United States Patent
Bersot et al.

(10) Patent No.: US 9,265,772 B2
(45) Date of Patent: Feb. 23, 2016

(54) CARBAZOLE-CONTAINING SULFONAMIDES AS CRYPTOCHROME MODULATORS

(71) Applicant: Reset Therapeutics, Inc., Burlingame, CA (US)

(72) Inventors: Ross Bersot, Orinda, CA (US); Paul Humphries, Santa Clara, CA (US)

(73) Assignee: RESET THERAPEUTICS, INC., South San Francisco, CA (US)

( * ) Notice: Subject to any disclaimer, the term of this patent is extended or adjusted under 35 U.S.C. 154(b) by 15 days.

(21) Appl. No.: 13/891,407

(22) Filed: May 10, 2013

(65) Prior Publication Data
US 2013/0303524 A1 Nov. 14, 2013

Related U.S. Application Data

(60) Provisional application No. 61/645,918, filed on May 11, 2012, provisional application No. 61/778,176, filed on Mar. 12, 2013.

(51) Int. Cl.
| | |
|---|---|
| *C07D 405/12* | (2006.01) |
| *C07D 405/14* | (2006.01) |
| *C07D 403/12* | (2006.01) |
| *C07D 401/12* | (2006.01) |
| *C07D 413/12* | (2006.01) |
| *C07D 417/12* | (2006.01) |
| *C07D 493/08* | (2006.01) |
| *C07D 209/86* | (2006.01) |
| *C07D 209/88* | (2006.01) |
| *A61K 31/403* | (2006.01) |
| *A61K 31/541* | (2006.01) |
| *A61K 31/549* | (2006.01) |
| *A61P 3/00* | (2006.01) |
| *A61K 31/4155* | (2006.01) |
| *A61K 31/427* | (2006.01) |
| *A61K 45/06* | (2006.01) |
| *C07D 417/06* | (2006.01) |
| *C07D 401/06* | (2006.01) |
| *C07D 403/06* | (2006.01) |
| *C07D 409/12* | (2006.01) |

(52) U.S. Cl.
CPC ............ *A61K 31/549* (2013.01); *A61K 31/403* (2013.01); *A61K 31/4155* (2013.01); *A61K 31/427* (2013.01); *A61K 31/541* (2013.01); *A61K 45/06* (2013.01); *C07D 209/86* (2013.01); *C07D 209/88* (2013.01); *C07D 401/06* (2013.01); *C07D 401/12* (2013.01); *C07D 403/06* (2013.01); *C07D 403/12* (2013.01); *C07D 405/12* (2013.01); *C07D 405/14* (2013.01); *C07D 409/12* (2013.01); *C07D 413/12* (2013.01); *C07D 417/06* (2013.01); *C07D 493/08* (2013.01)

(58) Field of Classification Search
CPC .. C07D 405/12; C07D 405/14; C07D 403/12; C07D 401/12; C07D 413/12; C07D 417/12; C07D 493/08; C07D 209/86; C07D 209/88; A61K 31/403; A61K 31/541; A61K 31/549
USPC ........ 514/222.2, 222.5, 411, 372, 226.5, 407, 514/451, 461; 548/444, 364.7, 214; 544/3, 544/8, 49
See application file for complete search history.

(56) References Cited

U.S. PATENT DOCUMENTS

| | | | |
|---|---|---|---|
| 4,105,776 A | 8/1978 | Ondetti et al. | |
| 4,230,767 A | 10/1980 | Isaka et al. | |

(Continued)

FOREIGN PATENT DOCUMENTS

| | | |
|---|---|---|
| EP | 0253310 A2 | 1/1988 |
| WO | WO-9500501 A2 | 1/1995 |

(Continued)

OTHER PUBLICATIONS

STN registry, CAS No. 865611-93-4, entered STN Oct. 19, 2005.*

(Continued)

*Primary Examiner* — Sreeni Padmanabhan
*Assistant Examiner* — Irina Neagu
(74) *Attorney, Agent, or Firm* — Cooley LLP; Ivor Elrifi; Christina Stock

(57) ABSTRACT

The subject matter herein is directed to carbazole-containing sulfonamide derivatives and pharmaceutically acceptable salts or hydrates thereof of structural formula I wherein the variable $R_1$, $R_2$, $R_3$, $R_4$, $R_5$, $R_6$, $R_7$, A, B, C, D, E, F, G, H, a, and b are accordingly described. Also provided are pharmaceutical compositions comprising the compounds of formula I to treat a Cry-mediated disease or disorder, such as diabetes, obesity, metabolic syndrome, Cushing's syndrome, and glaucoma.

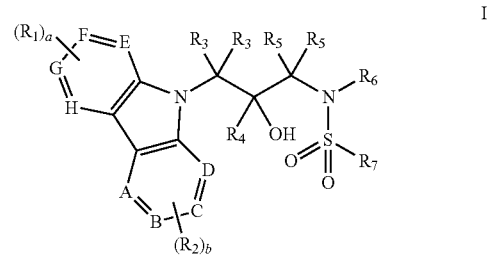

I

22 Claims, No Drawings

(56) References Cited

U.S. PATENT DOCUMENTS

| | | | |
|---|---|---|---|
| 4,231,938 A | 11/1980 | Monaghan et al. |
| 4,233,402 A | 11/1980 | Maggio et al. |
| 4,275,149 A | 6/1981 | Litman et al. |
| 4,276,890 A | 7/1981 | Fichera |
| 4,302,386 A | 11/1981 | Stevens |
| 4,316,906 A | 2/1982 | Ondetti et al. |
| 4,325,952 A | 4/1982 | Silvestrini et al. |
| 4,337,201 A | 6/1982 | Petrillo, Jr. |
| 4,344,949 A | 8/1982 | Hoefle et al. |
| 4,346,227 A | 8/1982 | Terahara et al. |
| 4,374,829 A | 2/1983 | Harris et al. |
| 4,376,110 A | 3/1983 | David et al. |
| 4,410,520 A | 10/1983 | Watthey |
| 4,444,784 A | 4/1984 | Hoffman et al. |
| 4,508,729 A | 4/1985 | Vincent et al. |
| 4,512,924 A | 4/1985 | Attwood et al. |
| 4,587,258 A | 5/1986 | Gold et al. |
| 4,659,678 A | 4/1987 | Forrest et al. |
| 4,727,022 A | 2/1988 | Skold et al. |
| 4,739,073 A | 4/1988 | Kathawala |
| 4,772,684 A | 9/1988 | Brunck et al. |
| 4,780,401 A | 10/1988 | Heusser et al. |
| 4,786,653 A | 11/1988 | Golwyn |
| 4,788,189 A | 11/1988 | Glazer |
| 4,816,463 A | 3/1989 | Blankley et al. |
| 4,845,079 A | 7/1989 | Luly et al. |
| 4,885,292 A | 12/1989 | Ryono et al. |
| 4,894,437 A | 1/1990 | TenBrink |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,825 A | 11/1991 | Chakravarty et al. |
| 5,064,965 A | 11/1991 | Ocain et al. |
| 5,066,643 A | 11/1991 | Abeles et al. |
| 5,071,837 A | 12/1991 | Doherty et al. |
| 5,073,566 A | 12/1991 | Lifer et al. |
| 5,075,451 A | 12/1991 | Ocain et al. |
| 5,081,127 A | 1/1992 | Carini et al. |
| 5,085,992 A | 2/1992 | Chen et al. |
| 5,087,634 A | 2/1992 | Reitz et al. |
| 5,089,471 A | 2/1992 | Hanson et al. |
| 5,095,006 A | 3/1992 | Bender et al. |
| 5,095,119 A | 3/1992 | Ocain et al. |
| 5,098,924 A | 3/1992 | Poss |
| 5,104,869 A | 4/1992 | Albright et al. |
| 5,106,835 A | 4/1992 | Albright et al. |
| 5,114,937 A | 5/1992 | Hamby et al. |
| 5,116,835 A | 5/1992 | Ruger et al. |
| 5,273,995 A | 12/1993 | Roth |
| 5,474,995 A | 12/1995 | Ducharme et al. |
| 5,521,213 A | 5/1996 | Prasit et al. |
| 5,536,752 A | 7/1996 | Ducharme et al. |
| 5,550,142 A | 8/1996 | Ducharme et al. |
| 5,552,422 A | 9/1996 | Gauthier et al. |
| 5,604,253 A | 2/1997 | Lau et al. |
| 5,604,260 A | 2/1997 | Guay et al. |
| 5,639,780 A | 6/1997 | Lau et al. |
| 5,643,933 A | 7/1997 | Talley et al. |
| 5,677,318 A | 10/1997 | Lau |
| 5,691,374 A | 11/1997 | Black et al. |
| 5,698,584 A | 12/1997 | Black et al. |
| 5,710,140 A | 1/1998 | Ducharme et al. |
| 5,723,591 A | 3/1998 | Livak et al. |
| 5,733,909 A | 3/1998 | Black et al. |
| 5,750,015 A | 5/1998 | Soane et al. |
| 5,789,413 A | 8/1998 | Black et al. |
| 5,801,155 A | 9/1998 | Kutyavin et al. |
| 5,817,700 A | 10/1998 | Dube et al. |
| 5,849,943 A | 12/1998 | Atkinson et al. |
| 5,861,419 A | 1/1999 | Dube et al. |
| 5,922,742 A | 7/1999 | Black et al. |
| 5,925,631 A | 7/1999 | Black et al. |
| 6,084,102 A | 7/2000 | Kutyavin et al. |
| 2002/0138208 A1 | 9/2002 | Paulse et al. |
| 2002/0193950 A1 | 12/2002 | Gavin et al. |
| 2003/0004402 A1 | 1/2003 | Hitt et al. |
| 2003/0055615 A1 | 3/2003 | Zhang et al. |
| 2005/0163545 A1 | 7/2005 | Cook et al. |
| 2009/0163454 A1 | 6/2009 | Hait et al. |
| 2011/0003836 A1* | 1/2011 | McKnight ............ A61K 31/404 514/275 |
| 2013/0040977 A1 | 2/2013 | McKnight et al. |

FOREIGN PATENT DOCUMENTS

| | | |
|---|---|---|
| WO | WO-9518799 A1 | 7/1995 |
| WO | WO-0131580 A2 | 5/2001 |
| WO | WO-2004056456 A1 | 7/2004 |
| WO | WO-2004088309 A2 | 10/2004 |
| WO | WO-2006023590 A1 | 3/2006 |

OTHER PUBLICATIONS

STN registry CAS No. 694499-58-6, entered STN Jun. 17, 2004.*
Akashi et al. "Noninvasive Method for Assessing the Human Circadian Clock Using Hair Follicle Cells." *PNAS.* 107.35(2010):15643-15648.
Balakin et al. "Property-Based Design of GPCR-Targeted Library." *J. Chem. Inf. Comput. Sci.* 42.6(2002):1332-1342.
Barker et al. "Association of Genetic Loci with Glucose Levels in Childhood and Adolescence: A Meta-Analysis of Over 6,000 Children." *Diabetes.* 60.6(2011):1805-1812.
Bjarnason et al. "Circadian Expression of Clock Genes in Human Oral Mucosa and Skin: Association with Specific Cell-Cycle Phases." *Am. J. Pathol.* 158.5(2001):1793-1801.
Boden et al. "Disruption of Circadian Insulin Secretion is Associated With Reduced Glucose Uptake in First-Degreee Relatives of Patients with Type 2 Diabetes." *Diabetes.* 48.11(1999):2182-2188.
Choi et al. "1,3-Diphenyl-1$H$-pryazole Derivatives as a New Series of Potent PPARγ Partial Agonists." *Bioorg. Med. Chem.* 18.23(2010):8315-8323.
Dupuis et al. "Erratum: New Genetic Loci Implicated in Fasting Glucose Homeostasis and Their Impact on Type 2 Diabetes Risk." *Nat. Genet.* 42.5(2010):464.
Dupuis et al. "New Genetic Loci Implicated in Fasting Glucose Homeostasis and Their Impact on Type 2 Diabetes Risk." *Nat. Genet.* 42.2(2010):105-116.
Eisen et al. "DNA Arrays for Analysis of Gene Expression." *Meth. Enzymol.* 303(1999):179-205.
Ekins et al. "Microarrays: Their Origins and Applications." *Trends Biotechnol.* 17.6(1999):217-218.
Green et al. "The Meter of Metabolism." *Cell.* 134.5(2008):728-742.
Hatori et al. "CRY Links the Circadian Clock and CREB-Mediated Gluconeogenesis." *Cell Res.* 20(2010):1285-1288.
Hirota et al. "Identification of Small Molecule Activators of Cryptochrome." *Science.* 337.6098(2012):1094-1097.
Jungblut et al. "Protein Identification from 2-DE Gels by MALDI Mass Spectrometry." *Mass. Spectrom. Rev.* 16.3(1997):145-162.
Lamia et al. "Crytochromes Mediate Rhythmic Repression of the Glucocorticoid Receptor." *Nature.* 480.7378(2011):552-556.
Lamia et al. "Physiological Significance of a Peripheral Tissue Circadian Clock." *PNAS.* 105.39(2008):15172-15177.
Liu et al. "Variants in *GLIS3* and *CRY2* are Associated with Type 2 Diabetes and Impaired Fasting Glucose in Chinese Hans." *PLoS One.* 6.6(2011):e21464.
Macmillan et al. "Development of Proneurogenic, Neuroprotective Small Molecules." *J. Am. Chem. Soc.* 133.5(2011):1428-1437.
Marcheva et al. "Disruption of the Clock Components Clock and BMAL1 Leads to Hypoinsulinaemia and Diabetes." *Nature.* 466.7306(2010):627-631.
Mohawk et al. "Central and Peripheral Circadian Clocks in Mammals." *Annu. Rev. Neurosci.* 35(2012):445-462.
Patani et al. "Bioisoterism: A Rational Approach in Drug Design." *Chem. Rev.* 96.8(1996):3147-3176.

(56) References Cited

OTHER PUBLICATIONS

Polonsky et al. "Abnormal Patterns of Insulin Secretion in Non-Insulin-Dependent Diabetes Mellitus." *N. Engl. J. Med.* 318.19(1988):1231-1239.

Scheer et al. "Adverse Metabolic and Cardiovascular Consequence of Circadian Misalignment." *PNAS.* 106.11(2009):4453-4458.

Shoemaker et al. "Experimental Annotation of the Human Genome Using Microarray Technology." *Nature.* 409.6822(2011):922-927.

Spiegel et al. "Impact of Sleep Debt on Metabolic and Endocrine Function." *Lancet.* 354.9188(1999):1435-1439.

Spiegel et al. "Sleep Loss: A Novel Risk for Insulin Resistance and Type 2 Diabetes." *J. Appl. Physiol.* 99.5(2005):2008-2019.

Stamenkovic et al. "Regulation of Core Clock Genes in Human Islets." *Metabolism.* 61.7(2012):978-985.

Tahira et al. "Obesity Alters the Expression Profile of Clock Genes in Peripheral Blood Mononuclear Cells." *Arch. Med. Sci.* 7.6(2011):933-940.

Takahashi et al. "The Genetics of Mammlian Circadian Order and Disorder: Implications for Physiology and Disease." *Nat. Rev. Genet.* 9.10(2008):764-775.

Wirth et al. "Post-Translational Modification Detection using Metastable Ions in Reflector Matrix-Assisted Laser Desorption/Ionization-Time of Flight Mass Spectrometry." *Proteomics.* 2.10(2002):1445-1451.

Wong et al. "Nonpeptide Agiotensin II Receptor Antagonists. I. Pharmacological Characterization of 2-$n$-Butyl-4-chloro-1-(2-chlorobenzyl)imidazole-5-acetic Acid, Sodium Salt (S-8307)." *J. Pharmacol. Exp. Ther.* 247.1(1988):1-7.

Yin et al. "Rev-erbα, a Heme Sensor that Coordinates Metabolic and Circadian Pathways." *Science.* 318.5857(2007):1786-1789.

Zhang et al. "Clocks Not Winding Down: Unravelling Circadian Networks." *Nat. Rev. Mol. Cell Biol.* 11.11(2010):764-776.

Zhang et al. "Cryptochrome Mediates Circadian Regulation of cAMP Signaling and Hepatic Gluconeogenesis." *Nat. Med.* 16.10(2010):1152-1156.

Turek et al. "Obesity and Metabolic Syndrome in Circadian *Clock* Mutant Mice." *Science.* 308.5724(2005):1043-1045.

\* cited by examiner

CARBAZOLE-CONTAINING SULFONAMIDES AS CRYPTOCHROME MODULATORS

RELATED APPLICATIONS

This application claims priority to and benefit of U.S. Provisional Application No. 61/645,918, filed on May 11, 2012 and U.S. Provisional Application No. 61/778,176, filed on Mar. 12, 2013, the contents of which are incorporated herein in their entireties.

INCORPORATION BY REFERENCE

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

TECHNICAL FIELD

The subject matter disclosed herein relates to, inter alia, carbazole-containing sulfonamide derivatives, pharmaceutical compositions containing these compounds, methods for their use in treating cryptochrome-mediated diseases or disorders, and processes for their production. Also provided are methods of diagnosing, detecting, or monitoring the progression of cryptochrome-dependent diseases in subjects receiving the compounds and compositions disclosed herein.

BACKGROUND

The circadian clock is an intrinsic time-keeping mechanism that controls the daily rhythms of many physiological processes, such as sleep/wake behavior, body temperature, hormone secretion, and metabolism (Takahashi, J. S. et al. *Nat. Rev. Genet.* 2008, 9, 764; Green, C. B. et al. *Cell*, 2008, 134, 728; Zhang, E. E. et al. *Nat. Rev. Mol. Cell. Biol.* 2010, 11, 764). Circadian rhythms are generated in a cell-autonomous manner through transcriptional regulatory networks of clock genes. In the core feedback loop, the transcription factors CLOCK and BMAL1 activate expression of Period (Per1 and Per2) and Cryptochrome (Cry1 and Cry2) genes. After translation and nuclear localization, PER and CRY proteins inhibit the function of CLOCK-BMAL1, resulting in sustained rhythmic gene expression. Many physiological pathways are under the control of the circadian clock (Panda, S. et al. *Cell*, 2002, 109, 307), including direct regulation of numerous hepatic processes (Rey, G. et al. *PLoS Biol.* 2011, 9, e1000595; Bugge, A. et al. *Genes Dev.* 2012, 26, 657).

Circadian desynchrony has been associated with impaired insulin sensitivity (Spiegel, K. et al. *J. Appl. Physiol.* 2005, 99, 2008; Spiegel, K. et al. *Lancet,* 1999, 354, 1435), decreased leptin levels and results in hyperglycemia, hyperinsulinemia and postprandial glucose responses comparable to those of a prediabetic state (Scheer, F. A. et al. *Proc. Natl. Acad. Sci. USA,* 2009, 106, 4453). Several genome-wide association studies led to the discovery that Cry2 may be important in the regulation of mammalian glucose levels (Dupuis, J. et al. *Nat. Genet.* 2010, 42, 105; Liu, C. et al. *PLoS One,* 2011, 6, e21464; Barker, A. et al. *Diabetes,* 2011, 60, 1805).

Glucose concentrations in the blood are highly rhythmic because of changes in insulin sensitivity and insulin secretory capacity of the endocrine pancreas (Polonsky, K. S. et al. *N. Engl. J. Med.* 1988, 318, 1231). Clock$^{\Delta 19}$ mutant mice develop age-dependent hyperglycemia and these animals also develop susceptibility to diet-induced obesity, have inappropriately low concentrations of insulin (Turek, F. W. et al. *Science,* 2005, 308, 1043) and display a steeper drop in blood sugar in response to treatment with insulin, indicating that these animals have enhanced insulin sensitivity, thereby masking their β-cell deficiency (Marcheva, B. et al. *Nature,* 2010, 466, 627). Liver-specific deletion of Bmal1 in mice results in impaired glucose tolerance and increased insulin sensitivity (Lamia, K. A. et al. *Proc. Natl. Acad. Sci. USA,* 2008, 105, 15172). Individuals with type 2 diabetes, and even their first-degree relatives not yet affected with the disease, display altered rhythmicity in glucose tolerance (Boden, G. et al. *Diabetes,* 1999, 48, 2182). Also, Per2, Per3, and Cry2 expression is significantly lower in humans with type 2 diabetes versus humans without the disease (Stamenkovich, J. A. et al. *Metabolism,* 2012, 61, 978). The gluconeogenic genes phosphoenol pyruvate carboxykinase (Pck1) and glucose 6-phosphatase (G6pc) are controlled by CRY and the Bmal1 gene regulator REV-ERB (Zhang, E. E. et al. *Nat. Med.* 2010, 16, 1152; Lamia, K. A. et al. *Nature,* 2011, 480, 552; Yin, L. et al. *Science,* 2007, 318, 1786). Gluconeogenesis is tightly controlled by multiple signaling mechanisms and moreover, studies in mice have revealed that modulation of Cry1 and Cry2 can perturb gluconeogenesis and regulate blood sugar levels (Zhang, E. E. et al. *Nat. Med.* 2010, 16, 1152).

In a monotherapeutic or combination therapy context, new and established oral antidiabetic agents have non-uniform and limited effectiveness. Oral antidiabetic therapies suffer from poor or limited glycemic control, or poor patient compliance due to unacceptable side effects, such as edema, weight gain, or even more serious complications like hypoglycemia. Metformin, a substituted biguanide, can cause diarrhea and gastrointestinal discomfort. Finally, edema, weight gain, and in some cases, hepatotoxicity and cardiotoxicity, have been linked to the administration of some thiazolidine-2,4-dione antidiabetic agents (e.g. Rosiglitazone and Pioglitazone). Combination therapy using two or more of the above agents is common, but generally only leads to incremental improvements in glycemic control.

Cry1 and Cry2 also interact with the glucocorticoid receptor (GR) to globally alter the transcriptional response to glucocorticoids (Lamia, K. A. et al. *Nature,* 2011, 480, 552). Loss of Cry1 and/or Cry2 results in glucose intolerance and constitutively high levels of circulating corticosterone, suggesting reduced suppression of the hypothalamic-pituitary-adrenal axis coupled with increased glucocorticoid transactivation in the liver. Genomically, Cry1 and Cry2 associate with a glucocorticoid response element in the Pck1 promoter in a hormone-dependent manner, and dexamethasone-induced transcription of the Pck1 gene was strikingly increased in cryptochrome-deficient livers. This suggests that the undesirable metabolic side effects of glucocorticoids (e.g. hyperglycemia, insulin resistance and suppression of adrenal function)

used to suppress inflammation may be alleviated by combining them with agents that can stabilize Cry1 and/or Cry2.

SUMMARY

The subject matter herein relates to cryptochrome (Cry) modulating compounds, pharmaceutical compositions comprising the Cry modulating compounds and methods of treating Cry-related diseases or disorders, such as, e.g. diabetes, obesity, metabolic syndrome, Cushing's syndrome and glaucoma, by administration of Cry modulating compounds.

In one aspect, the subject matter disclosed herein is directed to a compound of formula I:

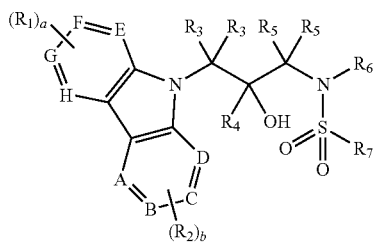

or a pharmaceutically acceptable salt or hydrate thereof, wherein:

each of A, B, C, D, E, F, G, and H is independently N or C;
each of $R_1$ and $R_2$, when A, B, C, D, E, F, G, or H is C, is independently selected from H, halo, cyano, nitro, $-CF_3$, $-CHF_2$, $-CH_2F$, trifluoromethoxy, azido, hydroxyl, $(C_1-C_6)$alkoxy, $(C_1-C_6)$alkyl, $(C_2-C_6)$alkenyl, $(C_2-C_6)$alkynyl, $-(C=O)-R_8$, $-(C=O)-O-R_8$, $-O-(C=O)-R_8$, $-NR_8(C=O)-R_{10}$, $-(C=O)-NR_8R_9$, $-NR_8R_9$, $-NR_8OR_9$, $-S(O)_cNR_8R_9$, $-S(O)_d(C_1-C_8)$alkyl, $-O-SO_2-R_8$, $NR_8-S(O)_c-$, $-(CR_8R_9)_d(3-10)$-membered cycloalkyl, $-(CR_8R_9)_e(C_6-C_{10})$aryl, $-(CR_8R_9)_e(4-10)$-membered heterocyclyl, $-(CR_8R_9)_f(C=O)(CR_8R_9)_e(C_6-C_{10})$aryl, $-(CR_8R_9)_f(C=O)(CR_8R_9)_e(4-10)$-membered heterocyclyl, $-(CR_8R_9)_eO(CR_8R_9)_f(C_6-C_{10})$aryl, $-(CR_8R_9)_eO(CR_8R_9)_f(4-10)$-membered heterocyclyl, $-(CR_8R_9)_fS(O)_d(CR_8R_9)_e(C_6-C_{10})$aryl, and $-(CR_8R_9)_fS(O)_d(CR_8R_9)_e(4-10)$-membered heterocyclyl;

each of $R_3$ and $R_5$ is independently selected from H, cyano, $-CF_3$, $-CHF_2$, $-CH_2F$, $(C_1-C_6)$alkyl, $(C_2-C_6)$alkenyl, $(C_2-C_6)$alkynyl, $-(C=O)-R_8$, $-(C=O)-O-R_8$, $-(C=O)-NR_8R_9$, $-S(O)_cNR_8R_9$, $-S(O)_d(C_1-C_8)$alkyl, $-(CR_8R_9)_d(3-10)$-membered cycloalkyl, $-(CR_8R_9)_e(C_6-C_{10})$aryl, $-(CR_8R_9)_e(4-10)$-membered heterocyclyl, $-(CR_8R_9)_f(C=O)(CR_8R_9)_e(C_6-C_{10})$aryl, $-(CR_8R_9)_f(C=O)(CR_8R_9)_e(4-10)$-membered heterocyclyl, $-(CR_8R_9)_eO(CR_8R_9)_f(C_6-C_{10})$aryl, $-(CR_8R_9)_eO(CR_8R_9)_f(4-10)$-membered heterocyclyl, $-(CR_8R_9)_fS(O)_d(CR_8R_9)_e(C_6-C_{10})$aryl, and $-(CR_8R_9)_fS(O)_d(CR_8R_9)_e(4-10)$-membered heterocyclyl;

wherein each of the $R_3$ groups are optionally linked to each other as a 4-12 membered mono- or bicyclic ring;

wherein each of the $R_5$ groups are optionally linked to each other as a 4-12 membered mono- or bicyclic ring;

$R_4$ is H, $-CF_3$, $-CHF_2$, $-CH_2F$, $(C_1-C_6)$alkyl, $(C_2-C_6)$alkenyl, $(C_2-C_6)$alkynyl, $-(C=O)-R_8$, $-(C=O)-O-R_8$, $-(C=O)-NR_8R_9$, $-(CR_8R_9)_d(3-10)$-membered cycloalkyl, $-(CR_8R_9)_e(C_6-C_{10})$aryl, $-(CR_8R_9)_e(4-10)$-membered heterocyclyl, $-(CR_8R_9)_f(C=O)(CR_8R_9)_e(C_6-C_{10})$aryl, $-(CR_8R_9)_f(C=O)(CR_8R_9)_e(4-10)$-membered heterocyclyl, $-(CR_8R_9)_eO(CR_8R_9)_f(C_6-C_{10})$aryl, $-(CR_8R_9)_eO(CR_8R_9)_f(4-10)$-membered heterocyclyl, $-(CR_8R_9)_fS(O)_d(CR_8R_9)_e(C_6-C_{10})$aryl, and $-(CR_8R_9)_fS(O)_d(CR_8R_9)_e(4-10)$-membered heterocyclyl;

$R_6$ is H, $-CF_3$, $-CHF_2$, $-CH_2F$, $(C_1-C_6)$alkyl, $(C_2-C_6)$alkenyl, $(C_2-C_6)$alkynyl, $-(C=O)-R_8$, $-(C=O)-O-R_8$, $-(C=O)-NR_8R_9$, $-(CR_8R_9)_d(3-10)$-membered cycloalkyl, $-(CR_8R_9)_e(C_6-C_{10})$aryl, $-(CR_8R_9)_e(4-10)$-membered heterocyclyl, $-(CR_8R_9)_f(C=O)_eCR_8R_9)_e(C_6-C_{10})$ aryl, $-(CR_8R_9)_f(C=O)(CR_8R_9)_e(4-10)$-membered heterocyclyl, $-(CR_8R_9)_eO(CR_8R_9)_f(C_6-C_{10})$aryl, $-(CR_8R_9)_eO(CR_8R_9)_f(4-10)$-membered heterocyclyl, $-(CR_8R_9)_fS(O)_d(CR_8R_9)_e(C_6-C_{10})$aryl, and $-(CR_8R_9)_fS(O)_d(CR_8R_9)_e(4-10)$-membered heterocyclyl;

wherein $R_5$ and $R_6$ are optionally linked to each other as a 4-12 membered mono- or bicyclic ring;

$R_7$ is $-CF_3$, $-CHF_2$, $-CH_2F$, $(C_1-C_6)$alkyl, $(C_2-C_6)$alkenyl, $(C_2-C_6)$alkynyl, $-(C=O)-R_8$, $-(C=O)-O-R_8$, $-NR_8(C=O)-R_{10}$, $-(C=O)-NR_8R_9$, $-NR_8R_9$, $-NR_8OR_9$, $-NR_8-S(O)_c-$, $-(CR_8R_9)_d(3-10)$-membered cycloalkyl, $-(CR_8R_9)_e(C_6-C_{10})$aryl, $-(CR_8R_9)_e(4-10)$-membered heterocyclyl, $-(CR_8R_9)_f(C=O)(CR_8R_9)_e(C_6-C_{10})$aryl, $-(CR_8R_9)_f(C=O)(CR_8R_9)_e(4-10)$-membered heterocyclyl, $-(CR_8R_9)_eO(CR_8R_9)_f(C_6-C_{10})$aryl, $-(CR_8R_9)_eO(CR_8R_9)_f(4-10)$-membered heterocyclyl, $-(CR_8R_9)_fS(O)_d(CR_8R_9)_e(C_6-C_{10})$aryl, and $-(CR_8R_9)_fS(O)_d(CR_8R_9)_e(4-10)$-membered heterocyclyl;

wherein $R_6$ and $R_7$ are optionally linked to each other as a 4-12 membered mono- or bicyclic ring;

each of $R_8$, $R_9$ and $R_{10}$ are independently selected from H, $(C_1-C_6)$alkyl, $-(CR_{11}R_{12})_e(3-10)$-membered cycloalkyl, $-(CR_{11}R_{12})_g(C_6-C_{10})$aryl, and $-(CR_{11}R_{12})_g(4-10)$-membered heterocyclyl;

any carbon atoms of the $(C_1-C_6)$alkyl, the (3-10)-membered cycloalkyl, the $(C_6-C_{10})$aryl and the (4-10)-membered heterocyclyl of the foregoing $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are independently optionally substituted with 1 to 3 $R_{14}$ substituents each independently selected from halo, cyano, nitro, $-CF_3$, $-CHF_2$, $-CH_2F$, trifluoromethoxy, azido, hydroxyl, $-O-R_{15}$, $-(CR_8R_9)e(C_1-C_6)$alkoxy, $(C_1-C_6)$alkoxy, $(C_1-C_6)$alkyl, $(C_2-C_6)$alkenyl, $(C_2-C_6)$alkynyl, $-(C=O)-R_{11}$, $-(C=O)-R_{15}$, $-(C=O)-O-R_{11}$, $-(C=O)-O-R_{15}$, $-O-(C=O)-R_{11}$, $-O-(C=O)-R_{15}$, $-NR11(C=O)-R_{13}$, $-(C=O)-NR_{11}R_{12}$, $-(C=O)-NR_{11}R_{15}$, $-NR_{11}R_{12}$, $-NR_{11}R_{15}$, $-NR_{11}OR_{12}$, $-NR_{11}OR_{15}$, $-S(O)_cNR_{11}R_{12}$, $-S(O)_cNR_{11}R_{15}$, $-S(O)_d(C_1-C_6)$alkyl, $-S(O)_dR_{15}$, $-O-SO_2-R_{11}$, $-O-SO_2-R_{15}$, $-NR_{11}-S(O)_c-$, $-NR_{15}-S(O)_c-$, $-(CR_{11}R_{12})_e(3-10)$- membered cycloalkyl, $-(CR_{11}R_{12})_e(C_6-C_{10})$aryl, $-(CR_{11}R_{12})_e(4-10)$-membered heterocyclyl, $-(CR_{11}R_{12})_f(C=O)(CR_{11}R_{12})_e(C_6-C_{10})$aryl, $-(CR_{11}R_{12})_f(C=O)(CR_{11}R_{12})_e(4-10)$-membered heterocyclyl, $-(CR_{11}R_{12})_eO(CR_{11}R_{12})_f(C_6-C_{10})$aryl, $-(CR_{11}R_{12})_eO(CR_{11}R_{12})_f(4-10)$-membered heterocyclyl, $-(CR_{11}R_{12})_fS(O)_d(CR_{11}R_{12})_e(C_6-C_{10})$aryl, and $-(CR_{11}R_{12})_fS(O)_d(CR_{11}R_{12})_e(4-10)$- membered heterocyclyl;

any carbon atoms of the $(C_1-C_6)$alkyl, the (3-10)-membered cycloalkyl, the $(C_6-C_{10})$aryl and the (4-10)-membered heterocyclyl of the foregoing $R_{14}$ are independently optionally substituted with 1 to 3 $R_{16}$ substituents each independently selected from halo, cyano, nitro, $-CF_3$, $-CHF_2$, $-CH_2F$, trifluoromethoxy, azido, $(CH_2)_eOH$, $(C_1-C_6)$alkoxy, $(C_1-C_6)$alkyl, $(C_2-C_6)$alkenyl, $(C_2-C_6)$alkynyl, $-(C=O)-R_{11}$, $-(C=O)-R_{15}$, $-(C=O)-O-R_{11}$, $-(C=O)-$ O—$R_{15}$, —O—(C=O)—$R_{11}$, —O—(C=O)—$R_{15}$, —$NR_{11}$(C=O)—$R_{13}$, —(C=O)—$NR_{11}R_{12}$, —$NR_{11}R_{12}$, and —$NR_{11}R_{15}$;

any nitrogen atoms of the (4-10)-membered heterocyclyl of the foregoing $R_1$, $R_2$, $R_3$, $R_4$, $R_5$, $R_6$, $R_7$, $R_8$, $R_9$, $R_{10}$, $R_{14}$, and $R_{15}$ are independently optionally substituted with ($C_1$-$C_6$)alkyl, ($C_2$-$C_6$)alkenyl, ($C_2$-$C_6$)alkynyl, —(C=O)—$R_{11}$, —(C=O)—O—$R_{11}$, —(C=O)—$NR_{11}R_{12}$, —$(CR_{11}R_{12})_e$(3-10)- membered cycloalkyl, —$(CR_{11}R_{12})_e(C_6$-$C_{10})$aryl, —$(CR_{11}R_{12})_e$(4-10)-membered heterocyclyl, —$(CR_{11}R_{12})_f$(C=O)$(CR_{11}R_{12})_e(C_6$-$C_{10})$aryl, or —$(CR_{11}R_{12})_f$(C=O)$(CR_{11}R_{12})_e$(4-10)-membered heterocyclyl;

each $R_{11}$, $R_{12}$, and $R_{13}$ are independently H or ($C_1$-$C_6$)alkyl;

$R_{15}$ is —$(CR_{11}R_{12})_e$(3-10)-membered cycloalkyl, —$(CR_{11}R_{12})_e(C_6$-$C_{10})$aryl, or —$(CR_{11}R_{12})_e$(4-10)-membered heterocyclyl;

a and b are each independently 1, 2, 3, or 4;

c is 1 or 2;

d is 0, 1, or 2; and e, f, and g are each independently 0, 1, 2, 3, 4, or 5.

In some embodiments, each of A, B, C, D, E, F, G, and H are C; each of $R_1$ and $R_2$ is independently selected from H or halo; $R_4$ is H or ($C_1$-$C_6$)alkyl, $R_3$ and $R_5$ are H; $R_6$ is —$CF_3$, —$CHF_2$, —$CH_2F$, ($C_1$-$C_6$)alkyl, ($C_2$-$C_6$)alkenyl, ($C_2$-$C_6$)alkynyl, —$(CR_8R_9)_d$ (3-10)-membered cycloalkyl, —$(CR_8R_9)_e(C_6$-$C_{10})$aryl, —$(CR_8R_9)_e$(4-10)-membered heterocyclyl, —$(CR_8R_9)_eO(CR_8R_9)_f(C_6$-$C_{10})$aryl, —$(CR_8R_9)_eO(CR_8R_9)_f$(4-10)-membered heterocyclyl, —$(CR_8R_9)_fS(O)_d(CR_8R_9)_e(C_6$-$C_{10})$aryl, and —$(CR_8R_9)_fS(O)_d(CR_8R_9)_e$(4-10)-membered heterocyclyl; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e(C_6$-$C_{10})$aryl, —$(CR_8R_9)_e$(4-10)-membered heterocyclyl, —$(CR_8R_9)_eO(CR_8R_9)_f(C_6$-$C_{10})$aryl, —$(CR_8R_9)_eO(CR_8R_9)_f$(4-10)-membered heterocyclyl, —$(CR_8R_9)_fS(O)_d(CR_8R_9)_e(C_6$-$C_{10})$aryl, and —$(CR_8R_9)_fS(O)_d(CR_8R_9)_e$(4-10)-membered heterocyclyl; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In other embodiments, each of A, B, C, D, E, F, G, and H are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic ring; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In other embodiments, each of A, B, C, D, E, F, G, and H are C; each of $R_1$ and $R_2$ is independently selected from H or halo; $R_4$ is H or ($C_1$-$C_6$)alkyl; $R_3$ and one $R_5$ are H; one $R_5$ and $R_6$ are linked to each other as a 4-12 membered mono- or bicyclic ring; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e(C_6$-$C_{10})$aryl, —$(CR_8R_9)_e$(4-10)-membered heterocyclyl, —$(CR_8R_9)_eO(CR_8R_9)_f(C_6$-$C_{10})$aryl, —$(CR_8R_9)_eO(CR_8R_9)_f$(4-10)-membered heterocyclyl, —$(CR_8R_9)_fS(O)_d(CR_8R_9)_e(C_6$-$C_{10})$aryl, and —$(CR_8R_9)_fS(O)_d(CR_8R_9)_e$(4-10)-membered heterocyclyl; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In some embodiments, the compound of formula I is a single enantiomer bearing an (S)-configuration or (R)-configuration at C-3, wherein each of A, B, C, D, E, F, G, and H are C; each of $R_1$ and $R_2$ is independently selected from H or halo; $R_4$ is H or ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e(C_6$-$C_{10})$aryl, —$(CR_8R_9)_e$(4-10)-membered heterocyclyl, —$(CR_8R_9)_eO(CR_8R_9)_f(C_6$-$C_{10})$aryl, —$(CR_8R_9)_eO(CR_8R_9)_f$(4-10)-membered heterocyclyl, —$(CR_8R_9)_fS(O)_d(CR_8R_9)_e(C_6$-$C_{10})$aryl, and —$(CR_8R_9)_fS(O)_d(CR_8R_9)_e$(4-10)-membered heterocyclyl; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e(C_6$-$C_{10})$aryl, —$(CR_8R_9)_e$(4-10)-membered heterocyclyl, —$(CR_8R_9)_eO(CR_8R_9)_f(C_6$-$C_{10})$aryl, —$(CR_8R_9)_eO(CR_8R_9)_f$(4-10)-membered heterocyclyl, —$(CR_8R_9)_fS(O)_d(CR_8R_9)_e(C_6$-$C_{10})$aryl, and —$(CR_8R_9)_fS(O)_d(CR_8R_9)_e$(4-10)-membered heterocyclyl; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In other embodiments of the subject matter disclosed herein, the compound of formula I is a single enantiomer bearing an (S)-configuration or (R)-configuration at C-3, wherein each of A, B, C, D, E, F, G, and H are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic ring; $R_8$, $R_9$, $R_{10}$, $R_{11}$, $R_{12}$, $R_{13}$, $R_{14}$, $R_{15}$, $R_{16}$, a, b, c, d, e, and f are as defined herein.

Other embodiments of the subject matter described herein are compounds selected from the group consisting of:

(S)—N-(3-(9H-Carbazol-9-yl)-2-hydroxypropyl)-1,2-thiazinane-1,1-dioxide;

N-(3-(3,6-Difluoro-9H-carbazol-9-yl)-2-hydroxypropyl)-isothiazolidine-1,1-dioxide;

(S)—N-(3-(9H-Carbazol-9-yl)-2-hydroxypropyl)isothiazolidine-1,1-dioxide;

2-(3-(9H-Carbazol-9-yl)-2-hydroxypropyl)-5-fluoro-isothiazolidine-1,1-dioxide;

2-(3-(3,6-Difluoro-9H-carbazol-9-yl)-2-hydroxypropyl)-1,2,6-thiadiazinane-1,1-dioxide;

N-(3-(9H-Carbazol-9-yl)-2-hydroxypropyl)-N-(1-methyl-cyclopentyl)methanesulfonamide;

N-(3-(9H-Carbazol-9-yl)-2-hydroxypropyl)isothiazolidine-1,1-dioxide;

N-(3-(9H-Carbazol-9-yl)-2-hydroxypropyl)-2,3-dihydrobenzo[d]isothiazole-1,1-dioxide;

N-(3-(2,6-Difluoro-9H-carbazol-9-yl)-2-hydroxypropyl)-1,2-thiazinane-1,1-dioxide;

2-(3-(9H-Carbazol-9-yl)-2-hydroxypropyl)-1,2,6-thiadiazinane-1,1-dioxide; or a pharmaceutically acceptable salt or hydrate thereof.

In another aspect, the compounds described herein modulate Cry1 or Cry2. Modulation of Cry1 or Cry2 includes any one of the following: binding to Cry1 or Cry2; inhibiting modification of Cry1 or Cry2; altering Cry1 or Cry2 localization; increasing or decreasing Cry1 or Cry2 stabilization; increasing or decreasing the binding between Cry1 or Cry2 to a target; increasing or decreasing Cry1 or Cry2 activity; and increasing or decreasing activity of a Cry1 or Cry2 target. Targets of Cry1 and/or Cry2 include, but are not limited to, Per1, Per2, glucocorticoid receptor (GR), CLOCK, BMAL1, or a CLOCK-BMAL1 promoter sequence.

In another aspect, the subject matter described herein provides a pharmaceutical composition comprising a compound according to claim 1, or a pharmaceutically acceptable salt or hydrate thereof, and a pharmaceutically acceptable carrier, adjuvant, or diluent. In some embodiments, the pharmaceutical composition further comprises one or more additional therapeutic agents.

In other aspects, a method of treating a Cry-mediated disease or disorder in a subject is provided, comprising administering to the subject a therapeutically effective amount of the pharmaceutical composition described herein. In a further aspect, the present invention provides a method for alleviating a symptom of a Cry-mediated disease or disorder in a subject, comprising administering to the subject a therapeutically effective amount of the pharmaceutical composition described herein. The disease or disorder may be selected from the group consisting of diabetes, metabolic syndrome, insulin resistance syndrome, obesity, glaucoma, Cushing's syndrome, psychotic depression, Alzheimer's disease, neuropathic pain, drug abuse, osteoporosis, cancer, macular degeneration, and myopathy. In some embodiments, the method may further comprise administering to the subject one or more additional therapeutic agents.

In another aspect, a method of monitoring progression or prognosis of a Cry-mediated disease or disorder in a subject is provided, comprising measuring an effective amount of one or more cryptochromes in a first sample from the subject at a first period of time; measuring an effective amount of one or more cryptochromes in a second sample from the subject at a second period of time; and comparing the amount of the one or more cryptochromes detected in the first sample to the amount of the one or more cryptochromes detected in the second sample, or to a reference value. In some embodiments, the monitoring comprises evaluating changes in the risk of developing the Cry-mediated disease or disorder in the subject.

The subject may comprise one who has been previously treated for the Cry-mediated disease or disorder, one who has not been previously treated for the Cry-mediated disease or disorder, or one who has not been previously diagnosed with the Cry-mediated disease or disorder. The sample can be whole blood, serum, plasma, blood cells, endothelial cells, tissue biopsies, lymphatic fluid, ascites fluid, interstitial fluid, bone marrow, cerebrospinal fluid (CSF), seminal fluid, saliva, mucous, sputum, sweat, or urine.

In some embodiments, the first sample is taken from the subject prior to being treated for the Cry-mediated disease or disorder and the second sample is taken from the subject after being treated for the Cry-mediated disease or disorder. In other embodiments, the subject is treated with the pharmaceutical composition comprising the compounds of formula I disclosed herein. In certain embodiments, the monitoring further comprises selecting a treatment for the subject and/or monitoring the effectiveness of a treatment for the Cry-mediated disease or disorder, wherein the treatment for the Cry-mediated disease or disorder comprises surgical intervention, administration of the pharmaceutical composition as defined herein alone or in combination with one or more additional therapeutic agents, surgical intervention following or preceded by administration of the pharmaceutical composition provided herein or in combination with one or more additional therapeutic agents, or taking no further action.

In other embodiments, the reference value comprises an index value, a value derived from one or more Cry-mediated disease or disorder risk prediction algorithms, a value derived from a subject not having a Cry-mediated disease or disorder, or a value derived from a subject diagnosed with a Cry-mediated disease or disorder. In some embodiments, the measuring comprises detecting the presence or absence of the one or more cryptochromes, quantifying the amount of the one or more cryptochromes, qualifying the type of the one or more cryptochromes, and assessing the ability of one or more cryptochromes to bind to a target. The target may be Per1, Per2, or a CLOCK-BMAL1 promoter sequence. As disclosed herein, the Cry-mediated disease or disorder may be selected from the group consisting of diabetes, obesity, metabolic syndrome, insulin resistance syndrome, Cushing's syndrome, and glaucoma, psychotic depression, Alzheimer's disease, neuropathic pain, drug abuse, osteoporosis, cancer, macular degeneration, and myopathy.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from the following detailed description and claims.

DETAILED DESCRIPTION

The features, structures, or characteristics described throughout this specification may be combined in any suitable manner in one or more embodiments. For example, the usage of the phrases "exemplary embodiments," "example embodiments," "some embodiments," or other similar language, throughout this specification refers to the fact that a particular feature, structure, or characteristic described in connection with an embodiment may be included in at least one embodiment described herein. Thus, appearances of the phrases "exemplary embodiments," "example embodiments," "in some embodiments," "in other embodiments," or other similar language, throughout this specification do not necessarily all refer to the same group of embodiments, and the described features, structures, or characteristics can be combined in any suitable manner in one or more embodiments.

To facilitate the understanding of this disclosure, a number of terms are defined below. Terms defined herein have meanings as commonly understood by a person of ordinary skill in the areas relevant to the subject matter described herein. Terms such as "a", "an" and "the" are not intended to refer to only a singular entity, but include the general class of which a specific example may be used for illustration. The terminology herein is used to describe specific embodiments of the subject matter described herein, but their usage does not delimit the subject matter, except as outlined in the claims.

As used herein, the terms "comprising", "including", or "having" are used in their open, non-limiting sense.

The term "halo", as used herein, unless otherwise indicated, means fluoro, chloro, bromo, or iodo.

The term "alkyl", as used herein, unless otherwise indicated, includes saturated monovalent hydrocarbon radicals having straight or branched moieties.

The term "alkenyl", as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkynyl", as used herein, represents monovalent straight or branched chain groups of from two to six carbon atoms containing a carbon-carbon triple bond and is exemplified by ethynyl, 1-propynyl, and the like.

The term "alkoxy", as used herein, unless otherwise indicated, includes O-alkyl groups wherein alkyl is as defined above.

The term "Me" means methyl, and "Et" means ethyl.

The term "cycloalkyl", as used herein, unless otherwise indicated, refers to a non-aromatic, saturated or partially saturated, monocyclic or fused, spiro or unfused bicyclic or tricyclic hydrocarbon referred to herein containing a total of from 3 to 10 carbon atoms. Illustrative examples of cycloalkyl are derived from, but not limited to, the following:

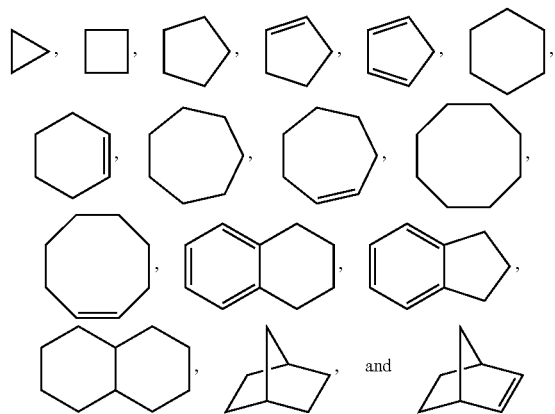

The term "aryl", as used herein, unless otherwise indicated, includes an organic radical derived from an aromatic hydrocarbon by removal of one hydrogen, such as phenyl or naphthyl.

The term "(4-12)-membered heterocyclyl", as used herein, unless otherwise indicated, includes aromatic and non-aromatic heterocyclic groups containing one to four heteroatoms each selected from O, S, and N, wherein each heterocyclic group has from 4-12 atoms, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3 membered heterocyclic group is aziridine, an example of a 4 membered ring heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Example of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, traizinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthridinyl, and furopyridinyl. The foregoing groups, as derived from the lists above, may be C-attached or N-attached where such is possible. For instance, a group derived from pyrrole may be pyrrol-1-yl (N-attached) or pyrrol-3-yl (C-attached). Further, a group derived from imidazole may be imidazole-1-yl (N-attached) or imidazole-3-yl (C-attached). The 4-12 membered heterocyclic may be optionally substituted on any ring carbon, sulfur, or nitrogen atom(s) by one or two oxo, per ring. An example of a heterocyclic group wherein 2 ring atoms are substituted with oxo moieties is 1,1-dioxo-thiomorpholinyl. Other illustrative example of 4-12 membered heterocyclic are derived from, but not limited to, the following:

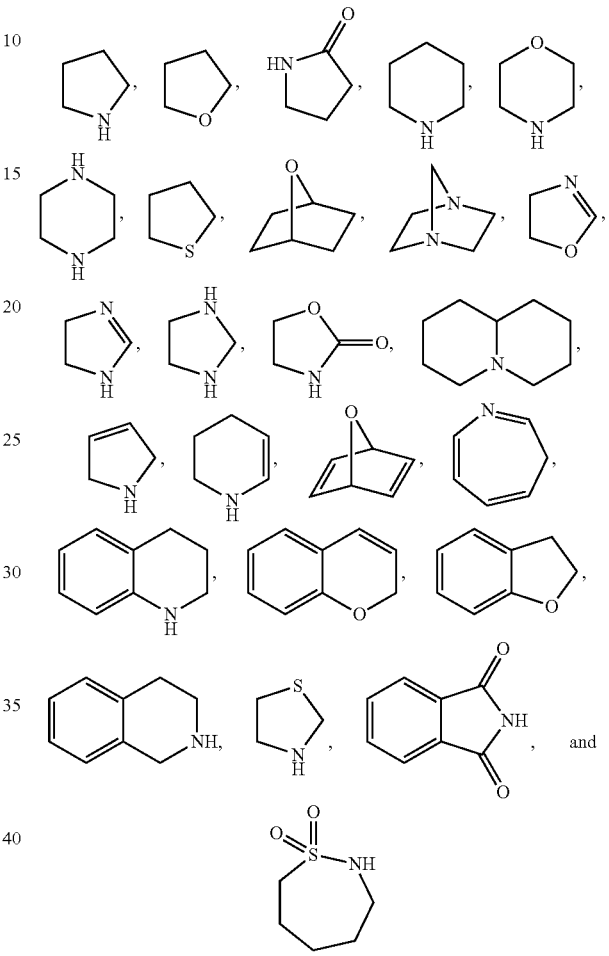

The term "4-12 membered mono- or bicyclic ring", as used herein represents, unless otherwise indicated, cycloalkyl, aryl, and (4-12)-membered heterocyclyl groups, wherein cycloalkyl, aryl, and (4-12)-membered heterocyclyl are as defined above.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). Non-limiting examples of such groups include, without limitation, H, $CH_3$, $NO_2$, $SO_2N(CH_3)_2$, $SO_2N((CH_3)SO_2)$, COOH, $COOCH_3$, $CO(N(CH_3))$, alkyl, alkenyl, alkynyl, aryl, aralkyl, cycloalkyl, heterocyclyl, alkylaryl, heteroaryl, heterocycloalkyl, alkoxy (i.e., methoxy, ethoxy, etc), alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, trifluoromethyl, pentafluoroethyl, halogen (i.e., chloro, fluoro, bromo, iodo), cyano, thio, amido, ether, ester, hydroxyl, hydroxyalkyl, saturated or unsaturated fatty acids, azido, phosphonamido, sulfonamido, lactam, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, guanidino, sulfhydryl, alkylthio, arylthio, thiocarboxylate, sulfates, alkylsulfinyl, sulfonato, sulfamoyl, sulfonamido, nitro, cyano, azido, etc.

The subject matter disclosed herein provides carbazole-containing sulfonamide compounds that modulate one or more cryptochrome molecules. These compounds have the general structure set forth in formula I:

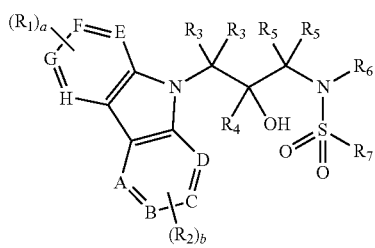

I or a pharmaceutically acceptable salt or hydrate thereof, wherein each of A, B, C, D, E, F, G, and H is independently N or C;

each of $R_1$ and $R_2$, when A, B, C, D, E, F, G, or H is C, is independently selected from H, halo, cyano, nitro, —$CF_3$, —$CHF_2$, —$CH_2F$, trifluoromethoxy, azido, hydroxyl, ($C_1$-$C_6$)alkoxy, ($C_1$-$C_6$)alkyl, ($C_2$-$C_6$)alkenyl, ($C_2$-$C_6$)alkynyl, —(C=O)—$R_8$, —(C=O)—O—$R_8$, —O—(C=O)—$R_8$, —$NR_8$(C=O)—$R_{10}$, —(C=O)—$NR_8R_9$, —$NR_8R_9$, —$NR_8OR_9$, —S(O)$_c NR_8R_9$, —S(O)$_d$($C_1$-$C_8$)alkyl, —O—$SO_2$—$R_8$, $NR_8$—S(O)$_c$, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_f$(C=O)($CR_8R_9$)$_e$($C_6$-$C_{10}$)aryl, —($CR_8R_9$)$_f$(C=O)($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_f$(O)$_d$($CR_8R_9$)$_e$($C_6$-$C_{10}$)aryl, and —($CR_8R_9$)$_f$S(O)$_d$($CR_8R_9$)$_e$(4-10)-membered heterocyclyl;

each of $R_3$ and $R_5$ is independently selected from H, cyano, —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O—$R_8$, —(C=O)—$NR_8R_9$, —S(O)$_c NR_8R_9$, —S(O)$_d$($C_1$-$C_8$)alkyl, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_f$(C=O)($CR_8R_9$)$_e$($C_6$-$C_{10}$)aryl, —($CR_8R_9$)$_f$(C=O)($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_f$S(O)$_d$($CR_8R_9$)$_e$($C_6$-$C_{10}$)aryl, and —($CR_8R_9$)$_f$S(O)$_d$($CR_8R_9$)$_e$(4-10)-membered heterocyclyl;

each of the $R_3$ groups are optionally linked to each other as a 4-12 membered mono- or bicyclic ring;

each of the $R_5$ groups are optionally linked to each other as a 4-12 membered mono- or bicyclic ring;

$R_4$ is H, —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O—$R_8$, —(C=O)—$NR_8R_9$, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_f$(C=O)($CR_8R_9$)$_e$($C_6$-$C_{10}$)aryl, —($CR_8R_9$)$_f$(C=O)($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_f$S(O)$_d$($CR_8R_9$)$_e$($C_6$-$C_{10}$)aryl, and —($CR_8R_9$)$_f$S(O)$_d$($CR_8R_9$)$_e$(4-10)-membered heterocyclyl;

$R_6$ is H, —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O—$R_8$, —(C=O)—$NR_8R_9$, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_f$(C=O)($CR_8R_9$)$_e$($C_6$-$C_{10}$)aryl, —($CR_8R_9$)$_f$(C=O)($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_f$S(O)$_d$($CR_8R_9$)$_e$($C_6$-$C_{10}$)aryl, and —($CR_8R_9$)$_f$S(O)$_d$($CR_8R_9$)$_e$(4-10)-membered heterocyclyl;

wherein $R_5$ and $R_6$ are optionally linked to each other as a 4-12 membered mono- or bicyclic ring;

$R_7$ is —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O—$R_8$, —$NR_8$(C=O)—$R_{10}$, —(C=O)—$NR_8R_9$, —$NR_8R_9$, —$NR_8OR_9$, —$NR_8$—S(O)$_c$, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_f$(C=O)($CR_8R_9$)$_e$($C_6$-$C_{10}$)aryl, —($CR_8R_9$)$_r$(C=O)($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_f$S(O)$_d$($CR_8R_9$)$_e$($C_6$-$C_{10}$)aryl, and —($CR_8R_9$)$_f$S(O)$_d$($CR_8R_9$)$_e$(4-10)-membered heterocyclyl;

wherein $R_6$ and $R_7$ are optionally linked to each other as a 4-12 membered mono- or bicyclic ring;

each of $R_8$, $R_9$ and $R_{10}$ are independently selected from H, ($C_1$-$C_6$)alkyl, —($CR_{11}R_{12}$)$_e$(3-10)-membered cycloalkyl, —($CR_{11}R_{12}$)$_g$($C_6$-$C_{10}$)aryl, and —($CR_{11}R_{12}$)$_g$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are independently optionally substituted with 1 to 3 $R_{14}$ substituents each independently selected from halo, cyano, nitro, —$CF_3$, —$CHF_2$, —$CH_2F$, trifluoromethoxy, azido, hydroxyl, —O—$R_{15}$, ($C_1$-$C_6$)alkoxy, —($CR_8R_9$)$_e$($C_1$-$C_6$)alkoxy, ($C_1$-$C_6$)alkyl, ($C_2$-$C_6$)alkenyl, ($C_2$-$C_6$)alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —NR11(C=O)—$R_{13}$, —(C=O)—$NR_{11}R_{12}$, —(C=O)—$NR_{11}R_{15}$, —$NR_{11}R_{12}$, —$NR_{11}R_{15}$, —$NR_{11}OR_{12}$, —$NR_{11}OR_{15}$, —S(O)$_c NR_{11}R_{12}$, —S(O)$_c NR_{11}R_{15}$, —S(O)$_d$($C_1$-$C_6$)alkyl, —S(O)$_d R_{15}$, —O—$SO_2$—$R_{11}$, —O—$SO_2$—$R_{15}$, —$NR_{11}$—S(O)$_c$, —$NR_{15}$—S(O)$_c$, —($CR_{11}R_{12}$)$_e$(3-10)-membered cycloalkyl, —($CR_{11}R_{12}$)$_e$($C_6$-$C_{10}$)aryl, —($CR_{11}R_{12}$)$_e$(4-10)-membered heterocyclyl, —($CR_{11}R_{12}$)$_f$(C=O)($CR_{11}R_{12}$)$_e$($C_6$-$C_{10}$)aryl, —($CR_{11}R_{12}$)$_f$(C=O)($CR_{11}R_{12}$)$_e$(4-10)-membered heterocyclyl, —($CR_{11}R_{12}$)$_e$O($CR_{11}R_{12}$)$_f$($C_6$-$C_{10}$)aryl, —($CR_{11}R_{12}$)$_e$O($CR_{11}R_{12}$)$_f$(4-10)-membered heterocyclyl, —($CR_{11}R_{12}$)$_f$S(O)$_d$($CR_{11}R_{12}$)$_e$($C_6$-$C_{10}$)aryl, and —($CR_{11}R_{12}$)$_f$S(O)$_d$($CR_{11}R_{12}$)$_e$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R_{14}$ are independently optionally substituted with 1 to 3 $R_{16}$ substituents each independently selected from halo, cyano, nitro, —$CF_3$, $CHF_2$, $CH_2F$, trifluoromethoxy, azido, $(CH_2)_e$OH, ($C_1$-$C_6$)alkoxy, ($C_1$-$C_6$)alkyl, ($C_2$-$C_6$)alkenyl, ($C_2$-$C_6$)alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —$NR_{11}$(C=O)—$R_{13}$, —(C=O)—$NR_{11}R_{12}$, —$NR_{11}R_{12}$, and —$NR_{11}R_{15}$;

any nitrogen atoms of the (4-10)-membered heterocyclyl of the foregoing $R_1$, $R_2$, $R_3$, $R_4$, $R_5$, $R_6$, $R_7$, $R_8$, $R_9$, $R_{10}$, $R_{14}$, and $R_{15}$ are independently optionally substituted with ($C_1$-$C_6$)alkyl, ($C_2$-$C_6$)alkenyl, ($C_2$-$C_6$)alkynyl, —(C=O)—$R_{11}$, —(C=O)—O—$R_{11}$, —(C=O)—$NR_{11}R_{12}$, —$(CR_{11}R_{12})_e$(3-10)-membered cycloalkyl, —$(CR_{11}R_{12})_e$($C_6$-$C_{10}$)aryl, —$(CR_{11}R_{12})_e$(4-10)-membered heterocyclyl, —$(CR_{11}R_{12})_f$(C=O)$(CR_{11}R_{12})_e$($C_6$-$C_{10}$)aryl, or —$(CR_{11}R_{12})_f$(C=O)$(CR_{11}R_{12})_e$(4-10)-membered heterocyclyl;

each $R_{11}$, $R_{12}$, and $R_{13}$ are independently H or ($C_1$-$C_6$)alkyl;

$R_{15}$ is —$(CR_{11}R_{12})_e$(3-10)-membered cycloalkyl, —$(CR_{11}R_{12})_e$($C_6$-$C_{10}$)aryl, or —$(CR_{11}R_{12})_e$(4-10)-membered heterocyclyl;

a and b are each independently 1, 2, 3, or 4;

c is 1 or 2;

d is 0, 1, or 2; and e, f, and g are each independently 0, 1, 2, 3, 4, or 5.

In exemplary embodiments of the compounds of formula I, each of A, B, C, D, E, F, G, and H are C; each of $R_1$ and $R_2$ is independently selected from H or halo; $R_4$ is H or ($C_1$-$C_6$)alkyl, $R_3$ and $R_5$ are H; $R_6$ is —$CF_3$, —$CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e$($C_6$-$C_{10}$)aryl, —$(CR_8R_9)_e$(4-10)-membered heterocyclyl, —$(CR_8R_9)_e$O$(CR_8R_9)_f$($C_6$-$C_{10}$)aryl, —$(CR_8R_9)_e$O$(CR_8R_9)_f$(4-10)-membered heterocyclyl, —$(CR_8R_9)_f$S(O)$_d$$(CR_8R_9)_e$($C_6$-$C_{10}$)aryl, and —$(CR_8R_9)_f$S(O)$_d$$(CR_8R_9)_e$(4-10)-membered heterocyclyl; $R_7$ is —$CF_3$, $CHF_2$, $CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e$($C_6$-$C_{10}$)aryl, —$(CR_8R_9)_e$(4-10)-membered heterocyclyl, —$(CR_8R_9)_e$O$(CR_8R_9)_f$($C_6$-$C_{10}$)aryl, —$(CR_8R_9)_e$O$(CR_8R_9)_f$(4-10)-membered heterocyclyl, —$(CR_8R_9)_f$S(O)$_d$$(CR_8R_9)_e$($C_6$-$C_{10}$)aryl, and —$(CR_8R_9)_f$S(O)$_d$$(CR_8R_9)_e$(4-10)-membered heterocyclyl; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In some embodiments, each of A, B, C, D, E, F, G, and H are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic ring; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In other embodiments, each of A, B, C, D, E, F, G, and H are C; each of $R_1$ and $R_2$ is independently selected from H or halo; $R_4$ is H or ($C_1$-$C_6$)alkyl; $R_3$ and one $R_5$ are H; one $R_5$ and $R_6$ are linked to each other as a 4-12 membered mono- or bicyclic ring; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e$($C_6$-$C_{10}$)aryl, —$(CR_8R_9)_e$(4-10)-membered heterocyclyl, —$(CR_8R_9)_e$O$(CR_8R_9)_f$($C_6$-$C_{10}$)aryl, —$(CR_8R_9)_e$O$(CR_8R_9)_f$(4-10)-membered heterocyclyl, —$(CR_8R_9)_f$S(O)$_d$$(CR_8R_9)_e$($C_6$-$C_{10}$) aryl, and —$(CR_8R_9)_f$S(O)$_d$$(CR_8R_9)_e$(4-10)-membered heterocyclyl; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In some embodiments of the subject matter disclosed herein, the compound of formula I is the single enantiomer bearing an (S)-configuration or (R)-configuration at C-3, wherein each of A, B, C, D, E, F, G, and H are C; each of $R_1$ and $R_2$ is independently selected from H or halo; $R_4$ is H or ($C_1$-$C_6$)alkyl, $R_3$ and $R_5$ are H; $R_6$ is —$CF_3$, —$CHF_2$, —$CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e$($C_6$-$C_{10}$)aryl, —$(CR_8R_9)_e$(4-10)-membered heterocyclyl, —$(CR_8R_9)_e$O$(CR_8R_9)_f$($C_6$-$C_{10}$)aryl, $(CR_8R_9)_e$O$(CR_8R_9)_f$(4-10)-membered heterocyclyl, —$(CR_8R_9)_f$S(O)$_d$$(CR_8R_9)_e$($C_6$-$C_{10}$)aryl, and —$(CR_8R_9)_f$S(O)$_d$$(CR_8R_9)_e$(4-10)-membered heterocyclyl; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —$(CR_8R_9)_d$(3-10)-membered cycloalkyl, —$(CR_8R_9)_e$($C_6$-$C_{10}$)aryl, —$(CR_8R_9)_e$(4-10)-membered heterocyclyl, —$(CR_8R_9)_e$O$(CR_8R_9)_f$($C_6$-$C_{10}$)aryl, $(CR_8R_9)_e$O$(CR_8R_9)_f$(4-10)-membered heterocyclyl, —$(CR_8R_9)_f$S(O)$_d$$(CR_8R_9)_e$($C_6$-$C_{10}$)aryl, and —$(CR_8R_9)_f$S(O)$_d$$(CR_8R_9)_e$(4-10)-membered heterocyclyl; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In other embodiments, the compound of formula I is a single enantiomer bearing an (S)-configuration or (R)-configuration at C-3, wherein each of A, B, C, D, E, F, G, and H are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic ring; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In certain embodiments, the compound may be selected from the group consisting of:

(S)—N-(3-(9H-Carbazol-9-yl)-2-hydroxypropyl)-1,2-thiazinane-1,1-dioxide;

N-(3-(3,6-Difluoro-9H-carbazol-9-yl)-2-hydroxypropyl)-isothiazolidine-1,1-dioxide;

(S)—N-(3-(9H-Carbazol-9-yl)-2-hydroxypropyl)isothiazolidine-1,1-dioxide;

2-(3-(9H-Carbazol-9-yl)-2-hydroxypropyl)-5-fluoro-isothiazolidine-1,1-dioxide;

2-(3-(3,6-Difluoro-9H-carbazol-9-yl)-2-hydroxypropyl)-1,2,6-thiadiazinane-1,1-dioxide;

N-(3-(9H-Carbazol-9-yl)-2-hydroxypropyl)-N-(1-methylcyclopentyl)methanesulfonamide;

N-(3-(9H-Carbazol-9-yl)-2-hydroxypropyl)isothiazolidine-1,1-dioxide;

N-(3-(9H-Carbazol-9-yl)-2-hydroxypropyl)-2,3-dihydrobenzo[d]isothiazole-1,1-dioxide;

N-(3-(2,6-Difluoro-9H-carbazol-9-yl)-2-hydroxypropyl)-1,2-thiazinane-1,1-dioxide;

2-(3-(9H-Carbazol-9-yl)-2-hydroxypropyl)-1,2,6-thiadiazinane-1,1-dioxide; or a pharmaceutically acceptable salt or hydrate thereof.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutically acceptable salt" as used herein, refers to salts that retain the biological effectiveness of the free acids and bases of the specified compound and that are not biologically or otherwise undesirable. Pharmaceutically acceptable salts of the compounds of formula I include the acid addition and base salts thereof. Suitable acid addition salts are formed from acids which form non-toxic salts. Examples include acetate, adipate, arabogalactanesulfonate, ascorbate, aspartate, benzoate, besylate, bicarbonate/carbonate, bisulfate/sulfate, borate, camsylate, cholate, citrate, edisylate, estolate, esylate, formate, fumarate, galacturonate, gluceptate, gluconate, glucuronate, glutamate, hexafluorophosphate, hibenzate, hippurate, hydrochloride/chloride, hydrobromide/bromide, hydroiodide/iodide, 3-hydroxy-2-naphthoate, 1-hydroxy-2-naphthoate, isethionate, lactate, lactobionate, malate, maleate, malonate, mandelate, mesylate, methylsulfate, mucate, napadisylate, naphthalate, 2-napsylate, nicotinate, nitrate, oleate, orotate, oxalate, plamitate, pamoate, phosphate/hydrogen phosphate/dihydrogen phosphate, saccharate, salicylate, stearate, succinate, sulfosalicylate, tartrate, tosylate, trifluoroacetate, and tryptophanate salts.

Suitable base salts are formed from bases which form non-toxic salts. Examples include adenine, aluminum, 2-amino-2-methylpropan-1-ol, arginine, benethamine, benzathine, calcium, choline, cytosine, diethylamine, diolamine, epolamine, erbumine, ethylenediamine, glucosamine, glycine, guanidine, guanine, hydrabamine, lysine, magnesium, meglumine, morpholine, nicotinamide, olamine, ornithine, piperazine, potassium, procaine, proline, pyridoxine, serine, silver, sodium, trolamine, tromethamine, tyrosine, valine and zinc salts. For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula I may be readily prepared by mixing together solutions of the compound of formula I and the desired acid or base, as appropriate. The salt may precipitate from solution and be collected by filtration or may be recovered by evaporation of the solvent. The degree of ionization in the salt may vary from completely ionized to almost non-ionized.

The compounds of Formula I may also exist in various crystalline forms, known as polymorphs. Polymorphs include the different crystal packing arrangements of the same elemental composition of a compound. Polymorphs may have different X-ray diffraction patterns, infrared spectra, melting points, density, hardness, crystal shape, optical and electrical properties, stability, solvates and solubility. Various factors such as the recrystallization solvent, rate of crystallization, and storage temperature may cause a single crystal form to dominate.

A "solvate" is intended to mean a pharmaceutically acceptable solvate form of a specified compound that retains the biological effectiveness of such compound. Examples of solvates include compounds of the invention in combination with water, isopropanol, ethanol, methanol, dimethylsulfoxide, ethyl acetate, acetic acid, or ethanolamine. The term "hydrate" refers to a solvate where the solvent is water. The term "alcoholate" refers to a solvate where the solvent is an alcohol. Hydrates are formed by the combination of one or more molecules of water with one molecule of the substance in which the water retains its molecular state as $H_2O$. Non-limiting examples of hydrates include monohydrates, dihydrates, etc.

The compounds of the invention include compounds of formula I as defined herein, polymorphs, prodrugs, and isomers, thereof (including optical, geometric, and tautomeric isomers) as well as isotopically-labeled compounds of formula I.

The compounds of the present invention may be administered as prodrugs. Thus certain derivatives of compounds of formula I which may have little or no pharmacological activity themselves can, when administered into or onto the body, be converted into compounds of formula I having the desired activity, for example, by hydrolytic cleavage. Such derivatives are referred to as 'prodrugs'. Further information on the use of prodrugs may be found in "Pro-drugs as Novel Delivery Systems, Vol. 14, ACS Symposium Series (T. Higuchi and W. Stella) and "Bioreversible Carriers in Drug Design", Pergamon Press, 1987 (Ed. E. B. Roche, American Pharmaceutical Association). Prodrugs can, for example, be produced by replacing appropriate functionalities present in the compounds of formula I with certain moieties known to those skilled in the art is 'pro-moieties' as described, for example, in "Design of Prodrugs" by H. Bundgaard (Elsevier, 1985).

Some examples of such prodrugs include where the compound of formula I contains a carboxylic acid functionality ($—CO_2H$), an ester thereof, for example, replacement of the hydrogen with ($C_1$-$C_8$)alkyl; where the compound of formula I contains an alcohol functionality (—OH), an ether thereof, for example, replacement of the hydrogen with ($C_1$-$C_8$)alkanoyloxymethyl; and where the compound of formula I contains a secondary amino functionality (—NHR where R is not H), an amide thereof, for example, replacement of one hydrogen with ($C_1$-$C_{10}$)alkanoyl. Further examples of replacement groups in accordance with the foregoing examples and examples of other prodrug types are known to those of ordinary skill in the art.

Compounds of formula I contain one or more asymmetric carbon atoms. It is to be understood that all the enantiomers and/or diastereomers corresponding to the compounds of formula I can be prepared by analogous methods. All optical isomers and stereoisomers of the compounds of formula I, and mixtures thereof, are considered to be within the scope of the invention. With respect to the compounds of formula I, the invention includes the use of a racemate, one or more enantiomeric forms, one or more diastereomeric forms, or mixtures thereof. The compounds of formula I may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini, et al. *Chem. Rev.* 1996, 96, 3147-3176 and references cited therein.

Included within the scope of the claimed compounds of formula I are pharmaceutically acceptable acid addition or base salts wherein the counterion is optically active, for example, D-lactate or L-lysine, or racemic, for example, DL-tartrate or DL-arginine. Cis/trans isomers may be separated by conventional techniques well known to those skilled in the art, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, an acid or base such as tartaric acid or 1-phenylethylamine. The resulting diastereomeric mixture may be separated by chromatography and/or fractional crystallization and the diastereomers converted to the corresponding pure enantiomers and/or diastereomers by means well known to a skilled person. The chiral compounds of the invention (and chiral precursors thereof) may be obtained in enantiomerically- and/or diastereomerically-enriched form using chromatography, typically HPLC, on an asymmetric resin with a mobile phase consisting of a hydrocarbon, typically heptane or hexane, containing from 0 to 50% isopropanol, typically 2 to 20%, and from 0 to 5% of an alkylamine, typically 0.1% diethylamine. Concentration of the eluate affords the enriched mixture. Mixtures of enantiomers and/or diastereomers may be separated by conventional techniques known to those skilled in the art. See, for example, "Stereochemistry of Organic Compounds" by E. L. Eliel (Wiley, New York, 1994).

The compounds of formula I may be isotopically-labeled, wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorous, such as $^{32}$P, and sulfur, such as $^{35}$S. Certain isotopically-labeled compounds of formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula I can be generally prepared by conventional techniques known to those skilled in the art or by processes analogous to those described in the accompanying Examples and Preparations using appropriate isotopically-labeled reagents in place of the non-labeled reagent previously employed.

The compounds of the present invention modulate Cry1 and/or Cry2. As used herein, "modulating" refers to increasing, decreasing, or altering Cry1 and Cry2 function, activity or intrinsic characteristics. Modulation of Cry1 or Cry2 includes any one of the following: binding to Cry1 or Cry2; inhibiting modification of Cry1 or Cry2; altering Cry1 or Cry2 localization; increasing or decreasing Cry1 or Cry2 stabilization; increasing or decreasing the binding between Cry1 or Cry2 to a target; increasing or decreasing Cry1 or Cry2 activity; and increasing or decreasing activity of a Cry1 or Cry2 target, or any combination thereof. Targets of Cry1 and/or Cry2 include, but are not limited to, Per1, Per2, glucocorticoid receptor (GR), CLOCK, BMAL1, or a CLOCK-BMAL1 promoter sequence.

Modulation of Cry1 and Cry2 includes: binding of a compound of the present invention to Cry1 and/or Cry2, either through direct interaction or indirect interaction. In some aspects, a compound of the present invention may bind to a complex containing Cry1 and/or Cry2. Methods for detecting interaction between small molecules and proteins are known in the art, for example, immunoprecipitation techniques, chromatography, and various array formats.

Intrinsic characteristics of Cry1 and Cry2, such as post-translational modification, stability, or localization, may be altered by the compounds of the present invention. Post-translational modification of Cry1 and Cry2 may play a critical role in determining the activity, stability, or cellular localization of Cry1 and Cry2. Some studies have shown that phosphorylation may alter Cry1 and Cry2 stability. Compounds of the present invention may prevent or increase post-translational modification of Cry1 and Cry2, for example, phosphorylation, ubiquitination, acetylation, glycosylation, ribosylation, or sumoylation. Methods for detecting post-translational modification of Cry1 or Cry2 can be readily performed by one skilled in the art. Such methods of detection include western blot and radioimmunoassays. Cry1 and Cry2 localize to the nucleus under particular conditions, for example, upon heterodimerization with Per1 and Per2. Once within the nucleus, Cry1 and Cry2 play a role in disrupting the nuclear CLOCK-BMAL1 complex from initiating transcription, thereby downregulating circadian rhythm genes in a negative feedback loop that is crucial for maintaining circadian oscillations. Localization of proteins can be readily determined by one in the art, for example, by immunofluorescence, subcellular fractionation and western blot assays. Downregulation of Cry1 and Cry2 is also critical for circadian oscillations, and is mediated at the transcriptional and protein level. Cry1 and Cry2 stability can be measured by methods known in the art, as well as those presented in Examples 5-8.

Cry1 and Cry2 activity, as used herein, includes the binding between Cry1 or Cry2 to a target and the activity of a downstream Cry1 or Cry2 target. Compounds of the present invention may increase or decrease the binding between Cry1 or Cry2 to a target. Targets that bind to Cry1 and/or Cry2 are known in the art, and include Per1, Per2, glucocorticoid receptor, the CLOCK-BMAL1 promoter sequence, and the VEGF promoter sequence. Cry1 and Cry2 targets referenced herein also include those targets that have yet to be identified. Binding between Cry1 or Cry2 and targets can be determined by, for example, immunoprecipitation, yeast two-hybrid, affinity chromatography. Downstream activity of Cry1 or Cry2 targets comprises CLOCK-BMAL1-mediated transcription, binding of Cry1 or Cry2 to the CLOCK-BMAL-1 promoter, binding of Cry1 or Cry2 to the VEGF promoter, Per1 or Per2 localization or stability, CLOCK-BMAL1 dimerization, expression of CLOCK-BMAL1 target genes, such as Cry1, Cry2, Per1, Per2, Rev-erb α and β, Rora, TIM proteins, and VEGF. Methods for detecting promoter activity can be determined by chromatin immunoprecipitation, electrophoretic mobility shift assay, or promoter-luciferase assays as described in Examples 3 and 4. Methods for determining expression of target genes include gene expression analysis and microarrays, which can be readily performed by one ordinarily skilled in the art.

In other aspects of the subject matter disclosed herein, a pharmaceutical composition is provided, comprising the compound according to formula I and a pharmaceutically acceptable carrier, adjuvant or diluent. Methods of preparing various pharmaceutical compositions with a specific amount of active compound are known, or will be apparent, to those skilled in the art. In addition, those of ordinary skill in the art are familiar with formulation and administration techniques. Such topics will be discussed, e.g. in Goodman and Gilman's "The Pharmaceutical Basis of Therapeutics", current edition, Pergamon Press; and "Remington's Pharmaceutical Sciences", current edition, Mack Publishing, Co., Easton, Pa. These techniques can be employed in appropriate aspects and embodiments of the methods and compositions described herein. Pharmaceutical compositions are preferably manufactured under GMP conditions. The following examples are provided for illustrative purposes only and are not meant to serve as limitations of the present invention.

Because the compounds described herein are intended for use in pharmaceutical compositions, it will readily be understood that they are each preferably provided in substantially pure form, for example at least 50% pure, at least 55% pure, at least 60% pure, at least 65% pure, at least 70% pure, at least 75% pure, at least 80% pure, at least 85%, at least 90% pure, at least 95% pure, at least 96% pure, at least 97% pure, at least 98% pure, or at least 99% pure. Percentages as provided herein are on a weight for weight basis. Impure preparations of the compounds may be used for preparing the more pure forms used in the pharmaceutical compositions; these less pure preparations of the compounds should contain at least 1%, more suitably at least 5%, e.g. 10 to 49% of a compound of the Formula I.

The compounds of formula I may be provided in suitable topical, oral, nasal, ocular, mucosal, rectal, vaginal, and parenteral pharmaceutical formulations for use in the treatment of Cry mediated diseases. The compounds of the present invention may be administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients, carriers, diluents, and adjuvants as an aid in the manufacture of such tablets. As is conventional in the art, these tablets may be coated with a pharmaceutically acceptable enteric coating, such as glyceryl monostearate or glyceryl distearate, to delay disintegration and absorption in the gastrointestinal tract to provide a sustained action over a longer period. The dissolution rate of poorly water-soluble compounds may be enhances by the use of spray-dried dispersion, such as those described by Takeuchi, H. et al. J. Pharm. Pharmacol. 1987, 39, 769-773.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients many be a suspending agent, such as Kolliphor, sodium carboxymethyl cellulose, methyl cellulose, hydroxypropylmethyl cellulose, sodium alginate, polyvinylpyrrolidone, gum tragancanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethyleneoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pharmaceutical compositions may be in the form of a sterile injectable aqueous or oleaginous suspension. This suspension may be formulated according to known methods as aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. The sterile injectable preparation may also be formulated as a suspension in a non-toxin parenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

The compounds of formula I may also be administered in the form of suppositories for rectal administration of the drug. These compositions can be prepared by mixing the drug with a suitable non-irritating excipient that is solid at about 25° C., but liquid at rectal temperature and will therefore melt in the rectum to release the drug. Such materials include cocoa butter and other glycerides.

For topical or transdermal use preparations, for example, creams, ointments, jellies solutions or suspensions containing the compounds of the present invention are employed. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations and iontophoresis devices can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The compounds of formula I may also be prepared in the form of liposome delivery systems such as small unilamellar vesicles, large unilamellar vesicles and multimellar vesicles. Liposomes can be formed from a variety of phospholipids, such as cholesterol, stearylamine or phosphatidylcholines.

Suitable extended release form of the either active pharmaceutical ingredient or both may be a matrix tablet or capsule composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticised according to the properties of the coating blend such as the glass transition temperature of the main component or mixture of components or the solvent used for applying the coating compositions. Suitable plasticisers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, MCC, or polacrilin potassium. The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water. Dosage levels of the compounds of the present invention are of the order of about 0.5 mg/kg body weight to about 100 mg/kg body weight, or any increment in between. A preferred dosage rate is between about 30 mg/kg body weight to about 100 mg/kg body weight. The total daily dose may be administered in single or divided doses. Suitable therapeutic doses of the compounds of formula I may be in the range of 1 microgram (µg) to 1000 milligrams (mg) per kilogram body weight of the recipient per day, and any increment in between, such as, e.g., 1, 2, 3, 5, 10, 25, 50, 75, 100, 200, 300, 400, 500, 600, 700, 800, 900, or 1000 µg (1 mg); 2, 3, 5, 10, 25, 50, 75, 100, 200, 300, 400, 500, 600, 700, 800, 900 or 1000 mg. It will be understood, however, that specific dose level for any particular patient will depend upon a number of factors including the activity of the particular compound being administered, the age, body weight, general health, sex, diet, time of administration, route of administration, rate of excretion, drug combination and the severity of the particular disease undergoing therapy.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals. Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can be temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

In another aspect of the subject matter disclosed herein, a method of treating a Cry-mediated disease or disorder is provided, comprising administering a therapeutically effective amount of a compound according to formula I as described in any of the preceding embodiments hereinabove. A preferred embodiment of the present invention is the method according to the preceding embodiment wherein the disease or disorder characterized by abnormal levels of Cry is selected from the group consisting of diabetes, metabolic syndrome, insulin resistance syndrome, obesity, glaucoma, Cushing's syndrome, psychotic depression, Alzheimer's disease, neuropathic pain, drug abuse, osteoporosis, cancer, macular degeneration, and myopathy. Yet another preferred embodiment is the method according to the preceding embodiment wherein the Cry-mediated disease or disorder is diabetes, metabolic syndrome, insulin resistance syndrome, obesity, Cushing's syndrome, glaucoma, psychotic depression, Alzheimer's disease, neuropathic pain, drug abuse, osteoporosis, cancer, macular degeneration, or myopathy. Particularly preferred cancers are solid tumor cancers or epithelial cancers, including but not limited to: lung cancer; brain cancer; pancreatic cancer; head and neck cancer (e.g., squamous cell carcinoma); breast cancer; colorectal cancer; liver cancer; stomach cancer; kidney cancer; ovarian cancer; prostate cancer; or an adenocarcinoma. Other preferred cancers are those with increased VEGF expression, increased angiogenesis, or hypoxic tumors.

The terms "administer," "administering", "administration," and the like, as used herein, refer to the methods that may be used to enable delivery of compounds or compositions to the desired site of biological action. These methods include, but are not limited to oral, parenteral, topical, mucosal, ocular, ophthalmic, vaginal, and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. As used herein, "parenteral administration" of a pharmaceutical composition includes any route of administration characterized by physical breaching of a tissue of a subject and administration of the pharmaceutical composition through the breach of the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of a Cry-mediated disease or disorder, such as ob/ob mice. A subject can be male or female. A subject can be one who has been previously diagnosed or identified as having a Cry-mediated disease or disorder, and optionally has already undergone, or is undergoing, a therapeutic intervention or treatment for the disease or disorder. Alternatively, a subject can also be one who has not been previously diagnosed as having a Cry-mediated disease or disorder. For example, a subject can be one who exhibits one or more risk factors for a Cry-mediated disease or disorder, or a subject who does not exhibit risk factors for a Cry-mediated disease or disorder, or a subject who is asymptomatic for a Cry-mediated disease or disorder. A subject can also be one who is suffering from or at risk of developing a Cry-mediated disease or disorder, or who is suffering from or at risk of developing a recurrence of a Cry-mediated disease or disorder. A subject can also be one who has been previously treated for a Cry-mediated disease or disorder, whether by administration of the compounds and compositions disclosed herein, either alone or in combination with other therapeutic agents, surgery, or any combination of the foregoing.

A "Cry-mediated disease or disorder" may include, without limitation, diabetes (including, without limitation, insulin-dependent "Type I" diabetes, non-insulin dependent "Type II" diabetes, gestational diabetes, and diabetes-related complications like diabetic neuropathy, diabetic retinopathy, diabetic cardiomyopathy, diabetic nephropathy, periodontal disease, and diabetic ketoacidosis), metabolic syndrome, insulin resistance syndrome, obesity, glaucoma, Cushing's syndrome, psychotic depression, Alzheimer's disease, neuropathic pain, drug abuse, osteoporosis, cancer, macular degeneration, and myopathy.

The term "treating", "treat", or "treatment" as used herein includes preventative (e.g. prophylactic), palliative, adjuvant, and curative treatment. For example, the treatment of type 2 diabetes, as used herein means that a patient having type 2 diabetes or at risk of having type 2 diabetes can be treated according to the methods described herein. For patients undergoing preventative treatment, a resulting reduction in the incidence of the disease state being preventively treated is the measurable outcome of the preventative treatment.

The term "alleviating" or "alleviate" as used herein describes a process by which the severity of a sign or symptom of a disorder is decreased, reduced, or inhibited. Importantly, a symptom can be alleviated without being eliminated. In a preferred embodiment, the administration of pharmaceutical compositions of the invention leads to the elimination of a symptom, however, elimination is not required. Therapeutically effective amounts of the compounds or pharmaceutical compositions described herein are expected to decrease the severity of a symptom.

As used herein the term "symptom" is defined as an indication of disease, illness, injury, or that something is not right in the body. Symptoms are felt or noticed by the individual experiencing the symptom, but may not easily be noticed by others. Others are defined by health-care or clinical professionals.

The term "metabolic syndrome", as used herein, unless otherwise indicated means psoriasis, diabetes mellitus, wound healing, inflammation, neurodegenerative diseases, galactosemia, maple syrup urine disease, phenylketonuria, hypersarcosinemia, thymine uraciluria, sulfinuria, isovaleric academia, saccharopurinuria, 4-hydroxybutyric aciduria, glucose-6-phosphate dehydrogenase deficiency, and pyruvate dehydrogenase deficiency.

The term "obesity" or "obese", as used herein, refers generally to individuals who are at least about 20-30% over the average weight for his/her age, sex and height. Technically, "obese" is defined, for males, as individuals whose body mass index is greater than 27.8 kg/m$^2$, and for females, as individuals whose body mass index is greater than 27.3 kg/m$^2$. Those of skill in the art readily recognize that the invention method is not limited to those who fall within the above criteria. Indeed, the method of the invention can also be advantageously practiced by individuals who fall outside of these traditional criteria, for example, by those who may be prone to obesity.

The term "inflammatory disorders", as used herein, refers to disorders such as rheumatoid arthritis, ankylosing spondylitis, psoriatic arthritis, psoriasis, chondrocalcinosis, gout, inflammatory bowel disease, ulcerative colitis, Crohn's disease, fibromyalgia, and cachexia.

The phrase "therapeutically effective amount", as used herein, refers to the amount of drug or pharmaceutical agent that will elicit the biological or medical response of a tissue, system, animal, or human that is being sought by a researcher, veterinarian, medical doctor or other.

The phrase "amount . . . effective to lower blood glucose levels", as used herein, refers to levels of compound sufficient to provide circulating concentrations high enough to accomplish the desired effect. Such a concentration typically falls in the range of about 10 nM up to 2 µM; with concentrations in the range of about 100 nM up to 500 nM being preferred. As noted previously, since the activity of different compounds which fall within the definition of formula I as set forth above may vary considerably, and since individual subjects may present a wide variation in severity of symptoms, it is up to the practitioner to determine a subject's response to treatment and vary the dosages accordingly.

The phrase "insulin resistance", as used herein, refers to the reduced sensitivity to the actions of insulin in the whole body or individual tissues, such as skeletal muscle tissue, myocardial tissue, fat tissue or liver tissue. Insulin resistance occurs in many individuals with or without diabetes mellitus.

The phrase "insulin resistance syndrome", as used herein, refers to the cluster of manifestations that include insulin resistance, hyperinsulinemia, non-insulin dependent diabetes mellits (NIDDM), arterial hypertension, central (visceral) obesity, and dyslipidemia.

The compounds of the present invention may also be useful in the treatment of other metabolic disorders associated with impaired glucose utilization and insulin resistance including major late-stage complications of NIDDM, such as diabetic angiopathy, atherosclerosis, non-alcoholic steatohepatitis (NASH), non-alcoholic fatty liver disease, diabetic nephropathy, diabetic neuropathy, and diabetic ocular complications such as retinopathy, cataract formation and glaucoma, and many other complications linked to NIDDM, including dyslipidemia, glucocorticoid-induced insulin resistance, polycystic ovarian syndrome, obesity, hyperglycemia, hyperlipidemia, hypercholesteremia, hypertriglyceridemia, hyperinsulinemia, and hypertension. Brief descriptions of these conditions are available in any medical dictionary, for instance, "Stedman's Medical Dictionary" (Xth Ed.).

Compounds and compositions disclosed herein can be administered in therapeutically effective amounts in combination with one or more additional therapeutic agents as defined herein. For example, synergistic effects can occur with other substances used in the treatment of Cry-mediated diseases or disorders. Where the compounds of the invention are administered in conjunction with other therapies, dosages of the co-administered compounds will of course vary depending on the type of co-drug employed, on the specific drug employed, on the condition being treated and so forth.

As used herein, the terms "combination treatment", "combination therapy", "combined treatment" or "combinatorial treatment", used interchangeably, refer to a treatment of an individual with at least two different therapeutic agents. The terms "co-administration" or "combined administration" or the like as utilized herein are meant to encompass administration of the selected therapeutic agents to a single subject, and are intended to include treatment regimens in which the agents are not necessarily administered by the same route of administration or at the same time. The term "pharmaceutical combination" means a product that results from the mixing or combining of more than one active ingredient and includes both fixed and non-fixed combinations of the active ingredients. A "fixed combination" means that the active ingredients, e.g. a compound as disclosed herein and an additional therapeutic agent, are both administered to a patient simultaneously in the form of a single entity or dosage. A "non-fixed combination" means that the active ingredients, e.g. a compound as disclosed herein and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Therapeutic agents for treating diabetes, metabolic syndrome, obesity, insulin resistance syndrome, diabetic complications or cancer include, without limitation of the following, insulin, hypoglycemic agents, anti-inflammatory agents, lipid reducing agents, anti-hypertensives such as calcium channel blockers, β-adrenergic receptor blockers, cyclooxygenase-2 inhibitors, angiotensin system inhibitors, ACE inhibitors, renin inhibitors, chemotherapeutic agents, radiotherapy, hormone-modulating agents, immunomodulating agents, anti-angiogenic agents, together with other common risk factor modifying agents.

Insulin includes rapid acting forms, such as Insulin lispro rDNA origin: HUMALOG (1.5 mL, 10 mL, Eli Lilly and Company, Indianapolis, Ind.), Insulin Injection (Regular Insulin) form beef and pork (regular ILETIN I, Eli Lilly], human: rDNA: HUMULIN R (Eli Lilly), NOVOLIN R (Novo Nordisk), Semisynthetic: VELOSULIN Human (Novo Nordisk), rDNA Human, Buffered: VELOSULIN BR, pork: regular Insulin (Novo Nordisk), purified pork: Pork Regular ILETIN II (Eli Lilly), Regular Purified Pork Insulin (Novo Nordisk), and Regular (Concentrated) ILETIN II U-500 (500 units/mL, Eli Lilly); intermediate-acting forms such as Insulin Zinc Suspension, beef and pork: LENTE ILETIN G I (Eli Lilly), Human, rDNA: HUMULIN L (Eli Lilly), NOVOLIN L (Novo Nordisk), purified pork: LENTE ILETIN II (Eli Lilly), Isophane Insulin Suspension (NPH): beef and pork: NPH ILETIN I (Eli Lilly), Human, rDNA: HUMULIN N (Eli Lilly), Novolin N (Novo Nordisk), purified pork: Pork NPH Iletin II (Eli Lilly), NPH-N (Novo Nordisk); and long-acting forms such as Insulin zinc suspension, extended (ULTRALENTE, Eli Lilly), human, rDNA: HUMULIN U (Eli Lilly).

Hypoglycemic agents include, without limitation, sulfonylureas: Acetohexamide (Dymelor), Chlorpropamide (Diabinese), Tolbutamide (Orinase); second-generation sulfonylureas: Glipizide (Glucotrol, Glucotrol XL), Glyburide (Diabeta; Micronase; Glynase), Glimepiride (Amaryl); Biguanides: Metformin (Glucophage); α-glucosidase inhibitors: Acarbose (Precose), Miglitol (Glyset), Thiazolidinediones: Rosiglitazone (Avandia), Pioglitazone (Actos), Troglitazone (Rezulin); Meglitinides: Repaglinide (Prandin); and other hypoglycemics such as Acarbose; Buformin; Butoxamine Hydrochloride; Camiglibose; Ciglitazone; Englitazone Sodium; Darglitazone Sodium; Etoformin Hydrochloride; Gliamilide; Glibomuride; Glicetanile Gliclazide Sodium; Gliflumide; Glucagon; Glyhexamide; Glymidine Sodium; Glyoctamide; Glyparamide; Linogliride; Linogliride Fumarate; Methyl Palmoxirate; Palmoxirate Sodium; Pirogliride Tartrate; Proinsulin Human; Seglitide Acetate; Tolazamide; Tolpyrramide; Zopolrestat.

Anti-inflammatory agents include Alclofenac; Alclometasone Dipropionate; Algestone Acetonide; α-Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. An important anti-inflammatory agent is aspirin.

Other anti-inflammatory agents are cytokine inhibitors including cytokine antagonists (e.g., IL-6 receptor antagonists), aza-alkyl lysophospholipids (AALP), and Tumor Necrosis Factor-α (TNF-α) inhibitors, such as anti-TNF-α antibodies, soluble TNF receptor, TNF-α, anti-sense nucleic acid molecules, multivalent guanylhydrazone (CNI-1493), N-acetylcysteine, pentoxiphylline, oxpentifylline, carbocyclic nucleoside analogues, RP 55778 (a TNF-α synthesis inhibitor), Dexanabinol (HU-211), MDL 201,449A (9-[(1R,3R)-trans-cyclopentan-3-ol]adenine, and trichodimerol (BMS-182123). Other TNF-α inhibitors include Etanercept (ENBREL, Immunex, Seattle) and Infliximab (REMICADE, Centocor, Malvern, Pa.).

Lipid reducing agents include gemfibrozil, cholystyramine, colestipol, nicotinic acid, and HMG-CoA reductase inhibitors. HMG-CoA reductase inhibitors useful for administration, or co-administration with other agents according to the invention include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), and cerivastatin.

Calcium channel blockers include dihydropyridines, such as nifedipine, phenyl alkyl amines, such as verapamil, and benzothiazepines, such as diltiazem. Other calcium channel blockers include, but are not limited to, aminone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

β-adrenergic receptor blocking agents include, but are not limited to, atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hyd-roxypropoxy)-3-pyridenecarbonitrilHCl, 1-butylamino-3-(2,5-dichlorophenoxy-)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

A number of selective COX-2 inhibitors are known in the art and include, but are not limited to, COX-2 inhibitors described in U.S. Pat. No. 5,474,995; U.S. Pat. No. 5,521,213; U.S. Pat. No. 5,536,752; U.S. Pat. No. 5,550,142; U.S. Pat. No. 5,552,422; U.S. Pat. No. 5,604,253; U.S. Pat. No. 5,604,260; U.S. Pat. No. 5,639,780; U.S. Pat. No. 5,677,318; U.S. Pat. No. 5,691,374; U.S. Pat. No. 5,698,584; U.S. Pat. No. 5,710,140; U.S. Pat. No. 5,733,909; U.S. Pat. No. 5,789,413; U.S. Pat. No. 5,817,700; U.S. Pat. No. 5,849,943; U.S. Pat. No. 5,861,419; U.S. Pat. No. 5,922,742; U.S. Pat. No. 5,925,631; and U.S. Pat. No. 5,643,933. A number of the above-identified COX-2 inhibitors are prodrugs of selective COX-2 inhibitors, and include those described in WO 95/00501, WO 95/18799, and U.S. Pat. No. 5,474,995, issued Dec. 12, 1995.

Examples of angiotensin II antagonists include: peptidic compounds (e.g., saralasin, [(San1) (Val5) (Ala8)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboylic acid and analog derivatives (U.S. Pat. No. 4,816,463); N2-tetrazole β-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP 253,310, Jan. 20, 1988); ES8891 (N-morpholinoacetyl-(-1-naphthyl)-L-alany-1-(4, thiazolyl)-L-alanyl (35,45)-4-amino-3-hydroxy-5-cyclohexapentanoyl-N-hexylamide, Sankyo Company, Ltd., Tokyo, Japan); SKF108566 (E-α-2-[2-butyl-1-(carboxy phenyl) methyl]1H-imidazole-5-yl[methylane]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche AG); $A_2$ agonists (Marion Merrill Dow) and certain nonpeptide heterocycles (G. D. Searle and Company).

Angiotensin converting enzyme (ACE) inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. Other ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors include amino acids and derivatives thereof, peptides and derivatives thereof, and antibodies to renin. Other rennin inhibitors include urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl β-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Other therapeutic agents useful in treating diabetes and related disorders include, but are not limited to, lipase inhibitors such as cetilistat (ATL-962); synthetic amylin analogs such as Symlin pramlintide with or without recombinant leptin; sodium-glucose cotransporter 2 (SGLT2) inhibitors like sergliflozin (869682; KGT-1251), YM543, dapagliflozin, GlaxoSmithKline molecule 189075, and Sanofi-Aventis molecule AVE2268; dual adipose triglyceride lipase and PI3 kinase activators like Adyvia (ID 1101); antagonists of neuropeptide Y2, Y4, and Y5 receptors like Nastech molecule PYY3-36, synthetic analog of human hormones PYY3-36 and pancreatic polypeptide (7TM molecule TM30338); Shionogi molecule S-2367; cannabinoid CB1 receptor antagonists such as rimonabant (Acomplia), taranabant, CP-945,598, Solvay molecule SLV319, Vernalis molecule V24343; hormones like oleoyl-estrone; inhibitors of serotonin, dopamine, and norepinephrine (also known in the art as triple monoamine reuptake inhibitors) like tesofensine (Neurosearch molecule NS2330); inhibitors of norepinephrine and dopamine reuptake, like Contrave (bupropion plus opioid antagonist naltrexone) and Excalia (bupropion plus anticonvulsant zonisamide); inhibitors of 11b-hydroxysteroid dehydrogenase type 1 (11b-HSD1) like Incyte molecule INCB13739; inhibitors of cortisol synthesis such as ketoconazole (DiObex molecule DIO-902); inhibitors of gluconeogenesis such as Metabasis/Daiichi molecule CS-917; glucokinase activators like Roche molecule R1440; antisense inhibitors of protein tyrosine phosphatase-1B such as ISIS 113715; as well as other agents like NicOx molecule NCX 4016; injections of gastrin and epidermal growth factor (EGF) analogs such as Islet Neogenesis Therapy (E1-I.N.T.); betahistine (Obecure molecule OBE101); bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., β-sitosterol and acylCoA-cholesterol acyltransferase (ACAT) inhibitors such as melinamide), HMG-CoA synthase inhibitors, squalene epoxidase inhibitors and squalene synthetase inhibitors.

Examples of analgesic agents frequently used to treat pain, including neuropathic pain, include, without limitation, opioid or non-opioid analgesic agents. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

Examples of therapeutic agents frequently used to treat glaucoma include cholinergic agonists (e.g., pilocarpine and carbachol), cholinesterase inhibitors (e.g., physostigmine, neostigmine, demacarium, echothiophate iodide and isofluorophate), carbonic anhydrase inhibitors (e.g., acetazolamide, dichlorphenamide, methazolamide, ethoxzolamide and dorzolamide), non-selective adrenergic agonists (e.g., epinephrine and dipivefrin), $\alpha_2$-selective adrenergic agonists (e.g., apraclonidine and brimonidine), β-blockers (e.g., timolol, betazolol, levobunolol, carteolol and metipranolol), prostaglandin analogs (e.g., latanoprost) and osmotic diuretics (e.g., glycerin, mannitol and isosorbide); corticosteroids, such as beclomethasone, methylprednisolone, betamethasone, prednisone, prenisolone, dexamethasone, fluticasone and hydrocortisone, and corticosteroid analogs such as budesonide.

Examples of therapeutic agents frequently used to treat Alzheimer's disease include β-secretase inhibitors or γ-secretase inhibitors; glycine transport inhibitors, tau phosphorylation inhibitors; blockers of Aβ oligomer formation; p25/CDK5 inhibitors; HMG-CoA reductase inhibitors; PPARγ agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A$ α5 receptor ligands; $GABA_B$ receptor ligands; potassium channel blockers; neuronal nicotinic agonists; P-450 inhibitors, such as ritonavir.

Examples of therapeutic agents frequently used to treat affective disorders such as depression include, without limitation, amitriptyline, amitriptyline oxide, desipramine, dibenzepin, dosulepin, doxepin, chloroimipramine, imipramine, nortriptyline, mianserin, maprotiline, trimipramine, CP-122721, elzasonan, PD-171729, MK-869, DOV-216303, DOV-21947, licarbazepine, amfebutamone, radafaxine, vilazodone, GSK-679769, GW-597599, NS-2359, GSK-876008, pramipexole, duloxetine, atomoxetine, LY-628535, desvenlafaxine, escitalopram, LU-AA21004, saredutant, SR-58611, SSR-149415, SSR-146977, moclobemide, R-673, R-1204, BMS-469458, DPC-368, Org-34517, Org-34850, inhibitors of the CRH receptors, ONO-2333Ms, NBI-876008, AAG-561, NBI-34041, DPC-368, PD-171729, SSR-125543, viloxazine, trazodone, nefazodone, mirtazapine, venlafaxine, reboxetine, tranylcypromine, brofaromine, moclobemide, citalopram, escitalopram, paroxetine, fluoxetine, fluvoxamine, sertraline, Hypericum (St. John's Wort), alprazolam, clonazepam, diazepam, lorazepam, halazepam, chlordiazepoxide, and other drugs such as buspirone, clonidine, pagoclone, risperidone, olanzapine, quetiapine, ziprasidone, celecoxib, piroxicam, parecoxib, valdecoxib, PMI-001, PH-686464, SC-58236, etoricoxib, rofecoxib, L-776967, lumiracoxib, GW-406381, GW-644784, meloxicam, SVT-2016, PAC-10649, CS-706, LAS-34475, cimicoxib, A-183827.0, or nimesulide.

Examples of therapeutic agents frequently used to treat addiction and drug abuse include, without limitation, phenelzine, phenylalkylhydrazine (U.S. Pat. No. 4,786,653), disulfuram ("Antabuse"), 2-imino-5-phenyl-4-oxazolidinone, α-methyl-para-tyrosine or fusaric acid, piperazine derivatives (U.S. Pat. No. 4,325,952), clonidine in conjunction with a tricyclic antidepressant drug (U.S. Pat. No. 4,788,189), γ-pyrones such as maltol or ethyl maltol (U.S. Pat. No. 4,276,890), acamprosate, gabapentin, vigabatrin, baclofen, N-acetylcysteine, nocaine, modanafil, paroxetine, bupropion, mirtazapine, topiramate, ondansetron, varenicline, antagonists of opioid receptors such as naltrexone, naloxone, nalmephine, antaxone, L-α-acetyl methadol, pentazocine, butorphanol, nalbuphine, buprenorphine, and methadone.

Examples of therapeutic agents frequently used in osteoporosis treatments, and may modulate bone mineral content include, but are not limited to, bisphosphonates such as alendronate (Fosamax®), risedronate (Actonel®), etidronate (Didronel®), pamidronate, tiludronate (Skelid®), clodronate (Bonefos®; Loron®), neridronate, olpadronate, zoledronate (Zometa®), and ibandronate (Boniva®), selective estrogen-receptor modulators (SERMs) such as raloxifene (Evista®), arzoxifene, clomifene, bazedoxifene, lasofoxifene, ormeloxifene, tamoxifen, and toremifine, anabolic therapies such as teriparatide (Forteo®; recombinant parathyroid hormone), and strontium ranelate, and recombinant peptide fragments of parathyroid hormone, estrogen/progesterone replacement therapies, monoclonal antibodies, inhibitors of receptor activator of nuclear factor kB ligand (RANKL) such as denosumab, osteoprotegerin and Pepstatin A, inhibitors of cathepsin K such as but not limited to OST-4077 (furan-2-carboxylic acid-(1-{1-[4-fluoro-2-(2-oxo-pyrrolidin-1-yl)-phenyl]-3-oxo-piperidin-3-ylcarbamoyl}-cyclohexyl)-amide), leupeptin, Cbz-Phe-Ala-CHN2, Cbz-Leu-Leu-Leu-aldehyde, cystatin, irreversible cysteine protease inhibitors like peptide halomethylketones, peptide diazomethylketones, and epoxides, quiescent irreversible cysteine protease inhibitors such as acyloxymethylketones, azapeptides, Michael acceptors like peptide vinyl esters, sulfones and sulfonates, reversible cysteine protease inhibitors such as peptide aldehydes, a-ketoesters and a-ketoamides, peptide methyl ketones and hydroxyl, alkyloxy, aryloxy, alkylthio, and arylthio derivatives thereof, 1,3-bis-(acylamino)-2-propanones, 1,3-bis-(acylhydrazino)-carbonyls, acylamino-pyrazolones, piperidinones, and thiazone-carbonyl-hydrazides, antagonists of integrin Avb3 (also known in the art as vitronectin), calcilytic compounds (Ca2+ receptor antagonists which increase the secretion of PTH), calcitonin (MiacalcinO), nitrates including but not limited to isosorbide mononitrate (ISMO) or nitroglycerin ointment (NTG), and dietary supplements such as calcium and vitamin D, and combinations thereof.

Another embodiment of the present invention is a method of identifying patients in need of treatment based on measuring clock gene (e.g. Cry1 and Cry2) expression levels in samples taken from a subject (Bjarnason, G. A. et al. *Am. J. Pathol.* 2001, 158, 1793; Akashi, M. et. al. *Proc. Natl. Acad. Sci. USA*, 2010, 107, 15643). Rhythmic mRNA expression profiles for human clock genes, including Cry1 and Cry2, measured in samples from a subject indicate a circadian clock is present in peripheral tissues (Mohawk, J. A. et al. *Ann. Rev. Neurosci.* 2012, Epub ahead of print). Expression of circadian clock related genes in these samples has been demonstrated to vary during the day. Furthermore, clock gene (e.g. Cry1 and Cry2) expression patterns in peripheral blood mononuclear cells are altered in humans by diseases such as obesity (Tahira, K. et al. *Arch. Med. Sci.* 2011, 7, 933). Changes in clock gene (e.g. Cry1 and Cry2) expression in peripheral mononuclear blood cells can be correlated with serum leptin, adiponectin, insulin and hsCRP levels, plasma lipid, glucose, melatonin and cortisol levels and, in animals, expression of clock genes (e.g. Cry1 and Cry2) in tissues including liver, adipose, pancreas and skeletal muscle. By contacting samples taken from a subject treated with a compound of formula I and measuring rhythmic mRNA or protein expression profiles, patients in need of treatment may be identified and pharmacological activity can be assessed. In other embodiments, the activities of one or more cryptochromes may be assessed, for example, the ability of cryptochromes to bind to a target such as Per1, Per2, glucocorticoid receptor (GR), or a promoter sequence containing Cry recognition sites, such as, e.g., the CLOCK-BMAL1 promoter.

Accordingly, one aspect of the subject matter disclosed herein relates to a method of monitoring progression or prognosis of a Cry-mediated disease or disorder in a subject, comprising measuring an effective amount of one or more cryptochromes in a first sample from the subject at a first period of time; measuring an affective amount of one or more cryptochromes in a second sample from the subject at a second period of time; and comparing the amount of the one or more cryptochromes detected in the first sample to the amount of the one or more cryptochromes detected in the second sample, or to a reference value.

"Diagnosis", "diagnose", "prognose" or "prognosis" is not limited to a definitive or near definitive determination that an individual has a disease, but also includes determining that an individual has an increased likelihood of having or developing the disease, compared to healthy individuals or to the general population.

As used herein, "expression" and "expression levels" include but are not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "algorithms" include sums, ratios, and regression operators, such as coefficients or exponents, value transformations and normalizations (including, without limitation, those normalization schemes based on clinical parameters, such as gender, age, body mass index, or ethnicity), rules and guidelines, statistical classification models, and neural networks trained on historical populations. Of particular use in measuring Cry as defined herein are linear and non-linear equations and statistical classification analyses to "correlate" the relationship between levels of Cry detected in a subject sample and the subject's risk of developing a Cry-mediated disease or disorder.

"Measuring" or "measurement" means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters. Measurement or measuring may also involve qualifying the type or identifying the substance. Measurement or measuring may also involve the ability of one or more Cry to bind to a target, wherein the target may be period genes or proteins Per1 and Per2, glucocorticoid receptor (GR), or the promoter region of the CLOCK-BMAL1 gene. Measurement of Cry may be used to diagnose, detect, or identify a Cry-mediated disease or disorder in a subject, to monitor the progression or prognosis of a Cry-mediated disease or disorder in a subject, to predict the recurrence of a Cry-mediated disease or disorder in a subject, or to classify a subject as having a low risk or a high risk of developing a Cry-mediated disease or disorder or a recurrence of a Cry-mediated disease or disorder.

"Risk" in the context of the present invention relates to the probability that an event will occur over a specific time period, as in the development of Cry-mediated disease or disorder, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion. Alternative continuous measures which may be assessed in the context of the present invention include time to development of a Cry-mediated disease or disorder, or progression to a different stage of a Cry-mediated disease or disorder, including progression or development of a Cry-mediated disease or disorder and therapeutic conversion risk reduction ratios.

"Risk evaluation," or "evaluation of risk" in the context of the subject matter disclosed herein encompasses making a prediction of the probability, odds, or likelihood that an event or disease state may occur, the rate of occurrence of the event or conversion from one disease state to another, i.e., from a "normal" condition to an at-risk condition for developing a Cry-mediated disease or disorder, or from an at-risk condition to a Cry-mediated disease or disorder, or development of recurrent disease or disorder. Risk evaluation can also comprise prediction of other indices of Cry-mediated disease or disorder, either in absolute or relative terms in reference to a previously measured population. The methods of the present invention may be used to make continuous or categorical measurements of the risk of conversion to a Cry-mediated disease or disorder, thus diagnosing and defining the risk spectrum of a category of subjects defined as at risk for developing the disease or disorder. In the categorical scenario, the invention can be used to discriminate between normal and at-risk subject cohorts. In other embodiments, the present invention may be used so as to discriminate at-risk conditions from disease conditions, or disease conditions from normal.

A "sample" as used herein is a biological sample isolated from a subject and can include, by way of example and not limitation, whole blood, serum, plasma, blood cells, endothelial cells, tissue biopsies, lymphatic fluid, ascites fluid, interstitial fluid (also known as "extracellular fluid" and encompasses the fluid found in spaces between cells, including, inter alia, gingival crevicular fluid), bone marrow, seminal fluid, cerebrospinal fluid (CSF), saliva, mucous, sputum, sweat, urine, or any other secretion, excretion, or other bodily fluids.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

The risk of a Cry-mediated disease or disorder can be detected by measuring an "effective amount" of one or more cryptochromes in a sample (e.g., a subject derived sample), and comparing the effective amounts to reference values, often utilizing mathematical algorithms or formulae in order to combine information from results of multiple individuals into a single measurement. Subjects identified as having an increased risk of a Cry-mediated disease or disorder can optionally be selected to receive treatment regimens or therapeutic interventions, such as administration of the compounds of formula I as defined herein as monotherapy or in combination with one or more additional therapeutic agents, or implementation of surgical interventions (which may follow or precede administration of the compounds of formula I, alone or in combination with additional therapeutic agents or other therapies).

The methods for detecting these cryptochromes in a sample have many applications. For example, one or more cryptochromes can be measured to aid diagnosis or prognosis of a Cry-mediated disease or disorder. In another example, the methods for detection of the cryptochromes can be used to monitor responses in a subject to treatment of a Cry-mediated disease or disorder. In another example, the methods can be used to assay for and to identify compounds that modulate expression of cryptochromes in vivo or in vitro.

The present invention may be used to make continuous or categorical measurements of the risk of conversion to a Cry-mediated disease or disorder, thus diagnosing and defining the risk spectrum of a category of subjects defined as being at-risk for developing the disease or disorder. In the categorical scenario, the methods of the present invention can be used to discriminate between normal and at-risk subject cohorts. In other embodiments, the present invention may be used so as to discriminate at-risk from disease, or disease from normal. Such differing use may require different combinations in individual panel or profile, mathematical algorithm, and/or cut-off points, but be subject to the same aforementioned measurements of accuracy for the intended use.

Identifying the at-risk subject enables the selection and initiation of various therapeutic interventions or treatment regimens in order to delay, reduce, or prevent that subject's conversion to a Cry-mediated disease or disorder. Levels of an effective amount of cryptochrome proteins, nucleic acids, polymorphisms, metabolites, or other analytes also allows for the course of treatment to be monitored. In this method, a biological sample can be provided from a subject undergoing treatment regimens, e.g., therapeutic treatments, for a Cry-mediated disease or disorder. Such treatment regimens can include, but are not limited to, surgical intervention and treatment with therapeutic agents used in subjects diagnosed or identified with a Cry-mediated disease or disorder, for example, the compounds of formula I described herein. If desired, biological samples are obtained from the subject at various time points before, during, or after treatment. For example, determining the disease status by comparison of a subject's cryptochrome profile to a reference cryptochrome profile can be repeated more than once, wherein the subject's profile can be obtained from a separate sample taken each time the method is repeated. Samples may be taken from the subject at defined time intervals, such as, e.g., 4 hours, 8 hours, 12 hours, 24 hours, 48 hours, 72 hours, or any suitable time interval as would be performed by those skilled in the art.

Differences in the genetic makeup of subjects can result in differences in their relative abilities to metabolize various drugs, which may modulate the symptoms or risk factors of a Cry-mediated disease or disorder. Subjects that have a Cry-mediated disease or disorder, or are at risk for developing a Cry-mediated disease or disorder can vary in age, ethnicity, and other parameters. Accordingly, measuring effective amounts of one or more cryptochromes as defined herein, both alone and together in combination with known genetic factors for drug metabolism, allow for a pre-determined level of predictability that a putative therapeutic or prophylactic to be tested in a selected subject will be suitable for treating or preventing a Cry-mediated disease or disorder in the subject.

To identify therapeutic agents or drugs that are appropriate for a specific subject, a test sample from the subject can also be exposed to a therapeutic agent or a drug, and the level or activity of one or more of cryptochrome proteins, nucleic acids, polymorphisms, splice variants, metabolites or other analytes can be determined. Other genes or proteins that are affected or which directly or indirectly bind to one or more cryptochromes (e.g., Per1, Per2, GR, CLOCK-BMAL1 promoter, etc.) may also be measured. The level of one or more cryptochromes can be compared to sample derived from the subject before and after subject management for a Cry-mediated disease or disorder, e.g., treatment or exposure to a therapeutic agent or a drug, or can be compared to samples derived from one or more subjects who have shown improvements in risk factors as a result of such treatment or exposure.

Nucleic acids may be obtained from the samples in many ways known to one of skill in the art, for example, extraction methods, including e.g., solvent extraction, affinity purification and centrifugation. Selective precipitation can also purify nucleic acids. Chromatography methods may also be utilized including, gel filtration, ion exchange, selective adsorption, or affinity binding. The nucleic acids may be, for example, RNA, DNA or may be synthesized into cDNA. The nucleic acids may be detected using microarray techniques that are well known in the art, for example, Affymetrix arrays followed by multidimensional scaling techniques. See R. Ekins, R. and Chu, F. W. (1999) Trends Biotechnol. 17: 217-218; D. D. Shoemaker, et al., (2001) Nature 409(6822): 922-927 and U.S. Pat. No. 5,750,015.

If desired, the sample can be prepared to enhance detectability of one or more cryptochromes by, for example, pre-fractionation. Methods of pre-fractionation include, for example, Cibacron blue agarose chromatography, size exclusion chromatography, ion exchange chromatography, heparin chromatography, lectin chromatography, affinity chromatography, single stranded DNA affinity chromatography, sequential extraction, gel electrophoresis and liquid chromatography. The analytes also may be modified prior to detection. A sample can be pre-fractionated by removing proteins that are present in a high quantity or that may interfere with the detection of molecules of interest in a sample. For example, in a blood serum sample, serum albumin is present in a high quantity and may obscure the analysis of one or more cryptochromes. Thus, a blood serum sample can be pre-fractionated by removing serum albumin using, for example, a substrate that comprises adsorbents that specifically bind serum albumin, an affinity column or anti-serum albumin antibodies can be used.

In other embodiments, molecules of interest in a sample can be separated by high-resolution electrophoresis, e.g., one or two-dimensional gel electrophoresis. A fraction can be isolated and further analyzed by gas phase ion spectrometry. Preferably, two-dimensional gel electrophoresis is used to generate two-dimensional array of spots, including one or more cryptochromes. See, e.g., Jungblut and Thiede, (1997) Mass Spectr. Rev. 16: 145-162. The two-dimensional gel electrophoresis can be performed using methods known in the art. See, e.g., Deutscher ed., Methods in Enzymology vol. 182. Typically, a sample may be separated by, e.g., isoelectric focusing, during which one or more cryptochromes in a sample are separated in a pH gradient until they reach a spot where their net charge is zero (i.e., isoelectric point). This first separation step results in one-dimensional array. The molecules in one-dimensional array are further separated using a technique generally distinct from that used in the first separation step. For example, in the second dimension, molecules of interest separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass. Typically, two-dimensional gel electrophoresis can separate chemically different molecules of interest in the molecular mass range from 1000-200,000 Da within complex mixtures.

Molecules of interest in the two-dimensional array can be detected using any suitable methods known in the art. For example, molecules of interest in a gel can be labeled or stained (e.g., Coomassie Blue or silver staining). If gel electrophoresis generates spots that correspond to the molecular weight of one or more cryptochromes of the invention, the spot can be excised and further analyzed by, for example, gas phase ion spectrometry, mass spectrometry, or high performance liquid chromatography. Alternatively, the gel containing molecules of interest can be transferred to an inert membrane by applying an electric field. Then a spot on the membrane that approximately corresponds to the molecular weight of a molecule of interest can be analyzed by e.g., gas phase ion spectrometry, mass spectrometry, or HPLC.

Optionally, a molecule of interest can be modified before analysis to improve its resolution or to determine its identity. For example, the sample may be subject to proteolytic digestion before analysis. Any protease can be used. Proteases, such as trypsin, that are likely to cleave proteins into a discrete number of fragments are particularly useful. The fragments that result from digestion may function as a fingerprint for the molecules of interest, thereby enabling their indirect detection. This is particularly useful where there are molecules of interest with similar molecular masses that might be confused for the preferred molecule, i.e., cryptochromes, in question. Also, proteolytic fragmentation is useful for high molecular weight molecules because smaller molecules are more easily resolved by mass spectrometry. In another example, molecules can be modified to improve detection resolution. For instance, neuraminidase can be used to remove terminal sialic acid residues from glycoproteins to improve binding to an anionic adsorbent (e.g., cationic exchange arrays) and to improve detection resolution. In another example, the molecules can be modified by the attachment of a tag of particular molecular weight that specifically binds to another molecular entity, further distinguishing them. Optionally, after detecting such modified molecules of interest, the identity of the molecules can be further determined by matching the physical and chemical characteristics of the modified versions in a protein database (e.g., SwissProt).

Once captured on a substrate, e.g., biochip or antibody, any suitable method, such as those described herein as well as other methods known in the art, can be used to measure one or more cryptochromes in a sample. The actual measurement of levels or amounts of the such molecules can be determined using any method known in the art. These methods include, without limitation, mass spectrometry (e.g., laser desorption/ionization mass spectrometry), fluorescence (e.g. sandwich immunoassay), surface plasmon resonance, ellipsometry and atomic force microscopy. Methods may further include, by one or more of microarrays, PCR methods, mass spectrometry (including, for example, and without limitation, ESI-MS, ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)n, atmospheric pressure photoionization mass spectrometry (APPI-MS), APPI-MS/MS, and APPI-(MS)n, quadrupole mass spectrometry, Fourier transform mass spectrometry (FTMS), and ion trap mass spectrometry), nucleic acid chips, Northern blot hybridization, TMA, SDA, NASBA, PCR, real time PCR, reverse transcriptase PCR, real time reverse transcriptase PCR, in situ PCR, chromatographic separation coupled with mass spectrometry, protein capture using immobilized antibodies or by traditional immunoassays. See for example, U.S. Pat. Nos. 5,723,591; 5,801,155 and 6,084,102 and Higuchi, 1992 and 1993. PCR assays may be done, for example, in a multi-well plate formats or in chips, such as the BioTrove OPEN ARRAY Chips (BioTrove, Woburn, Mass.).

For example, sequences within the sequence database entries corresponding to cryptochromes can be used to construct probes for detecting RNA sequences in, e.g., Northern blot hybridization analyses or methods which specifically, and, preferably, quantitatively amplify specific nucleic acid sequences. As another example, the sequences can be used to construct primers which specifically or selectively hybridize to cryptochrome sequences and which are used to amplifying such sequences in, e.g., amplification-based detection methods such as reverse-transcription based polymerase chain reaction (RT-PCR), e.g., quantitative real-time RT-PCR. When alterations in gene expression are associated with gene amplification, deletion, polymorphisms, and mutations, sequence comparisons in test and reference populations can be made by comparing relative amounts of the examined DNA sequences in subject and reference cell populations. As used herein, the term "specifically (or selectively) hybridizes" when referring to a nucleic acid, refers to a binding reaction that is determinative of the presence of the nucleic acid in a heterogeneous population of nucleic acids. Thus, under designated assay conditions, the specified nucleic acid probe (including inhibitory nucleic acids) may bind or hybridize to a particular nucleic acid of interest at least two times the background and do not substantially bind or hybridize in a significant amount to other nucleic acids present in the sample.

Levels of cryptochromes can also be determined by immunoassay. The antibody may be monoclonal, polyclonal, chimeric, or a fragment of the foregoing, as discussed in detail herein, and the step of detecting the reaction product may be carried out with any suitable immunoassay. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologies. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a cryptochrome from specific species such as rat, mouse, or human can be selected to obtain only those polyclonal antibodies that are specifically immunoreactive with that cryptochrome and not with other proteins, except for polymorphic variants and alleles of the cryptochrome. This selection may be achieved by subtracting out antibodies that cross-react with cryptochromes from other species.

Immunoassays carried out in accordance with the present invention may be homogeneous assays or heterogeneous assays. In a homogeneous assay the immunological reaction usually involves the specific antibody (e.g., anti-cryptochrome protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of detectable labels. Exemplary detectable labels include magnetic beads (e.g., DYNABEADS™), fluorescent dyes, enzymes (e.g., horse radish peroxide, alkaline phosphatase and others commonly used in an ELISA), radiolabels (e.g., $^{35}$S, $^{125}$I, $^{131}$I), and fluorescent labels (e.g., fluorescein, Alexa, green fluorescent protein, rhodamine) and colorimetric labels such as colloidal gold or colored glass or plastic beads in accordance with known techniques.

Alternatively, the molecule of interest in the sample can be detected using an indirect assay, wherein, for example, a second, labeled antibody is used to detect bound cryptochrome-specific antibody, and/or in a competition or inhibition assay wherein, for example, a monoclonal antibody which binds to a distinct epitope of the cryptochrome is incubated simultaneously with the mixture. For example, if the antigen to be detected contains a second binding site, an antibody which binds to that site can be conjugated to a detectable group and added to the liquid phase reaction solution before the separation step. The presence of the detectable label on the solid support indicates the presence of the antigen in the test sample. Methods for measuring the amount or the presence of antibody-antigen complexes include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Examples of suitable immunoassays include, but are not limited to immunoblotting (e.g., Western blotting, slot blot assay), immunoprecipitation, immunofluorescence methods, chemiluminescence methods, electrochemiluminescence (ECL) or enzyme-linked immunoassays, e.g., enzyme-linked immunosorbent assay (ELISA) and radioimmunoassay (RIA). See generally E. Maggio, Enzyme-Immunoassay, (1980) (CRC Press, Inc., Boca Raton, Fla.); see also U.S. Pat. Nos. 4,727,022; 4,659,678; 4,376,110; 4,275,149; 4,233,402; and 4,230,767. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra. All of these are incorporated by reference herein.

Immunoassays can be used to determine presence or absence of one or more cryptochromes in a sample as well as the quantity in a sample. The amount of an antibody-marker complex can be determined by comparing to a standard. A standard can be, e.g., a known compound or another protein known to be present in a sample. As noted above, the test amount of the one or more cryptochromes need not be measured in absolute units, as long as the unit of measurement can be compared to a control.

Proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. Antibodies can also be useful for detecting post-translational modifications of proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51). The collection of proteins including a specific protein and all modified forms of it is referred to herein as a "protein cluster." The collection of all modified forms of a specific protein, excluding the specific protein, itself, is referred to herein as a "modified protein cluster." Modified forms of any cryptochrome also may be used, themselves, in the methods disclosed herein. In certain cases the modified forms may exhibit better discriminatory power in diagnosis than the specific forms set forth herein. Modified forms can be initially detected by any methodology known in the art.

Alternatively, cryptochrome protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography (including high-performance liquid chromatography (HPLC)), which may be combined with mass spectrometry, matrix-assisted laser desorption ionization-time of flight (MALDI-TOF) combined with mass spectrometry, ion spray spectroscopy combined with mass spectrometry, capillary electrophoresis, ion mobility spectrometry, surface-enhanced laser desorption/ionization (SELDI), optical methods, electrochemical methods, atomic force microscopy, radiofrequency methods, surface Plasmon resonance, ellipsometry, NMR and IR detection. (See, International Application Publication Nos. WO 04/056456 and WO 04/088309, each of which are hereby incorporated by reference in their entireties). In this regard, other analytes can be measured using the above-mentioned detection methods, or other methods known to the skilled artisan. For example, circulating calcium ions (Ca2+) can be detected in a sample using fluorescent dyes such as the Fluo series, Fura-2A, Rhod-2, among others. Other metabolites can be similarly detected using reagents that specifically designed or tailored to detect such metabolites.

A Cry-mediated disease or disorder may involve changes in the activity of one or more cryptochromes, or ability of one or more cryptochromes to bind to a target. Without wishing to be bound by theory, cryptochrome proteins are believed to bind to Period proteins Per 1 and/or Per2 as a heterodimer, which then bind to the promoter region of the CLOCK-BMAL1 gene to facilitate transcriptional repression in a feedback loop that can impinge upon numerous metabolic processes. Thus, measuring an effective amount of one or more cryptochromes according to the methods of the invention may involve assessing an increase or decrease in the ability of Cry proteins to bind to Per1 and/or Per2, to the glucocorticoid receptor (GR), or any other binding target of Cry known to those skilled in the art. Measurement of protein-protein interactions may be facilitated by any method known in the art, including co-immunoprecipitation, yeast two-hybrid assay, surface Plasmon resonance, bimolecular fluorescence complementation, tandem affinity purification, phage display, fluorescence polarization/anisotropy, dual polarization interferometry, fluorescence correlation spectroscopy, fluorescence resonance energy transfer, and the like.

The activity of one or more cryptochromes may also be measured by an increase or decrease in the ability to bind to a DNA sequence, i.e., the promoter region of the CLOCK-BMAL1 gene, or other gene that contains binding sites recognized by one or more cryptochromes. "Promoter", "promoter sequence", or "promoter region" refers to a DNA sequence capable of binding RNA polymerase in a cell, initiating transcription of a downstream (3' direction) coding sequence, thereby controlling its expression. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Promoters may be derived in their entirety from a native gene, or be composed of different elements derived from different promoters found in nature, or even comprise synthetic DNA segments. In most cases the exact boundaries of regulatory sequences have not been completely defined, DNA fragments of different lengths may have identical promoter activity.

The CLOCK-BMAL1 promoter (or any other promoter region containing binding or recognition sites for Cry) may be "operably linked" to a reporter gene. The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), alkaline phosphatase (ALP), chloramphenicol acetyltransferase (CAT), β-galactosidase (LacZ), β-glucuronidase (Gus), and the like. Selectable marker genes may also be considered reporter genes. The promoter-reporter gene construct may be contained in a plasmid or expression vector that is transferred or transfected into a cell. The expression of the reporter gene can be detected by determining the activity of the gene product, for example, an enzyme activity in the case of using a reporter gene exemplified above.

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. The term "expression vector" means a vector, plasmid or vehicle designed to enable the expression of an inserted nucleic acid sequence following transformation into the host. Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter. Any cell may be used to carry out reporter assays, such as a prokaryotic cell or eukaryotic cell. Preferably, the cell may be a bacterial cell, a fungal cell, a yeast cell, a nematode cell, an insect cell, a fish cell, a plant cell, an avian cell, an animal cell, and a mammalian cell. Cells may be primary cells or may be continuously passaged as cell lines. Exemplary cells and cell lines are known to those skilled in the art.

Other methods of measuring the activity or ability of one or more cryptochromes to bind to a DNA sequence include chromatin immunoprecipitation assay, electrophoretic mobility shift assay, DNA pull-down assay, microplate capture and detection, and the like.

Levels of an effective amount of cryptochrome proteins, nucleic acids, polymorphisms, metabolites, or other analytes, or the activities of cryptochrome proteins or targets that are directly or indirectly bound to cryptochrome proteins, can then be determined and compared to a reference value, e.g. a control subject or population whose disease status is known, or an index value or baseline value. The reference sample or index value or baseline value may be taken or derived from one or more subjects who have been exposed to the treatment, or may be taken or derived from one or more subjects who are at low risk of developing a Cry-mediated disease or disorder, or may be taken or derived from subjects who have shown improvements in disease risk factors as a result of exposure to treatment. Alternatively, the reference sample or index value or baseline value may be taken or derived from one or more subjects who have not been exposed to the treatment. For example, samples may be collected from subjects who have received initial treatment for a Cry-mediated disease or disorder and subsequent treatment for the disease or disorder to monitor the progress of the treatment. In some embodiments, a first sample may be taken from a subject at a first period of time, e.g., prior to treatment with a compound of formula I as defined herein, either alone or in combination with one or more additional therapeutic agents, followed by measuring or detecting one or more cryptochromes (or cryptochrome targets) as described herein. Thereafter, a second sample may be taken from a subject at a second period of time, e.g., after treatment with a compound of formula I as defined herein, either alone or in combination with one or more additional therapeutic agents, and measuring the one or more cryptochromes or cryptochrome targets. Any number of samples may be taken at any time interval throughout the course of treatment to assess its effectiveness.

A reference value can also comprise a value derived from risk prediction algorithms or computed indices from population studies such as those disclosed herein. A similar term in this context is a "control", which can be, e.g., the average or median amount of cryptochromes present in comparable samples of normal subjects in normal subjects or in non-disease subjects such as where a Cry-mediated disease or disorder is undetectable. The control amount is measured under the same or substantially similar experimental conditions as in measuring the test amount. The correlation may take into account the presence or absence of the cryptochromes in a test sample and the frequency of detection of the same molecules in a control. The correlation may take into account both of such factors to facilitate determination of disease status.

A reference profile of those subjects who do not have a Cry-mediated disease or disorder, and would not be expected to develop a Cry-mediated disease or disorder may also be prepared according to methods disclosed herein. Measurement of one or more cryptochromes can also be used to generate a "subject profile" taken from subjects who have a Cry-mediated disease or disorder. The subject profiles can be compared to a reference profile to diagnose or identify subjects at risk for developing a Cry-mediated disease or disorder, to monitor the progression of disease, as well as the rate of progression of disease, and to monitor the effectiveness of treatment modalities or subject management.

The reference and subject profiles of the present invention can be contained in a machine-readable medium, such as but not limited to, analog or digital tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other risk algorithms and computed indices such as those described herein.

In any of the methods disclosed herein, the data from the sample may be fed directly from the detection means into a computer containing the diagnostic algorithm. Alternatively, the data obtained can be fed manually, or via an automated means, into a separate computer that contains the diagnostic algorithm. Accordingly, embodiments of the invention include methods involving correlating the detection of the cryptochromes with a probable diagnosis of a Cry-mediated disease or disorder. The correlation may take into account the amount of the one or more cryptochromes in the sample compared to a control amount (up or down regulation of the cryptochromes) (e.g., in normal subjects in whom a Cry-mediated disease or disorder is undetectable). The correlation may take into account the presence or absence of the cryptochromes in a test sample and the frequency of detection of the same molecules in a control. The correlation may take into account both of such factors to facilitate determination of whether a subject has a Cry-mediated disease or disorder or not.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. The signal strength detected for each molecule of interest can be displayed in the form of relative intensities in the scale desired (e.g., 100). Alternatively, a standard (e.g., a serum protein) may be admitted with the sample so that a peak from the standard can be used as a reference to calculate relative intensities of the signals observed for each molecule of interest detected.

The resulting data can be transformed or converted into various formats for displaying. In one format, referred to as "spectrum view or retentate map," a standard spectral view can be displayed, wherein the view depicts the quantity of molecule reaching the detector at each particular molecular weight. In another format, referred to as "peak map," only the peak height and mass information are retained from the spectrum view, yielding a cleaner image and enabling molecules of interest with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique molecules of interest which are up- or down-regulated between samples. Profiles (spectra) from any two samples may be compared visually. In yet another format, Spotfire Scatter Plot can be used, wherein molecules of interest that are detected are plotted as a dot in a plot, wherein one axis of the plot represents the apparent molecular weight of the cryptochromes detected and another axis represents the signal intensity of cryptochromes detected. For each sample, molecules of interest that are detected and the amount of molecules present in the sample can be saved in a computer readable medium. This data can then be compared to a control or reference profile or reference value (e.g., a profile or quantity of molecules detected in control, e.g., subjects in whom a Cry-mediated disease or disorder is undetectable).

The data that are generated in the methods disclosed herein can be classified using a pattern recognition process that uses a classification model. In some embodiments, data generated using samples such as "known samples" can then be used to "train" a classification model. A "known sample" is a sample that is pre-classified (e.g., disease or no disease). Data generated using known samples can then be used to "train" a classification model. A "known sample" is a sample that is pre-classified. The data can be used to form the classification model can be referred to as a "training data set". Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased vs. non diseased). The training data set that is used to form the classification model may comprise raw data or pre-processed data. In some embodiments, raw data can be obtained directly from time-of-flight spectra or mass spectra, and then may be optionally "pre-processed" in any suitable manner. Pre-processing steps such as these can be used to reduce the amount of data that is used to train the classification model.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety. In supervised classification, training data containing examples of known categories are presented to a learning mechanism, which learns one more sets of relationships that define each of the known classes. New data may then be applied to the learning mechanism, which then classifies the new data using the learned relationships.

Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines). A preferred supervised classification method is a recursive partitioning process (U.S. Patent Application Publication No. 20020138208). Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm. Learning algorithms asserted for use in classifying biological information are described in, for example, International Application Publication No. WO 01/31580 and U.S. Patent Application Publication Nos. 20020193950, 20030004402, and 20030055615. Another classification method involves multivariate predictive models using a non-linear version of Unified Maximum Separability Analysis ("USMA") classifiers. Details of USMA classifiers are described in U.S. Patent Application Publication No. 20030055615.

Other classification algorithms and formulae include, but are not limited to, Principal Component Analysis (PCA), cross-correlation, factor rotation, Logistic Regression (LogReg), Linear Discriminant Analysis (LDA), Eigengene Linear Discriminant Analysis (ELDA), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, Leave-One-Out (LOO), 10-Fold cross-validation (10-Fold CV), and Hidden Markov Models, among others.

Detection and correlation of one or more cryptochromes may also be analyzed using any suitable means, including software packages, for example, Applied Maths, GenExplore™, 2-way cluster analysis, principal component analysis, discriminant analysis, self-organizing maps; BioDiscovery, Inc., Los Angeles, Calif. (ImaGene™, special image processing and data extraction software, powered by MatLab®; GeneSight: hierarchical clustering, artificial neural network (SOM), principal component analysis, time series; AutoGene™; CloneTracker™); GeneData AG (Basel, Switzerland); Molecular Pattern Recognition web site at MIT's Whitehead Genome Center; Rosetta Inpharmatics, Kirkland, Wash. Resolver™ Expression Data Analysis System; Scanalytics, Inc., Fairfax, Va. Its MicroArray Suite enables researchers to acquire, visualize, process, and analyze gene expression microarray data; TIGR (The Institute for Genome Research) offers software tools for array analysis. For example, see also Eisen and Brown, (1999) Methods Enzymol. 303: 179-205.

In certain embodiments of the methods of qualifying disease status, the methods further comprise managing or modifying clinical treatment of a subject based on the status of the disease or disorder. For example, if the result of the methods of the present invention is inconclusive or there is reason that confirmation of status is necessary, the physician may order more tests (e.g., CT scans, PET scans, MRI scans, PET-CT scans, X-rays, biopsies, blood tests. Alternatively, if the status indicates that treatment is appropriate, the physician may schedule the subject for treatment. In other instances, the subject may receive therapeutic treatments (such as administration of therapeutic agents (such as, e.g., the compounds of formula I defined herein, either alone or in combination with one or more additional therapeutic agents), either in lieu of, or in addition to, surgery. No further action may be warranted. Furthermore, if the results show that treatment has been successful, a maintenance therapy or no further management may be necessary.

The subject matter disclosed herein also provides for such methods where the cryptochromes are measured again after clinical treatment of a subject. In these cases, the methods are used to monitor the status of a Cry-mediated disease or disorder, e.g., response to treatment, remission of the disease or progression of the disease. The methods can be repeated after each treatment the subject receives, allowing the physician to follow the effectiveness of the course of treatment. If the results show that the treatment is not effective, the course of treatment can be altered accordingly.

The invention provides kits for qualifying disease status and/or detecting or diagnosing disease, wherein the kits can be used to detect one or more cryptochromes. For example, the kits can be used to detect any one or more of the cryptochromes described herein, which the one or more cryptochromes are differentially present in samples of disease subjects and normal subjects. The kits of the invention have many applications. For example, the kits can be used in any one of the methods of the invention described herein, such as, inter alia, to differentiate if a subject has a Cry-mediated disease or disorder or has a negative diagnosis, thus aiding a diagnosis. In another example, the kits can be used to identify compounds that modulate expression of one or more of the cryptochromes, compounds that modulate the activity of one or more cryptochromes (i.e., that affect the ability of one or more cryptochromes to bind to a target such as Per1, Per2, the glucocorticoid receptor (GR), or a promoter sequence recognized by cryptochromes such as the CLOCK-BMAL1 promoter or any other promoter sequence) by using in vitro or in vivo animal models for a Cry-mediated disease or disorder. In another example, the kits can be used to identify binding targets of one or more cryptochrome proteins as defined herein.

Kits of the present invention may include a detection reagent, e.g., nucleic acids that specifically identify one or more cryptochrome nucleic acids by having homologous nucleic acid sequences, such as oligonucleotide sequences, primers, or aptamers, complementary to a portion of the nucleic acids or antibodies to proteins encoded by the nucleic acids packaged together. The oligonucleotides can be fragments of the genes. The oligonucleotides may be single stranded or double stranded. For example the oligonucleotides can be 200, 150, 100, 50, 25, 10 or less nucleotides in length. Alternatively, the detection reagent may be one or more antibodies that specifically or selectively bind to one or more cryptochrome proteins or targets thereof. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay and for correlation to disease status may be included in the kit.

For example, detection reagents can be immobilized on a solid matrix such as a porous strip to form at least one detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of cryptochromes present in the sample. The detection sites may be configured in any suitably detectable shape and are typically in the shape of a bar or dot spanning the width of a test strip. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.). The kit may also contain reagents, and/or enzymes for amplifying or isolating sample DNA. The kits may include reagents for real-time PCR, for example, TaqMan probes and/or primers, and enzymes.

In some embodiments, a kit comprises: (a) a substrate comprising an adsorbent thereon, wherein the adsorbent retains or is otherwise suitable for binding a cryptochrome, and (b) instructions to detect the cryptochrome by contacting a sample with the adsorbent and detecting the cryptochrome retained by the adsorbent. In some embodiments, the kit may comprise an eluant (as an alternative or in combination with instructions) or instructions for making an eluant, wherein the combination of the adsorbent and the eluant allows detection of the cryptochrome using gas phase ion spectrometry.

In other embodiments, the kit may comprise a first substrate comprising an adsorbent thereon (e.g., a particle functionalized with an adsorbent) and a second substrate onto which the first substrate can be positioned to form a probe, which may be removed and inserted into machine, such as, e.g., a gas phase ion spectrometer. In other embodiments, the kit may comprise a single substrate, which is in the form of a probe with adsorbents on the substrate that can be removed and inserted into a machine. In yet another embodiment, the kit may further comprise a pre-fractionation spin column (e.g., Cibacron blue agarose column, anti-HSA agarose column, K-30 size exclusion column, Q-anion exchange spin column, single stranded DNA column, lectin column, etc.). In another embodiment, a kit comprises (a) an antibody that specifically binds to one or more cryptochromes; and (b) a detection reagent. An antibody may be, for example, an antibody directed against the gene products of a cryptochrome gene.

Optionally, the kit may further comprise a standard or control information so that the test sample can be compared with the control information standard to determine if the test amount of one or more cryptochromes detected in a sample is a diagnostic amount consistent with a diagnosis of a Cry-mediated disease or disorder.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow described herein does not require the particular order shown, or sequential order, to achieve desirable results. Other embodiments may be within the scope of the claims.

EXAMPLES

Example 1

Reaction Schemes for Synthesis of Compounds

The following reaction schemes, Reaction Scheme I, II, and III, depicts methods of synthesis for compounds of formula I. In the general methods for preparation of the compounds of formula I, the variable $R_1$, $R_2$, $R_3$, $R_4$, $R_5$, $R_6$, $R_7$, a, and b are as previously defined for a compound of formula I unless otherwise stated. The Reaction Schemes herein described are intended to provide a general description of the methodology employed in the preparation of many of the Examples given. However, it will be evident from the detailed descriptions given in the Experimental section that the modes of preparation employed extend further than the general procedures described herein. In particular, it is noted that the compounds prepared according to the Schemes may be modified further to provide new Examples within the scope of this invention. The reagents and intermediates used in the following examples are either commercially available or can be prepared according to the standard literature procedures by those skilled in the art of organic synthesis.

Reaction Scheme I, below, depicts the synthesis of compounds of formula I. Treatment of an appropriately substituted bromide derivative of formula VI with an appropriate carbazole of formula VII, in an appropriate solvent, such as N,N-dimethylformamide or N,N-dimethylacetamide, within a temperature range of approximately 0° C. to 150° C. for a period of approximately 5 minutes to 24 hours provides the corresponding oxirane compound of formula V. Preferred conditions for reacting the bromide compound of formula VI with the carbazole of formula VII to provide compounds of formula V include carrying out the reaction in N,N-dimethylformamide at 0° C. to room temperature in the presence of potassium hydroxide for 20 to 24 hours followed by an extractive workup. Treatment of the compound of formula V with an appropriate amine of formula IV, in an appropriate solvent, such as ethanol, within a temperature range of approximately room temperature to 150° C. for a period of approximately 5 mins to 24 hours provides the corresponding amino alcohol compound of formula III. Preferred conditions for reacting the oxirane compound of formula V to provide compounds of formula III include carrying out the reaction in ethanol at 40° C. for 20 to 24 hours followed by extractive workup. Alternatively, the oxirane compound of formula V can be reacted with the amine of formula IV in an appropriate solvent, such as ethanol, under microwave irradiation to provide the compound of formula III. Treatment of the compound of formula III with an appropriate sulfonyl chloride of formula II, in an appropriate solvent, such as methylene chloride, within a temperature range of 0° C. to 150° C. for a period of approximately 5 minutes to 24 hours provides the corresponding sulfonamide compound of formula I. Preferred conditions for reacting amino alcohol compound of formula III with the sulfonyl chloride of formula II to provide the compounds of formula I include carrying out the reaction in methylene chloride at 0° C. to room temperature in the presence of triethylamine or pyridine for 1 to 24 hours followed by an extractive workup.

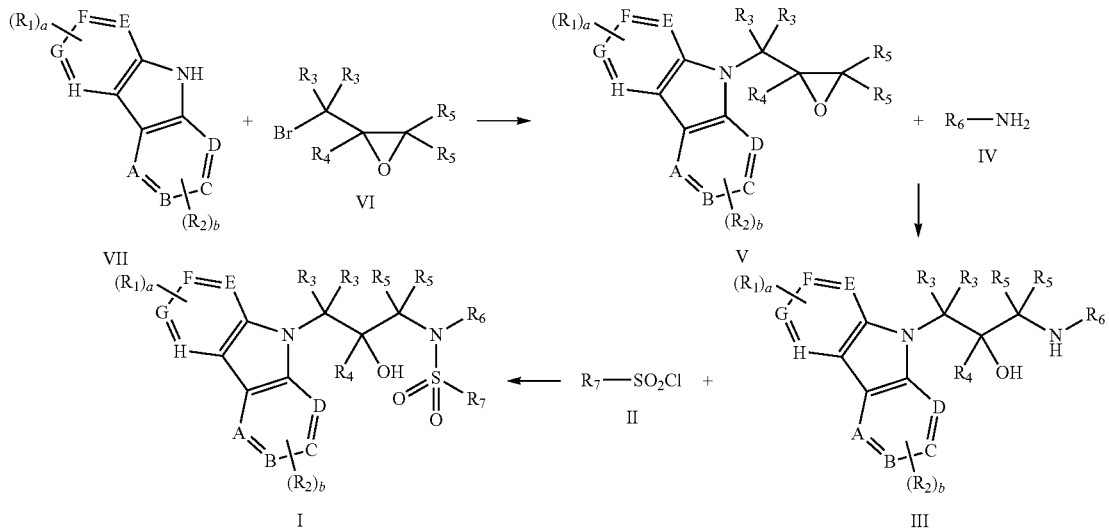

Reaction Scheme I

Reaction Scheme II, below, depicts an alternative synthesis of compounds of formula I. Treatment of an appropriately substituted oxirane derivative of formula V with an appropriate sulfonamide of formula VIII, in an appropriate solvent, such as N,N-dimethylformamide or N,N-dimethylacetamide, within a temperature range of 0° C. to 150° C. for a period of approximately 5 minutes to 24 hours provides the corresponding sulfonamide compound of formula I. Preferred conditions for reacting oxirane compound of formula V with the sulfonamide of formula VIII to provide compounds of formula I include carrying out the reaction in N,N-dimethylformamide at room temperature to 70° C. in the presence of sodium hydride for 20 to 24 hours. Alternatively, the oxirane compound of formula V can be reacted with the sulfonamide of formula VIII in an appropriate solvent, such as N,N-dimethylacetamide, at 100° C. in the presence of cesium carbonate for 20 to 24 hours.

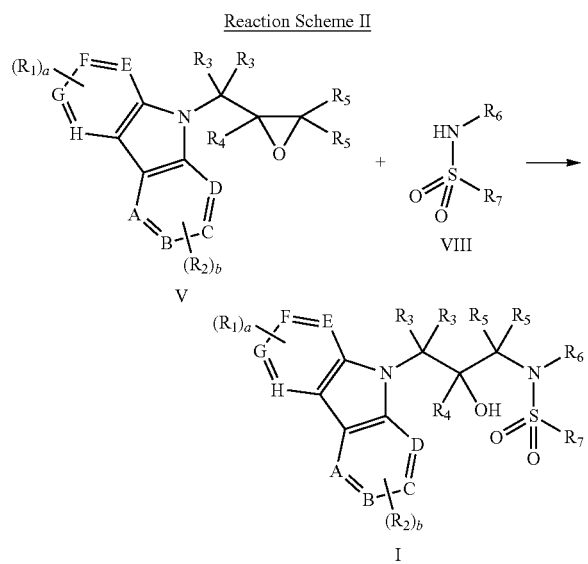

Reaction Scheme III, below, depicts an alternative synthesis of compounds of formula I. Treatment of the amine compound of formula IV with an appropriate sulfonyl chloride of formula II, in an appropriate solvent, such as methylene chloride, within a temperature range of 0° C. to 150° C. for a period of approximately 5 minutes to 24 hours provides the corresponding sulfonamide compound of formula VIII. Preferred conditions for reacting amine compound of formula IV with the sulfonyl chloride of formula II to provide the compounds of formula VIII include carrying out the reaction in methylene chloride at 0° C. to room temperature in the presence of triethylamine or pyridine for 1 to 24 hours followed by an extractive workup. Treatment of the compound of formula VIII with an appropriate bromide of formula X, in an appropriate solvent, such as N,N-dimethylformamide or N,N-dimethylacetamide, within a temperature range of 0° C. to 150° C. for a period of approximately 5 minutes to 24 hours provides the corresponding oxirane compound of formula IX. Preferred conditions for reacting sulfonamide compound of formula VIII with the bromide of formula X to provide compounds of formula IX include carrying out the reaction in N,N-dimethylformamide at room temperature to 70° C. in the presence of sodium hydride for 20 to 24 hours. Treatment of the compound of formula IX with an appropriate carbazole of formula VII, in an appropriate solvent, such as N,N-dimethylformamide or N,N-dimethylacetamide, within a temperature range of 0° C. to 150° C. for a period of approximately 5 minutes to 24 hours provides the corresponding sulfonamide compound of formula I. Preferred conditions for reacting oxirane compound of formula IX with the carbazole of formula VII to provide compounds of formula I include carrying out the reaction in N,N-dimethylformamide at room temperature to 115° C. in the presence of cesium carbonate for 1 to 24 hours. Alternatively, the oxirane compound of formula IX can be reacted with the carbazole of formula VII in an appropriate solvent, such as N,N-dimethylformamide, under microwave irradiation to provide the compound of formula I.

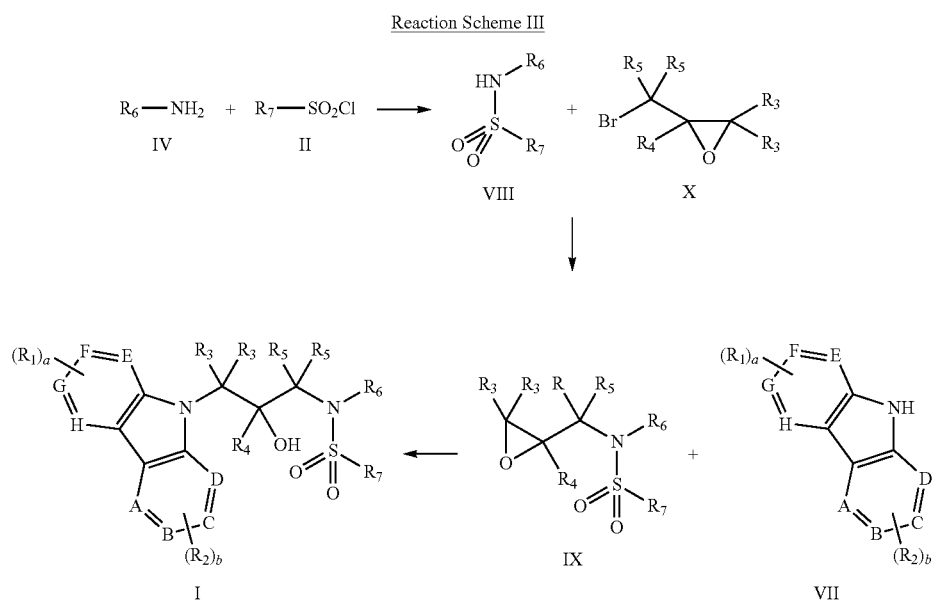

Reaction Scheme IV, below, depicts an alternative synthesis of compounds of formula I. Treatment of the amino ester compound of formula XIV with an appropriate sulfonyl chloride of formula II, in an appropriate solvent, such as methylene chloride, within a temperature range of 0° C. to 150° C. for a period of approximately 5 minutes to 24 hours provides the corresponding sulfonamide compound of formula XIII. Preferred conditions for reacting amino ester compound of formula XIV with the sulfonyl chloride of formula II to provide the compounds of formula XIII include carrying out the reaction in methylene chloride at 0° C. to room temperature in the presence of triethylamine for 1 to 24 hours followed by an extractive workup. Treatment of the compound of formula XIII with an appropriate reducing agent, in an appropriate solvent, such as tetrahydrofuran, within a temperature range of 0° C. to 150° C. for a period of approximately 5 minutes to 24 hours provides the corresponding alcohol compound of formula XII. Preferred conditions for reducing ester compound of formula XIII to provide the compounds of formula XII include carrying out the reaction in tetrahydrofuran at 0° C. to room temperature in the presence of lithium aluminum hydride for 1 to 24 hours followed by an extractive workup. Treatment of the compound of formula XII with an appropriate oxidizing agent, in an appropriate solvent, such as methylene chloride, within a temperature range of 0° C. to 150° C. for a period of approximately 5 minutes to 24 hours provides the corresponding aldehyde compound of formula XI. Preferred conditions for oxidizing alcohol compound of formula XII to provide the compounds of formula XI include carrying out the reaction in methylene chloride at 0° C. to room temperature in the presence of Dess-Martin periodinane for 24 to 48 hours followed by a filtration. Treatment of the compound of formula XI with a trimethylsulfoxonium iodide, in an appropriate solvent, such as dimethylsulfoxide, within a temperature range of 0° C. to 150° C. for a period of approximately 5 minutes to 24 hours provides the corresponding oxirane compound of formula IX. Preferred conditions for conversion of aldehyde compound of formula XI to provide the compounds of formula IX include carrying out the reaction in dimethylsulfoxide at 0° C. to room temperature in the presence of trimethylsulfoxonium iodide and sodium hydride for 2 to 24 hours followed by an extractive workup. Treatment of the compound of formula IX with an appropriate carbazole of formula VII, in an appropriate solvent, such as N,N-dimethylformamide or N,N-dimethylacetamide, within a temperature range of 0° C. to 150° C. for a period of approximately 5 minutes to 24 hours provides the corresponding sulfonamide compound of formula I. Preferred conditions for reacting oxirane compound of formula IX with the carbazole of formula VII to provide compounds of formula I include carrying out the reaction in N,N-dimethylformamide at room temperature to 115° C. in the presence of cesium carbonate for 1 to 24 hours. Alternatively, the oxirane compound of formula IX can be reacted with the carbazole of formula VII in an appropriate solvent, such as N,N-dimethylformamide, under microwave irradiation to provide the compound of formula I.

Reaction Scheme IV

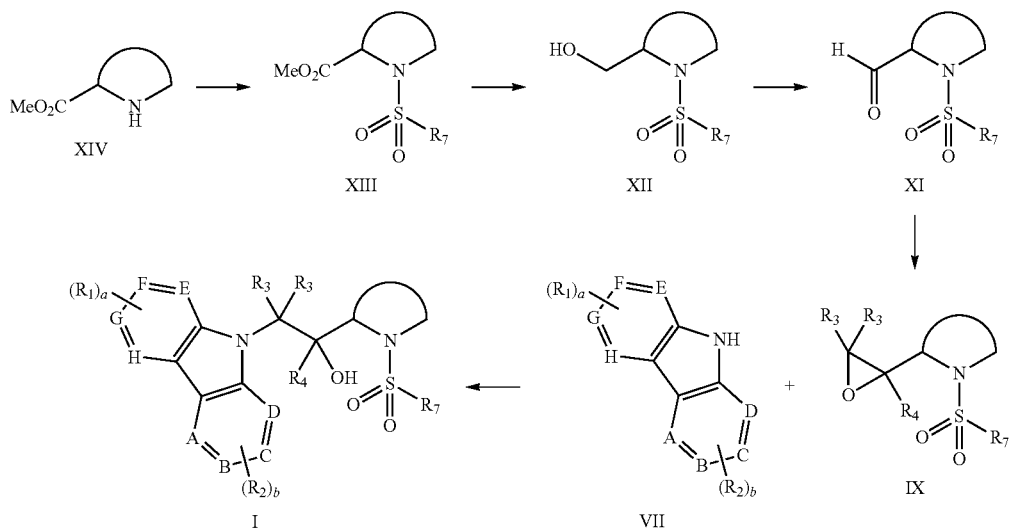

Reaction Scheme V, below, depicts an alternative synthesis of compounds of formula I. Treatment of an appropriately substituted oxirane derivative of formula XV or XVI with an appropriate sulfonamide of formula VIII, in an appropriate solvent, such as N,N-dimethylformamide or N,N-dimethylacetamide, within a temperature range of 0° C. to 150° C. for a period of approximately 5 minutes to 24 hours provides the corresponding sulfonamide compound of formula I. Preferred conditions for reacting oxirane compound of formula XV or XVI with the sulfonamide of formula VIII to provide compounds of formula I include carrying out the reaction in N,N-dimethylformamide at room temperature to 70° C. in the presence of sodium hydride for 20 to 24 hours. Alternatively, the oxirane compound of formula XV or XVI can be reacted with the sulfonamide of formula VIII in an appropriate solvent, such as N,N-dimethylacetamide, at 100° C. in the presence of cesium carbonate for 20 to 24 hours.

Reaction Scheme V

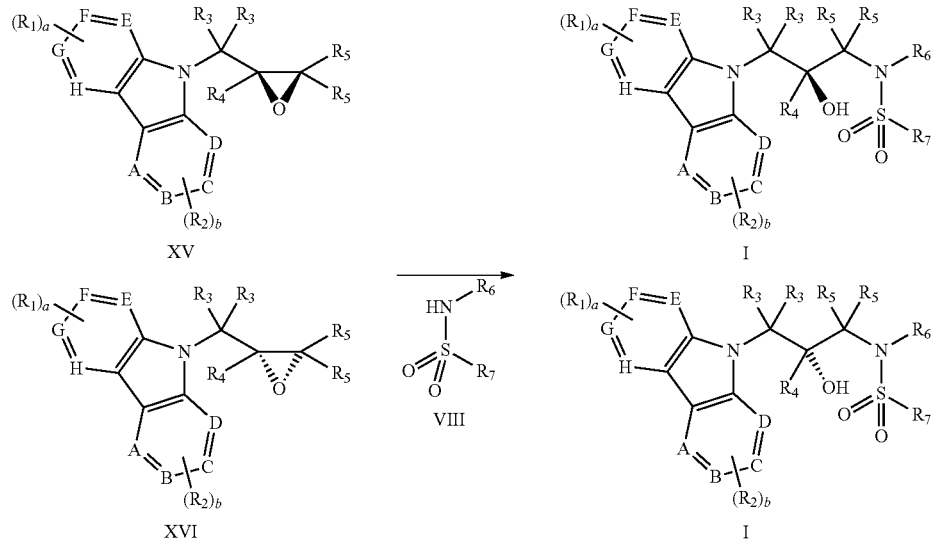

In the reaction schemes described herein it is to be understood that hydroxyl groups in intermediates useful for preparing compounds of formula I may be protected by conventional groups known to those skilled in the art, as required. For example, intermediates containing a hydroxyl group may be protected as the corresponding tert-butyldimethylsilyl ether and subsequently deprotected by treatment with tetra-n-butylammonium fluoride to provide the free hydroxyl derivative. Suitable protecting groups and methods for their removal are illustrated in "Protective Groups in Organic Synthesis", $3^{rd}$ Ed., T. W. Greene and P. G. M. Wuts (Wiley & Sons, 1999).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionization (ESI) or atmospheric pressure chemical ionization (APCI). Where thin layer chromatography (TLC) has been used it refers to silica gel TLC using silica gel 60 $F_{254}$ plates, $R_f$ is the distance traveled by a compound divided by the distance traveled by the solvent front on a TLC plate. HPLC refers to high performance liquid chromatography.

The following specific examples are included for illustrative purposes and are not to be construed as a limitation to this disclosure.

Preparation 1: 2-Fluoro-N-phenylaniline

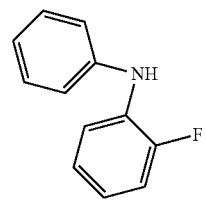 [SMILES: Fc1ccccc1Nc1ccccc1]

A reaction vessel was charged with iodobenzene (1.42 g, 7 mmol), palladium(II) acetate (0.079 g, 0.35 mmol), 2,2'-bis (diphenylphosphino)-1,1'-binaphthyl (0.217 g, 0.35 mmol), cesium carbonate (6.8 g, 21 mmol), 2-fluoroaniline (0.777 g, 7 mmol) in anhydrous toluene (18 mL). Under a nitrogen atmosphere, the mixture was heated at 115° C. for 24 hours. The cooled mixture was diluted with water and ether. The organic layer was isolated, washed with saturated aqueous sodium chloride, dried (anhydrous sodium sulfate), filtered, and concentrated to a residue. The crude product was purified by silica gel column chromatography (0-30% ethyl acetate in hexanes) to give the desired product as a clear oil (1.1 g, 81%).
$^1$H NMR (CDCl$_3$, 300 MHz) δ 7.36-7.29 (m, 3H), 7.20-7.14 (m, 3H), 7.09-7.00 (m, 2H), 6.88-6.85 (m, 1H), 5.82 (br s, 1H). ESI m/z: 188.2 (M+H).

Preparation 2: 1-Fluoro-9H-carbazole

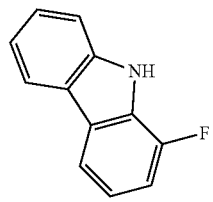 [SMILES: Fc1cccc2c1[nH]c1ccccc12]

A reaction vessel was charged with 2-fluoro-N-phenylaniline (0.4 g, 2.1 mmol), palladium diacetate (0.025 g, 0.1 mmol), potassium carbonate (0.030 g, 0.21 mmol), and pivalic acid (1.8 g), placed under an oxygen balloon, and heated at 120° C. Additional portions of palladium diacetate (0.025 g, 0.1 mmol) were added at 48 hours and 72 hours, and the mixture was heated for 4 days. The cooled reaction mixture was diluted with methylene chloride, washed with saturated aqueous sodium carbonate, dried (anhydrous sodium sulfate), filtered through a pad of silica gel, and concentrated. The crude product was purified by silica gel column chromatography (5-30% methylene chloride in hexanes) to give the desired product as a white solid (0.181 g, 46%). $^1$H NMR (d6-DMSO, 300 MHz) δ 11.65 (s, 1H), 8.13-8.11 (dd, 1H, J=0.6, 7.5 Hz), 7.94-7.91 (d, 1H, J=7.8 Hz), 7.50-7.38 (m, 2H), 7.25-7.07 (m, 3H). HPLC analysis (C18, 5-95% acetonitrile in H$_2$O+0.1% trifluoroacetic acid over 20 min: retention time, % area at 254 nm): 9.65 min, 100%.

Preparation 3: 4-Fluoro-2-nitro-1,1'-biphenyl

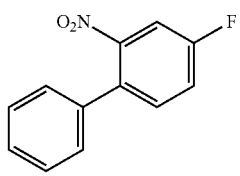 [SMILES: O=[N+]([O-])c1cc(F)ccc1-c1ccccc1]

A microwave reaction vessel was charged with 2-chloro-5-fluoronitrobenzene (0.175 g, 1 mmol), phenylboronic acid (0.134 g, 1.1 mmol), sodium carbonate (0.317 g, 3 mmol), palladium diacetate (0.009 g, 0.04 mmol), tetrabutylammonium bromide (0.322 g, 1 mmol) in water (2 mL). The mixture was heated to 165° C. in a microwave reactor for 7.5 minutes. The reaction was cooled and poured into ether and 0.1N aqueous sodium hydroxide. The ether layer was washed with saturated aqueous sodium chloride, dried (anhydrous sodium sulfate), filtered, and concentrated. The crude product was purified by silica gel column chromatography (5-30% methylene chloride in hexanes) to give the desired product as a pale yellow oil (0.179 g, 82%). $^1$H NMR (CDCl$_3$, 300 MHz) δ 7.62-7.58 (dd, 1H, J=2.7, 8.1 Hz), 7.46-7.40 (m, 4H), 7.38-7.34 (m, 1H), 7.31-7.26 (m, 2H). HPLC analysis (C18, 5-95% acetonitrile in H$_2$O+0.1% trifluoroacetic acid over 20 min: retention time, % area at 254 nm): 9.95 min, 96.3%.

Preparation 4: 2-Fluoro-9H-carbazole

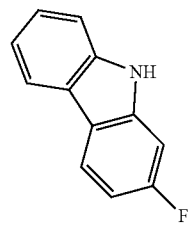 [SMILES: Fc1ccc2c(c1)[nH]c1ccccc12]

A solution of 4-fluoro-2-nitro-1,1'-biphenyl (0.170 g, 0.78 mmol) and triphenylphosphine (0.513 g, 1.9 mmol) in anhydrous 1,2-dichlorobenzene (1.5 mL) was heated to 175° C. in a microwave reactor for 8 hours. The cooled mixture was concentrated in vacuo and purified by silica gel column chromatography (7-50% methylene chloride in hexanes) to give an off-white solid (0.129 g, 89%). $^1$H NMR (CDCl$_3$, 300 MHz) δ 8.06 (br s, 1H), 8.03-7.95 (m, 2H), 7.43-7.39 (m, 2H), 7.26-7.21 (m, 1H), 7.12-7.08 (dd, 1H, J=2.3, 9.3 Hz), 7.00-6.93 (m, 1H). HPLC analysis: (C18, 5-95% acetonitrile in H$_2$O+0.1% trifluoroacetic acid over 20 min: retention time, % area at 254 nm): 9.67 min, 98.8%.

Preparation 5: 4-Fluorophenyl trifluoromethanesulfonate

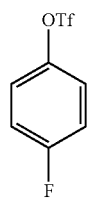

To a 0° C. solution of 4-fluorophenol (1.5 g, 13.3 mmol) in anhydrous methylene chloride (44 mL) was added pyridine (2.2 mL, 27 mmol) and trifluoromethanesulfonic anhydride (2.7 mL, 16 mmol). The solution was slowly allowed to warm to ambient temperature and stirred for 16 hours. The solution was diluted with ether, and successively washed with 1N aqueous hydrochloric acid twice, saturated aqueous sodium bicarbonate, and saturated aqueous sodium chloride solutions. The organic solution was dried (anhydrous sodium sulfate), filtered, and concentrated to give a tan liquid (3.2 g, 99%). ¹H NMR (CDCl₃, 300 MHz) δ 7.28-7.24 (m, 2H), 7.16-7.11 (m, 2H).

Preparation 6: 3-Fluoro-9H-carbazole

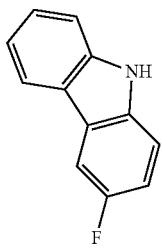 [SMILES: Fc1ccc2[nH]c3ccccc3c2c1]

A mixture of 4-fluorophenyl trifluoromethanesulfonate (0.753 g, 3 mmol) aniline (0.307 g, 3.3 mmol), palladium acetate (0.067 g, 0.3 mmol), cesium carbonate (1.17 g, 3.6 mmol), and 2-dicyclohexylphosphino-2',4',6'-triisopropylbiphenyl (0.215 g, 0.45 mmol) in anhydrous toluene (7.5 mL) was placed under a nitrogen environment, evacuating and backfilling with nitrogen twice, and heated at 100° C. for 2 hours. To the cooled reaction mixture was added acetic acid (25 mL), and the reaction was placed under an oxygen environment (balloon) and heated at 100° C. for 48 hours. The mixture was concentrated to a residue, dissolved in ethyl acetate, washed with saturated aqueous sodium bicarbonate and saturated sodium chloride solutions, dried (anhydrous sodium sulfate), filtered, and concentrated. The crude product was purified by silica gel column chromatography to give the desired product as a tan solid (0.1 g, 18%). ¹H NMR (d6-DMSO, 300 MHz) δ 11.26 (s, 1H), 8.11-8.08 (d, 1H, J=7.5 Hz), 7.94-7.90 (dd, 1H, J=2.4, 9.3 Hz), 7.47-7.35 (m, 3H), 7.23-7.10 (m, 2H).

Preparation 7: 2-Chloro-3-fluoro-N-phenylaniline

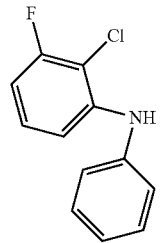 [SMILES: Fc1cccc(Nc2ccccc2)c1Cl]

A reaction vessel was charged with 2-chloro-3-fluoroaniline (1.5 g, 10.3 mmol), palladium(II) acetate (0.140 g, 0.62 mmol), 2,2'-bis(diphenylphosphino)-1,1'-binaphthyl (0.386 g, 0.62 mmol), cesium carbonate (6.7 g, 20.6 mmol), and iodobenzene (2.1 g, 10.3 mmol) in anhydrous toluene (28 mL). The vessel was purged with nitrogen and the mixture heated at reflux for 24 hours. The mixture was cooled, diluted with methylene chloride, filtered through a silica pad, concentrated, and purified by silica gel column chromatography (10-50% methylene chloride in hexanes) to give the desired product as a clear liquid (1.24 g, 54%). ¹H NMR (CDCl₃, 300 MHz) δ 7.38-7.32 (m, 2H), 7.20-7.19 (m, 2H), 7.16-6.98 (m, 3H), 6.67-6.61 (m, 1H), 6.17 (br s, 1H). ESI m/z: 222.1 (M+H). HPLC analysis: (C18, 5-95% acetonitrile in H₂O+ 0.1% trifluoroacetic acid over 20 min: retention time, % area at 254 nm): 11.03 min, 98.6%.

Preparation 8: 4-Fluoro-9H-carbazole

A mixture of 2-chloro-3-fluoro-N-phenylaniline (0.300 g, 1.3 mmol), potassium carbonate (0.374 g, 2.7 mmol), palladium diacetate (0.024 g, 0.1 mmol), tricyclohexylphosphonium tetrafluoroborate (0.079 g, 0.2 mmol) in anhydrous N,N-dimethylacetamide (6.7 mL) was evacuated and back-filled with argon and heated at 150° C. for 45 mins. The mixture was cooled, diluted with ethyl acetate and water. The organic layer was washed with water and saturated aqueous sodium chloride, dried (anhydrous sodium sulfate), filtered, and concentrated. The crude product was purified by silica gel column chromatography (7-50% ether in hexanes) to give an off-white solid (0.06 g, 24%). ¹H NMR (CDCl₃, 300 MHz) δ 8.23-8.20 (d, 1H, J=7.8 Hz), 8.10 (br s, 1H), 7.48-7.25 (m, 4H), 7.20-7.17 (d, 1H, J=8.1 Hz), 6.95-6.89 (dd, 1H, J=7.8, 9.9 Hz). HPLC analysis: (C18, 5-95% acetonitrile in H₂O+ 0.1% trifluoroacetic acid over 20 min: retention time, % area at 254 nm): 9.84 min, 96.5%.

Preparation 9: 9-(Oxiran-2-ylmethyl)-9H-carbazole

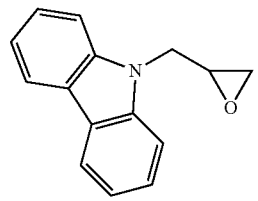 [SMILES: c1ccc2c(c1)c1ccccc1n2CC1CO1]

Powdered potassium hydroxide (3.36 g, 60 mmol) was added to a solution of carbazole (8.36 g, 50 mmol) in anhydrous N,N-dimethylformamide (50 mL) and stirred at ambient temperature for 1 hour. The reaction mixture was cooled in an ice bath and epibromohydrin (10.3 mL, 125 mmol) was added. The ice bath was removed and the reaction was stirred at room temperature for 20 hours. The mixture was partitioned between ethyl acetate and water. The organic layer was washed successively with water and saturated aqueous sodium chloride solutions, dried (anhydrous sodium sulfate), filtered, and concentrated. The crude material was triturated with hexanes, and recrystallized from ethyl acetate/hexanes to yield the desired product as white needles (6.41 g, 58% yield). A second crop of crystals was crystallized from the mother liquor to give additional product (1.2 g, 11%). ¹H NMR (CDCl₃, 300 MHz) δ 8.11-8.08 (m, 2H), 7.46-7.44 (m, 4H), 7.28-7.25 (m, 2H), 4.68-4.62 (dd, 1H, J=3.1, 15.8 Hz) 4.45-4.38 (dd, 1H, J=4.8, 15.9 Hz), 3.37 (m, 1H), 2.84-2.81 (dd, 1H, J=4.2, 4.3 Hz), 2.60-2.57 (dd, 1H, J=2.5, 5.0 Hz).

HPLC analysis: (C18, 5-95% acetonitrile in H$_2$O+0.1% trifluoroacetic acid over 20 min: detention time, % area at 254 nm): 7.83 min, 98.7%.

Preparation 10:
(S)-9-(Oxiran-2-ylmethyl)-9H-carbazole

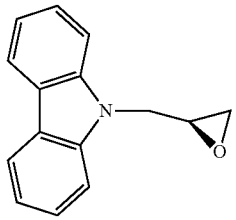 [SMILES: c1ccc2c(c1)c1ccccc1n2C[C@H]1CO1]

To a stirred solution of carbazole (2.0 g, 12 mmol) in anhydrous N,N-dimethylformamide (20 mL) was added 85% aqueous potassium hydroxide (0.95 g, 14.4 mmol) and the mixture was stirred at room temperature for 1 hour. The mixture was cooled in an ice bath and (R)-(−)-2-(chloromethyl)oxirane (2.77 g, 29.9 mmol) was added. The mixture was stirred overnight at room temperature, and then partitioned between water and ethyl acetate. The organic layer was washed with saturated aqueous sodium chloride, dried (anhydrous sodium sulfate), filtered, and concentrated. The residue was purified by recrystallization from ethyl acetate/hexanes to afford the desired product as white crystals (0.8 g, 30%). $^1$H NMR (300 MHz, CDCl$_3$) δ 8.10 (d, 2H, J=7.5 Hz), 7.55-7.40 (m, 4H), 7.32-7.22 (m, 2H), 4.66 (dd, 1H, J=15.9, 3.3 Hz), 4.43 (dd, 1H, J=15.9, 4.8 Hz), 3.38 (m, 1H), 2.83 (t, 1H, J=4.5 Hz), 2.60 (dd, 1H, J=4.8, 2.4 Hz).

Preparation 11:
(R)-9-(Oxiran-2-ylmethyl)-9H-carbazole

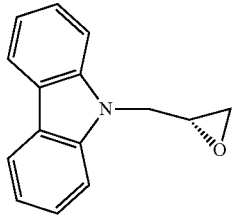 [SMILES: c1ccc2c(c1)c1ccccc1n2C[C@@H]1CO1]

To a stirred solution of carbazole (5.0 g, 29.9 mmol) in anhydrous N,N-dimethylformamide (20 mL) was added 85% aqueous potassium hydroxide (2.171 g, 32.9 mmol) and the mixture was stirred at room temperature for 1 hour. The mixture was cooled in an ice bath and (S)-(+)-epichlorohydrin (4.68 mL, 59.8 mmol) was added. The mixture was stirred overnight at room temperature, and then partitioned between water and ethyl acetate. The organic layer was washed with saturated aqueous sodium chloride, dried (anhydrous sodium sulfate), filtered, and concentrated. The residue was purified by silica gel column chromatography (30% methylene chloride/hexanes) to afford the desired product as a white solid (3.9 g, 58%). [α]$_D$-10.4 (c 1.92, CHCl$_3$). $^1$H NMR (300 MHz, CDCl$_3$) δ 8.10 (d, 2H, J=7.5 Hz), 7.60-7.40 (m, 4H), 7.35-7.20 (m, 2H), 4.64 (dd, 1H, J=15.9, 3.3 Hz), 4.41 (dd, 1H, J=15.9, 4.8 Hz), 3.37 (m, 1H), 2.82 (t, 1H, J=4.2 Hz), 2.59 (dd, 1H, J=4.5, 2.4 Hz).

Preparation 12: 1-(9H-Carbazol-9-yl)-3-((furan-2-ylmethyl)amino)propan-2-ol

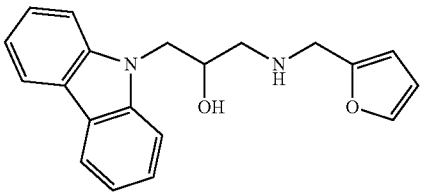 [SMILES: OC(CNCc1ccco1)Cn1c2ccccc2c2ccccc21]

A suspension of 9-(oxiran-2-ylmethyl)-9H-carbazole (2.97 g, 13.3 mmol) in a solution of furfurylamine (5.3 mL, 60 mmol) and ethanol (11 mL) was heated to 110° C. for 15 minutes in a Biotage Initiator microwave reactor. The resulting solution was diluted with methanol and cooled in an ice bath to precipitate a white solid. The solid was recrystallized by dissolving in a minimal volume of hot methanol and slowly cooled to give the desired product as a fine crystalline white solid (2.4 g, 57%). $^1$H NMR (CDCl$_3$, 300 MHz) δ 8.10-8.08 (d, 2H, J=8.1 Hz), 7.46-7.44 (m, 3H), 7.32-7.25 (m, 4H), 6.29-6.27 (dd, 1H, J=1.8, 3.3 Hz), 6.11-6.10 (d, 1H, J=3 Hz), 4.39-4.38 (d, 1H, J=2.1 Hz), 4.37 (d, 1H, J=0.9 Hz), 4.21-4.17 (m, 1H), 3.75 (s, 2H), 2.85-2.79 (dd, 1H, J=3.8, 12.3 Hz), 2.69-2.62 (dd, 1H, J=8.4, 12.3 Hz), 2.00 (br s, 2H). ESI m/z: 321.1 (M+H). HPLC analysis: (C18, 10-90% acetonitrile in water+0.1% trifluoroacetic acid over 10 min: retention time, % area at 254 nm): 6.1 min, 99.0%.

Preparation 13: 2-((tert-Butyldimethylsilyl)oxy)-3-(9H-carbazol-9-yl)-N-(furan-2-ylmethyl)propan-1-amine

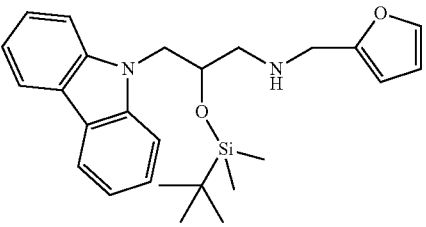 [SMILES: CC(C)(C)[Si](C)(C)OC(CNCc1ccco1)Cn1c2ccccc2c2ccccc21]

To a stirred solution of 1-(9H-carbazol-9-yl)-3-((furan-2-ylmethyl)amino)propan-2-ol (1.80 g, 5.6 mmol) and imidazole (1.912 g, 28.1 mmol) in anhydrous methylene chloride (50 mL) was added tert-butyldimethylsilyl chloride (2.117 g, 14.0 mmol). The reaction mixture was stirred overnight at 70° C. The reaction mixture was washed with saturated aqueous sodium chloride and saturated aqueous sodium carbonate, dried (anhydrous sodium sulfate), filtered, and concentrated. The residue was purified by silica gel column chromatography (0-40% ethyl acetate in hexanes) to afford the product as a thick oil (2.4 g, 98%). $^1$H NMR (300 MHz, CDCl$_3$) δ 8.08 (d, 2H, J=7.8 Hz), 7.53-7.40 (m, 4H), 7.37 (d, 1H, J=1.5 Hz), 7.22 (t, 2H, J=7.2 Hz), 6.32 (dd, 1H, J=3.3, 1.8 Hz), 6.16 (d, 1H, J=3.3 Hz), 4.56 (dd, 1H, J=14.4, 6.0 Hz), 4.41-4.22 (m, 2H), 3.85 and 3.75 (dd, 2H, J=14.4, 14.4 Hz), 2.74 (dd, 1H, J=12.0, 4.5 Hz), 2.61 (dd, 1H, J=12.0, 3.6 Hz), 1.60 (br s, 2H), 0.80 (s, 9H), −0.13 (s, 3H), −0.42 (s, 3H). ESI m/z: 435.2 [M+H].

Preparation 14:
N-(Furan-2-ylmethyl)methanesulfonamide

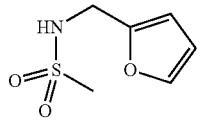

Methanesulfonyl chloride (3.2 mL, 42 mmol) was slowly added to a stirring solution of furfurylamine (4.2 g, 43.2 mmol) and triethylamine (6 mL, 43 mmol) in anhydrous methylene chloride (110 mL). The reaction was stirred overnight at ambient temperature and then diluted with ethyl acetate. The organic solution was successively washed with 1N aqueous hydrochloric acid three times, saturated aqueous sodium bicarbonate and saturated aqueous sodium chloride solutions, dried (anhydrous sodium sulfate), and filtered. The solution was concentrated under reduced pressure to give the desired product as a tan liquid (6.6 g, 89%). $^1$H NMR (CDCl$_3$, 300 MHz) δ 7.39-7.38 (m, 1H), 6.33-6.31 (m, 2H), 5.02 (br s, 1H), 4.33-4.31 (d, 2H, J=6 Hz).

Preparation 15:
N-(2-Methoxyethyl)methanesulfonamide

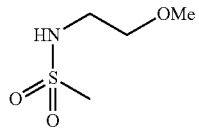

To a stirred solution of 2-methoxyethylamine (2.67 mL, 31.0 mmol) in anhydrous methylene chloride (100 mL) and N,N-diisopropylethyl amine (8.54 mL, 51.7 mmol) at 0° C. was slowly added methanesulfonyl chloride (2.0 mL, 25.8 mmol). The reaction mixture was slowly warmed to room temperature and stirred overnight. The mixture was concentrated and the residue was purified by silica gel column chromatography (0-100% ethyl acetate in hexanes) to afford the product as a colorless oil (2.8 g, 71%). $^1$H NMR (300 MHz, CDCl$_3$) δ 4.66 (br s, 1H), 3.54 (t, 2H, J=4.8 Hz), 3.39 (s, 3H), 6.37-3.29 (m, 2H), 3.00 (s, 3H).

Preparation 16: 2,3-Dihydrobenzo[d]isothiazole 1,1-dioxide

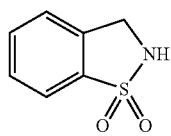 [SMILES: O=S1(=O)NCc2ccccc21]

To a cold solution of lithium aluminum hydride (0.414 g) in anhydrous tetrahydrofuran (30 mL), kept at 0° C. with an external ice bath, was added sulfobenzimide (1 g, 5.5 mmol). The reaction was allowed to warm to ambient temperature and stirred overnight. The reaction was quenched with the addition of water and 2.5M aqueous sulfuric acid. The mixture was filtered through Celite and washed with ethyl acetate. The organic layer was washed with 1M aqueous sulfuric acid, dried (anhydrous magnesium sulfate), filtered, and concentrated to afford an off-white solid (0.75 g, 81%). $^1$H NMR (CDCl$_3$, 300 MHz) δ 7.81-7.78 (d, 1H, J=7.8 Hz), 7.64-7.59 (dt, 1H, J=1.2, 7.5 Hz), 7.52-7.49 (dt, 1H, J=0.75, 7.5 Hz), 7.41-7.37 (d, 1H, J=8.1 Hz), 4.8 (br s, 1H), 4.55-4.54 (d, 1H, J=3.6 Hz).

Preparation 17: 1,3-Dihydrobenzo[c]isothiazole 2,2-dioxide

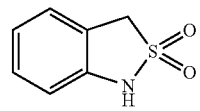 [SMILES: O=S1(=O)Cc2ccccc2N1]

The title compound was prepared using the method described in WO 98/32438 A1. To a solution of 2-nitro-alpha-toluenesulfonyl chloride (5.1 g, 21.6 mmol) in anhydrous ethyl acetate (250 mL) was added tin (II) chloride (19.3 g, 86 mmol). The reaction was stirred overnight at 70° C., then poured onto ice and neutralized with saturated aqueous sodium bicarbonate. The solution was filtered through Celite, extracted with ethyl acetate, and the organic layer concentrated. To the crude residue was added anhydrous methylene chloride (200 mL) and triethylamine (5 mL). The solution was stirred overnight at room temperature and concentrated under reduced pressure. The product was obtained by silica gel column chromatography (30-100% ethyl acetate in hexanes) followed by recrystallization from methylene chloride/hexanes to give a white solid. (0.24 g, 6.5%). $^1$H NMR (CDCl$_3$, 300 MHz) δ 7.30-7.22 (m, 2H), 7.07-7.02 (t, 1H, J=7.4 Hz), 6.89-6.86 (dd, 1H, J=0.6, 8.1 Hz), 6.66 (br s, 1H), 4.39 (s, 1H).

Preparation 18:
3,4-Dihydro-1H-benzo[d][1,2]thiazine 2,2-dioxide

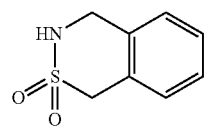 [SMILES: O=S1(=O)Cc2ccccc2CN1]

The title compound was prepared according to the method described in Bravo, R. D. et al. Synth. Commun. 2002, 32, 3675. A flask was charged with alpha-toluenesulfonamide (1 g, 5.8 mmol) and 1,3,5-trioxane (0.175 g, 1.9 mmol) in anhydrous dichloroethane (23 mL) and amberlyst 15H+ resin (3.7 g). The mixture was stirred at 80° C. overnight, after which the resin was filtered off and washed with methylene chloride.

The organic solution was concentrated to afford a white solid (0.848 g, 79%). $^1$H NMR (d6-DMSO, 300 MHz) δ 7.41-7.37 (t, 1H, J=6.8 Hz), 7.30-7.24 (m, 2H), 7.19-7.16 (m, 1H), 7.12-7.09 (m, 1H), 4.42-4.40 (d, 2H, J=6.6 Hz), 4.35 (s, 2H).

Preparation 19:
N-(2-(Hydroxymethyl)phenyl)methanesulfonamide

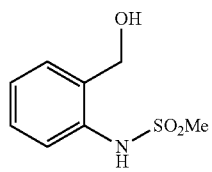 [SMILES: CS(=O)(=O)Nc1ccccc1CO]

The title compound was synthesized according to the method described in WO 2008/073956 A2. A solution of methanesulfonyl chloride (3.4 mL, 44 mmol) in anhydrous methylene chloride (40 mL) was added dropwise to a stirring solution of 2-aminobenzylalcohol (5 g, 40.6 mmol) and anhydrous pyridine (16 mL, 203 mmol) in anhydrous methylene chloride (80 mL). The resulting mixture was stirred at room temperature for 24 hours and concentrated to ⅓ volume and diluted with ethyl acetate. The organic solution was successively washed twice with 1N aqueous hydrochloric acid, water, saturated aqueous sodium bicarbonate, and saturated aqueous sodium chloride solutions, dried (anhydrous sodium sulfate), filtered, and concentrated. The crude residue was passed through a pad of silica gel, washing with ethyl acetate/hexanes to give a yellow oil (6.1 g, 75%). $^1$H NMR (CDCl$_3$, 300 MHz) δ 7.84 (br s, 1H), 7.53 (d, 1H, J=8.1 Hz), 7.36-7.30 (dt, 1H, J=1.5, 7.8 Hz), 7.25-7.21 (dd, 1H, J=1.5, 7.8 Hz), 7.16-7.11 (dt, 1H, J=1.2, 7.5 Hz), 4.77-4.75 (d, 2H, J=5.1 Hz), 3.04 (s, 3H), 2.60 (t, 1H, J=5.2 Hz).

Preparation 20:
N-(2-Formylphenyl)methanesulfonamide

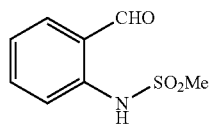

The title compound was synthesized according to the method described in WO 2008/073956 A2. To a solution of N-(2-(hydroxymethyl)phenyl)methanesulfonamide (3.44 g, 17.1 mmol) in anhydrous methylene chloride (68 mL) was added manganese dioxide (85% Aldrich, 17 g) and the mixture was stirred at ambient temperature overnight. Additional manganese dioxide (1.6 g) was added and the mixture stirred at 30° C. for 8 hours. The mixture was filtered through Celite, washing with methylene chloride, and the organic solution concentrated. The crude residue was purified by silica gel column chromatography (40-60% ethyl acetate in hexanes) to give a white solid (2.1 g, 62%). $^1$H NMR (CDCl$_3$, 300 MHz) δ 10.59 (br s, 1H), 9.91 (s, 1H), 7.75-7.59 (m, 3H) 7.28-7.23 (t, 1H, J=7.5 Hz), 3.12 (s, 3H).

Preparation 21:
1-(4-Methoxybenzyl)-1H-benzo[c][1,2]thiazine 2,2-dioxide

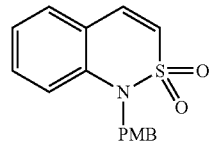

The title compound was synthesized according to the method described in WO 2008/073956 A2. To a solution of N-(2-formylphenyl)methanesulfonamide (2.0 g, 10 mmol) in anhydrous acetonitrile (45 mL) was added cesium carbonate (6.5 g, 20 mmol) and 4-methoxybenzylchloride (2.7 mL, 20 mmol). The mixture was heated to 50° C. and stirred for 48 hours, diluted with ethyl acetate, filtered through Celite, and concentrated. The crude product was purified by silica gel column chromatography (50-100% methylene chloride in hexanes) to give the product (0.9 g, 31%). $^1$H NMR (CDCl$_3$, 300 MHz) δ 7.40-7.32 (m, 2H), 7.28-7.24 (m, 3H), 7.16-7.11 (m, 2H), 6.85-6.81 (m, 3H), 5.15 (s, 2H), 3.77 (s, 3H).

Preparation 22: 1H-Benzo[c][1,2]thiazine 2,2-dioxide

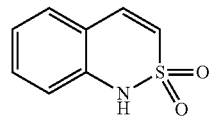

The title compound was synthesized according to the method described in WO 2008/073956 A2. To a solution of 1-(4-methoxybenzyl)-1H-benzo[c][1,2]thiazine 2,2-dioxide (0.9 g, 3 mmol) in anhydrous methylene chloride was added trifluoroacetic acid (18 mL). The mixture was stirred at room temperature for 5 hours and then concentrated under reduced pressure. The crude product was purified by silica gel column chromatography (25-70% ethyl acetate in hexanes) to give a white solid. (0.6 g, 72%). $^1$H NMR (CDCl$_3$, 300 MHz) δ 7.43-7.38 (m, 2H), 7.29 (m, 1H), 7.20-7.14 (dt, 1H, J=1.2, 7.5 Hz), 7.02-6.99 (d, 1H, J=7.8 Hz), 6.78-6.75 (dd, 1H, J=2.4, 10.5 Hz).

Preparation 23:
3,4-Dihydro-1H-benzo[c][1,2]thiazine 2,2-dioxide

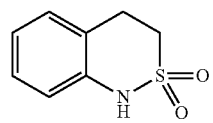 [SMILES: O=S1(=O)CCc2ccccc2N1]

A solution of 1H-benzo[c][1,2]thiazine 2,2-dioxide (0.381 g, 2.1 mmol) and 10% palladium on carbon (0.05 g) in anhydrous methanol (6 mL) was placed under a hydrogen filled balloon and stirred at room temperature for 17 hours. The mixture was filtered through Celite and concentrated to give a white solid (0.366 g, 95%). $^1$H NMR (CDCl$_3$, 300 MHz) δ 7.25-7.16 (m, 2H), 7.07-7.01 (m, 1H), 6.76-6.73 (d, 1H, J=8.4 Hz), 3.51-3.46 (t, 2H, J=6.8 Hz), 3.34-3.29 (br t, 1H, J=6.9 Hz).

Preparation 24:
N-(2-Bromoethyl)-4-chlorobenzenesulfonamide

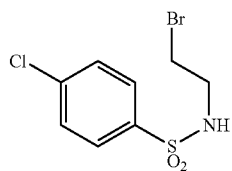 [SMILES: O=S(=O)(NCCBr)c1ccc(Cl)cc1]

To a stirred mixture of 4-chlorobenzenesulfonyl chloride (5.0 g, 23.7 mmol) and 2-bromoethylamine hydrobromide (5.4 g, 26.3 mmol) in anhydrous methylene chloride (50 mL) at 0° C. was slowly added N,N-diisopropylethyl amine (8.6 mL, 52.1 mmol) and the mixture was stirred at 0° C. for 1 hour. The reaction mixture was washed sequentially with water, 2N aqueous hydrochloric acid, saturated aqueous sodium carbonate, and saturated aqueous sodium chloride. The organic layer was dried (anhydrous sodium sulfate), filtered, and concentrated in vacuo to afford a white solid (7 g, 99%). $^1$H NMR (300 MHz, CDCl$_3$) δ 7.82 (d, 2H, J=8.7 Hz), 7.52 (d, 2H, J=8.7 Hz), 4.96 (s, 1H), 3.50-3.30 (m, 4H).

Preparation 25:
6-Chloro-3,4-dihydro-2H-benzo[e][1,2]thiazine 1,1-dioxide

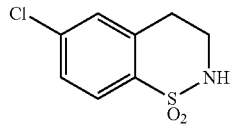 [SMILES: O=S1(=O)NCCc2cc(Cl)ccc21]

A two-necked flask equipped with a condenser and a rubber septum was charged with N-(2-bromoethyl)-4-chlorobenzenesulfonamide (2.80 g, 9.4 mmol) and anhydrous benzene (50 mL). The reaction vessel was degassed and backfilled with argon and then heated to reflux. Under reflux, a solution of tributyltin hydride (5.05 mL, 18.8 mmol) and 2,2'-azobis(2-methylpropionitrile) (0.77 g, 4.7 mmol) in anhydrous benzene (25 mL) was added slowly over 8 hours using a syringe pump, and the mixture was refluxed for a further 12 hours. After cooling, the reaction mixture was concentrated and the residue purified by silica gel column chromatography (0-40% ethyl acetate in methylene chloride) followed by preparative TLC (1:2 ethyl acetate in hexanes) to afford the pure product as a white foam (0.085 g, 4%). $^1$H NMR (300 MHz, CDCl$_3$) δ 7.77 (d, 1H, J=8.4 Hz), 7.37 (dd, 1H, J=8.1, 2.1 Hz), 7.26 (s, 1H), 4.47 (t, 1H, J=7.5 Hz), 3.83 (dt, 2H, J=7.5, 6.0 Hz), 3.00 (t, 2H, J=6.0 Hz).

Preparation 26: N-(Furan-2-ylmethyl)-N-(oxiran-2-ylmethyl)methanesulfonamide

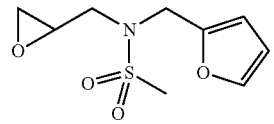

Sodium hydride (60% mineral oil dispersion, 0.524 g, 13.1 mmol) was added in portions to a 0° C. solution of N-(furan-2-ylmethyl)methanesulfonamide (2.0 g, 11.4 mmol) in 38 ml anhydrous N,N-dimethylformamide (38 mL), and the resultant mixture was allowed to warm to room temperature and stirred for 1 hour. Epibromohydrin (1.2 mL, 14.3 mmol) was added slowly, and the reaction was stirred for 3 hours at room temperature and 16 hours at 70° C. The reaction was cooled, diluted with ethyl acetate, and successively washed twice with water and once with saturated aqueous sodium chloride solutions. The organic layer was dried (anhydrous sodium sulfate), filtered, and concentrated under reduced pressure. The crude residue was purified by silica gel column chromatography (25-60% ethyl acetate in hexanes) to give a pale yellow liquid (2.2 g, 84%). $^1$H NMR (CDCl$_3$, 300 MHz) δ 7.40-7.39 (m, 1H), 6.37-6.35 (m, 2H), 4.64-4.50 (br dd, 2H, J=25.8, 16.5 Hz), 3.61-3.55 (m, 1H), 3.22-3.12 (m, 2H), 2.82 (s, 3H), 2.82-2.79 (m, 1H), 2.62-2.60 (m, 1H). ESI (m/z): 232.0 (M+H).

Preparation 27: N-(Furan-2-ylmethyl)-N-(2-methylallyl)methanesulfonamide

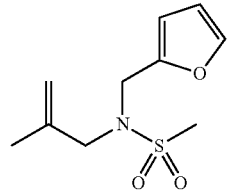

Sodium hydride (60% mineral oil dispersion, 0.284 g, 7.1 mmol) was added in portions to a stirring solution of N-(furan-2-ylmethyl)methanesulfonamide (1.0 g, 5.7 mmol) in anhydrous N,N-dimethylformamide (12 mL), which was kept at 0° C. by an external ice bath. The ice bath was removed and the mixture was stirred for 50 mins at ambient temperature. 3-bromo-2-methylpropane (1.15 g, 8.6 mmol) was added in one portion, and the resulting mixture was stirred overnight at 65° C. before being diluted with ethyl acetate. The organic layer was successively washed with water and saturated aqueous sodium chloride solutions, dried (anhydrous sodium sulfate), filtered, and concentrated. The crude material was purified by silica gel column chromatography (0-50% ethyl acetate in hexanes) to give a clear liquid (1.24 g, 95%). $^1$H NMR (CDCl$_3$, 300 MHz) δ 7.41-7.40 (m, 1H), 6.38-6.34 (m, 1H), 6.29-6.28 (m, 1H), 5.03-5.00 (m, 2H), 4.37 (s, 2H), 3.73 (s, 2H), 2.76 (s, 3H), 1.77 (s, 3H).

Preparation 28: N-(Furan-2-ylmethyl)-N-((2-methyloxiran-2-yl)methyl)methanesulfonamide

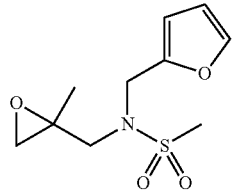 [SMILES: CC1(CN(Cc2ccco2)S(C)(=O)=O)CO1]

To a stirring solution of N-(furan-2-ylmethyl)-N-(2-methylallyl)methanesulfonamide (1.0 g, 4.3 mmol) in anhydrous methylene chloride (20 mL) was added 3-chloroperbenzoic acid (70%, 2.1 g, 8.6 mmol). The mixture was stirred at ambient temperature for 2 hours and at 40° C. for 18 hours. The mixture was diluted with methylene chloride and successively washed with saturated aqueous sodium sulfite, saturated aqueous sodium bicarbonate, and saturated aqueous sodium chloride solutions. The organic layer was dried (anhydrous sodium sulfate), filtered, and concentrated. The crude residue was purified by silica gel column chromatography (10-60% ethyl acetate in hexanes) to give a clear oil (0.278 g, 26%). $^1$H NMR (CDCl$_3$, 300 MHz) δ 7.40-7.35 (dd, 1H, J=0.9, 1.8 Hz), 6.33-6.30 (m, 2H), 4.52-4.51 (m, 2H), 3.48-3.43 (d, 1H, J=15 Hz), 3.13-3.09 (d, 1H, J=15 Hz), 2.73-2.72 (d, 1H, J=4.5 Hz), 2.70 (s, 3H), 2.62-2.61 (d, 1H, J=4.5 Hz), 1.35 (s, 3H).

Preparation 29: Methyl 1-(methylsulfonyl)pyrrolidine-2-carboxylate

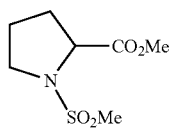

Methanesulfonyl chloride (2.3 mL, 30 mmol) was slowly added to a stirring solution of D/L-proline methyl ester hydrochloride (5.0 g, 30.2 mmol) and triethylamine (8.4 mL, 60 mmol) in anhydrous methylene chloride (75 mL). The reaction was stirred overnight at ambient temperature and then diluted with ethyl acetate. The organic layer was successively washed with water, 1N aqueous hydrochloric acid twice, saturated aqueous sodium bicarbonate, and saturated aqueous sodium chloride solutions, dried (anhydrous sodium sulfate), and filtered. The solution was concentrated under reduced pressure to give the desired product as a tan liquid (4.45 g, 72%). $^1$H NMR (CDCl$_3$, 300 MHz) δ 4.53-4.49 (dd, 1H, J=8.7, 3.6 Hz), 3.75 (s, 3H), 3.57-3.54 (m, 1H), 3.52-3.42 (m, 1H), 3.01 (s, 3H), 2.32-2.22 (m, 1H), 2.11-1.98 (m, 3H).

Preparation 30: (1-(Methylsulfonyl)pyrrolidin-2-yl)methanol

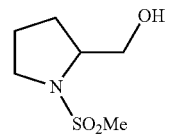 [SMILES: CS(=O)(=O)N1CCCC1CO]

Methyl 1-(methylsulfonyl)pyrrolidine-2-carboxylate (1.1 g, 4.6 mmol) in anhydrous tetrahydrofuran (10 mL) was added slowly to a stirring suspension of lithium aluminum hydride (0.259 g, 6.8 mmol) in anhydrous tetrahydrofuran (10 mL) kept at 0° C. with an external ice bath. After fifteen minutes, the ice bath was removed and the reaction was allowed to warm to ambient temperature and stirred for an additional hour. The mixture was cooled to 0° C., and water (1 mL) was added dropwise, followed by 15% aqueous sodium hydroxide (1 mL), and water (3 mL). The mixture was stirred for 15 mins at room temperature, followed by the addition of magnesium sulfate and additional stirring. The mixture was filtered through Celite, washed three times with ether, and the combined organic fractions concentrated under reduced pressure to afford a yellow oil (0.7 g, 77%). $^1$H NMR (CDCl$_3$, 300 MHz) δ 3.78-3.57 (m, 3H), 3.49-3.36 (m, 2H), 2.87 (s, 3H), 2.64 (br s, 1H), 2.09-1.82 (m, 4H).

Preparation 31: 1-(Methylsulfonyl)pyrrolidine-2-carbaldehyde

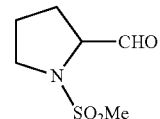

Dess-Martin periodinane (1.7 g, 4 mmol) was added to a solution of (1-(methylsulfonyl)pyrrolidin-2-yl)methanol (0.570 g, 3.18 mmol) in anhydrous methylene chloride (20 mL). The reaction was stirred for 24 hours and a second portion of Dess-Martin periodinane (1 g, 2.3 mmol) was added. The resulting suspension was stirred for 24 hours, filtered, and concentrated. The crude residue was purified by silica gel column chromatography (1-15% ethyl acetate in methylene chloride) to provide a white waxy solid (0.44 g, 78%). $^1$H NMR (CDCl$_3$, 300 MHz) δ 9.58 (d, 1H, J=1.2 Hz), 4.25-4.20 (td, 1H, J=6.9, 1.2 Hz), 3.55-3.44 (m, 2H), 2.97 (s, 3H), 2.21-2.13 (m, 2H), 2.05-1.90 (m, 2H).

Preparation 32: 1-(Methylsulfonyl)-2-(oxiran-2-yl)pyrrolidine

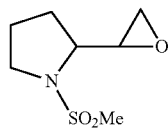

Anhydrous dimethylsulfoxide (0.750 mL) was added to trimethylsulfoxonium iodide (0.187 g, 0.85 mmol) and sodium hydride (60% mineral oil dispersion, 0.034 g, 0.85 mmol), and the resulting suspension was stirred for 1 hour. To the stirring solution was added 1-(methylsulfonyl)pyrrolidine-2-carbaldehyde (0.100 g, 0.56 mmol) in anhydrous tetrahydrofuran (1 mL) and the mixture was stirred for 2 hours at room temperature. Saturated aqueous sodium chloride (3 mL) was added, and the mixture was extracted with ethyl acetate (3×30 mL). The combined organics were dried (anhydrous sodium sulfate), filtered, and concentrated under reduced pressure to give a dimethylsulfoxide solution (0.473 g) containing crude product, which was used directly in the next step.

Preparation 33: Ethyl 1-(methylsulfonyl)piperidine-2-carboxylate

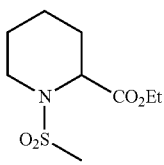

Methanesulfonyl chloride (4.0 g, 35 mmol) was slowly added to a stirring solution of ethyl pipecolinate, (5.5 g, 35 mmol) and triethylamine (4.9 mL, 35 mmol) in anhydrous methylene chloride (88 mL). The reaction was stirred overnight at ambient temperature and then diluted with ethyl acetate. The organic layer was successively washed with water, twice with 1N aqueous hydrochloric acid, saturated aqueous sodium bicarbonate, and saturated aqueous sodium chloride solutions, dried (anhydrous sodium sulfate), and filtered. The solution was concentrated under reduced pressure to give the desired product as a tan liquid (6.9 g, 84%). $^1$H NMR (CDCl$_3$, 300 MHz) δ 4.72-4.71 (br d, 1H, J=3.6 Hz), 4.24-4.16 (qd, 2H, J=6.9, 2.6 Hz), 3.74-3.68 (m, 1H), 3.22-3.13 (td, 1H, J=12.3, 3.0 Hz), 2.93 (s, 3H), 2.31-2.25 (m, 1H), 1.83-1.51 (m, 5H), 1.32-1.27 (td, 3H, J=7.0, 0.6 Hz), 3.52-3.42 (m, 1H), 3.01 (s, 3H), 2.32-2.22 (m, 1H), 2.11-1.98 (m, 3H). ESI (m/z): 235.9 (M+H).

Preparation 34: (1-(Methylsulfonyl)piperidin-2-yl)methanol

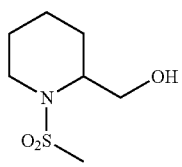

Ethyl 1-(methylsulfonyl)piperidine-2-carboxylate (6.9 g, 29.3 mmol) in anhydrous tetrahydrofuran (40 mL) was added slowly to a stirring suspension of lithium aluminum hydride (1.5 g, 40 mmol) in anhydrous tetrahydrofuran (80 mL) kept at 0° C. with an external ice bath. After fifteen minutes, the ice bath was removed and the reaction was allowed to warm to ambient temperature and stirred for an additional 4.5 hours. The mixture was cooled to 0° C., and water (1.5 mL) was added dropwise, followed by aqueous sodium hydroxide (1.5 mL), and water (4.5 mL). The mixture was stirred for 15 mins at room temperature, followed by the addition of magnesium sulfate and additional stirring. The mixture was filtered through Celite, washed three times with ether, and the combined organic fractions concentrated under reduced pressure. The crude residue was passed through a pad of silica gel, washing with ethyl acetate, to give the desired product as a clear liquid (4.9 g, 87%). $^1$H NMR (CDCl$_3$, 300 MHz) δ 4.06-4.03 (m, 1H), 3.96-3.92 (dd, 1H, J=11.1, 9.3 Hz), 3.73-3.68 (br d, 1H, J=14.1 Hz), 3.61-3.56 (dd, 1H, J=11.1, 4.8 Hz), 3.12-3.03 (br t, 1H, J=12.1 Hz), 2.96 (s, 3H), 2.17 (br s, 1H), 1.74-1.47 (m, 6H).

Preparation 35: 1-(Methylsulfonyl)piperidine-2-carbaldehyde

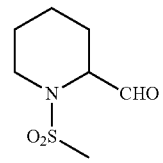

Dess-Martin periodinane (21 g, 50 mmol) was added to a solution of (1-(methylsulfonyl)piperidin-2-yl)methanol (4.9 g, 25.4 mmol) in anhydrous methylene chloride (125 mL). The reaction was stirred for 24 hours, filtered, and concentrated in vacuo. The crude residue was purified by silica gel column chromatography (25-75% ethyl acetate in hexanes) to provide a white waxy solid (1.1 g, 24% yield). $^1$H NMR (CDCl$_3$, 300 MHz) δ 9.56 (s, 1H), 4.61-4.58 (br d, 1H, J=6.3 Hz), 3.75-3.68 (m, 1H), 3.13-3.04 (td, 1H, J=12.0, 3.2 Hz), 2.97 (s, 3H), 2.33-2.22 (m, 1H), 1.89-1.55 (m, 4H), 1.27-1.21 (m, 1H).

Preparation 36: 1-(Methylsulfonyl)-2-vinylpiperidine

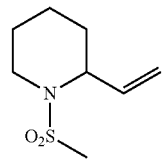

n-Butyllithium (2.5N in hexanes, 1.96 mL, 4.92 mmol) was added to a cold suspension of triphenylphosphonium bromide (1.76 g, 4.92 mmol) in anhydrous tetrahydrofuran (10 mL), which was kept at −78° C. with an external cold bath. The mixture was allowed to warm to 0° C. and stirred for 1 hour, then cooled to −78° C. 1-(methylsulfonyl)piperidine-2-carbaldehyde (0.626 g, 3.28 mmol) in anhydrous tetrahydrofuran (5 mL) was added. The resulting mixture was stirred for 10 mins at −78° C., then warmed to 0° C. and stirred for 3 hours. Saturated aqueous sodium chloride (10 mL) was added, and the mixture extracted with ethyl acetate (3×50 mL). The combined organics were dried (anhydrous sodium sulfate), filtered, and concentrated under reduced pressure. The crude residue was purified by silica gel column chromatography (25-70% ethyl acetate in hexanes) to provide a clear oil (0.369 g, 60%). $^1$H NMR (CDCl$_3$, 300 MHz) δ 6.08-5.97

(m, 1H), 5.33-5.26 (m, 2H), 4.52 (br s, 1H), 3.69-3.63 (m, 1H), 3.05-3.00 (m, 1H), 2.81 (s, 3H), 1.86-1.55 (m, 6H).

Preparation 37:
1-(Methylsulfonyl)-2-(oxiran-2-yl)piperidine

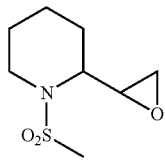

To a solution of 1-(methylsulfonyl)-2-vinylpiperidine (0.369 g, 2.0 mmol) in anhydrous methylene chloride (10 mL) was added purified 3-chloroperbenzoic acid (100%, 1.0 g, 6 mmol). The reaction was stirred at room temperature for 65 hours. The reaction mixture was filtered, saturated aqueous sodium sulfite added, and the biphasic solution was stirred for 5 mins. The mixture was diluted with ethyl acetate, and the organic layer successively washed with saturated aqueous sodium bicarbonate and saturated aqueous sodium chloride solutions, dried (anhydrous sodium sulfate), filtered, and concentrated. The crude product was purified by silica gel column chromatography (30-60% ethyl acetate in hexanes) to give a white semi-solid (0.128 g, 31%). $^1$H NMR (CDCl$_3$, 300 MHz) δ 3.78-3.74 (br d, 1H, J=13.2 Hz), 3.66-3.61 (m, 1H), 3.37-3.32 (m, 1H), 3.24-3.15 (m, 1H), 2.98 (s, 3H), 2.88-2.85 (dd, 1H, J=4.8, 4.2 Hz), 2.68-2.66 (dd, 1H, J=4.8, 2.6 Hz), 1.81-1.60 (m, 6H). ESI (m/z): 205.9 (M+H).

Preparation 38:
2-Chloro-4-fluoro-N-(4-fluorophenyl)aniline

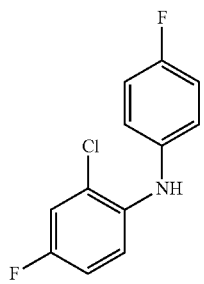 [SMILES: Fc1ccc(Nc2ccc(F)cc2Cl)cc1]

A round bottom flask was charged with 1-bromo-4-fluorobenzene (6.011 g, 34.4 mmol), 2-chloro-4-fluoroaniline (5.000 g, 34.3 mmol), Xantphos (0.795 g, 1.4 mmol), anhydrous toluene (200 mL), and sodium tert-butoxide (4.952 g, 51.5 mmol). The mixture was degassed and filled with nitrogen, and then tris(dibenzylideneacetone)dipalladium(0) (0.944 g, 1.0 mmol) was added and the reaction was stirred under nitrogen at 100° C. for 16 hrs. After cooling to room temperature, the mixture was filtered through Celite and the filter cake washed with methylene chloride. The filtrate was concentrated and the residue purified by silica gel chromatography (0-20% ethyl acetate/hexanes) to afford a yellowish oil (5.63 g, 68%). $^1$H NMR (300 MHz, CDCl$_3$) δ 7.14 (dd, 1H, J=8.4, 3.0 Hz), 7.12-6.98 (m, 5H), 6.88 (td, 1H, J=8.7, 3.0 Hz), 5.80 (br s, 1H).

Preparation 39: 3,6-Difluoro-9H-carbazole

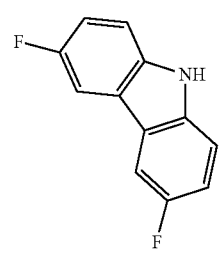 [SMILES: Fc1ccc2[nH]c3ccc(F)cc3c2c1]

A reaction tube was charged with sodium tert-butoxide (7.218 g, 75.1 mmol), 2-chloro-4-fluoro-N-(4-fluorophenyl)aniline (3.600 g, 15.0 mmol), tri-tert-butylphosphonium tetrafluoroborate (0.305 g, 1.1 mmol), palladium diacetate (0.169 g, 0.8 mmol), and anhydrous 1,4-dioxane (80 mL). The tube was sealed under nitrogen and heated in an oil bath at 110° C. for 20 hrs. After cooling to room temperature, the mixture was treated with 2M aqueous hydrochloric acid (90 mL) and extracted with methylene chloride (3×50 mL). The combined organic layers were washed with saturated aqueous sodium chloride, dried (anhydrous sodium sulfate), and concentrated in vacuo. The residue was purified by silica gel chromatography (20-50% methylene chloride/hexanes). The solids were rinsed with hexanes and dried to afford pure compound as a white powder (1.1 g, 36%). $^1$H NMR (300 MHz, CDCl$_3$) δ 7.99 (br s, 1H), 7.67 (dd, 2H, J=8.7, 2.4 Hz), 7.36 (dd, 2H, J=8.7, 4.2 Hz), 7.19 (td, 2H, J=9.0, 2.4 Hz).

Preparation 40:
3,6-Difluoro-9-(oxiran-2-ylmethyl)-9H-carbazole

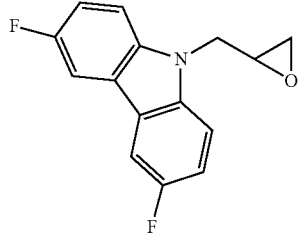 [SMILES: Fc1ccc2c(c1)c1cc(F)ccc1n2CC1CO1]

To a stirred solution of 3,6-difluoro-9H-carbazole (0.500 g, 2.5 mmol) in N,N-dimethylformamide (5 mL) at 0° C. was added 85% potassium hydroxide (0.195 g, 3.0 mmol) and the mixture was stirred for 1 hr. Epibromohydrin (0.407 mL, 4.9 mmol) was added and the mixture was slowly warmed to room temperature and stirred for 16 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-50% methylene chloride/hexanes) to afford the desired product as a white solid (0.575 g, 90%). $^1$H NMR (300 MHz, CDCl$_3$) δ 7.69 (dd, 2H, J=8.7, 2.7 Hz), 7.39 (dd, 2H, J=9.0, 3.9 Hz), 7.24 (td, 2H, J=9.0, 2.7 Hz), 4.68 (dd, 1H, J=15.9, 3.0 Hz), 4.33 (dd, 1H, J=15.9, 5.1 Hz), 3.35 (m, 1H), 2.84 (t, 1H, J=4.5 Hz), 2.55 (dd, 1H, J=4.8, 2.4 Hz).

Preparation 41: 4,4'-Difluoro-2-nitro-1,1'-biphenyl

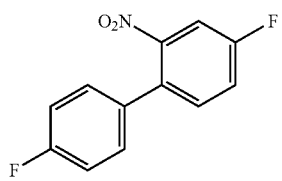

A microwave reaction vessel was charged with 2-chloro-5-fluoronitrobenzene (0.878 g, 5.0 mmol), 4-fluorophenylboronic acid (0.770 g, 5.5 mmol), sodium carbonate (1.590 g, 15.0 mmol), palladium diacetate (0.045 g, 0.2 mmol), tetrabutylammonium bromide (1.612 g, 5.0 mmol) in water (10 mL). The mixture was heated to 165° C. in a microwave reactor for 10 mins. The reaction was cooled to room temperature and poured into diethyl ether and 0.1N aqueous sodium hydroxide. The organic layer was washed with saturated aqueous sodium chloride, dried (anhydrous sodium sulfate), filtered, and concentrated in vacuo. The residue was purified by silica gel chromatography (10-30% methylene chloride/hexanes) to give the desired product as a yellow solid (0.61 g, 52%). $^1$H NMR (CDCl$_3$, 300 MHz) δ 7.61 (dd, 1H, J=8.1, 2.7 Hz), 7.44-7.30 (m, 2H), 7.30-7.21 (m, 2H), 7.16-7.07 (m, 2H).

Preparation 42: 2,7-Difluoro-9H-carbazole

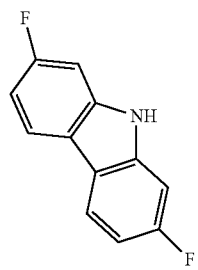 [SMILES: Fc1ccc2c(c1)[nH]c1cc(F)ccc12]

A solution of 4,4'-difluoro-2-nitro-1,1'-biphenyl (0.580 g, 2.5 mmol) and triphenylphosphine (1.617 g, 6.2 mmol) in anhydrous 1,2-dichlorobenzene (5 mL) was heated to 175° C. in a microwave reactor for 4 hrs. The mixture was cooled to room temperature and concentrated to a black residue under high vacuum. The crude product was purified by silica gel chromatography (5-50% methylene chloride/hexanes) to afford the product as a light brown powder (0.41 g, 82%). $^1$H NMR (CDCl$_3$, 300 MHz) δ 8.10 (br s, 1H), 7.93 (dd, 2H, J=8.7, 5.4 Hz), 7.11 (dd, 2H, J=9.3, 2.4 Hz), 6.99 (ddd, 2H, J=9.6, 9.0, 2.4 Hz).

Preparation 43: 2,7-Difluoro-9-(oxiran-2-ylmethyl)-9H-carbazole

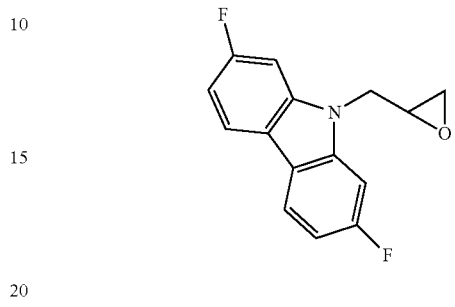

To a stirred solution of 2,7-difluoro-9H-carbazole (0.400 g, 2.0 mmol) in N,N-dimethylformamide (5 mL) at 0° C. was added 85% potassium hydroxide (0.156 g, 2.4 mmol) and the mixture was stirred for 1 hr. Epibromohydrin (0.326 mL, 3.9 mmol) was added and the mixture was slowly warmed to room temperature and stirred for 16 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-50% methylene chloride/hexanes) to afford the desired product as a white solid (0.47 g, 92%). $^1$H NMR (300 MHz, CDCl$_3$) δ 7.93 (dd, 2H, J=8.4, 5.4 Hz), 7.14 (dd, 2H, J=9.9, 2.4 Hz), 6.99 (td, 2H, J=9.0, 2.4 Hz), 4.60 (dd, 1H, J=15.9, 2.7 Hz), 4.25 (dd, 1H, J=15.9, 5.1 Hz), 3.35 (m, 1H), 2.86 (t, 1H, J=4.5 Hz), 2.57 (dd, 1H, J=4.8, 2.7 Hz).

Preparation 44: 2,4'-Difluoro-6-nitro-1,1'-biphenyl

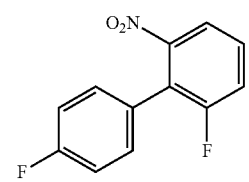 [SMILES: O=[N+]([O-])c1cccc(F)c1-c1ccc(F)cc1]

A microwave reaction vessel was charged with 2-chloro-3-fluoronitrobenzene (1.500 g, 8.5 mmol), 4-fluorophenylboronic acid (1.315 g, 9.4 mmol), sodium carbonate (2.717 g, 25.6 mmol), palladium diacetate (0.077 g, 0.3 mmol), tetrabutylammonium bromide (2.755 g, 8.5 mmol) in water (10 mL) and 1,4-dioxane (1 mL). The mixture was heated to 100° C. in a microwave reactor for 1 hr. The reaction was cooled to room temperature and poured into diethyl ether and 0.1N aqueous sodium hydroxide. The organic layer was washed with saturated aqueous sodium chloride, dried (anhydrous sodium sulfate), filtered, and concentrated in vacuo. The residue was purified by silica gel chromatography (10-30% methylene chloride/hexanes) to give the desired product as a

Preparation 45: 2,5-Difluoro-9H-carbazole

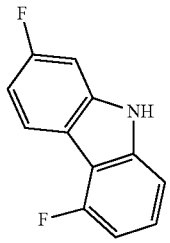 [SMILES: Fc1ccc2c(c1)[nH]c1cccc(F)c12]

A solution of 2,4'-difluoro-6-nitro-1,1'-biphenyl (1.100 g, 4.7 mmol) and triphenylphosphine (3.067 g, 11.7 mmol) in anhydrous 1,2-dichlorobenzene (2 mL) was heated to 175° C. in a microwave reactor for 4 hrs. The mixture was cooled to room temperature and concentrated in vacuo. The crude residue was then purified by silica gel chromatography (5-50% methylene chloride/hexanes) to afford the product as a white solid (0.84 g, 88%). $^1$H NMR (CDCl$_3$, 300 MHz) δ 8.17 (br s, 1H), 8.12 (dd, 1H, J=8.7, 5.1 Hz), 7.33 (td, 1H, J=8.1, 5.1 Hz), 7.20 (d, 1H, J=8.1 Hz), 7.12 (dd, 1H, J=9.3, 2.4 Hz), 7.02 (td, 1H, J=9.3, 2.4 Hz), 6.93 (dd, 1H, J=9.6, 7.8 Hz).

Preparation 46: 2,5-Difluoro-9-(oxiran-2-ylmethyl)-9H-carbazole

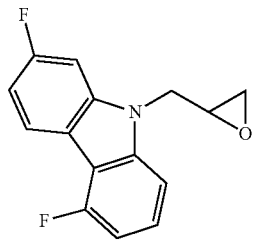 [SMILES: Fc1ccc2c3c(F)cccc3n(CC3CO3)c2c1]

To a stirred solution of 2,5-difluoro-9H-carbazole (0.530 g, 2.6 mmol) in N,N-dimethylformamide (5 mL) at 0° C. was added 85% potassium hydroxide (0.207 g, 3.1 mmol) and the mixture was stirred for 1 hr. Epibromohydrin (0.432 mL, 5.2 mmol) was added and the mixture was slowly warmed to room temperature and stirred for 16 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-50% methylene chloride/hexanes) to afford the desired product as a white solid (0.59 g, 87%). $^1$H NMR (300 MHz, CDCl$_3$) δ 8.13 (dd, 1H, J=8.7, 5.7 Hz), 7.38 (td, 1H, J=8.1, 5.4 Hz), 7.23 (d, 1H, J=8.4 Hz), 7.15 (dd, 1H, J=9.6, 2.1 Hz), 7.03 (ddd, 1H, J=9.6, 9.0, 2.4 Hz), 6.95 (ddd, 1H, J=9.9, 8.1, 0.6 Hz), 4.64 (dd, 1H, J=15.9, 3.0 Hz), 4.31 (dd, 1H, J=15.9, 5.1 Hz), 3.36 (m, 1H), 2.85 (t, 1H, J=4.5 Hz), 2.57 (dd, 1H, J=4.5, 2.4 Hz).

Preparation 47: 2-Chloro-5-fluoro-N-(4-fluorophenyl)aniline

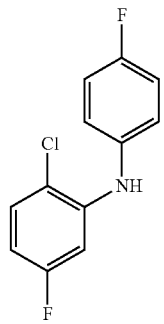 [SMILES: Fc1ccc(Nc2cc(F)ccc2Cl)cc1]

A round bottom flask was charged with 1-bromo-4-fluorobenzene (4.809 g, 27.5 mmol), 2-chloro-5-fluoroaniline (4.000 g, 27.5 mmol), Xantphos (0.636 g, 1.1 mmol), anhydrous toluene (100 mL), and sodium tert-butoxide (3.961 g, 41.2 mmol). The mixture was degassed and filled with argon, and then tris(dibenzylideneacetone)dipalladium(0) (0.755 g, 0.8 mmol) was added and the reaction was stirred under argon at 110° C. for 5 hrs. After cooling to room temperature, the mixture was treated with water and extracted with diethyl ether. The organic layer was washed with saturated aqueous sodium chloride, dried (anhydrous magnesium sulfate), filtered, and concentrated in vacuo. The residue was purified by silica gel chromatography (0-20% ethyl acetate/hexanes) to afford the product as a colorless oil (5.75 g, 87%). $^1$H NMR (300 MHz, CDCl$_3$) δ 7.27 (dd, 1H, J=9.0, 5.4 Hz), 7.23-7.03 (m, 4H), 6.71 (dd, 1H, J=10.8, 2.4 Hz), 6.47 (td, 1H, J=8.1, 3.0 Hz), 6.09 (br s, 1H).

Preparation 48: 2,6-Difluoro-9H-carbazole

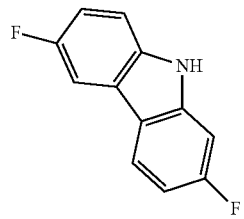 [SMILES: Fc1ccc2c(c1)[nH]c1ccc(F)cc12]

A mixture of sodium tert-butoxide (11.429 g, 118.9 mmol), 2-chloro-5-fluoro-N-(4-fluorophenyl)aniline (5.700 g, 23.8 mmol) and anhydrous 1,4-dioxane (120 mL) was degassed and back-filled with argon. Tri-tert-butylphosphonium tetrafluoroborate (0.483 g, 1.7 mmol) and palladium diacetate (0.267 g, 1.2 mmol) were added and the mixture was stirred in an oil bath at 110° C. for 20 hrs. After cooling to room temperature, the mixture was treated with 2M aqueous hydro- (yellow solid (1.15 g, 57%). $^1$H NMR (CDCl$_3$, 300 MHz) δ 7.70 (dt, 1H, J=8.4, 1.5 Hz), 7.51 (td, 1H, J=8.4, 5.4 Hz), 7.41 (td, 1H, J=8.4, 1.2 Hz), 7.35-7.26 (m, 2H), 7.22-7.11 (m, 2H).)

chloric acid (90 mL) and extracted with methylene chloride (3×50 mL). The combined organic layers were washed with saturated aqueous sodium chloride, dried (anhydrous sodium sulfate), filtered, and concentrated in vacuo. The residue was purified by silica gel chromatography (20-50% methylene chloride/hexanes). The solids were rinsed with hexanes and dried to afford the pure compound as a white powder (0.80 g, 17%). $^1$H NMR (300 MHz, CDCl$_3$) δ 8.05 (br s, 1H), 7.94 (dd, 1H, J=8.7, 5.7 Hz), 7.67 (dd, 1H, J=8.7, 2.7 Hz), 7.35 (dd, 1H, J=9.0, 4.5 Hz), 7.14 (td, 1H, J=9.0, 2.7 Hz), 7.11 (dd, 1H, J=9.3, 2.4 Hz), 6.98 (ddd, 1H, J=9.3, 8.4, 2.4 Hz).

Preparation 49:
2,6-Difluoro-9-(oxiran-2-ylmethyl)-9H-carbazole

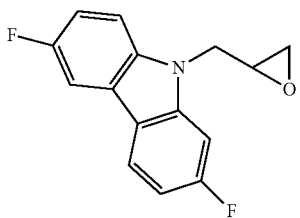 [SMILES: Fc1ccc2c(c1)c1ccc(F)cc1n2CC1CO1]

To a stirred solution of 2,6-difluoro-9H-carbazole (0.460 g, 2.3 mmol) in N,N-dimethylformamide (5 mL) at 0° C. was added 85% potassium hydroxide (0.179 g, 2.7 mmol) and the mixture was stirred for 1 hr. Epibromohydrin (0.375 mL, 4.5 mmol) was added and the mixture was slowly warmed to room temperature and stirred for 16 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-50% methylene chloride/hexanes) to afford the desired product as a white solid (0.55 g, 94%). $^1$H NMR (300 MHz, CDCl$_3$) δ 7.95 (dd, 1H, J=8.7, 5.7 Hz), 7.68 (dd, 1H, J=8.7, 2.7 Hz), 7.38 (dd, 1H, J=8.7, 4.2 Hz), 7.20 (td, 1H, J=9.0, 2.7 Hz), 7.13 (dd, 1H, J=9.9, 2.1 Hz), 6.98 (ddd, 1H, J=9.6, 9.0, 2.4 Hz), 4.64 (dd, 1H, J=15.9, 2.7 Hz), 4.29 (dd, 1H, J=15.9, 5.1 Hz), 3.35 (m, 1H), 2.85 (t, 1H, J=4.5 Hz), 2.56 (dd, 1H, J=4.8, 2.4 Hz).

Preparation 50: 2,2'-Difluoro-6-nitro-1,1'-biphenyl

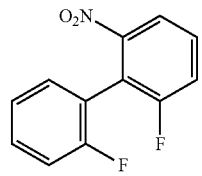 [SMILES: O=[N+]([O-])c1cccc(F)c1-c1ccccc1F]

To a solution of 2-bromo-3-fluoronitrobenzene (1.500 g, 6.8 mmol), 2-fluorophenylboronic acid (1.145 g, 8.2 mmol), N,N-dimethylformamide (50 mL), and 2.0 M aqueous potassium carbonate (10 mL) under argon was added tetrakis (triphenylphosphine)palladium (0) (0.394 g, 0.3 mmol). The mixture was stirred at 110° C. for 16 hrs. After cooling to room temperature, the mixture was diluted with ethyl acetate (100 mL) and washed with saturated aqueous sodium chloride, dried (anhydrous sodium sulfate), filtered, and concentrated in vacuo. The residue was purified by silica gel chromatography (0-30% methylene chloride/hexanes) to afford a pale yellow solid (0.780 g, 49%). $^1$H NMR (300 MHz, CDCl$_3$) δ 7.86 (dt, 1H, J=7.8, 1.2 Hz), 7.56 (td, 1H, J=8.1, 5.7 Hz), 7.52-7.40 (m, 2H), 7.35-7.15 (m, 3H).

Preparation 51: 4,5-Difluoro-9H-carbazole

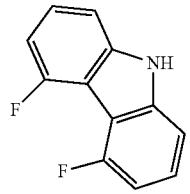

A solution of 2,2'-difluoro-6-nitro-1,1'-biphenyl (0.740 g, 3.1 mmol) and triphenylphosphine (2.063 g, 7.9 mmol) in anhydrous 1,2-dichlorobenzene (1.5 mL) was heated to 175° C. in a microwave reactor for 3 hrs. The mixture was cooled to room temperature and purified by silica gel chromatography (5-50% methylene chloride/hexanes) to afford the product as a white solid (0.28 g, 44%). $^1$H NMR (CDCl$_3$, 300 MHz) δ 8.26 (br s, 1H), 7.39 (tt, 2H, J=8.1, 2.4 Hz), 7.22 (d, 2H, J=8.1 Hz), 6.97 (dt, 2H, J=8.1, 5.1 Hz).

Preparation 52:
4,5-Difluoro-9-(oxiran-2-ylmethyl)-9H-carbazole

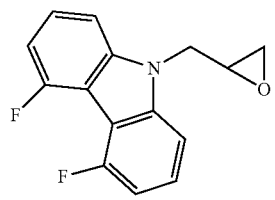 [SMILES: Fc1cccc2c1c1c(F)cccc1n2CC1CO1]

To a stirred solution of 4,5-difluoro-9H-carbazole (0.270 g, 1.3 mmol) in N,N-dimethylformamide (5 mL) at 0° C. was added 85% potassium hydroxide (0.105 g, 1.6 mmol) and the mixture was stirred for 1 hr. Epibromohydrin (0.220 mL, 2.7 mmol) was added and the mixture was slowly warmed to room temperature and stirred for 4 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-50% methylene chloride/hexanes) to afford the desired product as a white solid (0.315 g, 91%). $^1$H NMR (300 MHz, CDCl$_3$) δ 7.45 (tt, 2H, J=8.1, 2.4 Hz), 7.25 (d, 2H, J=8.1 Hz), 6.99 (dt, 2H, J=9.9, 4.2 Hz), 4.68 (dd, 1H, J=15.9, 3.0 Hz), 4.38 (dd, 1H, J=15.9, 5.1 Hz), 3.37 (m, 1H), 2.85 (t, 1H, J=4.5 Hz), 2.57 (dd, 1H, J=4.5, 2.4 Hz).

Preparation 53: 2',5-Difluoro-2-nitro-1,1'-biphenyl

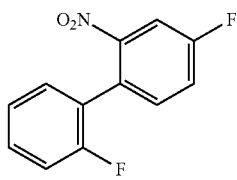 [SMILES: O=[N+]([O-])c1cc(F)ccc1-c1ccccc1F]

To a solution of 2-bromo-4-fluoronitrobenzene (1.500 g, 6.8 mmol), 2-fluorophenylboronic acid (1.145 g, 8.2 mmol), N,N-dimethylacetamide (50 mL), and 2.0 M aqueous potassium carbonate (10 mL) under argon was added tetrakis(triphenylphosphine)palladium (0) (0.394 g, 0.3 mmol). The mixture was stirred at 110° C. for 6 hrs. After cooling to room temperature, the mixture was partitioned between ethyl acetate (100 mL) and water. The organic layer was washed with saturated aqueous sodium chloride, dried (anhydrous sodium sulfate), filtered, and concentrated in vacuo. The residue was purified by silica gel chromatography (0-30% methylene chloride/hexanes) to afford a light yellow oil (1.5 g, 94%). $^1$H NMR (300 MHz, CDCl$_3$) δ 8.12 (dd, 1H, J=9.0, 5.1 Hz), 7.44 (m, 1H), 7.34 (td, 1H, J=7.5, 2.1 Hz), 7.31-7.10 (m, 4H).

Preparation 54: 3,5-Difluoro-9H-carbazole

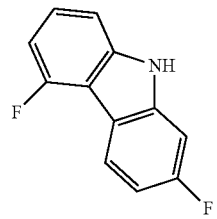 [SMILES: Fc1ccc2c(c1)[nH]c1cccc(F)c12]

A solution of 2',5-difluoro-2-nitro-1,1'-biphenyl (1.400 g, 6.0 mmol) and triphenylphosphine (3.903 g, 14.9 mmol) in anhydrous 1,2-dichlorobenzene (5 mL) was heated to 175° C. in a microwave reactor for 4 hrs. The mixture was cooled to room temperature and purified by silica gel chromatography (5-50% methylene chloride/hexanes) to afford the product as a light brown solid (0.62 g, 51%). $^1$H NMR (CDCl$_3$, 300 MHz) δ 8.12 (br s, 1H), 7.87 (dd, 1H, J=9.0, 2.4 Hz), 7.41-7.31 (m, 2H), 7.24-7.15 (m, 2H), 6.91 (dd, 1H, J=10.2, 8.1 Hz).

Preparation 55: 3,5-Difluoro-9-(oxiran-2-ylmethyl)-9H-carbazole

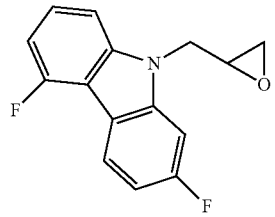 [SMILES: Fc1ccc2c3c(F)cccc3n(CC3CO3)c2c1]

To a stirred solution of 3,5-difluoro-9H-carbazole (0.300 g, 1.5 mmol) in N,N-dimethylformamide (5 mL) at 0° C. was added 85% potassium hydroxide (0.117 g, 1.8 mmol) and the mixture was stirred for 1 hr. Epibromohydrin (0.244 mL, 3.0 mmol) was added and the mixture was slowly warmed to room temperature and stirred for 4 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-50% methylene chloride/hexanes) to afford the desired product as an off-white solid (0.36 g, 94%). $^1$H NMR (300 MHz, CDCl$_3$) δ 7.88 (dd, 1H, J=8.7, 2.7 Hz), 7.46-7.36 (m, 2H), 7.29-7.20 (m, 2H), 6.92 (dd, 1H, J=9.9, 7.8 Hz), 4.68 (dd, 1H, J=15.9, 3.0 Hz), 4.35 (dd, 1H, J=15.9, 5.1 Hz), 3.36 (m, 1H), 2.85 (t, 1H, J=4.5 Hz), 2.56 (dd, 1H, J=4.5, 2.7 Hz).

Preparation 56: 6-Methyl-1,2-thiazinane 1,1-dioxide

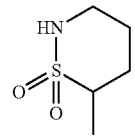

To a stirred solution of 3-chloropropylamine hydrochloride (3.000 g, 23.1 mmol) in anhydrous acetonitrile (60 mL) and triethylamine (7.056 mL, 50.8 mmol) at 0° C. was slowly added ethanesulfonyl chloride (2.967 g, 23.1 mmol). The reaction mixture was slowly warmed to room temperature and stirred for 16 hrs. The triethylamine hydrochloride was removed by filtration and the filter cake washed with tetrahydrofuran. The filtrate was concentrated and the residue was dissolved in ethyl acetate and washed with saturated aqueous sodium bicarbonate and saturated aqueous sodium chloride, dried (anhydrous sodium sulfate), filtered, and concentrated to afford the halosulfonamide intermediate (4.35 g) which was dissolved in anhydrous tetrahydrofuran (60 mL) and cooled to −30° C. After addition of diisopropylamine (0.584 g, 5.8 mmol) and 1,10-phenanthroline (0.010 g), a solution n-BuLi in hexanes (50 mmol, 2.5 M) was slowly added via a dropping funnel over period of 30 mins maintaining the internal temperature range of −30° C. to −10° C. The resulting solution was slowly warmed to 0° C. over 2 hrs. After a further 2 hrs at 0° C., the reaction was quenched by addition of 2N aqueous hydrochloric acid (pH adjusted to 5). After addition of saturated aqueous sodium chloride, the mixture was extracted with ethyl acetate. The organic layer was washed with saturated aqueous sodium chloride, dried (anhydrous magnesium sulfate), filtered, and concentrated to afford the product as a yellow oil (2.73 g, 79%). $^1$H NMR (300 MHz, CDCl$_3$) δ 4.20 (br s, 1H), 3.54-3.28 (m, 2H), 3.06 (m, 1H), 2.13 (m, 1H), 1.98 (m, 1H), 1.77 (m, 1H), 1.65 (m, 1H), 1.41 (d, 3H, J=6.6 Hz).

Preparation 57: But-3-ene-1-sulfonamide

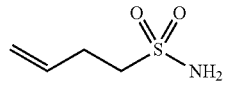

A mixture of 4-bromo-1-butene (3.000 g, 22.2 mmol) and sodium sulfite (3.356 g, 26.6 mmol) in water (15 mL) was heated under reflux for 16 hrs. After cooling to room temperature, the aqueous solution was washed with diethyl ether and concentrated in vacuo to afford a white powder which was dried under vacuum at 100° C. to give a mixture of the crude but-3-ene-1-sulfonic acid and salts (ca. 6.2 g) which was then treated with phosphorus oxychloride (20.7 mL, 222.2 mmol). The mixture was heated at 130° C. for 6 hrs and then concentrated. The residue was treated with acetonitrile (50 mL) and ammonia gas was slowly introduced at 0° C. The mixture was stirred at 0° C. for 1 hr and then diluted with water and extracted with ethyl acetate (100 mL). The organic layer was washed with saturated aqueous sodium chloride, dried (anhydrous sodium sulfate), filtered, and concentrated to afford a yellow oil (2.1 g, 70%). $^1$H NMR (300 MHz, CDCl$_3$) δ 5.85 (m, 1H), 5.19 (d, 1H, J=17.4 Hz), 5.15 (d, 1H, J=9.9 Hz), 4.69 (br s, 2H), 3.24 (t, 2H, J=7.5 Hz), 2.65 (q, 2H, J=7.5 Hz).

Preparation 58: 2-Thia-1-azabicyclo[3.1.0]hexane 2,2-dioxide

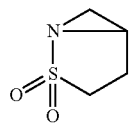

To a mixture of but-3-ene-1-sulfonamide (1.300 g, 9.6 mmol), iodosobenzene diacetate (3.252 g, 10.1 mmol), aluminum oxide (1.030 g, 10.1 mmol), and methylene chloride (50 mL) under argon at room temperature was added rhodium (II) acetate (0.80 g). The resulting suspension was stirred vigorously at 40° C. for 5 hrs. The mixture was filtered through a pad of Celite and the filter cake washed with methylene chloride. The filtrate was evaporated, and the residue purified by silica gel chromatography (0-100% ethyl acetate/hexanes) to afford the product as a white solid (0.61 g, 48%). $^1$H NMR (300 MHz, CDCl$_3$) δ 3.21 (m, 1H), 3.15 (dt, 1H, J=13.2, 4.5 Hz), 2.82 (m, 1H), 2.72-2.62 (m, 2H), 2.49 (dd, 1H, J=5.1, 2.4 Hz), 2.31 (dd, 1H, J=4.5, 3.0 Hz).

Preparation 59: 4-Methoxy-1,2-thiazinane 1,1-dioxide

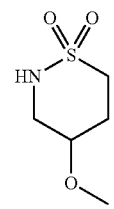

A mixture of 2-thia-1-azabicyclo[3.1.0]hexane 2,2-dioxide (0.600 g, 4.5 mmol), p-toluenesulfonic acid hydrate (0.086 g, 0.5 mmol) and methanol (50 mL) was stirred at room temperature for 3 days. The reaction was concentrated and the residue purified by silica gel chromatography (0-100% ethyl acetate/hexanes) to afford the product as a white solid (0.56 g, 75%). $^1$H NMR (300 MHz, CDCl$_3$) δ 4.43 (br s, 1H), 3.65-3.40 (m, 2H), 3.40 (s, 3H), 3.36-3.23 (m, 2H), 3.08 (dt, 1H, J=13.5, 3.9 Hz), 2.50-2.23 (m, 2H).

Preparation 60: 9-(2-Methylbut-3-yn-2-yl)-9H-carbazole

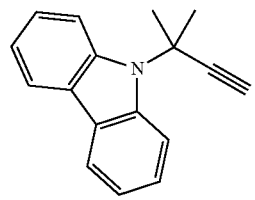 [SMILES: C#CC(C)(C)n1c2ccccc2c2ccccc21]

To a stirred solution of carbazole (2.500 g, 15.0 mmol) in anhydrous N,N-dimethylformamide (30 mL) at 0° C. was added 60% sodium hydride in mineral oil (0.718 g, 17.9 mmol) and the mixture was stirred at 0° C. for 1 hr. 3-Chloro-3-methyl-1-butyne (2.300 g, 22.4 mmol) was added and the reaction mixture was stirred at 0° C. for 1 hr and then slowly warmed to room temperature and stirred for 16 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-70% methylene chloride/hexanes) to afford the desired product as a light brown solid (1.7 g, 49%). $^1$H NMR (300 MHz, CDCl$_3$) δ 8.10 (d, 2H, J=7.5 Hz), 8.04 (d, 2H, J=8.7 Hz), 7.41 (td, 2H, J=8.1, 1.5 Hz), 7.24 (t, 2H, J=7.5 Hz), 2.67 (s, 1H), 2.28 (s, 6H).

Preparation 61:
9-(2-Methylbut-3-en-2-yl)-9H-carbazole

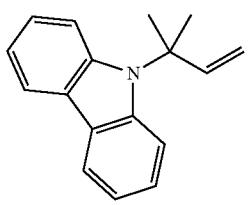 [SMILES: C=CC(C)(C)n1c2ccccc2c2ccccc21]

A mixture of 9-(2-methylbut-3-yn-2-yl)-9H-carbazole (1.600 g, 6.9 mmol), quinoline (0.810 mL, 6.9 mmol), benzene (70.0 mL) and 5% palladium on barium sulfate (0.190 g) was stirred under an atmosphere of hydrogen at room temperature. Once the desired amount of hydrogen was consumed (~45 mins), the reaction was stopped and filtered through Celite and the filtrate concentrated in vacuo. The residue was purified by silica gel chromatography (0-20% methylene chloride/hexanes) to afford the desired product as a colorless oil (1.55 g, 96%). $^1$H NMR (300 MHz, CDCl$_3$) δ 8.10 (d, 2H, J=7.5 Hz), 7.81 (d, 2H, J=8.4 Hz), 7.35 (t, 2H, J=8.1 Hz), 7.21 (t, 2H, J=7.5 Hz), 6.41 (dd, 1H, J=17.7, 10.5 Hz), 5.32-5.20 (m, 2H), 2.06 (s, 6H).

Preparation 62:
3-(9H-Carbazol-9-yl)-3-methylbutane-1,2-diol

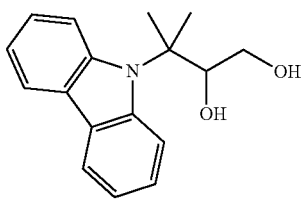 [SMILES: CC(C)(C(O)CO)n1c2ccccc2c2ccccc21]

To a stirred solution of 9-(2-methylbut-3-en-2-yl)-9H-carbazole (0.400 g, 1.7 mmol), and 4-methylmorpholine N-oxide (0.398 g, 3.4 mmol) in acetonitrile (10 mL) and water (3 mL) was added 4% osmium tetroxide solution (0.540 mL, 0.1 mmol). The mixture was stirred at room temperature for 48 hrs. The reaction was concentrated and the residue partitioned between ethyl acetate and water. The organic layer was washed with saturated aqueous sodium chloride, dried (anhydrous sodium sulfate), filtered, and concentrated to give a yellow solid (0.43 g, 94%). $^1$H NMR (300 MHz, CDCl$_3$) δ 8.10 (d, 2H, J=7.5 Hz), 7.84 (d, 2H, J=8.4 Hz), 7.37 (t, 2H, J=7.5 Hz), 7.23 (t, 2H, J=7.5 Hz), 4.84 (m, 1H), 3.80-3.50 (m, 2H), 2.30 (br s, 1H), 2.11 (s, 3H), 2.05 (s, 3H), 1.82 (br s, 1H). ESI m/z: 269.8 (M+H).

Preparation 63: 9-(2-(Oxiran-2-yl)propan-2-yl)-9H-carbazole

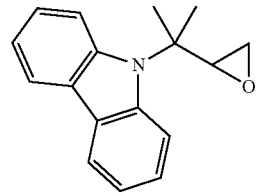 [SMILES: CC(C)(C1CO1)n1c2ccccc2c2ccccc21]

To a stirred solution of 3-(9H-carbazol-9-yl)-3-methylbutane-1,2-diol (0.430 g, 1.6 mmol) in pyridine (5.0 mL, 61.8 mmol) and methylene chloride (5 mL) at 0° C. was slowly added p-toluenesulphonyl chloride (0.609 g, 3.2 mmol). The reaction mixture was warmed to room temperature and stirred for 16 hrs. The mixture was concentrated and the residue dissolved in ethyl acetate. The organic phase was washed with saturated aqueous sodium chloride, 1N aqueous hydrochloric acid and then saturated aqueous sodium bicarbonate, dried (anhydrous sodium sulfate), filtered, and concentrated to afford the crude tosylate (0.650 g). To a stirred mixture of the crude tosylate (0.650 g, 1.5 mmol) in methanol (20 mL) at 0° C. was added potassium carbonate (0.255 g, 1.8 mmol). The resulting mixture was stirred at 0° C. for 2 hrs and then slowly warmed to room temperature. The mixture was concentrated and the residue was partitioned between water and ethyl acetate. The organic layer was washed with saturated aqueous sodium chloride, dried (anhydrous sodium sulfate), filtered, and concentrated in vacuo. The residue was purified by silica gel chromatography (0-50% methylene chloride/hexanes) to afford the desired product as a white solid (0.295 g, 76%). $^1$H NMR (300 MHz, CDCl$_3$) δ 8.10 (d, 2H, J=7.5 Hz), 7.91 (d, 2H, J=8.7 Hz), 7.39 (t, 2H, J=7.5 Hz), 7.23 (t, 2H, J=7.5 Hz), 3.66 (m, 1H), 3.09 (t, 1H, J=4.2 Hz), 2.98 (m, 1H), 1.96 (s, 3H), 1.86 (s, 3H).

Preparation 64: 2-(2-Methylbut-3-yn-2-yl)-isothiazolidine-1,1-dioxide

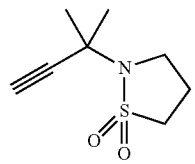

To a stirred solution of 1,3-propanesultam (2.000 g, 16.5 mmol) in anhydrous N,N-dimethylformamide (30 mL) at 0° C. was added 60% sodium hydride in mineral oil (1.981 g, 49.5 mmol) and the mixture was stirred at 0° C. for 1 hr. 3-Chloro-3-methyl-1-butyne (2.300 g, 22.4 mmol) was added and the reaction mixture was stirred at 0° C. for 1 hr and then slowly warmed to room temperature and stirred for 16 hrs. The reaction was carefully quenched with water and extracted with ethyl acetate. The organic layer was washed with saturated aqueous sodium chloride, dried (anhydrous sodium sulfate), and concentrated in vacuo. The residue was purified by silica gel chromatography (0-70% ethyl acetate/hexanes) to afford the desired product as a yellow oil (1.35 g, 44%). $^1$H NMR (300 MHz, CDCl$_3$) δ 3.52 (t, 2H, J=6.6 Hz), 3.23 (t, 2H, J=7.5 Hz), 2.46 (s, 1H), 2.42-2.28 (m, 2H), 1.74 (s, 6H).

Preparation 65: 2-(2-Methylbut-3-en-2-yl)-isothiazolidine-1,1-dioxide

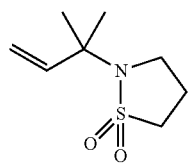

A mixture of 2-(2-methylbut-3-yn-2-yl)-isothiazolidine-1,1-dioxide (1.350 g, 7.2 mmol), quinoline (0.852 mL, 7.2 mmol), benzene (70.0 mL) and 5% palladium on barium sulfate (0.20 g) was stirred under an atmosphere of hydrogen at room temperature. Once the desired amount of hydrogen was consumed (~1 hr), the reaction was stopped and filtered through Celite and the filtrate concentrated. The residue was purified by silica gel chromatography (0-70% ethyl acetate/hexanes) to afford the product as a yellowish oil (2.22 g) containing about 40% quinoline. $^1$H NMR (300 MHz, CDCl$_3$) δ 6.04 (dd, 1H, J=17.4, 10.5 Hz), 5.16 (d, 1H, J=17.4 Hz), 5.15 (d, 1H, J=10.8 Hz), 3.29 (t, 2H, J=6.6 Hz), 3.21 (t, 2H, J=7.5 Hz), 2.35-2.20 (m, 2H), 1.56 (s, 6H).

Preparation 66: 2-(2-(Oxiran-2-yl)propan-2-yl)-isothiazolidine-1,1-dioxide

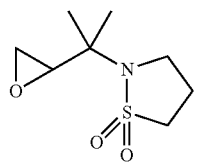

To a stirred solution of 60% 2-(2-methylbut-3-en-2-yl) isothiazolidine 1,1-dioxide (1.0 g, 3.2 mmol), 4-methylmorpholine N-oxide (0.743 g, 6.3 mmol) in acetonitrile (10 mL) and water (3 mL) was added 4% osmium tetroxide solution (1.007 mL, 0.2 mmol). The mixture was stirred at room temperature for 48 hrs. The reaction was concentrated and the residue was partitioned between ethyl acetate and water. The organic layer was washed with saturated aqueous sodium chloride, dried (anhydrous sodium sulfate), filtered, and concentrated to give the crude diol. To a stirred solution of 2-(3,4-dihydroxy-2-methylbutan-2-yl)-isothiazolidine-1,1-dioxide (0.065 g, 0.3 mmol) in pyridine (1.0 mL, 12.4 mmol) and methylene chloride (2 mL) at 0° C. was slowly added p-toluenesulphonyl chloride (0.111 g, 0.6 mmol). The reaction mixture was warmed to room temperature and stirred for 16 hrs. The mixture was concentrated and the residue was dissolved in ethyl acetate. The organic phase was washed with saturated aqueous sodium chloride, 1N aqueous hydrochloric acid, saturated aqueous sodium bicarbonate, dried (anhydrous sodium sulfate), filtered, and concentrated to afford the crude tosylate (0.040 g). To a stirred mixture of the crude tosylate (0.040 g, 0.1 mmol) in methanol (5 mL) at 0° C. was added potassium carbonate (0.048 g, 0.3 mmol) and the mixture was stirred at 0° C. for 2 hrs and then slowly warmed to room temperature The mixture was concentrated and the residue was partitioned between water and ethyl acetate. The organic layer was washed with saturated aqueous sodium chloride, dried (anhydrous sodium sulfate), filtered, and concentrated to give the crude epoxide (0.02 g), which was used without further purification.

Preparation 67: 3,6-Difluoro-9-((2-methyloxiran-2-yl)methyl)-9H-carbazole

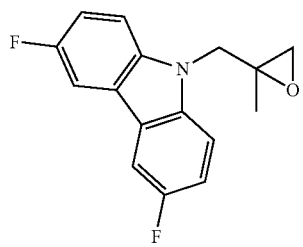 [SMILES: CC1(Cn2c3ccc(F)cc3c3cc(F)ccc32)CO1]

To a stirred solution of 3,6-difluoro-9H-carbazole (2.0 g, 9.8 mmol) in N,N-dimethylformamide (50 mL) at 0° C. was added 85% potassium hydroxide (0.780 g, 11.8 mmol) and the mixture was stirred for 1 hr. 2-(Chloromethyl)-2-methyloxirane (2.098 g, 19.7 mmol) was added and the mixture was slowly warmed to room temperature and stirred for 16 hrs. The mixture was partitioned between water and ethyl acetate. The organic layer was washed with saturated aqueous sodium chloride, dried (anhydrous sodium sulfate), filtered, and concentrated in vacuo. The residue was purified by silica gel chromatography (10-50% methylene chloride/hexanes) to afford the desired product as a white solid (1.7 g, 63%). $^1$H NMR (300 MHz, CDCl$_3$) δ 7.68 (dd, 2H, J=8.4, 2.4 Hz), 7.41 (dd, 2H, J=9.0, 4.2 Hz), 7.23 (td, 2H, J=9.0, 2.4 Hz), 4.62 and 4.22 (AB, 2H, J=15.6 Hz), 2.71 & 2.66 (AB, 2H, J=4.5 Hz), 1.33 (s, 3H).

Preparation 68: N-Isopropylmethanesulfonamide

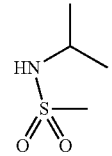

To a stirred solution of 2-aminopropane (1.200 g, 20.3 mmol), N,N-diisopropylethylamine (3.355 mL, 20.3 mmol) and pyridine (1.642 mL, 20.3 mmol) in methylene chloride (30 mL) at 0° C. was slowly added methanesulfonyl chloride (1.571 mL, 20.3 mmol). The reaction mixture was slowly warmed to room temperature and stirred for 16 hrs. The mixture was concentrated and the residue purified by silica gel chromatography (0-80% ethyl acetate/hexanes) to afford the product low melting solid (2.7 g, 97%). ¹H NMR (300 MHz, CDCl₃) δ 4.25 (br s, 1H), 3.67 (m, 1H), 2.99 (s, 3H), 1.27 (d, 6H, J=6.6 Hz).

Preparation 69: N-Cyclopropylmethanesulfonamide

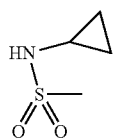

To a stirred solution of cyclopropylamine (1.200 g, 21.0 mmol), N,N-diisopropylethylamine (3.474 mL, 21.0 mmol) and pyridine (1.700 mL, 21.0 mmol) in methylene chloride (30 mL) at 0° C. was slowly added methanesulfonyl chloride (1.627 mL, 21.0 mmol). The reaction mixture was slowly warmed to room temperature and stirred for 16 hrs. The mixture was concentrated and the residue purified by silica gel chromatography (0-80% ethyl acetate/hexanes) to afford the product as a low melting solid (2.7 g, 95%). ¹H NMR (300 MHz, CDCl₃) δ 4.86 (br s, 1H), 3.02 (s, 3H), 2.60 (m, 1H), 0.85-0.65 (m, 4H).

Preparation 70: N-Cyclobutylmethanesulfonamide

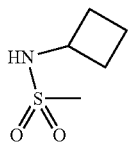

To a stirred solution of cyclobutylamine (0.400 g, 5.6 mmol), N,N-diisopropylethylamine (0.930 mL, 5.6 mmol) and pyridine (0.455 mL, 5.6 mmol) in methylene chloride (10 mL) at 0° C. was slowly added methanesulfonyl chloride (0.435 mL, 5.6 mmol). The reaction mixture was slowly warmed to room temperature and stirred for 16 hrs. The mixture was concentrated and the residue purified by silica gel chromatography (0-80% ethyl acetate/hexane) to afford the product as a low melting solid (0.82 g, 98%). ¹H NMR (300 MHz, CDCl₃) δ 4.62 (br s, 1H), 3.94 (m, 1H), 2.94 (s, 3H), 2.50-2.30 (m, 2H), 2.10-1.85 (m, 2H), 1.85-1.60 (m, 2H).

Preparation 71: 2-(2,4-Dimethoxybenzyl)-isothiazolidine-1,1-dioxide

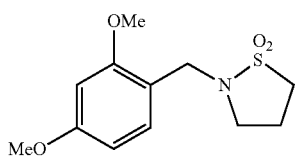 [SMILES: COc1ccc(CN2CCCS2(=O)=O)c(OC)c1]

A solution of 1,1-(azodicarbonyl) dipiperidine (1.874 g, 7.4 mmol) in anhydrous tetrahydrofuran (10 mL) was added dropwise to a 0° C. solution of 1,3-propanesultam (0.6 g, 4.95 mmol), triphenylphosphine (1.95 g, 7.4 mmol), and 2,4-dimethoxybenzyl alcohol (1.0 g, 6.2 mmol) in anhydrous tetrahydrofuran (20 mL). The resultant solution was stirred at 0° C. for 3 hrs, warmed to room temperature and stirred for a further 16 hrs. The solution was concentrated under reduced pressure and suspended in ethyl acetate/hexanes to precipitate a white solid. The solid was removed by filtration and the filtrate purified by silica gel chromatography (25-70% ethyl acetate/hexanes) to give a pale yellow oil (0.505 g). ¹H NMR (CDCl₃, 300 MHz) δ 7.31-7.28 (dd, 1H, J=0.6, 7.8 Hz), 6.49-6.44 (m, 2H), 4.17 (s, 2H), 3.81 (s, 3H), 3.80 (s, 3H), 3.19-3.13 (m, 4H), 2.32-2.23 (m, 2H).

Preparation 72: 2-(2,4-Dimethoxybenzyl)-5-fluoro-isothiazolidine-1,1-dioxide

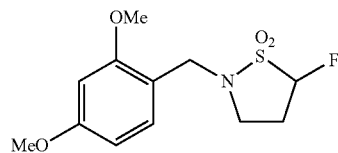

To a solution of 2-(2,4-dimethoxybenzyl)-isothiazolidine-1,1-dioxide (4.0 g, 14.7 mmol) in anhydrous tetrahydrofuran (200 mL), under an atmosphere of nitrogen & cooled to −78° C., was slowly added n-butyl lithium (11.5 mL, 2.5 N in hexanes) and the resultant solution was stirred for 1.5 hrs. A solution of N-fluorobenzene sulfonimide (10.5 g, 33 mmol) in anhydrous tetrandrofuran (60 mL), cooled to 0° C., was added slowly over 30 mins, stirred at −78° C. for 3 hrs, then warmed to room temperature and stirred for an additional 2.5 hrs. Saturated aqueous ammonium chloride (250 mL) was added and the mixture extracted with ethyl acetate (250 mL). The organic layer was washed with saturated aqueous sodium chloride, dried (anhydrous sodium sulfate), filtered, and concentrated in vacuo. The crude product was extracted with diethyl ether, filtering through a sintered glass filter to remove insoluble products. The solids were extracted with a small amount of methylene chloride, and the filtrate passed through a silica gel plug (washing with 50% ethyl acetate/hexanes) and combined with the diethyl ether extract. The combined organic solutions were concentrated and purified by silica gel chromatography (20-60% ethyl acetate/hexanes). This material was further purified by preparative HPLC, (C18 column with acetonitrile/water gradient) to give a low melting tan solid (0.519 g). ¹H NMR (CDCl₃, 300 MHz) δ 7.24-7.21 (d, 1H, J=7.5 Hz), 6.49-6.44 (m, 2H), 5.51-5.31 (ddd, 1H, J=1.8, 5.1, 54 Hz), 4.44-4.39 (d, 1H, J=2.7 Hz), 4.20-4.15 (d, 1H, J=2.7 Hz), 3.82 (s, 3H), 3.81 (s, 3H), 3.27-3.18 (m, 2H), 2.65-2.35 (m, 2H). HPLC analysis: (C18, 25-95% acetonitrile in water+0.1% trifluoroacetic acid over 10 mins: retention time, % area at 254 nm): 7.51 min, 97%.

Preparation 73: 5-Fluoro-isothiazolidine-1,1-dioxide

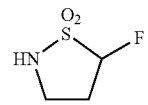

To a solution of 2-(2,4-dimethoxybenzyl)-5-fluoro-isothiazolidine-1,1-dioxide (0.519 g, 1.9 mmol) in methylene chloride (50 mL), cooled to 0° C., was added trifluoroacetic acid (25 mL). The solution was stirred at 0° C. for 2.5 hrs and concentrated in vacuo. The crude product was purified by silica gel chromatography (20-70% ethyl acetate/hexanes) to give a tan solid (0.212 g). ¹H NMR (CDCl₃, 300 MHz) δ 5.52-5.50 (ddd, 1H, J=1.5, 4.5, 53.1 Hz), 4.57 (br s, 1H), 3.57-3.33 (m, 2H), 2.78-2.48 (m, 2H).

Preparation 74:
2-(2,4-Dimethoxybenzyl)-1,2-thiazinane-1,1-dioxide

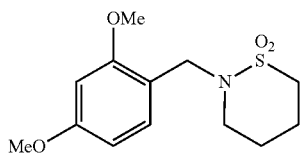

To a 0.5 M solution of 2,4-dimethoxybenzyl alcohol (4.94 g, 29.3 mmol) in anhydrous diethyl ether was added anhydrous pyridine (4.75 mL, 58.7 mmol). The mixture was cooled to 0° C. and thionyl chloride (5.98 mL, 80.7 mmol) was added slowly over 5-10 mins and the reaction stirred at 0° C. for 1.5 hrs. The reaction mixture was poured into ice water (120 mL) and the layers separated. The aqueous layer was extracted with diethyl ether (2×60 mL) and the combined organic layers washed with ice water (60 mL) and a solution of 5:1 saturated aqueous sodium chloride:saturated aqueous sodium bicarbonate (2×60 mL), dried (anhydrous sodium sulfate), filtered, and concentrated to ~5 mL of liquid. The crude solution was dissolved in benzene (200 mL) and reconcentrated to 10-15 mL of liquid, which was used immediately in the next step. 1,4-butanesultam (2.800 g, 20.7 mmol) in anhydrous N,N-dimethylformamide (50 mL) was cooled to 0° C. and sodium hydride was added in small portions, stirring for 5 min at 0° C. and 1 hr at room temperature. The reaction became a slurry, and was cooled to 0° C. and a solution of 1-(chloromethyl)-2,4-dimethoxybenzene in benzene was added, stirring at 0° C. and slowly warming to room temperature and stirring for 16 hrs. The mixture was poured into water (300 mL) and extracted with ethyl acetate (3×). The combined organic layers were washed with water, saturated aqueous sodium chloride, dried (anhydrous sodium sulfate), filtered, and concentrated in vacuo. The crude material was purified by silica gel chromatography (15-60% ethyl acetate/hexanes) to give a white solid (4.78 g). ¹H NMR (300 MHz, CDCl₃) δ 7.28-7.25 (d, 1H, J=8.4 Hz), 6.48-6.45 (dd, 1H, J=2.4, 8.1 Hz), 6.43-6.42 (d, 1H, J=2.1 Hz), 4.29 (s, 2H), 3.79 (s, 6H), 3.31-3.27 (m, 2H), 3.04-3.00 (m, 2H), 2.18-2.15 (m, 2H), 1.60-1.56 (m, 2H). HPLC analysis: (C18, 25-99% acetonitrile in water+0.1% trifluoroacetic acid over 10 mins: retention time, % area at 254 nm): 6.93 min, 98%.

Preparation 75: 2-(2,4-Dimethoxybenzyl)-6-fluoro-1,2-thiazinane-1,1-dioxide

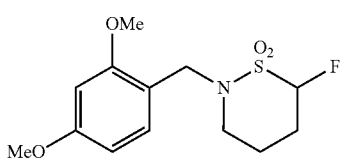 [SMILES: COc1ccc(CN2CCCC(F)S2(=O)=O)c(OC)c1]

2-(2,4-Dimethoxybenzyl)-1,2-thiazinane-1,1-dioxide (4.780 g, 16.8 mmol) in anhydrous tetrahydrofuran (250 mL) was cooled to -78° C. and n-butyllithium (13 mL, 2.5N in hexanes) was added dropwise. The reaction was stirred at -78° C. for 1 hr and a solution of N-fluorobenzene sulfonimide (11.885 g, 37.7 mmol) in anhydrous tetrahydrofuran (50 mL) was added slowly over 20 mins. The resulting solution stirred at -78° C. for 3 hrs and for 1 hr at room temperature. The reaction mixture was poured into saturated aqueous ammonium chloride, and extracted with ethyl acetate (2×). The combined organic layers were washed with water, saturated aqueous sodium chloride, dried (anhydrous sodium sulfate), filtered, and concentrated under reduced pressure. The crude residue was extracted with ethyl acetate/hexanes, filtering off solid precipitate, and the solution concentrated. The crude material was purified by silica gel chromatography (20-60% ethyl acetate/hexanes) followed by preparative HPLC(C18, 25-95% acetonitrile/water+0.1% diethylamine) to give a pale yellow oil (0.99 g). ¹H NMR (300 MHz, CDCl₃) δ 7.26-7.24 (d, 1H, J=8.1 Hz), 6.49-6.46 (dd, 1H, J=8.1, 2.4 Hz), 6.44-6.43 (d, 1H, J=2.4 Hz), 5.35-5.16 (m, 1H), 4.55-4.37 (dd, 2H, J=15.0, 38.4 Hz), 3.81 (s, 3H), 3.80 (s, 3H), 3.50-3.46 (m, 1H), 3.26-3.22 (m, 1H), 2.60-2.42 (m, 2H), 2.02-1.97 (m, 1H), 1.47-1.39 (m, 1H). ¹⁹F NMR (CDCl₃, 400 MHz) δ -156.7 (t, 1F, J=42 Hz). HPLC analysis: (C18, 10-95% acetonitrile in water+0.1% trifluoroacetic acid over 20 mins: retention time, % area at 254 nm): 13.5 min, 97%.

Preparation 76: 6-Fluoro-1,2-thiazinane-1,1-dioxide

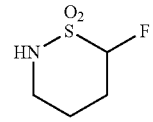

2-(2,4-Dimethoxybenzyl)-6-fluoro-1,2-thiazinane-1,1-dioxide (0.532 g, 1.8 mmol) in methylene chloride (40 mL) was cooled to 0° C. Trifluoroacetic acid (25 mL) was added and the resultant red solution stirred for 1.5 hrs at 0° C., concentrated under reduced pressure. The crude product was purified by silica gel chromatography (20-70% ethyl acetate/hexanes) to give a clear liquid (0.213 g, 79%). ¹H NMR (300 MHz, CDCl₃) δ 5.35-5.33 (dd, 0.5H, J=5.0, 2.4 Hz), 5.19-5.17 (t, 0.5H, J=3.6 Hz), 4.76 (br s, 1H), 3.52-3.32 (m, 2H), 2.56-2.40 (m, 2H), 1.91-1.81 (m, 1H), 1.59-1.52 (m, 1H).

Preparation 77: 2-(2,4-Dimethoxybenzyl)-6,6-difluoro-1,2-thiazinane-1,1-dioxide

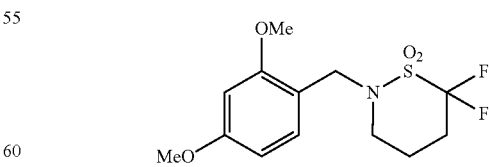

To a solution of 2-(2,4-dimethoxybenzyl)-6-fluoro-1,2-thiazinane-1,1-dioxide (0.500 g, 1.8 mmol) in anhydrous tetrahydrofuran (30 mL), cooled to -78° C., was slowly added 2.5 N n-butyl lithium in hexanes (1.262 mL, 3.2 mmol). The solution was stirred at -78° C. for 1 hr, a solution of N-fluorobenzene sulfonimide (1.243 g, 3.9 mmol) in anhydrous tetrahydrofuran (5 mL) was slowly added over 10 mins, and the mixture stirred at −78° C. for 3 hrs and at room temperature for 3 hrs. The reaction mixture was poured into saturated aqueous ammonium chloride and extracted with ethyl acetate (2×). The combined organic layers were washed with water, saturated aqueous sodium chloride, dried (anhydrous sodium sulfate), filtered, and concentrated in vacuo. The crude product was purified by silica gel chromatography (15-60% ethyl acetate/hexanes) to give a yellow oil (0.09 g). $^1$H NMR (CDCl$_3$, 300 MHz) δ 7.25-7.21 (d, 1H, J=8.4 Hz), 6.50-6.47 (dd, 1H, J=2.4, 8.4 Hz), 6.45-6.44 (d, 1H, J=2.4 Hz), 4.43 (s, 2H), 3.82 (s, 3H), 3.81 (s, 3H), 3.38-3.37 (t, 2H, J=5.1 Hz), 2.58-2.45 (m, 2H), 2.00-1.92 (m, 2H).

Preparation 78:
6,6-Difluoro-1,2-thiazinane-1,1-dioxide

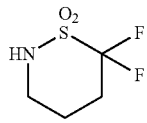

To a solution of 2-(2,4-dimethoxybenzyl)-6,6-difluoro-1,2-thiazinane-1,1-dioxide (0.090 g, 0.3 mmol) in methylene chloride (7 mL) was added trifluoroacetic acid (4 mL), and the resultant red solution stirred for 3 hrs at room temperature. The mixture was concentrated in vacuo to afford the crude residue. The crude product was purified by silica gel chromatography (10-60% ethyl acetate/hexanes) to give a clear oil (0.034 g). $^1$H NMR (CDCl$_3$, 300 MHz) δ 4.85 (br s, 1H), 3.46-3.40 (m, 2H), 2.60-2.47 (m, 2H), 2.01-1.93 (m, 2H).

Preparation 79:
N-(Furan-2-ylmethyl)propane-2-sulfonamide

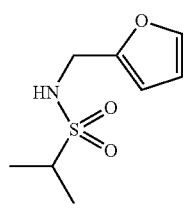

To a stirred solution of furfurylamine (1.040 g, 10.7 mmol) in pyridine (10 mL) at 0° C. was slowly added 2-propanesulfonyl chloride (1.0 mL, 8.9 mmol). The reaction mixture was warmed to room temperature and stirred for 16 hrs. The mixture was concentrated and the residue was dissolved in ethyl acetate. The organic layer was washed with 1N aqueous hydrochloric acid, saturated aqueous sodium bicarbonate, saturated aqueous sodium chloride, dried (anhydrous sodium sulfate), filtered, and concentrated in vacuo. The residue was purified by silica gel chromatography (0-50% ethyl acetate/hexanes) to afford the product (0.84 g, 46%) as a yellowish thick oil. $^1$H NMR (300 MHz, CDCl$_3$) δ 7.40 (dd, 1H, J=1.8, 0.9 Hz), 6.35 (dd, 1H, J=3.3, 1.8 Hz), 6.29 (d, 1H, J=3.3 Hz), 4.42 (br s, 1H), 4.33 (d, 2H, J=5.7 Hz), 3.08 (m, 1H), 1.35 (d, 6H, J=6.9 Hz).

Preparation 80:1,1,1-Trifluoro-N-(furan-2-ylmethyl)methanesulfonamide

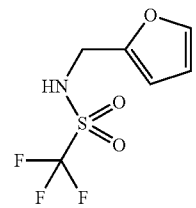

To a stirred solution of furfurylamine (0.899 g, 9.3 mmol) in pyridine (10 mL) at 0° C. was slowly added trifluoromethanesulfonyl chloride (1.300 g, 7.7 mmol). The reaction mixture was warmed to room temperature and stirred for 16 hrs. The mixture was concentrated and the residue was dissolved in ethyl acetate. The organic layer was washed with 1N aqueous hydrochloric acid, saturated aqueous sodium bicarbonate, saturated aqueous sodium chloride, dried (anhydrous sodium sulfate), filtered, and concentrated in vacuo. The residue was purified by silica gel chromatography (0-50% ethyl acetate/hexanes) to afford the product (1.5 g, 85%) as a yellowish oil. $^1$H NMR (300 MHz, CDCl$_3$) δ 7.43 (dd, 1H, J=1.8, 0.9 Hz), 6.38 (dd, 1H, J=3.3, 1.8 Hz), 6.36 (d, 1H, J=3.3 Hz), 5.10 (br s, 1H), 4.48 (s, 2H).

Preparation 81:
N-(Furan-2-ylmethyl)cyclohexanesulfonamide

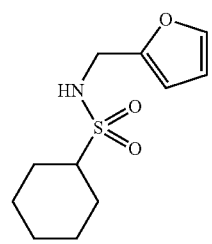 [SMILES: O=S(=O)(NCc1ccco1)C1CCCCC1]

To a stirred solution of furfurylamine (0.319 g, 3.3 mmol) in pyridine (5 mL) at 0° C. was slowly added cyclohexanesulfonyl chloride (0.500 g, 2.7 mmol). The reaction mixture was warmed to room temperature and stirred for 16 hrs. The mixture was concentrated and the residue was dissolved in ethyl acetate. The organic layer was washed with 1N aqueous hydrochloric acid, saturated aqueous sodium bicarbonate, saturated aqueous sodium chloride, dried (anhydrous sodium sulfate), filtered, and concentrated in vacuo. The residue was purified by silica gel chromatography (0-50% ethyl acetate/hexanes) to afford the product (0.325 g, 49%) as a white solid. $^1$H NMR (300 MHz, CDCl$_3$) δ 7.40 (dd, 1H, J=1.8, 0.9 Hz), 6.35 (dd, 1H, J=3.3, 2.1 Hz), 6.30 (d, 1H, J=3.0 Hz), 4.43 (m, 1H), 4.32 (d, 2H, J=5.7 Hz), 2.75 (tt, 1H, J=12.0, 3.3 Hz), 2.15-2.05 (m, 2H), 1.95-1.80 (m, 2H), 1.70 (m, 1H), 1.60-1.40 (m, 2H), 1.30-1.10 (m, 3H).

Preparation 82:
N-(Furan-2-ylmethyl)tetrahydrofuran-3-sulfonamide

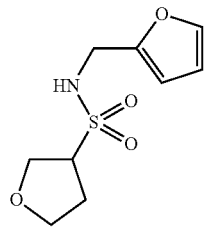 [SMILES: O=S(=O)(NCc1ccco1)C1CCOC1]

To a stirred solution of furfurylamine (0.171 g, 1.8 mmol) in pyridine (2 mL) at 0° C. was slowly added tetrahydrofuran-3-sulfonyl chloride (0.250 g, 1.5 mmol). The reaction mixture was warmed to room temperature and stirred for 16 hrs. The mixture was concentrated and the residue was dissolved in ethyl acetate. The organic layer was washed with 1N aqueous hydrochloric acid, saturated aqueous sodium bicarbonate, saturated aqueous sodium chloride, dried (anhydrous sodium sulfate), filtered, and concentrated in vacuo. The residue was purified by silica gel chromatography (0-50% ethyl acetate/hexanes) to afford the product (0.220 g, 65%) as a thick oil. $^1$H NMR (300 MHz, CDCl$_3$) δ 7.41 (s, 1H), 6.36 (dd, 1H, J=3.3, 2.1 Hz), 6.31 (d, 1H, J=3.3 Hz), 4.68 (t, 1H, J=5.4 Hz), 4.36 (d, 2H, J=6.0 Hz), 4.05 (dd, 1H, J=10.2, 5.7 Hz), 4.02-3.78 (m, 3H), 3.65 (m, 1H), 2.36-2.10 (m, 2H).

Preparation 83: 1,2,6-Thiadiazinane-1,1-dioxide

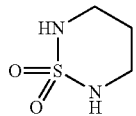

To a stirred mixture of 1,3-diaminopropane (1.0 mL, 11.9 mmol) in pyridine (20 mL) was added sulfamide (2.282 g, 23.7 mmol). The mixture was heated in an oil bath at 120° C. for 16 hrs. After cooling to room temperature, the mixture was concentrated and the residue partitioned between ethyl acetate and saturated aqueous sodium chloride. The organic layer was washed with 1N aqueous hydrochloric acid, saturated aqueous sodium chloride, dried (anhydrous sodium sulfate, filtered, and concentrated to afford a white solid (0.085 g, 5%). $^1$H NMR (300 MHz, CDCl$_3$) δ 4.26 (br s, 2H), 3.70-3.50 (m, 4H), 1.80-1.60 (m, 2H).

Preparation 84:
2-Methyl-1,2,6-thiadiazinane-1,1-dioxide

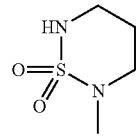

To a stirred mixture of N-methyl-1,3-diaminopropane (1.70 mL, 16.3 mmol) in pyridine (20 mL) was added sulfamide (1.877 g, 19.5 mmol). The mixture was heated in an oil bath at 120° C. for 16 hrs. After cooling to room temperature, the mixture was concentrated and the residue partitioned between ethyl acetate and saturated aqueous sodium chloride. The organic layer was washed with 1N aqueous hydrochloric acid, saturated aqueous sodium chloride, dried (anhydrous sodium sulfate, filtered, and concentrated to afford a colorless oil (1.3 g, 53%). $^1$H NMR (300 MHz, CDCl$_3$) δ 4.11 (br s, 1H), 3.60-3.48 (m, 2H), 3.32 (t, 2H, J=5.7 Hz), 2.78 (s, 3H), 1.85-1.72 (m, 2H).

Preparation 85: 3-Methoxycyclohexanamine

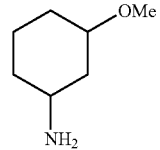

A mixture of 3-methoxycyclohexanecarboxylic acid, mixture of cis and trans 97% (1.50 g, 9.5 mmol), diphenylphosphoryl azide (2.043 mL, 9.5 mmol), and triethylamine (1.582 mL, 11.4 mmol) in anhydrous toluene (65 mL) was heated at reflux for 3 hrs. The mixture was cooled to 0° C., sodium trimethylsilanolate (18.964 mL of a 1 M solution in tetrahydrofuran, 19.0 mmol) was added, and the mixture stirred for 30 mins at room temperature. The reaction was quenched with 5% aqueous citric acid (100 mL), stirred, concentrated to approximately half volume under reduced pressure, washed with diethyl ether (2×), adjusted to basic pH with sodium hydroxide, and extracted with methylene chloride (3×). The combined organic layers were washed with saturated aqueous sodium chloride, dried (anhydrous sodium sulfate), filtered, and concentrated in vacuo. The crude material was purified by silica gel chromatography (5-12% methanol/methylene chloride) to give partially purified material. The residue was dissolved in methylene chloride and extracted with 1 N aqueous hydrochloric acid (3×). The combined aqueous layers were adjusted to basic pH with 15% aqueous sodium hydroxide and extracted with methylene chloride (3×). The combined organic fractions were dried (anhydrous sodium sulfate), filtered, concentrated, suspended in hexanes/methylene chloride, and filtered. Concentration of the organics gave a yellow liquid (0.272 g). ¹H NMR (300 MHz, CDCl₃) (mixture of diastereomers) δ 3.52 (m, 1H), 3.28 (s, 3H), 2.99 (m, 1H), 1.95-1.00 (m, 10H).

Preparation 86: 7-Oxabicyclo[2.2.1]heptan-2-amine

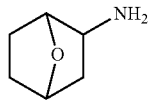

A mixture of 7-oxabicyclo[2.2.1]heptane-2 carboxylic acid (0.233 g, 1.6 mmol) in anhydrous toluene (10 mL), triethylamine (0.273 mL, 2.0 mmol), and diphenylphosphoryl azide (0.353 mL, 1.6 mmol) was heated at reflux temperature for 3 hrs, then cooled to 0° C. and sodium trimethylsilanolate (3.278 mL of a 1 M solution in tetrahydrofuran, 3.3 mmol) was added and stirred at room temperature for 1 hr. A solution of 5% aqueous citric acid (15 mL) was added and the mixture concentrated to approximately half the volume under reduced pressure. The mixture was washed with diethyl ether (2×), and once with ethyl acetate, and the aqueous layer was adjusted to basic pH with 15% aqueous sodium hydroxide and extracted with methylene chloride (3×). The combined organic layers were washed with saturated aqueous sodium chloride (+3 drops sodium hydroxide), dried (anhydrous sodium sulfate), filtered, and concentrated to give a clear liquid (0.121 g). ¹H NMR (300 MHz, CDCl₃) (mixture of diastereomers) δ 4.6-4.14 (m, 2H), 3.48-3.42 (m, 1H), 2.21-0.86 (m, 8H).

Preparation 87: Benzyl (3,3-difluorocyclobutyl)carbamate

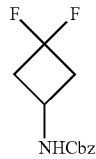

To a solution of benzyl (3-oxocyclobutyl)carbamate (0.900 g, 4.1 mmol) in anhydrous methylene chloride (9 mL) was added diethylaminosulfur trifluoride (2.170 mL, 16.4 mmol) dropwise. The resulting solution was stirred at room temperature for 16 hrs. The mixture was poured into cold saturated aqueous sodium bicarbonate and stirred for 5 mins. The mixture was extracted with methylene chloride (3×), and the combined organic layers successively washed with water, saturated aqueous sodium chloride, dried (anhydrous sodium sulfate), filtered, and concentrated in vacuo. The crude product was purified by silica gel chromatography (5-30% ethyl acetate/hexanes) to give a tan solid (0.6 g). ¹H NMR (300 MHz, CDCl₃) δ 7.36-7.34 (m, 5H), 5.10 (s, 2H), 4.99 (br m, 1H), 4.10 (m, 1H), 2.97 (m, 2H), 2.48 (m, 2H).

Preparation 88: 3,3-Difluorocyclobutanaminium chloride

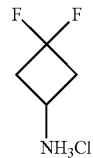

A suspension of benzyl (3,3-difluorocyclobutyl)carbamate (0.600 g, 2.5 mmol) and 10% palladium on carbon (0.350 g, 50% wet) in methanol (8 mL) was placed under an atmosphere of hydrogen. After 24 hrs, an additional 10% palladium on carbon (0.25 g, 50% wet) was added and the mixture stirred for a further 24 hrs. The reaction mixture was filtered through Celite, washing with methanol, and concentrated hydrochloric acid (0.3 mL) was added to the methanolic solution. The crude solution was concentrated under vacuum to give an off-white semi-solid (0.303 g). ¹H NMR (d6-DMSO, 300 MHz) δ 8.61 (br s, 3H), 3.65-3.58 (m, 1H), 2.93-2.81 (m, 4H).

Preparation 89: Benzyl (3-oxocyclohexyl)carbamate

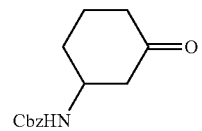

To a solution of 2-cyclohexen-1-one (1.442 g, 15.0 mmol) in anhydrous methylene chloride (15 mL) was added bis(acetonitrile)dichloro-palladium(II) (0.231 g, 1.0 mmol) and benzyl carbamate (1.497 g, 9.9 mmol) and stirred under nitrogen for 24 hrs. The reaction mixture was filtered through a pad of silica gel, washing with ethyl acetate, and concentrated in vacuo. The crude product was purified by silica gel chromatography (20-65% ethyl acetate/hexanes) to give a pale yellow low melting solid (1.9 g). ¹H NMR (300 MHz, CDCl₃) δ 7.34 (m, 5H), 5.09 (s, 2H), 4.81 (br s, 1H), 3.99 (br s, 1H), 2.73 (m, 1H), 2.36-2.26 (m, 3H), 2.11-1.97 (m, 2H), 1.67-1.64 (m, 2H). ESI m/z: 248.0 (M+H).

Preparation 90: Benzyl (3,3-difluorocyclohexyl)carbamate

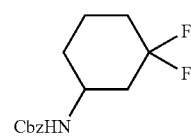 [SMILES: O=C(NC1CCCC(F)(F)C1)OCc1ccccc1]

To a solution of benzyl (3-oxocyclohexyl)carbamate (1.0 g, 4 mmol) in anhydrous dichloroethane (8 mL), was added Deoxo-Fluor® (1.1 mL) and the mixture was heated at 65° C. in a sealed vial for 16 hrs. The mixture was cooled to 0° C. and cold saturated aqueous sodium bicarbonate was added. The mixture was extracted with ethyl acetate (3×), and the combined organic layers washed with saturated aqueous sodium chloride, dried (anhydrous sodium sulfate), filtered, and concentrated in vacuo. The crude product was purified by silica gel chromatography (5-40% ethyl acetate/hexanes) to give a white solid (0.435 g). $^1$H NMR (300 MHz, CDCl$_3$) δ 7.41-7.28 (m, 5H), 5.09 (s, 2H), 4.89 (br s, 1H), 3.92 (br s, 1H), 2.34 (m, 1H), 2.05-1.67 (m, 6H), 1.40 (m, 1H). ESI (m/z): 269.9 (M+H).

Preparation 91: 3,3-Difluorocyclohexanaminium formate

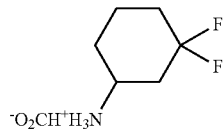

To a suspension of benzyl (3,3-difluorocyclohexyl)carbamate (0.43 g, 1.6 mmol) in 4% formic acid in methanol (25 mL) was added 10% palladium on carbon (0.4 g, 50% wet). The resulting mixture stirred under an atmosphere of hydrogen for 20 hrs. The mixture was filtered through Celite, washing with methanol, and concentrated under vacuum to give an off-white solid (0.3 g). $^1$H NMR (d6-DMSO, 300 MHz) δ 8.36 (s, 1H), 3.03 (m, 1H), 2.97 (m, 1H), 1.97-1.63 (m, 5H), 1.39-1.22 (m, 2H). $^{19}$F NMR (d6-DMSO, 400 MHz) −60.33-−60.97 (d, 1F, J=252 Hz), −70.73-71.54 (dt, 1F, J=252, 36 Hz). ESI (m/z) 136.2 (M+H).

Preparation 92: Benzyl 2-hydroxycyclohexylcarbamate

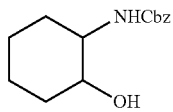

A solution of 2-aminocyclohexanol (3.524 g, 30.6 mmol) in anhydrous tetrahydrofuran (85 mL) was cooled to 0° C. and triethylamine (3.402 mL, 24.5 mmol) followed by benzyloxycarbonyl N-succinimide (6.100 g, 24.5 mmol) were added in portions. The resulting mixture was stirred at 0° C. and slowly warmed to room temperature and stirred for 16 hrs. The mixture was diluted with water and ethyl acetate, the organic layer isolated, and successively washed with 1 N aqueous hydrochloric acid (2×), saturated aqueous sodium bicarbonate, saturated aqueous sodium chloride, dried (anhydrous sodium sulfate), filtered, and concentrated in vacuo. The crude product was purified by silica gel chromatography (25-60% ethyl acetate/hexanes) to give a white solid (4.2 g). $^1$H NMR (400 MHz, CDCl$_3$) δ 7.35 (m, 5H), 5.09 (m, 3H), 3.96 (m, 1H), 3.67 (m, 1H), 1.82-1.28 (m, 8H).

Preparation 93: Benzyl (2-oxocyclohexyl)carbamate

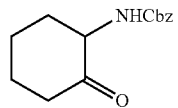 [SMILES: O=C(NC1CCCCC1=O)OCc1ccccc1]

Jones reagent was prepared with chromium trioxide (1.7 g) suspended in sulfuric acid (1.7 mL), which was added to cold water (13 mL) to make the active solution.

To a solution of benzyl (2-hydroxycyclohexyl)carbamate (4.200 g, 16.8 mmol) in acetone (15 mL) was added Jones reagent dropwise over several minutes (with room temperature water bath cooling of reaction), and the reaction mixture was stirred at room temperature for 2.5 hrs. Solutions of saturated aqueous sodium carbonate and then saturated aqueous sodium bicarbonate were added until the solution was adjusted to neutral pH, and the resulting mixture extracted with ethyl acetate (3×). The combined organic layers were washed with saturated aqueous sodium chloride, dried (anhydrous sodium sulfate), filtered, and concentrated in vacuo. The crude product was purified by silica gel chromatography (10-50% ethyl acetate/hexanes) to give a clear liquid (3.3 g). $^1$H NMR (300 MHz, CDCl$_3$) δ 7.36-7.29 (m, 5H), 5.75 (br s, 1H), 5.10 (s, 2H), 4.29-4.25 (m, 1H), 2.65 (m, 1H), 2.57-2.50 (m, 1H), 2.43-2.33 (m, 1H), 2.17-2.10 (m, 1H), 1.88-1.60 (m, 3H), 1.48-1.34 (m, 1H). ESI (m/z): 248.0 (M+H).

Preparation 94: Benzyl (2,2-difluorocyclohexyl)carbamate

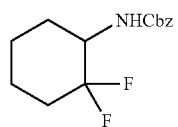 [SMILES: O=C(NC1CCCCC1(F)F)OCc1ccccc1]

To a solution of benzyl (2-oxocyclohexyl)carbamate (1.25 g, 5.0 mmol) in anhydrous methylene chloride (20 mL) was added diethylaminosulfur trifluoride (2 mL) and the resulting solution was stirred at room temperature for 16 hrs. The reaction mixture was cooled to 0° C. and poured into cold saturated aqueous sodium bicarbonate. The mixture was extracted with ethyl acetate (3×) and the organic layers washed with saturated aqueous sodium bicarbonate, saturated aqueous sodium chloride, dried (anhydrous sodium sulfate), filtered, and concentrated in vacuo. The crude product was purified by silica gel chromatography (5-55% ethyl acetate/hexanes) to give a yellow solid. This material was recrystallized from diethyl ether/hexanes to give a white solid (0.227 g). $^1$H NMR (CDCl$_3$, 300 MHz) δ 7.41-7.25 (m, 5H), 5.17-5.07 (m, 2H), 4.99 (m, 1H), 3.99-3.85 (m, 1H), 2.20-2.16 (m, 1H), 2.00 (m, 1H), 1.78-1.38 (m, 6H). ESI (m/z): 269.9 (M+H).

Preparation 95: 2,2-Difluorocyclohexanaminium formate

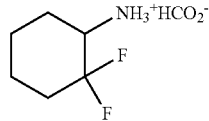

To a solution of benzyl (2,2-difluorocyclohexyl)carbamate (0.200 g, 0.7 mmol) in 4% formic acid in methanol (10 mL) was added 10% palladium on carbon (0.15 g, 50% wet). The reaction mixture was stirred under an atmosphere of hydrogen for 18 hrs, filtered through Celite, washing with methanol, and concentrated under vacuum to give an off-white solid (0.1 g). $^1$H NMR (d6-DMSO, 300 MHz) δ 8.21 (s, 1H), 3.03-2.95 (m, 1H), 2.07-2.04 (m, 1H), 1.76-1.34 (m, 7H). ESI (m/z): 136.2 (M+H).

Preparation 96: N-Propylmethanesulfonamide

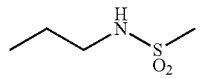

To a cooled, 0° C., solution of 1-propylamine (1.0 g, 16.9 mmol) and triethylamine (2.587 mL, 18.6 mmol) in anhydrous methylene chloride (30 mL) was added methanesulfonyl chloride (1.309 mL, 16.9 mmol) dropwise. The reaction mixture was allowed to slowly warm to room temperature & stirred for 16 hrs. The mixture was diluted with ethyl acetate and successively washed with 1.0 N aqueous hydrochloric acid, saturated aqueous sodium bicarbonate, saturated aqueous sodium chloride, dried (anhydrous sodium sulfate), filtered, and concentrated to give pure product (1.730 g, 75%). $^1$H NMR (CDCl$_3$, 300 MHz) δ 4.49 (br s, 1H), 3.12-3.08 (q, 2H, J=7.5 Hz), 1.67-1.54 (sext, 2H, J=7.5 Hz), 0.99-0.94 (t, 3H, J=7.5 Hz).

Preparation 97: N-Ethylmethanesulfonamide

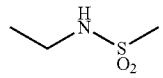

To a cooled, 0° C., solution of ethylamine (0.763 g, 16.9 mmol) in anhydrous methylene chloride (20 mL), was added triethylamine (2.587 mL, 18.6 mmol) and methanesulfonyl chloride (1.309 mL, 16.9 mmol) dropwise. The mixture was allowed to slowly warm to room temperature and stirred for 16 hrs. The resulting mixture was diluted with ethyl acetate and washed with 1 N aqueous hydrochloric acid (2×), saturated aqueous sodium bicarbonate, and saturated aqueous sodium chloride. The organic layer was dried (anhydrous sodium sulfate), filtered, and concentrated to give a semi-solid (0.633 g, 30%). $^1$HNMR (CDCl$_3$, 300 MHz) δ 4.60 (br s, 1H), 3.21-3.12 (qd, 2H, J=6.0, 7.2 Hz), 1.28-1.19 (t, 3H, J=7.2 Hz).

Preparation 98: 2-Methyl-1,2,5-thiadiazolidine-1,1-dioxide

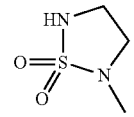

To a stirred mixture of N-methylethylenediamine (1.200 g, 16.2 mmol) in pyridine (20 mL) was added sulfamide (1.867 g, 19.4 mmol). The mixture was heated in an oil bath at 120° C. for 16 hrs. After cooling to room temperature, the mixture was concentrated and the residue was partitioned between ethyl acetate and saturated aqueous sodium chloride. The organic layer was washed with 1 N aqueous hydrochloric acid, saturated aqueous sodium chloride, dried (anhydrous sodium sulfate), filtered, and concentrated to afford a colorless oil (0.61 g, 28%). $^1$H NMR (300 MHz, CDCl$_3$) δ 4.30 (br s, 1H), 3.53 (m, 2H), 3.40 (m, 2H), 2.76 (s, 3H).

Preparation 99: 2-Benzyl-1,2,5-thiadiazolidine-1,1-dioxide

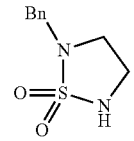

To a stirred mixture of N-benzylethylenediamine (2.000 g, 13.3 mmol) in pyridine (20 mL) was added sulfamide (1.919 g, 20.0 mmol). The mixture was heated in an oil bath at 120° C. for 16 hrs. After cooling to room temperature, the mixture was concentrated and the residue was partitioned between ethyl acetate and saturated aqueous sodium chloride. The organic layer was washed with 1 N aqueous hydrochloric acid, saturated aqueous sodium chloride, dried (anhydrous sodium sulfate), filtered, and concentrated. The residue was purified by silica gel chromatography (0-80% ethyl acetate/hexanes) to afford the product as a light yellow thick oil (1.4 g, 50%). $^1$H NMR (300 MHz, CDCl$_3$) δ 7.40-7.30 (m, 5H), 4.38 (br s, 1H), 4.20 (s, 2H), 3.50 (q, 2H, J=6.6 Hz), 3.29 (t, 2H, J=6.6 Hz).

Preparation 100: 1,2,5-Thiadiazolidine-1,1-dioxide

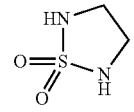

A mixture of 2-benzyl-1,2,5-thiadiazolidine-1,1-dioxide (1.000 g, 4.7 mmol) and 20% palladium hydroxide (0.200 g) in methanol (20 mL) was stirred under a hydrogen atmosphere (1 atm) for 16 hrs. The mixture was filtered through Celite and the filtrate concentrated to afford a white solid (0.570 g, 99%). $^1$H NMR (300 MHz, d6-DMSO) δ 6.68 (s, 2H), 3.30-3.25 (m, 4H).

Preparation 101: 2-(2,4-Dimethoxybenzyl)-5-methylisothiazolidine-1,1-dioxide

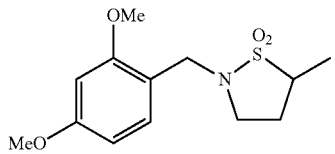 [SMILES: COc1ccc(CN2CCC(C)S2(=O)=O)c(OC)c1]

To a −78° C. solution of 2-(2,4-dimethoxybenzyl)isothiazolidine-1,1-dioxide (0.600 g, 2.2 mmol) in anhydrous tetrahydrofuran (29 mL) was slowly added n-butyl lithium (1.725 mL of a 2.5 N solution in hexanes, 4.3 mmol). The reaction mixture was stirred for 1 hr at −78° C., iodomethane (0.688 mL, 11.1 mmol) was added, and the resulting mixture stirred for 2.5 hrs at −78° C. and 30 mins at room temperature. The mixture was poured into saturated aqueous ammonium chloride and extracted with ethyl acetate. The organic layer was washed with saturated aqueous sodium chloride, dried (anhydrous sodium sulfate), filtered, and concentrated in vacuo. The crude material was purified by silica gel chromatography (20-60% ethyl acetate/hexanes) to give the product as a clear oil (0.3 g). $^1$H NMR (CDCl$_3$, 300 MHz) δ 7.25-7.22 (d, 1H, J=8.1 Hz), 6.48-6.43 (m, 2H), 4.27-4.13 (q, 2H, J=14.1 Hz), 3.80 (s, 3H), 3.79 (s, 3H), 3.25-3.02 (m, 3H), 2.43-2.32 (m, 1H), 1.95-1.83 (m, 1H), 1.42-1.40 (d, 3H, J=6.6 Hz).

Preparation 102: 2-(2,4-Dimethoxybenzyl)-5,5-dimethylisothiazolidine-1,1-dioxide

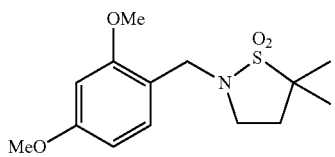 [SMILES: COc1ccc(CN2CCC(C)(C)S2(=O)=O)c(OC)c1]

Using the above procedure, the title compound was also obtained as a clear oil (0.237 g). $^1$H NMR (CDCl$_3$, 300 MHz) δ 7.26-7.23 (d, 1H, J=7.8 Hz), 6.48-6.43 (m, 2H), 4.23 (s, 2H), 3.80 (s, 6H), 3.07-3.03 (t, 2H, J=7.1 Hz), 2.10-2.05 (t, 2H, J=6.9 Hz), 1.42 (s, 3H).

Preparation 103: 5-Methylisothiazolidine-1,1-dioxide

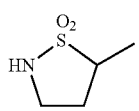

To a 0° C. solution of 2-(2,4-dimethoxybenzyl)-5-methylisothiazolidine-1,1-dioxide (0.292 g, 1.0 mmol) in methylene chloride (10 mL) was added trifluoroacetic acid (5.000 mL, 67.3 mmol) and the resulting red solution was stirred at 0° C. for 3 hrs, and concentrated in vacuo. The crude product was purified by silica gel chromatography (30-75% ethyl acetate/hexanes) to give a clear oil (0.117 g, 90%). $^1$HNMR (CDCl$_3$, 300 MHz) 4.38 (br s, 1H), 3.38-3.32 (m, 2H), 3.21-3.14 (m, 1H), 2.60-2.47 (m, 1H), 2.13-2.00 (m, 1H), 1.43-1.40 (d, 3H, J=7.2 Hz).

Preparation 104: 5,5-Dimethylisothiazolidine-1,1-dioxide

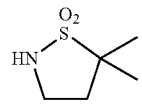

To a 0° C. solution of 2-(2,4-dimethoxybenzyl)-5,5-dimethylisothiazolidine-1,1-dioxide (0.220 g, 0.7 mmol) in methylene chloride (10 mL) was added trifluoroacetic acid (3.591 mL, 48.3 mmol) and the resulting red solution was stirred at 0° C. for 3 hrs and concentrated under reduced pressure. The crude product was purified by silica gel chromatography (20-80% ethyl acetate/hexanes) to give a clear oil (0.087 g, 86%). $^1$HNMR (300 MHz, CDCl$_3$) δ 4.61 (br s, 1H), 3.32-3.26 (td, 2H, J=5.1, 7.1 Hz), 2.25-2.20 (t, 2H, J=7.2 Hz), 1.43 (s, 6H).

Preparation 105: N-Allylethenesulfonamide

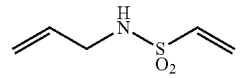

To a cooled, 0° C., solution of allylamine (1.926 g, 33.7 mmol) and triethylamine (12.789 mL, 92.0 mmol) in anhydrous methylene chloride (50 mL) was slowly added a solution of 2-chloroethanesulfonyl chloride (5.000 g, 30.7 mmol) in methylene chloride (10 mL). The resulting mixture was allowed to warm to room temperature and stirred for 4 hrs. The mixture was successively extracted with 1 N aqueous hydrochloric acid (2×), water, saturated aqueous sodium chloride, dried (anhydrous sodium sulfate), filtered, and concentrated to give a yellow liquid. $^1$H NMR (300 MHz, CDCl$_3$) δ 6.57-6.48 (dd, 1H, J=9.9, 16.8 Hz), 6.28-6.22 (d, 1H, J=16.8 Hz), 5.96-5.92 (d, 1H, J=9.6 Hz), 5.90-5.77 (m, 1H), 5.30-5.29 (m, 1H), 5.24-5.17 (m, 1H), 4.44 (br s, 1H), 3.69-3.64 (tt, 2H, J=1.5, 6.0 Hz).

Preparation 106: 2,3-Dihydroisothiazole-1,1-dioxide

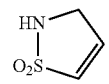

A solution N-allylethenesulfonamide (0.700 g, 4.8 mmol) in anhydrous methylene chloride (7 mL) was placed under argon, and (1,3-bis(2,4,6-trimethylphenyl)-2-imidazolidinylidene)dichloro(phenylmethylene)(tricyclohexylphosphine)ruthenium (0.02 g) was added. The mixture was heated to reflux under and additional portions (0.02 g each) of (1,3-bis(2,4,6-trimethylphenyl)-2-imidazolidinylidene)dichloro (phenylmethylene)(tricyclohexylphosphine)ruthenium were added at 30 min intervals, until a total of 0.1 g (2.5 mol %) had been added. The reaction was refluxed for a total of 6 hrs, cooled to room temperature, and concentrated in vacuo. The crude material was purified by silica gel chromatography (50-100% ethyl acetate/hexanes) to give a brown oil (0.46 g). $^1$H NMR (CDCl$_3$, 300 MHz) δ 6.90-6.86 (dt, 1H, J=2.4, 6.6 Hz), 6.75-6.6.71 (dt, 1H, J=2.4, 6.3 Hz), 4.92 (br s, 1H), 4.15-4.12 (m, 2H).

Preparation 107:
4-Methoxyisothiazolidine-1,1-dioxide

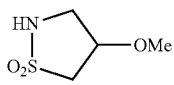

To a solution of 2,3-dihydroisothiazole-1,1-dioxide (0.100 g, 0.8 mmol) in methanol (1 mL) was added 25% sodium methoxide in methanol (0.181 g, 0.8 mmol) and the solution stirred at 60° C. for 2 hrs and at 70° C. for 3 hrs. The mixture was concentrated and suspended in 1 N aqueous hydrochloric acid. The aqueous mixture was extracted with ethyl acetate (3×), and the organic layers dried (anhydrous sodium sulfate), filtered, and concentrated in vacuo. The crude material was purified by silica gel chromatography (0-6% methanol/methylene chloride) to give the product (0.011 g, 13%). $^1$H NMR (300 MHz, CDCl$_3$) δ 4.53 (br s, 1H), 4.33-4.29 (m, 1H), 3.48-3.30 (m, 3H), 3.37 (s, 3H), 3.19-3.13 (m, 1H). $^{13}$C NMR (100 MHz, CDCl$_3$) δ 80.8, 57.1, 53.3, 48.7.

Preparation 108: 2-(2,4-Dimethoxybenzyl)-5,5-difluoroisothiazolidine-1,1-dioxide

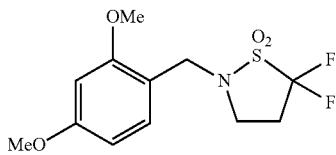 [SMILES: COc1ccc(CN2CCC(F)(F)S2(=O)=O)c(OC)c1]

To a solution of 2-(2,4-dimethoxybenzyl)-5-fluoroisothiazolidine-1,1-dioxide (5.700 g, 19.7 mmol) in anhydrous tetrahydrofuran (225 mL), cooled to −78° C., was slowly added n-butyl lithium (14.973 mL of a 2.5 N solution in hexanes, 37.4 mmol) and the resulting dark orange/red solution stirred for 1 hr. A solution of N-fluorobenzene sulfonamide (14.6 g, 46.3 mmol) in anhydrous tetrahydrofuran (60 mL) was added slowly over 30 mins, stirring at −78° C. for 3 hrs and at room temperature for 2.5 hrs. The reaction was poured into saturated aqueous ammonium chloride, diluted with ethyl acetate, and the organic layer isolated. The organic layer was washed with saturated aqueous sodium chloride, dried (anhydrous sodium sulfate), filtered, and concentrated in vacuo. The crude material was suspended in methylene chloride and filtered through a pad of silica gel, washing with methylene chloride, and concentrating the solution. The crude material was purified by silica gel chromatography (20-75% ethyl acetate/hexanes) and then by preparative HPLC (C18, 32-95% acetonitrile/water over 17 mins) to give a tan oil (0.106 g, 2%). $^1$H NMR (CDCl$_3$, 300 MHz) δ 7.21-7.18 (d, 1H, J=8.4 Hz), 6.49-6.45 (m, 2H), 4.28 (s, 2H), 3.82 (s, 3H), 3.14 (s, 3H), 3.19-3.15 (m, 2H), 2.70-2.55 (m, 2H).

Preparation 109:
5,5-Difluoroisothiazolidine-1,1-dioxide

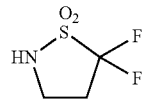

To a 0° C. solution of 2-(2,4-dimethoxybenzyl)-5,5-difluoroisothiazolidine-1,1-dioxide (0.100 g, 0.3 mmol) in methylene chloride (6 mL) was added trifluoroacetic acid (2.182 mL, 29.4 mmol). The resulting red/purple solution was stirred at 0° C. for 3.5 hrs and concentrated in vacuo. The crude material was purified by silica gel chromatography (30-75% ethyl acetate/hexanes) to give a tan oil (0.036 g). $^1$H NMR (CDCl$_3$, 300 MHz) δ 4.78 (br s, 1H), 3.46-3.40 (q, 2H, J=6.6 Hz), 2.79-2.65 (m, 2H). $^{19}$F NMR (CDCl$_3$, 282 MHz)-105.96-106.07 (t, J=15.4 Hz).

Preparation 110: 3-(1,1-Dioxidoisothiazolidin-2-yl)-3-methylbutan-2-one

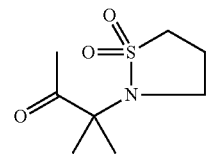

A mixture of 2-(2-methylbut-3-yn-2-yl)isothiazolidine-1,1-dioxide (3.500 g, 18.7 mmol) and mercury(II) oxide (0.810 g, 3.7 mmol) in methanol (100 mL) and 2 N aqueous sulfuric acid (50 mL) was heated at 90° C. for 3 hrs. The reaction mixture was filtered through Celite and the filtrate concentrated in vacuo. The residue was treated with water and extracted with ethyl acetate. The organic layer was washed with saturated aqueous sodium chloride, dried (anhydrous sodium sulfate, filtered, and concentrated in vacuo. The residue was purified by silica gel chromatography (0-100% ethyl acetate/hexanes) to afford the desired product as a yellow oil (1.65 g, 43%). $^1$H NMR (300 MHz, CDCl$_3$) δ 3.38 (t, 2H, J=6.6 Hz), 3.21 (t, 2H, J=7.5 Hz), 2.42-2.30 (m, 2H), 2.28 (s, 3H), 1.60 (s, 6H).

Preparation 111: 2-(2-(2-Methyloxiran-2-yl)propan-2-yl)isothiazolidine-1,1-dioxide

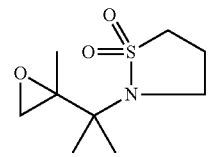

To a stirred suspension of 60% sodium hydride in mineral oil (0.039 g, 1.0 mmol) in anhydrous dimethyl sulfoxide (5 mL), under nitrogen, was added trimethylsulfoxonium iodide (0.214 g, 1.0 mmol). The mixture was stirred at 70° C. for 1 hr and then cooled to room temperature. 3-(1,1-Dioxidoisothiazolidin-2-yl)-3-methylbutan-2-one (0.100 g, 0.5 mmol) was added and the reaction mixture was stirred at room temperature for 16 hrs and then heated at 70° C. for 4 hrs. The mixture was cooled to 0° C. and quenched with water and extracted with ethyl acetate. The organic layer was washed with saturated aqueous sodium chloride, dried (anhydrous sodium sulfate), filtered, and concentrated in vacuo. The residue was purified by silica gel chromatography (0-80% ethyl acetate/hexanes) to afford the product as a thick oil (0.065 g, 61%). $^1$H NMR (300 MHz, CDCl$_3$) δ 3.52-3.12 (m, 4H), 2.76 (d, 1H, J=4.5 Hz), 2.54 (d, 1H, J=4.5 Hz), 2.42-2.20 (m, 2H), 1.60 (s, 3H), 1.43 (s, 3H), 1.35 (s, 3H).

Preparation 112:
N-(1-Methylcyclobutyl)methanesulfonamide

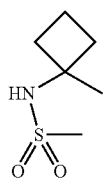

To a stirred solution of 1-methyl-cyclobutylamine hydrochloride (0.100 g, 0.8 mmol) in pyridine (1 mL) was added methanesulfonyl chloride (0.095 mL, 1.2 mmol). The reaction mixture was stirred at room temperature for 16 hrs. The mixture was diluted with ethyl acetate and washed with 2 N aqueous hydrochloric acid, saturated aqueous sodium bicarbonate, saturated aqueous sodium chloride, dried (anhydrous sodium sulfate), filtered, and concentrated to afford the product as a brown oil (0.090 g, 67%). $^1$H NMR (300 MHz, CDCl$_3$) δ 4.49 (br s, 1H), 3.03 (s, 3H), 2.40-2.25 (m, 2H), 2.12-2.00 (m, 2H), 1.95-1.75 (m, 2H), 1.58 (s, 3H).

Preparation 113:
N-(1-Methylcyclopropyl)methanesulfonamide

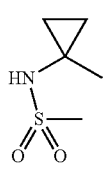

To a stirred solution of 1-methylcyclopropan-1-amine hydrochloride (0.100 g, 0.9 mmol) in pyridine (1 mL) was added methanesulfonyl chloride (0.108 mL, 1.4 mmol). The reaction mixture was stirred at room temperature for 16 hrs. The mixture was diluted with ethyl acetate and washed with 2 N aqueous hydrochloric acid, saturated aqueous sodium bicarbonate, saturated aqueous sodium chloride, dried (anhydrous sodium sulfate), filtered, and concentrated to afford the product as a yellow oil (0.105 g, 76%). $^1$H NMR (300 MHz, CDCl$_3$) δ 4.68 (br s, 1H), 3.02 (s, 3H), 1.50 (s, 3H), 1.02-0.94 (m, 2H), 0.71-0.64 (m, 2H).

Preparation 114:
N-(3-Methylcyclobutyl)methanesulfonamide

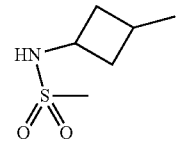

To a stirred solution of 3-methylcyclobutanamine hydrochloride (0.100 g, 0.8 mmol) in pyridine (1 mL) was added methanesulfonyl chloride (0.095 mL, 1.2 mmol). The reaction mixture was stirred at room temperature for 16 hrs. The mixture was diluted with ethyl acetate and washed with 2 N aqueous hydrochloric acid, saturated aqueous sodium bicarbonate, saturated aqueous sodium chloride, dried (anhydrous sodium sulfate), filtered, and concentrated to afford the product as a brown solid (0.125 g, 93%). The material was used without further purification.

Preparation 115:
N-(2-Methylcyclopentyl)methanesulfonamide

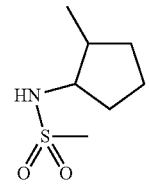

To a stirred solution of 2-methylcyclopentanamine hydrochloride (0.100 g, 0.7 mmol) in pyridine (1 mL) was added methanesulfonyl chloride (0.095 mL, 1.2 mmol). The reaction mixture was stirred at room temperature for 16 hrs. The mixture was diluted with ethyl acetate and washed with 2 N aqueous hydrochloric acid, saturated aqueous sodium bicarbonate, saturated aqueous sodium chloride, dried (anhydrous sodium sulfate), filtered, and concentrated to afford the product as a brown solid (0.100 g, 84%). The material was used without further purification.

Preparation 116:
N-(2-Methylallyl)ethenesulfonamide

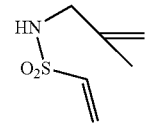

To a stirred solution of 2-methylprop-2-en-1-amine (0.500 g, 7.0 mmol), N,N-diisopropylethylamine (3.486 mL, 21.1 mmol) and N,N-4-dimethylaminopyridine (0.043 g, 0.4 mmol) in methylene chloride (20 mL) at 0° C. was slowly added 2-chloroethanesulfonyl chloride (0.734 mL, 7.0 mmol). The reaction mixture was slowly warmed to room temperature and stirred for 16 hrs. The mixture was concentrated and the residue purified by silica gel chromatography (0-80% ethyl acetate/hexanes) to afford the product as a colorless oil (0.59 g, 52%). $^1$H NMR (300 MHz, CDCl$_3$) δ 6.54 (dd, 1H, J=16.5, 9.6 Hz), 6.27 (d, 1H, J=16.5 Hz), 5.96 (d, 1H, J=9.6 Hz), 4.97 (s, 1H), 4.93 (s, 1H), 4.37 (br s, 1H), 3.60 (d, 2H, J=6.3 Hz), 1.79 (s, 3H).

Preparation 117:
4-Methyl-2,3-dihydroisothiazole-1,1-dioxide

A solution of N-(2-methylallyl)ethenesulfonamide (0.700 g, 4.3 mmol) in anhydrous methylene chloride (10 mL) was stirred under argon and (1,3-bis(2,4,6-trimethylphenyl)-2-imidazolidinylidene)dichloro(phenylmethylene)(tricyclohexylphosphine)ruthenium (0.02 g) was added. The mixture was heated to reflux under and additional portions (0.02 g each) of (1,3-bis(2,4,6-trimethylphenyl)-2-imidazolidinylidene)dichloro(phenylmethylene)(tricyclohexylphosphine)ruthenium were added at 30 min intervals, until a total of 0.1 g (2.5 mol %) had been added. The reaction was refluxed for a total of 72 hrs, cooled to room temperature, and concentrated in vacuo. The crude material was purified by silica gel chromatography (0-100% ethyl acetate/hexanes) to afford the desired product as a brown oil (0.380 g, 66%). $^1$H NMR (CDCl$_3$, 300 MHz) δ 6.45 (s, 1H), 4.55 (br s, 1H), 3.99 (m, 2H), 2.06 (s, 3H).

Preparation 118:
4-Methylisothiazolidine-1,1-dioxide

A mixture of 4-methyl-2,3-dihydroisothiazole-1,1-dioxide (0.380 g, 2.9 mmol) and 20% palladium hydroxide on carbon (0.050 g) in methanol (10 mL) was stirred under a hydrogen atmosphere for 2 hrs. The mixture was filtered through Celite and the filtrate concentrated to afford the product as a brown oil (0.385 g, 100%). $^1$H NMR (300 MHz, CDCl$_3$) δ 4.25 (br s, 1H), 3.53 (m, 1H), 3.34 (dd, 1H, J=12.0, 7.5 Hz), 3.05-2.70 (m, 3H), 1.27 (d, 3H, J=6.6 Hz).

Preparation 119:
N-(1-Methylcyclopentyl)methanesulfonamide

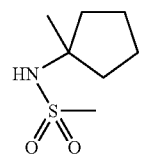

To a stirred solution of 1-amino-1-methylcyclopentane hydrochloride (0.165 g, 1.2 mmol) in pyridine (1 mL) was added methanesulfonyl chloride (0.169 mL, 2.2 mmol). The reaction mixture was stirred at room temperature for 16 hrs and then concentrated. The mixture was diluted with ethyl acetate and washed with 1 N aqueous hydrochloric acid, saturated aqueous sodium bicarbonate, saturated aqueous sodium chloride, dried (anhydrous sodium sulfate), filtered, and concentrated to afford the product as a brown oil (0.100 g, 46%). $^1$H NMR (300 MHz, CDCl$_3$) δ 4.27 (br s, 1H), 3.04 (s, 3H), 2.00-1.60 (m, 8H), 1.50 (s, 3H).

Preparation 120:
N-(3-Methoxycyclohexyl)methanesulfonamide

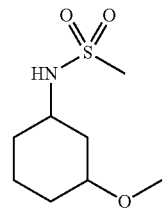

To a stirred solution of 3-methoxycyclohexanamine (0.200 g, 1.5 mmol) in pyridine (1 mL) was added methanesulfonyl chloride (0.144 mL, 1.9 mmol). The reaction mixture was stirred at room temperature for 16 hrs and then concentrated. The mixture was diluted with ethyl acetate and washed with 1 N aqueous hydrochloric acid, saturated aqueous sodium bicarbonate, saturated aqueous sodium chloride, dried (anhydrous sodium sulfate), filtered, and concentrated to afford the product as a brown oil (0.140 g, 44%). The material was used without further purification.

Preparation 121: N1-Cyclobutylethane-1,2-diamine

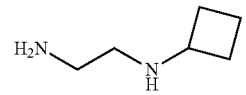

To a solution of cyclobutanone (5.830 g, 83.2 mmol), ethylenediamine (39.711 mL, 594.0 mmol), acetic acid (34.006 mL, 594.0 mmol), and 4 Å molecular sieves (25 g) in anhydrous methanol (250 mL) was added sodium cyanoborohydride (7.466 g, 118.8 mmol). The mixture was stirred for 48 hrs, filtered to remove the solids, and concentrated in vacuo. The residue was dissolved in 3 N aqueous sodium hydroxide (300 mL) and extracted with methylene chloride (3×500 mL). The combined organic layers were washed with basic saturated aqueous sodium chloride, dried (anhydrous sodium sulfate), filtered, and concentrated to give the crude product. The material was vacuum distilled to give the desired product as a clear liquid (4.8 g, 50%). $^1$H NMR (300 MHz, CDCl$_3$) δ

3.24-3.17 (m, 1H), 2.76-2.72 (t, 2H, J=6.0 Hz), 2.57-2.53 (td, 2H, J=0.8, 6.0 Hz), 2.23-2.14 (m, 2H), 1.71-1.58 (m, 4H), 1.22 (br s, 3H).

Preparation 122: N1-Cyclopentylethane-1,2-diamine

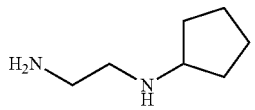

To a solution of cyclopentanone (2.000 mL, 22.6 mmol), ethylenediamine (10.860 g, 180.7 mmol), acetic acid (10.345 mL, 180.7 mmol), and 4 Å molecular sieves (10 g) in anhydrous methanol (113 mL) was added sodium cyanoborohydride (2.839 g, 45.2 mmol). The mixture was stirred for 48 hrs, filtered to remove the solids, and concentrated in vacuo. The residue was dissolved in 3 N aqueous sodium hydroxide (150 mL) and extracted with methylene chloride (3×300 mL). The combined organic layers were washed with basic saturated aqueous sodium chloride, dried (anhydrous sodium sulfate), filtered, and concentrated to give the crude product. The material was vacuum distilled to give the desired product as a clear liquid (1.0 g, 35%). $^1$H NMR (300 MHz, CDCl$_3$) δ 3.08-2.99 (quint, 1H, J=6.8 Hz), 2.80-2.76 (t, 2H, J=5.9 Hz), 2.65-2.61 (t, 2H, J=5.9 Hz), 1.87-1.77 (m, 2H), 1.72-1.60 (m, 2H), 1.57-1.46 (m, 2H), 1.35-1.24 (m, 5H).

Preparation 123: N1-Cyclohexylethane-1,2-diamine

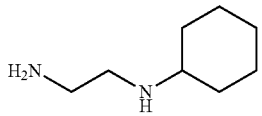

To a solution of cyclohexanone (6.260 g, 63.8 mmol), ethylenediamine (42.640 mL, 637.8 mmol), acetic acid (36.515 mL, 637.8 mmol), and 4 Å molecular sieves (25 g) in anhydrous methanol (250 mL) was added sodium cyanoborohydride (8.017 g, 127.6 mmol). The mixture was stirred for 48 hrs, filtered to remove the solids, and concentrated in vacuo. The residue was dissolved in 3 N aqueous sodium hydroxide (150 mL) and extracted with methylene chloride (3×300 mL). The combined organic layers were washed with basic saturated aqueous sodium chloride, dried (anhydrous sodium sulfate), filtered, and concentrated to give the crude product. The material was vacuum distilled to give the desired product as a clear liquid (4.1 g, 45%). $^1$H NMR (300 MHz, CDCl$_3$) δ 2.80-2.76 (td, 2H, J=0.9, 6.0 Hz), 2.68-2.64 (td, 2H, J=0.9, 6.0 Hz), 2.43-2.34 (m, 1H), 1.89-1.83 (m, 2H), 1.74-1.70 (m, 2H), 1.62-1.57 (m, 1H), 1.32-0.98 (m, 8H).

Preparation 124: 3-(Cyclobutylamino)propanenitrile

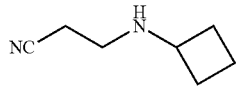

At room temperature, cyclobutylamine (5.90 mL, 59.8 mmol) was added dropwise, over 15 mins, to a solution of acrylonitrile (4.76 g, 89.7 mmol) in methanol (7 mL). The mixture was stirred at room temperature for 30 mins and at reflux for 1 hr, cooled to room temperature, concentrated under reduced pressure. The desired product was obtained by distillation under vacuum to provide a clear liquid (7.7 g, 98%). $^1$H NMR (CDCl$_3$, 300 MHz) δ 3.29-3.21 (m, 1H), 2.88-2.83 (t, 2H, J=6.6 Hz), 2.50-2.46 (t, 2H, J=6.6 Hz), 2.26-2.20 (m, 2H), 1.76-1.63 (m, 4H), 1.30 (br s, 1H).

Preparation 125: N1-Cyclobutylpropane-1,3-diamine

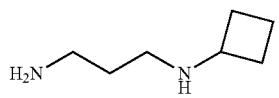

To a cooled (0° C.) suspension of lithium aluminum hydride (3.056 g, 80.5 mmol) in anhydrous diethyl ether (120 mL) was added a solution of 3-(cyclobutylamino)propanenitrile (5.000 g, 40.3 mmol) in anhydrous diethyl ether (40 mL), dropwise over 45 mins. The reaction mixture was stirred at room temperature for 15 mins and at reflux for 4 hrs, cooled to room temperature and stirred for 1 hr. The mixture was cooled to 0° C. and vigorously stirred while water (3.1 mL) was added dropwise, followed by 15% aqueous sodium hydroxide (3.1 mL), and finally water (9.3 mL). The resultant slurry was warmed to room temperature, stirred for 15 mins, and anhydrous magnesium sulfate added, stirring for an additional 15 mins. Solid materials were removed by filtration, washing multiple times with warm methylene chloride, and the filtrate concentrated under reduced pressure to give the desired product as a pale yellow liquid (3.44 g, 66%). $^1$H NMR (CDCl$_3$, 300 MHz) 3.14 (m, 1H), 2.69-2.62 (m, 2H), 2.53-2.45 (m, 2H), 2.13-2.10 (m, 2H), 1.56-1.48 (m, 6H), 1.33 (br s, 3H).

Preparation 126: 3-(Cyclopentylamino)propanenitrile

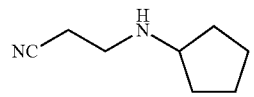

At room temperature, cyclopentylamine (5.794 mL, 58.7 mmol) was added dropwise to a solution of acrylonitrile (5.79 mL, 88.1 mmol) in methanol (7 mL). The solution was stirred at room temperature for 30 mins and at reflux for 1 hr, cooled to room temperature, and concentrated under reduced pressure. The desired product as obtained by distillation under vacuum to provide a clear liquid (7.4 g, 91%). $^1$H NMR (CDCl$_3$, 300 MHz) δ 3.14-3.04 (quint, 1H, J=6.3 Hz), 2.91-

2.87 (t, 2H, J=6.9 Hz), 2.53-2.48 (td, 2H, J=0.9, 6.9 Hz), 1.88-1.78 (m, 2H), 1.73-1.49 (m, 4H), 1.36-1.24 (m, 2H), 1.19 (br s, 1H).

Preparation 127:
N1-Cyclopentylpropane-1,3-diamine

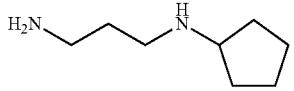

To a cooled (0° C.) suspension of lithium aluminum hydride (3.295 g, 86.8 mmol) in anhydrous diethyl ether (150 mL) was added a solution of 3-(cyclopentylamino)propanenitrile (6.000 g, 43.4 mmol) in anhydrous diethyl ether (40 mL), dropwise over 45 mins. The reaction mixture was stirred at room temperature for 15 mins and at reflux for 4 hrs, cooled to room temperature and stirred for 1 hr. The mixture was cooled to 0° C. and vigorously stirred while water (3.4 mL) was added dropwise, followed by 15% aqueous sodium hydroxide (3.4 mL), and finally water (10.2 mL). The resultant slurry was warmed to room temperature, stirred for 15 mins, and anhydrous magnesium sulfate was added, stirring for an additional 15 mins. Solid materials were removed by filtration, washing multiple times with warm methylene chloride, and the filtrate concentrated under reduced pressure to give the desired product as a clear oil (4.5 g, 73%). $^1$H NMR (CDCl$_3$, 300 MHz) δ 3.05-2.96 (quint, 1H, J=6.6 Hz), 2.74-2.71 (t, 2H, J=6.6 Hz), 2.68-2.58 (t, 2H, J=6.9 Hz), 1.85-1.68 (m, 2H), 1.62-1.42 (m, 6H), 1.34 (br s, 3H), 1.30-1.21 (m, 2H).

Preparations 128 to 138

Preparations 128 to 138 were prepared according to the following general procedure:

To a stirred solution of diamine (1.0 equiv., 0.5 M) in anhydrous pyridine was added sulfamide (1.2 equiv.). The mixture was heated at 120-125° C. for 18-24 hrs in a sealed tube. After cooling to room temperature, the mixture was concentrated under reduced pressure and the residue partitioned between ethyl acetate and water. The organic layer was successively washed with 1 N aqueous hydrochloric acid (2×), saturated aqueous sodium chloride, dried (anhydrous sodium sulfate), filtered, and concentrated under reduced pressure to afford the desired product. Products were typically used directly in the next step without any additional purification.

| Prep. # | Structure | Name | $^1$H NMR |
|---|---|---|---|
| 128 | 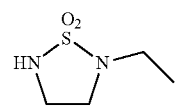 | 2-Ethyl-1,2,5-thiadiazolidine-1,1-dioxide | (300 MHz, CDCl$_3$) δ .4.45 (br s, 1H), 3.54-3.48 (t, 2H, J = 6.0 Hz), 3.42-3.37 (t, 2H, J = 6.9 Hz), 3.15-3.08 (q, 2H, J = 6.9 Hz), 1.30-1.25 (t, 3H, J = 7.2 Hz) |
| 129 | 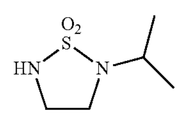 | 2-Isopropyl-1,2,5-thiadiazolidine-1,1-dioxide | (300 MHz, CDCl$_3$) δ 4.54 (br m, 1H), 3.70-3.61 (quint, 1H, J = 6.6 Hz), 3.52-3.36 (m, 4H), 1.29-1.27 (d, 6H, J = 6.0 Hz) |
| 130 | 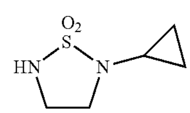 | 2-Cyclopropyl-1,2,5-thiadiazolidine-1,1-dioxide | (300 MHz, CDCl$_3$) δ 4.53 (br s, 1H), 3.50-3.46 (m, 4H), 2.32-2.28 (m, 1H), 0.80-0.69 (m, 4H) |
| 131 | 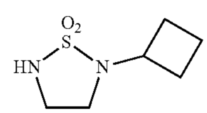 [SMILES: O=S1(=O)NCCN1C1CCC1] | 2-Cyclobutyl-1,2,5-thiadiazolidine-1,1-dioxide | (300 MHz, CDCl$_3$) δ 4.38 (br s, 1H), 3.81-3.70 (quint, 1H, J = 7.8 Hz), 3.53-3.46 (m, 2H), 3.38-3.34 (m, 2H), 2.27-2.19 (m, 4H), 1.87-1.75 (m, 2H) |
| 132 | 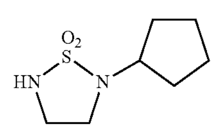 [SMILES: O=S1(=O)NCCN1C1CCCC1] | 2-Cyclopentyl-1,2,5-thiadiazolidine-1,1-dioxide | (300 MHz, CDCl$_3$) δ 4.32 (br s, 1H), 3.51-3.41 (m, 5H), 2.05-1.95 (m, 2H), 1.76-1.58 (m, 6H) |
| 133 | 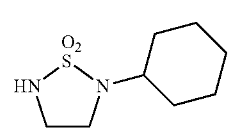 [SMILES: O=S1(=O)NCCN1C1CCCCC1] | 2-Cyclohexyl-1,2,5-thiadiazolidine-1,1-dioxide | (300 MHz, CDCl$_3$) δ 4.29 (br s, 1H), 3.53-3.40 (m, 4H), 3.30-3.22 (m, 1H), 2.06-2.01 (m, 2H), 1.83-1.78 (m, 2H), 1.68-1.59 (m, 1H), 1.51-1.14 (m, 5H) |
| 134 | 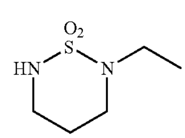 | 2-Ethyl-1,2,6-thiadiazinane-1,1-dioxide | (300 MHz, CDCl$_3$) δ 4.17 (br s, 1H), 3.51-3.47 (q, 2H, J = 6.1 Hz), 3.33-3.31 (t, 2H, J = 5.6 Hz), 3.19-3.11 (m, 2H), 1.80-1.72 (quint, 2H, J = 5.6 Hz), 1.21-1.16 (m, 3H) |

-continued

| Prep. # | Structure | Name | $^1$H NMR |
|---|---|---|---|
| 135 | 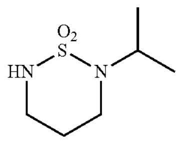 | 2-Isopropyl-1,2,6-thiadiazinane-1,1-dioxide | (300 MHz, CDCl$_3$) δ 4.22-4.13 (sept, 1H, J = 6.8 Hz), 3.94 (br s, 1H), 3.55-3.49 (m, 2H), 3.62-3.22 (t, 2H, J = 6.0 Hz), 1.83-1.76 (quint, 2H, J = 5.6 Hz), 1.18-1.16 (d, J = 6.9 Hz) |
| 136 | 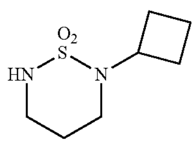 | 2-Cyclobutyl-1,2,6-thiadiazinane-1,1-dioxide | (300 MHz, CDCl$_3$) δ 4.17 (br s, 1H), 3.90-3.79 (m, 1H), 3.52-3.46 (m, 2H), 3.25-3.21 (m, 2H), 2.21-2.05 (m, 4H), 1.77-1.64 (m, 4H) |
| 137 | 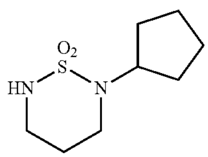 [SMILES: O=S1(=O)NCCCN1C1CCCC1] | 2-Cyclopentyl-1,2,6-thiadiazinane-1,1-dioxide | (300 MHz, CDCl$_3$) δ 4.19-4.10 (quint, 1H, J = 7.8 Hz), 3.99-3.96 (br t, 1H, J = 6.9 Hz), 3.54-3.48 (m, 2H), 3.28-3.24 (t, 2H, J = 5.7 Hz), 1.91-1.78 (m, 4H), 1.76-1.51 (m, 6H) |
| 138 | 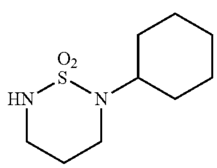 [SMILES: O=S1(=O)NCCCN1C1CCCCC1] | 2-Cyclohexyl-1,2,6-thiadiazinane-1,1-dioxide | (300 MHz, CDCl$_3$) δ 3.96-3.91 (t, 1H, J = 7.5 Hz), 3.75-3.67 (m, 1H), 3.55-3.38 (m, 2H), 3.16-3.27 (t, 2H, J = 5.7 Hz), 1.87-1.59 (m, 7H), 1.43-1.28 (m, 4H), 1.13-1.00 (m, 1H) |

Example 2

Preparation of Compounds of Formula I

Compound 1: N-(3-(9H-Carbazol-9-yl)-2-hydroxypropyl)-N-(furan-2-ylmethyl)methanesulfonamide

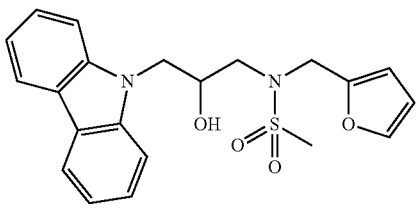 [SMILES: CS(=O)(=O)N(Cc1ccco1)CC(O)Cn1c2ccccc2c2ccccc21]

Methanesulfonyl chloride (0.650 mL, 8.4 mmol) was added dropwise to a cold stirring solution of 1-(9H-carbazol-9-yl)-3-((furan-2-ylmethyl)amino)propan-2-ol (2.7 g, 8.4 mmol) and triethylamine (1.3 mL, 9.2 mmol) in anhydrous methylene chloride (55 mL), which was kept at 0-5° C. with an external ice bath. The solution was stirred at 0° C. for 2 hours and then diluted with methylene chloride and successively washed with 0.25N aqueous hydrochloric acid twice, water, and saturated aqueous sodium chloride. The organics were dried (anhydrous sodium sulfate), filtered, and concentrated in vacuo. The crude residue was purified by silica gel column chromatography (0-10% ethyl acetate in methylene chloride) to give the desired product as a white solid (1.5 g, 45%). $^1$H NMR (d6-DMSO, 300 MHz) δ 8.09-8.06 (d, 2H, J=8.1 Hz), 7.42-7.37 (m, 5H), 7.18-7.14 (m, 2H), 6.37-6.35 (dd, 1H, J=1.8, 3 Hz), 6.31-6.30 (d, 1H, J=3 Hz), 4.52-4.39 (dd, 2H, J=15.9, 24.6 Hz), 4.39-4.30 (dd, 1H, J=3.3, 14.4 Hz), 4.22-4.10 (m, 1H), 4.20-4.05 (br m, 1H), 3.40-3.33 (m, 1H) 3.26-3.17 (m, 1H), 2.90 (s, 3H). ESI (m/z): 398.9 (M+H). HPLC analysis: (C18, 10-90% acetonitrile in water+0.1% trifluoroacetic acid over 10 min: retention time, % area at 254 nm): 8.6 min, 97.9%.

Compounds 2 to 12

Compounds 2 to 12 were prepared by procedures analogous to those used for Compound 1 or by using pyridine (4 equiv.) instead of triethylamine.

| Cpd # | Structure | Name | $^1$H NMR | ESI (m/z) |
|---|---|---|---|---|
| 2 | 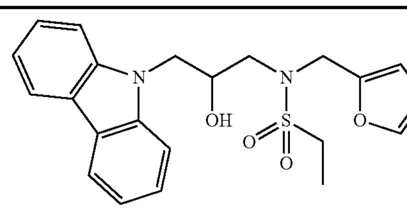 | N-(3-(9H-Carbazol-9-yl)-2-hydroxypropyl)-N-(furan-2-ylmethyl)ethanesulfonamide | (300 MHz, CDCl$_3$) δ 8.11 (d, 2H, J = 7.8 Hz), 7.52-7.38 (m, 4H), 7.27 (t, 2H, J = 7.2 Hz), 7.19 (d, 1H, J = 1.8 Hz), 6.13 (dd, 1H, J = 3.3, 1.8 Hz), 5.86 (d, 1H, J = 3.3 Hz), 4.52-4.25 (m, 5H), 3.47 (dd, 1H, J = 15.0, 7.5 Hz), 3.27 (dd, 1H, J = 15.0, 2.4 Hz), 3.03 (m, 2H), 2.77 (d, 1H, J = 2.7 Hz), 1.33 (t, 3H, J = 7.5 Hz) | 413.0 (M + H) |

| Cpd # | Structure | Name | ¹H NMR | ESI (m/z) |
|---|---|---|---|---|
| 3 | 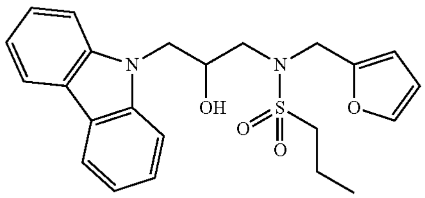 [SMILES: CCCS(=O)(=O)N(Cc1ccco1)CC(O)Cn1c2ccccc2c2ccccc21] | N-(3-(9H-Carbazol-9-yl)-2-hydroxypropyl)-N-(furan-2-ylmethyl)propane-1-sulfonamide | (300 MHz, CDCl$_3$) δ 8.11 (d, 2H, J = 7.8 Hz), 7.52-7.38 (m, 4H), 7.27 (td, 2H, J = 7.2, 1.5 Hz), 7.19 (d, 1H, J = 2.1 Hz), 6.13 (dd, 1H, J = 3.3, 2.1 Hz), 5.86 (d, 1H, J = 3.3 Hz), 4.52-4.24 (m, 5H), 3.46 (dd, 1H, J = 15.0, 7.5 Hz), 3.26 (dd, 1H, J = 15.0, 2.7 Hz), 3.05-2.85 (m, 2H), 2.76 (d, 1H, J = 3.0 Hz), 1.90-1.70 (m, 2H), 1.03 (t, 3H, J = 7.5 Hz) | 427.0 (M + H) |
| 4 | 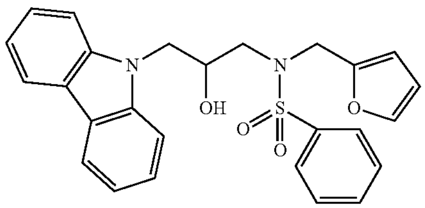 [SMILES: O=S(=O)(c1ccccc1)N(Cc1ccco1)CC(O)Cn1c2ccccc2c2ccccc21] | N-(3-(9H-Carbazol-9-yl)-2-hydroxypropyl)-N-(furan-2-ylmethyl)benzenesulfonamide | (300 MHz, CDCl$_3$) δ 8.09 (d, 2H, J = 7.8 Hz), 7.75 (d, 2H, J = 7.2 Hz), 7.59 (t, 1H, J = 7.5 Hz), 7.53-7.41 (m, 4H), 7.38 (d, 2H, J = 7.8 Hz), 7.30-7.20 (m, 2H), 7.03 (d, 1H, J = 1.8 Hz), 6.04 (dd, 1H, J = 3.3, 1.8 Hz), 5.85 (d, 1H, J = 3.3 Hz), 4.42-4.25 (m, 4H), 4.17 (m, 1H), 3.34 (dd, 1H, J = 15.0, 8.1 Hz), 3.15 (dd, 1H, J = 14.7, 3.6 Hz), 2.78 (d, 1H, J = 2.7 Hz) | 460.9 (M + H) |
| 5 | 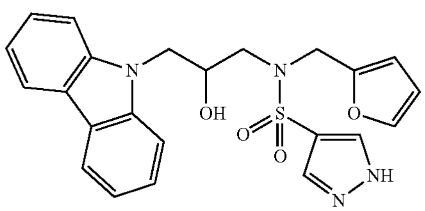 [SMILES: O=S(=O)(c1cn[nH]c1)N(Cc1ccco1)CC(O)Cn1c2ccccc2c2ccccc21] | N-(3-(9H-Carbazol-9-yl)-2-hydroxypropyl)-N-(furan-2-ylmethyl)-1H-pyrazole-4-sulfonamide | (300 MHz, CDCl$_3$) δ 10.20 (br s, 1H), 8.10 (d, 2H, J = 7.5 Hz), 7.74 (s, 2H), 7.50-7.36 (m, 4H), 7.30-7.22 (m, 2H), 7.10 (s, 1H), 6.10 (dd, 1H, J = 3.3, 1.8 Hz), 5.94 (d, 1H, J = 3.0 Hz), 4.40-4.30 (m, 4H), 4.25 (m, 1H), 3.32 (dd, 1H, J = 15.0, 7.8 Hz), 3.15 (dd, 1H, J = 15.0, 3.6 Hz), 2.82 (br s, 1H) | 451.0 (M + H) |
| 6 | 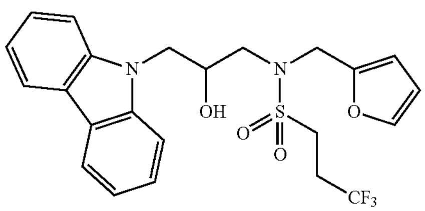 [SMILES: O=S(=O)(CCC(F)(F)F)N(Cc1ccco1)CC(O)Cn1c2ccccc2c2ccccc21] | N-(3-(9H-Carbazol-9-yl)-2-hydroxypropyl)-3,3,3-trifluoro-N-(furan-2-ylmethyl)propane-1-sulfonamide | (300 MHz, CDCl$_3$) δ 8.12 (d, 2H, J = 7.8 Hz), 7.49 (t, 2H, J = 7.2 Hz), 7.42 (d, 2H, J = 7.8 Hz), 7.32-7.24 (m, 3H), 6.20 (dd, 1H, J = 3.0, 2.1 Hz), 5.96 (d, 1H, J = 3.0 Hz), 4.53 (dd, 1H, J = 16.2, 16.2 Hz), 4.46-4.28 (m, 4H), 3.51 (m, 1H), 3.36-3.15 (m, 3H), 2.60 (m, 2H), 2.48 (d, 1H, J = 2.7 Hz) | 481.0 (M + H) |
| 7 | 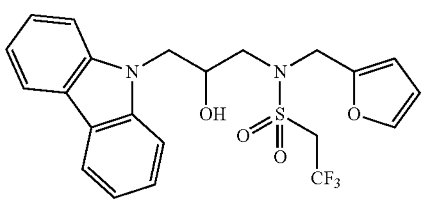 [SMILES: O=S(=O)(CC(F)(F)F)N(Cc1ccco1)CC(O)Cn1c2ccccc2c2ccccc21] | N-(3-(9H-Carbazol-9-yl)-2-hydroxypropyl)-2,2,2-trifluoro-N-(furan-2-ylmethyl)ethanesulfonamide | (300 MHz, CDCl$_3$) δ 8.11 (d, 2H, J = 7.8 Hz), 7.49 (t, 2H, J = 7.5 Hz), 7.41 (d, 2H, J = 7.8 Hz), 7.32-7.24 (m, 3H), 6.23 (dd, 1H, J = 3.3, 2.1 Hz), 6.05 (d, 1H, J = 2.7 Hz), 4.60 and 4.45 (dd, 2H, J = 15.6, 15.6 Hz), 4.42-4.26 (m, 3H), 3.88 (q, 2H, J = 9.3 Hz), 3.59 (dt, 1H, J = 15.3, 3.9 Hz), 3.35 (d, 1H, J = 15.6 Hz), 2.32 (s, 1H) | 467.2 (M + H) |
| 8 | 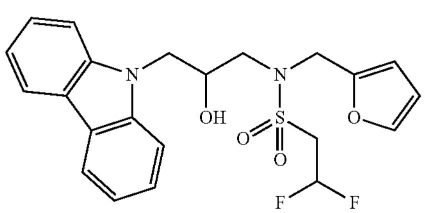 [SMILES: O=S(=O)(CC(F)F)N(Cc1ccco1)CC(O)Cn1c2ccccc2c2ccccc21] | N-(3-(9H-Carbazol-9-yl)-2-hydroxypropyl)-2,2-difluoro-N-(furan-2-ylmethyl)ethanesulfonamide | (300 MHz, CDCl$_3$) δ 8.12 (d, 2H, J = 7.5 Hz), 7.49 (t, 2H, J = 7.2 Hz), 7.41 (d, 2H, J = 8.1 Hz), 7.32-7.24 (m, 3H), 6.21 (dd, 1H, J = 3.3, 1.8 Hz), 6.18 (tt, 1H, J = 54.9, 4.5 Hz), 6.01 (d, 1H, J = 3.0 Hz), 4.55 and 4.42 (dd, 2H, J = 15.9, 15.9 Hz), 4.42-4.24 (m, 3H), 3.68-3.48 (m, 3H), 3.30 (dd, 1H, J = 15.9, 2.4 Hz), 2.43 (d, 1H, J = 2.4 Hz) | 449.0 (M + H) |
| 9 | 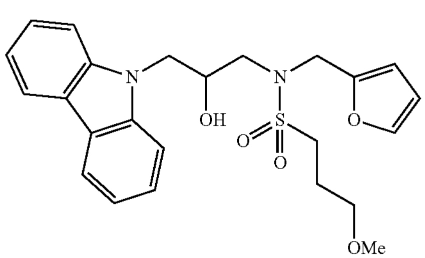 [SMILES: COCCCS(=O)(=O)N(Cc1ccco1)CC(O)Cn1c2ccccc2c2ccccc21] | N-(3-(9H-Carbazol-9-yl)-2-hydroxypropyl)-N-(furan-2-ylmethyl)-3-methoxypropane-1-sulfonamide | (300 MHz, CDCl$_3$) δ 8.12 (d, 2H, J = 7.5 Hz), 7.52-7.40 (m, 4H), 7.31-7.23 (m, 2H), 7.18 (d, 1H, J = 1.8 Hz), 6.12 (dd, 1H, J = 3.3, 1.8 Hz), 5.86 (d, 1H, J = 3.3 Hz), 4.52-4.24 (m, 5H), 3.53-3.40 (m, 3H), 3.32 (s, 3H), 3.25 (dd, 1H, J = 15.0, 2.7 Hz), 3.11 (t, 2H, J = 7.5 Hz), 2.85 (d, 1H, J = 3.0 Hz), 2.12-1.98 (m, 2H) | 457.1 (M + H) |

-continued

| Cpd # | Structure | Name | ¹H NMR | ESI (m/z) |
|---|---|---|---|---|
| 10 | 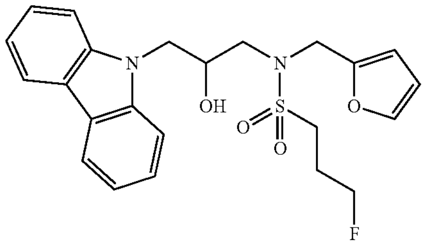 [SMILES: O=S(=O)(CCCF)N(Cc1ccco1)CC(O)Cn1c2ccccc2c2ccccc21] | N-(3-(9H-Carbazol-9-yl)-2-hydroxypropyl)-3-fluoro-N-(furan-2-ylmethyl)propane-1-sulfonamide | (300 MHz, CDCl₃) δ 8.12 (d, 2H, J = 7.5 Hz), 7.53-7.40 (m, 4H), 7.32-7.24 (m, 2H), 7.22 (d, 1H, J = 1.8 Hz), 6.15 (dd, 1H, J = 3.3, 2.1 Hz), 5.89 (d, 1H, J = 3.0 Hz), 4.66-4.26 (m, 7H), 3.48 (dd, 1H, J = 15.0, 7.2 Hz), 3.27 (dd, 1H, J = 15.0, 2.4 Hz), 3.22-3.04 (m, 2H), 2.67 (d, 1H, J = 2.7 Hz), 2.30-2.08 (m, 2H) | 445.0 (M + H) |
| 11 | 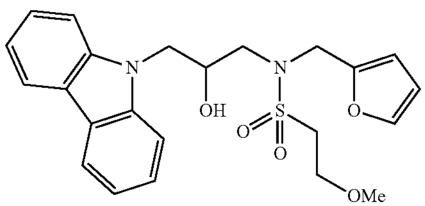 [SMILES: COCCS(=O)(=O)N(Cc1ccco1)CC(O)Cn1c2ccccc2c2ccccc21] | N-(3-(9H-Carbazol-9-yl)-2-hydroxypropyl)-N-(furan-2-ylmethyl)-2-methoxyethanesulfonamide | (300 MHz, CDCl₃) δ 8.11 (d, 2H, J = 7.5 Hz), 7.52-7.38 (m, 4H), 7.31-7.23 (m, 2H), 7.17 (d, 1H, J = 1.8 Hz), 6.13 (dd, 1H, J = 3.3, 1.8 Hz), 5.92 (d, 1H, J = 3.3 Hz), 4.50-4.20 (m, 5H), 3.84-3.68 (m, 2H), 3.50 (dd, 1H, J = 15.3, 8.7 Hz), 3.41 (m, 1H), 3.32 (s, 3H), 3.32-3.22 (m, 2H), 3.18 (dd, 1H, J = 15.3, 2.4 Hz) | 443.0 (M + H) |
| 12 | 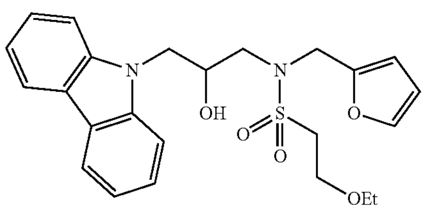 [SMILES: CCOCCS(=O)(=O)N(Cc1ccco1)CC(O)Cn1c2ccccc2c2ccccc21] | N-(3-(9H-Carbazol-9-yl)-2-hydroxypropyl)-2-ethoxy-N-(furan-2-ylmethyl)ethanesulfonamide | (300 MHz, CDCl₃) δ 8.11 (d, 2H, J = 7.5 Hz), 7.52-7.38 (m, 4H), 7.30-7.22 (m, 2H), 7.12 (s, 1H), 6.09 (dd, 1H, J = 3.0, 1.8 Hz), 5.87 (d, 1H, J = 3.0 Hz), 4.52-4.20 (m, 5H), 3.90-3.73 (m, 2H), 3.56-3.40 (m, 5H), 3.30 (m, 1H), 3.15 (dd, 1H, J = 15.0, 2.1 Hz), 1.16 (t, 3H, J = 7.2 Hz) | 457.0 (M + H) |

Compounds 13 to 19

Compounds 13 to 19 were prepared by the following general method:

To a stirred solution of 2-((tert-butyldimethylsilyl)oxy)-3-(9H-carbazol-9-yl)-N-(furan-2-ylmethyl)propan-1-amine (0.100 g, 0.2 mmol) in anhydrous pyridine (1 mL) was added the corresponding sulfonyl chloride (0.9 mmol). The reaction mixture was stirred overnight at room temperature and the mixture concentrated in vacuo. The crude residue was treated with water and extracted with ethyl acetate (20 mL). The organic layer was washed with saturated aqueous sodium chloride and saturated aqueous sodium carbonate, dried (anhydrous sodium sulfate), filtered, and concentrated. The residue was purified by silica gel column chromatography (0-80% ethyl acetate in hexanes) to afford the TBS-protect product. The product was dissolved in anhydrous tetrahydrofuran (5 mL) and aqueous tetrabutylammonium fluoride (0.040 g, 0.1 mmol) in water was added. The mixture was stirred overnight at room temperature and then concentrated. The crude residue was purified by silica gel column chromatography (0-50% ethyl acetate in hexanes) to afford the pure product.

| Cpd # | Structure | Name | ¹H NMR | ESI (m/z) |
|---|---|---|---|---|
| 13 | 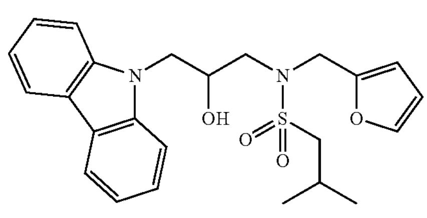 [SMILES: CC(C)CS(=O)(=O)N(Cc1ccco1)CC(O)Cn1c2ccccc2c2ccccc21] | N-(3-(9H-Carbazol-9-yl)-2-hydroxypropyl)-N-(furan-2-ylmethyl)-2-methylpropane-1-sulfonamide | (300 MHz, CDCl₃) δ 8.11 (d, 2H, J = 7.5 Hz), 7.52-7.40 (m, 4H), 7.30-7.22 (m, 2H), 7.19 (d, 1H, J = 1.8 Hz), 6.13 (dd, 1H, J = 3.3, 1.8 Hz), 5.85 (d, 1H, J = 3.0 Hz), 4.50-4.25 (m, 5H), 3.44 (dd, 1H, J = 15.0, 7.8 Hz), 3.24 (dd, 1H, J = 15.0, 2.4 Hz), 2.90-2.72 (m, 3H), 2.25 (m, 1H), 1.13-1.05 (m, 6H) | 441.0 (M + H) |

| Cpd # | Structure | Name | ¹H NMR | ESI (m/z) |
|---|---|---|---|---|
| 14 | 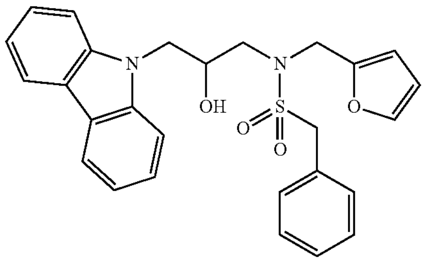 [SMILES: O=S(=O)(Cc1ccccc1)N(Cc1ccco1)CC(O)Cn1c2ccccc2c2ccccc21] | N-(3-(9H-Carbazol-9-yl)-2-hydroxypropyl)-N-(furan-2-ylmethyl)-1-phenylmethane-sulfonamide | (300 MHz, CDCl₃) δ 8.10 (d, 2H, J = 7.5 Hz), 7.46 (t, 2H, J = 7.5 Hz), 7.42-7.18 (m, 8H), 7.11 (d, 2H, J = 7.2 Hz), 6.16 (dd, 1H, J = 3.3, 2.1 Hz), 5.79 (d, 1H, J = 3.0 Hz), 4.43-4.00 (m, 7H), 2.95 (m, 2H), 2.69 (d, 1H, J = 2.4 Hz). | 474.9 (M + H) |
| 15 | 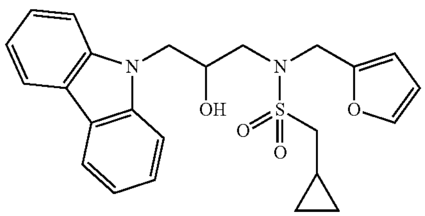 [SMILES: O=S(=O)(CC1CC1)N(Cc1ccco1)CC(O)Cn1c2ccccc2c2ccccc21] | N-(3-(9H-Carbazol-9-yl)-2-hydroxypropyl)-1-cyclopropyl-N-(furan-2-ylmethyl)methane-sulfonamide | (300 MHz, CDCl₃) δ 8.11 (d, 2H, J = 7.8 Hz), 7.52-7.38 (m, 4H), 7.30-7.23 (m, 2H), 7.16 (d, 1H, J = 1.8 Hz), 6.12 (dd, 1H, J = 3.3, 1.8 Hz), 5.80 (d, 1H, J = 3.3 Hz), 4.51-4.22 (m, 5H), 3.53 (dd, 1H, J = 15.0, 7.8 Hz), 3.28 (dd, 1H, J = 15.0, 2.7 Hz), 3.01 (dd, 1H, J = 14.4, 6.6 Hz), 2.87 (dd, 1H, J = 14.4, 7.8 Hz), 2.81 (d, 1H, J = 2.7 Hz), 1.04 (m, 1H), 0.60 (m, 2H), 0.26 (m, 1H), 0.15 (m, 1H). | 439.0 (M + H) |
| 16 | 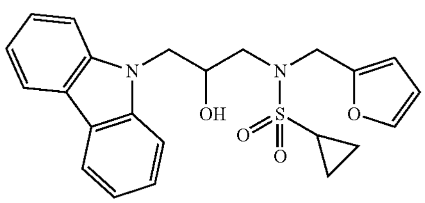 [SMILES: O=S(=O)(C1CC1)N(Cc1ccco1)CC(O)Cn1c2ccccc2c2ccccc21] | N-(3-(9H-Carbazol-9-yl)-2-hydroxypropyl)-N-(furan-2-ylmethyl)cyclopropanesulfonamide | (300 MHz, CDCl₃) δ 8.11 (d, 2H, J = 7.5 Hz), 7.52-7.40 (m, 4H), 7.26 (t, 2H, J = 7.2 Hz), 7.18 (d, 1H, J = 1.8 Hz), 6.13 (dd, 1H, J = 3.0, 1.8 Hz), 5.93 (d, 1H, J = 3.3 Hz), 4.50-4.20 (m, 5H), 3.50 (dd, 1H, J = 15.0, 7.8 Hz), 3.30 (dd, 1H, J = 15.0, 3.3 Hz), 2.74 (d, 1H, J = 2.7 Hz), 2.30 (m, 1H), 1.18 (m, 2H), 0.95 (m, 2H). | 425.0 (M + H) |
| 17 | 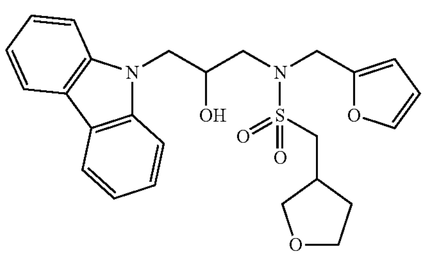 [SMILES: O=S(=O)(CC1CCOC1)N(Cc1ccco1)CC(O)Cn1c2ccccc2c2ccccc21] | N-(3-(9H-Carbazol-9-yl)-2-hydroxypropyl)-N-(furan-2-ylmethyl)-1-(tetrahydrofuran-3-yl)methanesulfonamide | (300 MHz, CDCl₃) δ 8.12 (d, 2H, J = 7.8 Hz), 7.52-7.40 (m, 4H), 7.31-7.24 (m, 2H), 7.22 (s, 1H), 6.16 (s, 1H), 5.89 (s, 1H), 4.54-4.25 (m, 5H), 4.02-3.70 (m, 3H), 3.58-3.40 (m, 2H), 3.25 (d, 1H, J = 15.0 Hz), 3.12-2.90 (m, 2H), 2.80-2.60 (m, 2H), 2.20 (m, 1H), 1.71 (m, 1H). | 469.0 (M + H) |
| 18 | 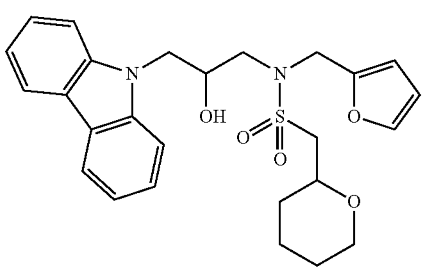 [SMILES: O=S(=O)(CC1CCCCO1)N(Cc1ccco1)CC(O)Cn1c2ccccc2c2ccccc21] | N-(3-(9H-Carbazol-9-yl)-2-hydroxypropyl)-N-(furan-2-ylmethyl)-1-(tetrahydro-2H-pyran-2-yl)methanesulfonamide | (300 MHz, CDCl₃) (diasteromeric mixture) δ 8.10 (d, 2H, J = 7.5 Hz), 7.51-7.38 (m, 4H), 7.30-7.22 (m, 2H), 7.18 and 7.07 (d, 1H, J = 1.8 Hz), 6.13 and 6.07 (dd, 1H, J = 3.3, 2.1 Hz), 5.99 and 5.86 (d, 1H, J = 3.3 Hz), 4.60-2.95 (m, 13H), 1.88 (m, 1H), 1.70-1.20 (m, 5H). | 483.1 (M + H) |
| 19 | 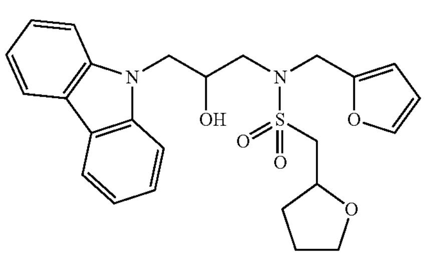 [SMILES: O=S(=O)(CC1CCCO1)N(Cc1ccco1)CC(O)Cn1c2ccccc2c2ccccc21] | N-(3-(9H-Carbazol-9-yl)-2-hydroxypropyl)-N-furan-2-ylmethyl)-1-(tetrahydrofuran-2-yl)methanesulfonamide | (300 MHz, CDCl₃) (diasteromeric mixture) δ 8.11 (d, 2H, J = 7.5 Hz), 7.52-7.39 (m, 4H), 7.30-7.22 (m, 2H), 7.17 and 7.10 (d, 1H, J = 1.8 Hz), 6.13 and 6.08 (dd, 1H, J = 3.0, 1.8 Hz), 5.96 and 5.87 (d, 1H, J = 3.0 Hz), 4.62-3.00 (m, 13H), 2.15 (m, 1H), 1.92 (m, 2H), 1.63 (m, 1H). | 469.1 (M + H) |

Compound 20: N-(3-(9H-Carbazol-9-yl)-2-hydroxypropyl)isothiazolidine 1,1-dioxide

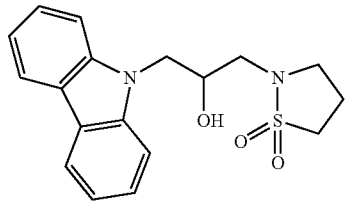 [SMILES: O=S1(=O)CCCN1CC(O)Cn1c2ccccc2c2ccccc21]

To a stirred solution of 1,3-propanesultam (0.80 g, 6.6 mmol) in anhydrous N,N-dimethylformamide (20 mL) was added sodium hydride (60% in mineral oil, 0.053 g, 1.3 mmol) and the mixture was stirred at room temperature for 1 hour. 9-(Oxiran-2-ylmethyl)-9H-carbazole (1.622 g, 7.3 mmol) was added and the mixture was stirred at 70° C. overnight. After cooling, the reaction was diluted with water and extracted three times with ethyl acetate. The combined organic layers were washed with saturated aqueous sodium chloride, dried (anhydrous sodium sulfate), filtered, and concentrated. The residue was purified by silica gel column chromatography (0-70% ethyl acetate in hexanes) and then recrystallized from ethyl acetate/hexanes to give the pure compound as a white solid (1.6 g, 70%). $^1$H NMR (300 MHz, CDCl$_3$) δ 8.10 (d, 2H, J=7.5 Hz), 7.48 (d, 4H, J=3.9 Hz), 7.30-7.22 (m, 2H), 4.55-4.35 (m, 3H), 3.42-3.12 (m, 6H), 2.59 (d, 1H, J=3.0 Hz), 2.37 (m, 2H). ESI (m/z): 344.9 (M+H). HPLC analysis: (C18, 10-90% acetonitrile in water+ 0.1% trifluoroacetic acid over 10 min: retention time, % area at 254 nm): 11.8 min, >98%.

Compounds 21 to 235

Compounds 21 to 235 were prepared by procedures analogous to those used for Compound 20 or by using cesium carbonate (1 equiv.) in N,N-dimethylacetamide at 100° C. overnight.

Enantiomeric excesses of optically active examples were obtained by HPLC using a Chiralpak AD-H column, 0.46 cm×25 cm, 0-30 min elution with 25% isopropanol in hexanes; flow rate: 1 mL/min, UV 254 nM.

| Cpd # | Structure | Name | $^1$H NMR | ESI (m/z) |
|---|---|---|---|---|
| 21 | 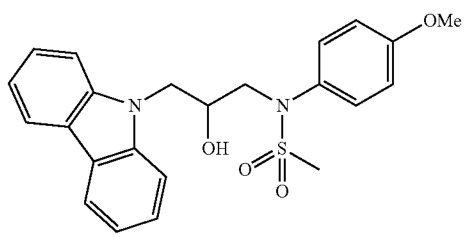 [SMILES: COc1ccc(N(CC(O)Cn2c3ccccc3c3ccccc32)S(C)(=O)=O)cc1] | N-(3-(9H-Carbazol-9-yl)-2-hydroxypropyl)-N-(4-methoxyphenyl)methanesulfonamide | (CDCl$_3$, 300 MHz) δ 8.11-8.08 (dt, 2H, J = 0.9, 7.5 Hz), 7.45-7.74 (m, 2H), 7.37-7.35 (m, 2H), 7.37-7.35 (br d, 2H, J = 7.8 Hz), 7.29-7.26 (d, 2H, J = 9.0 Hz), 7.25-7.20 (m, 2H), 6.90-6.87 (d, 2H, J = 8.7 Hz), 4.48-4.42 (dd, 1H, J = 4.1, 14.7 Hz), 4.38-4.22 (m, 2H), 3.96-3.89 (dd, 1H, J = 6.9, 17.1 Hz), 3.8 (s, 3H), 3.80-3.74 (dd, 1H, J = 5.0, 14 Hz), 2.91 (s, 3H), 2.29-2.28 (d, 1H, J = 3.6 Hz). | 424.9 (M + H) |
| 22 | 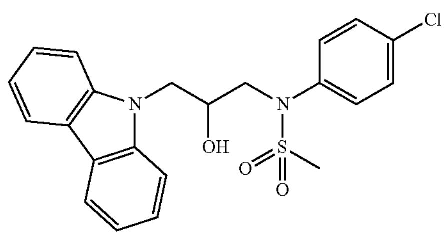 [SMILES: CS(=O)(=O)N(CC(O)Cn1c2ccccc2c2ccccc21)c1ccc(Cl)cc1] | N-(3-(9H-Carbazol-9-yl)-2-hydroxypropyl)-N-(4-chlorophenyl)methanesulfonamide | (CDCl$_3$, 300 MHz) δ 8.08-8.08 (br d, 2H, J = 7.5 Hz), 7.47-7.39 (m, 2H), 7.36-7.31 (m, 4H), 7.29-7.21 (m, 4H), 4.45-4.24 (m, 3H), 3.96-3.89 (dd, 1H, J = 6.9, 14.2 Hz), 3.81-3.75 (dd, 1H, J = 4.2, 14.4 Hz), 2.91 (s, 3H), 2.27-2.26 (d, 1H, J = 3.3 Hz). | N/A |
| 23 | 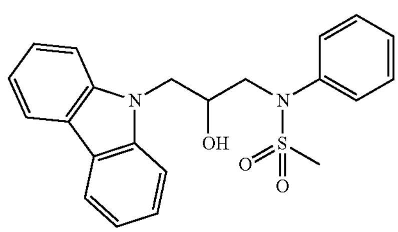 [SMILES: CS(=O)(=O)N(CC(O)Cn1c2ccccc2c2ccccc21)c1ccccc1] | N-(3-(9H-Carbazol-9-yl)-2-hydroxypropyl)-N-phenylmethanesulfonamide | (CDCl$_3$, 300 MHz) δ 8.08-8.08 (br d, 2H, J = 7.5 Hz), 7.47-7.33 (m, 8H), 7.25-7.20 (m, 2H), 4.45-4.44 (dd, 1H, J = 3.3, 14.1 Hz), 4.39-4.25 (m, 2H), 4.00-3.94 (dd, 1H, J = 6.9, 14.4 Hz), 3.88-3.82 (dd, 1H, J = 5.1, 14.1 Hz), 2.93 (s, 3H), 2.27-2.26 (d, 1H, J = 3.6 Hz). | 395.0 (M + H) |
| 24 | 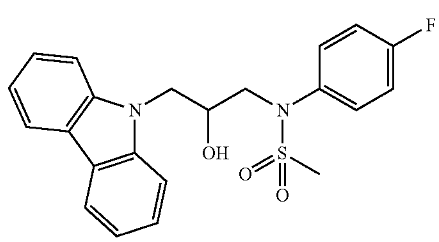 [SMILES: CS(=O)(=O)N(CC(O)Cn1c2ccccc2c2ccccc21)c1ccc(F)cc1] | N-(3-(9H-Carbazol-9-yl)-2-hydroxypropyl)-N-(4-fluorophenyl)methanesulfonamide | (CDCl$_3$, 300 MHz) δ 8.08-8.08 (dt, 2H, J = 0.9, 7.6 Hz), 7.46-7.41 (m, 2H), 7.37-7.30 (m, 4H), 7.26-7.21 (m, 2H), 7.09-7.03 (dd, 2H, J = 8.1, 8.7 Hz), 4.47-4.24 (m, 3H), 3.97-3.90 (dd, 1H, J = 7.8, 14.1 Hz), 3.80-3.74 (dd, 1H, J = 4.5, 14.5 Hz), 2.93 (s, 3H), 2.27-2.26 (d, 1H, J = 3.3 Hz). | 413.0 (M + H) |

-continued

| Cpd # | Structure | Name | ¹H NMR | ESI (m/z) |
|---|---|---|---|---|
| 25 | 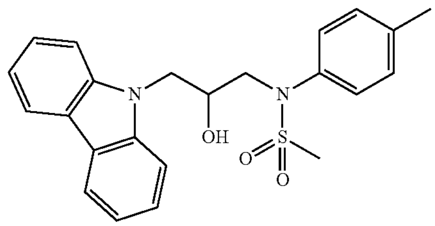 [SMILES: Cc1ccc(N(CC(O)Cn2c3ccccc3c3ccccc32)S(C)(=O)=O)cc1] | N-(3-(9H-Carbazol-9-yl)-2-hydroxypropyl)-N-p-tolylmethane-sulfonamide | (CDCl₃, 300 MHz) δ 8.08-8.08 (br d, 2H, J = 7.5 Hz), 7.45-7.40 (m, 2H), 7.37-7.34 (br d, 2H, J = 8.4 Hz), 7.25-7.18 (m, 6H), 4.49-4.43 (dd, J = 3.7, 14.5 Hz), 4.38-4.24 (m, 2H), 3.98-3.91 (dd, 1H, J = 6.9, 14.1 Hz), 3.85-3.78 (dd, 1H, J = 5.1, 14.1 Hz), 2.92 (s, 3H), 2.36 (s, 3H), 2.27-2.26 (d, 1H, J = 3.6 Hz). | 409.0 (M + H) |
| 26 | 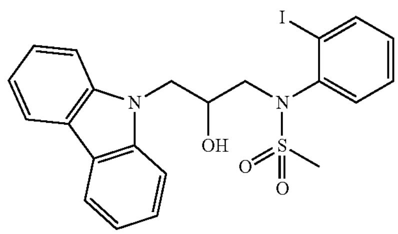 [SMILES: CS(=O)(=O)N(CC(O)Cn1c2ccccc2c2ccccc21)c1ccccc1I] | N-(3-(9H-Carbazol-9-yl)-2-hydroxypropyl)-N-(2-iodophenyl)meth-anesulfonamide | (300 MHz, CDCl₃) (rotomers) δ 8.12-8.05 (m, 2H), 7.91 (m, 1H), 7.50-7.18 (m, 8H), 7.05 (m, 1H), 4.52-4.18 (m, 3H), 4.01 (dd, 0.6H, J = 15.0, 9.0 Hz), 3.90-3.72 (m, 1.4H), 3.13 and 3.12 (s, 3H), 2.72 (d, 0.6H, J = 4.2 Hz), 2.52 (d, 0.4H, J = 3.3 Hz). | 520.9 (M + H) |
| 27 | 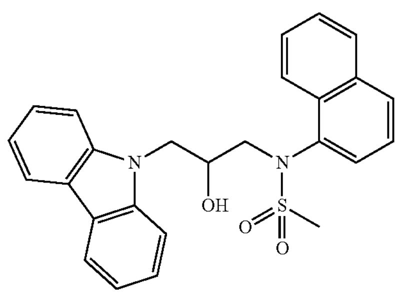 [SMILES: CS(=O)(=O)N(CC(O)Cn1c2ccccc2c2ccccc21)c1cccc2ccccc12] | N-(3-(9H-Carbazol-9-yl)-2-hydroxypropyl)-N-(naphthalen-1-yl)methanesulfon-amide | (300 MHz, CDCl₃) (rotomers) δ 8.27 and 8.22 (d, 1H, J = 8.4 Hz), 8.10-8.02 (m, 2H), 7.94 and 7.89 (d, 2H, J = 7.5 Hz), 7.70-7.18 (m, 10H), 4.50-3.80 (m, 5H), 3.15 and 3.05 (s, 3H), 2.52 (d, 0.4H, J = 3.6 Hz), 2.29 (d, 0.6H, J = 2.7 Hz). | 444.9 (M + H) |
| 28 | 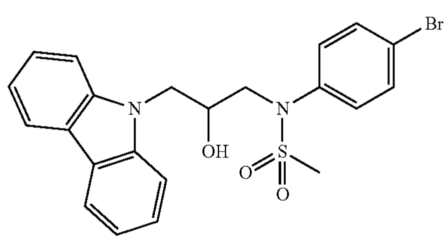 [SMILES: CS(=O)(=O)N(CC(O)Cn1c2ccccc2c2ccccc21)c1ccc(Br)cc1] | N-(3-(9H-Carbazol-9-yl)-2-hydroxypropyl)-N-(4-bromophenyl)methanesulfonamide | (300 MHz, CDCl₃) δ 8.09 (d, 2H, J = 8.1 Hz), 7.55-7.20 (m, 10H), 4.52-4.24 (m, 3H), 3.95 (dd, 1H, J = 14.4, 7.2 Hz), 3.81 (dd, 1H, J = 14.4, 4.5 Hz), 2.94 (s, 3H), 2.26 (d, 1H, J = 3.6 Hz). | N/A |
| 29 | 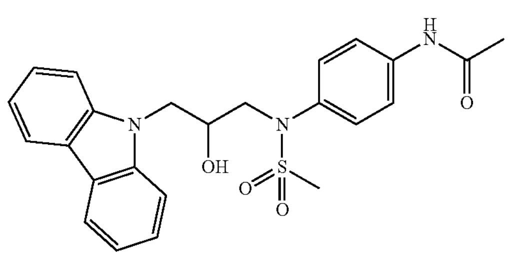 [SMILES: CC(=O)Nc1ccc(N(CC(O)Cn2c3ccccc3c3ccccc32)S(C)(=O)=O)cc1] | N-(4-(N-(3-(9H-Carbazol-9-yl)-2-hydroxypropyl)methylsulfonamido)phenyl)acetamide | (300 MHz, CDCl₃) δ 8.08 (d, 2H, J = 8.1 Hz), 7.58-7.18 (m, 11H), 4.50-4.22 (m, 3H), 3.95 (dd, 1H, J = 14.1, 7.2 Hz), 3.81 (dd, 1H, J = 14.1, 4.8 Hz), 2.94 (s, 3H), 2.31 (d, 1H, J = 3.6 Hz), 2.21 (s, 3H). | 451.8 (M + H) |
| 30 | 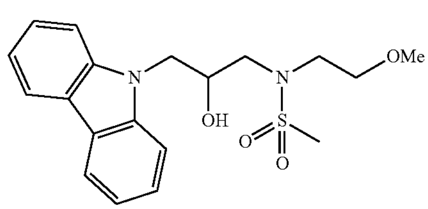 [SMILES: COCCN(CC(O)Cn1c2ccccc2c2ccccc21)S(C)(=O)=O] | N-(3-(9H-Carbazol-9-yl)-2-hydroxypropyl)-N-(2-methoxyethyl)methanesulfonamide | N/A | N/A |

-continued

| Cpd # | Structure | Name | ¹H NMR | ESI (m/z) |
|---|---|---|---|---|
| 31 | 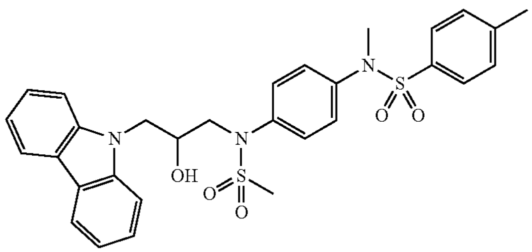 [SMILES: Cc1ccc(S(=O)(=O)N(C)c2ccc(N(CC(O)Cn3c4ccccc4c4ccccc43)S(C)(=O)=O)cc2)cc1] | N-(4-(N-(3-(9H-Carbazol-9-yl)-2-hydroxypropyl) methylsulfonamido) phenyl)-N,4-dimethylbenzene-sulfonamide | (300 MHz, CDCl₃) δ 8.10 (d, 2H, J = 7.5 Hz), 7.50-7.10 (m, 14H), 4.50-4.22 (m, 3H), 3.98 (dd, 1H, J = 14.4, 7.5 Hz), 3.84 (dd, 1H, J = 14.4, 4.5 Hz), 3.15 (s, 3H), 2.97 (s, 3H), 2.39 (s, 3H), 2.27 (d, 1H, J = 3.6 Hz). | 578.0 (M + H) |
| 32 | 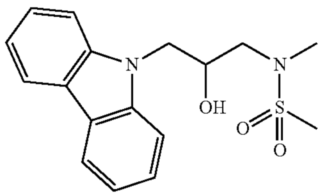 [SMILES: CN(CC(O)Cn1c2ccccc2c2ccccc21)S(C)(=O)=O] | N-(3-(9H-Carbazol-9-yl)-2-hydroxypropyl)-N-methylmethane-sulfonamide | (300 MHz, CDCl₃) δ 8.11 (d, 2H, J = 7.5 Hz), 7.53-7.44 (m, 4H), 7.31-7.24 (m, 2H), 4.54-4.36 (m, 3H), 3.45 (dd, 1H, J = 14.4, 7.5 Hz), 3.25 (dd, 1H, J = 15.0, 3.3 Hz), 2.94 (s, 3H), 2.87 (s, 3H), 2.41 (d, 1H, J = 3.0 Hz). | 333.1 (M + H) |
| 33 | 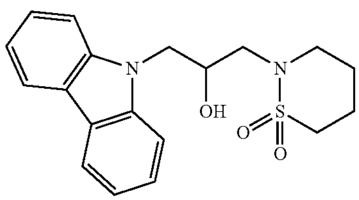 [SMILES: O=S1(=O)CCCCN1CC(O)Cn1c2ccccc2c2ccccc21] | N-(3-(9H-Carbazol-9-yl)-2-hydroxypropyl)-1,2-thiazinane 1,1-dioxide | (300 MHz, CDCl₃) δ 8.10 (d, 2H, J = 7.8 Hz), 7.55-7.40 (m, 4H), 7.32-7.20 (m, 2H), 4.50-4.30 (m, 3H), 3.50-3.35 (m, 3H), 3.29 (dd, 1H, J = 14.4, 4.2 Hz), 3.16-2.98 (m, 2H), 2.47 (d, 1H, J = 3.3 Hz), 2.28-2.14 (m, 2H), 1.70-1.58 (m, 2H). | 359.0 (M + H) |
| 34 | 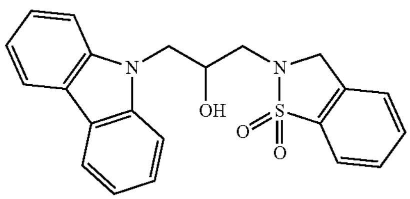 [SMILES: O=S1(=O)c2ccccc2CN1CC(O)Cn1c2ccccc2c2ccccc21] | N-(3-(9H-Carbazol-9-yl)-2-hydroxypropyl)-2,3-dihydrobenzo[d] isothiazole 1,1-dioxide | (CDCl₃, 300 MHz) δ 8.11-8.08 (dt, 2H, J = 0.9, 8.4 Hz), 7.85-7.83 (d, 1H, J = 7.2 Hz), 7.63-7.4 (m, 6H), 7.36-7.34 (d, 1H, J = 6.9 Hz), 7.28-7.23 (m, 2H), 4.60-4.47 (m, 5H), 3.62-3.54 (dd, 1H, J = 14.4, 6.9 Hz), 2.64-2.63 (d, 1H), J = 3.3 Hz). | 393.1 (M + H) |
| 35 | 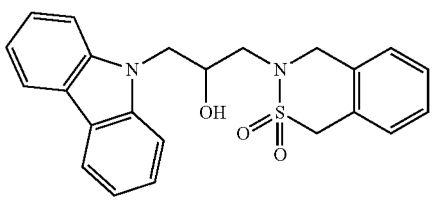 [SMILES: O=S1(=O)Cc2ccccc2CN1CC(O)Cn1c2ccccc2c2ccccc21] | N-(3-(9H-Carbazol-9-yl)-2-hydroxypropyl)-3,4-dihydro-1H-benzo[d][1,2] thiazine 2,2-dioxide | (CDCl₃, 300 MHz) δ 8.10-8.07 (d, 2H, J = 7.5 Hz), 7.46-7.45 (m, 4H), 7.30-7.22 (m, 4H), 7.10-7.06 (m, 2H), 4.71 (s, 2H), 4.46 (s, 2H), 4.40 (m, 1H), 4.37-4.36 (d, 2H, J = 3.3 Hz), 3.43-3.41 (d, 2H, J = 4.2 Hz), 2.28-2.27 (d, 1H, J = 2.7 Hz). | 407.1 (M + H) |
| 36 | 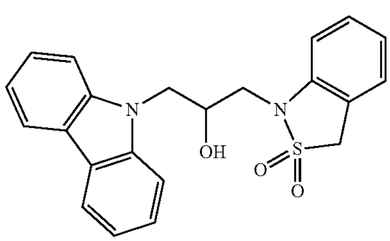 [SMILES: O=S1(=O)Cc2ccccc2N1CC(O)Cn1c2ccccc2c2ccccc21] | N-(3-(9H-Carbazol-9-yl)-2-hydroxypropyl)-1,3-dihydrobenzo[c] isothiazole 2,2-dioxide | (CDCl₃, 300 MHz) δ 8.12-8.10 (d, 1H, J = 6.6 Hz), 7.48-7.46 (m, 4H), 7.23-7.25 (m, 2H), 7.20-7.17 (d, 1H, J = 7.8 Hz), 7.08-7.03 (t, 1H, J = 7.8 Hz), 6.95-6.90 (t, 1H, J = 7.4 Hz), 6.24-6.21 (d, 1H, J = 8.1 Hz), 4.58 (m, 3H), 4.37 (s, 2H), 3.86-3.79 (dd, 1H, J = 7.1, 15.5 Hz), 3.67 (dd, 1H, J = 3.0, 15.3 Hz), 2.81-2.80 (d, 1H, J = 3.0 Hz). | 393.0 (M + H) |
| 37 | 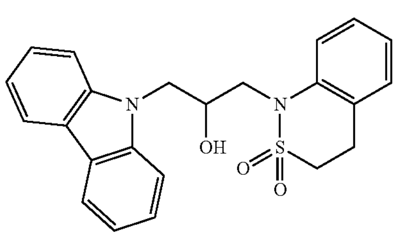 [SMILES: O=S1(=O)CCc2ccccc2N1CC(O)Cn1c2ccccc2c2ccccc21] | N-(3-(9H-Carbazol-9-yl)-2-hydroxypropyl)-3,4-dihydro-1H-benzo[c][1,2] thiazine 2,2-dioxide | (CDCl₃, 300 MHz) δ 8.12-8.09 (dt, 2H, J = 0.9, 7.5 Hz), 7.46-7.42 (m, 4H), 7.29-7.25 (m, 2H), 7.11-7.08 (m, 1H), 6.97-6.93 (m, 2H), 6.60-6.57 (m, 1H), 4.49-4.54 (m, 1H), 4.49-4.67 (d, 2H, J = 6.6 Hz), 4.07-3.99 (dd, 1H, J = 8.3, 15.5 Hz), 3.88-3.83 (dd, 1H, J = 3.2, 15.6 Hz), 3.45-3.30 (m, 4H), 2.52-2.51 (d, 1H, J = 3.9 Hz). | 407.0 (M + H) |

| Cpd # | Structure | Name | ¹H NMR | ESI (m/z) |
|---|---|---|---|---|
| 38 | 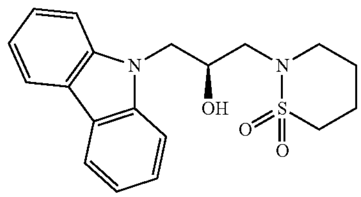 | (S)-N-(3-(9H-Carbazol-9-yl)-2-hydroxypropyl)-1,2-thiazinane 1,1-dioxide (61.7% ee) | (300 MHz, CDCl₃) δ 8.09 (d, 2H, J = 8.1 Hz), 7.55-7.40 (m, 4H), 7.32-7.20 (m, 2H), 4.50-4.30 (m, 3H), 3.50-3.35 (m, 3H), 3.29 (dd, 1H, J = 14.4, 3.9 Hz), 3.16-2.98 (m, 2H), 2.44 (d, 1H, J = 3.0 Hz), 2.28-2.14 (m, 2H), 1.70-1.58 (m, 2H). | 359.0 (M + H) |
| 39 | 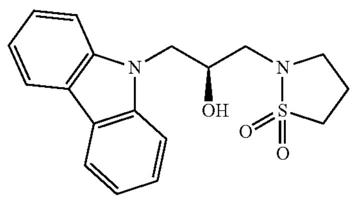 [SMILES: O=S1(=O)CCCN1C[C@@H](O)Cn1c2ccccc2c2ccccc21] | (S)-N-(3-(9H-Carbazol-9-yl)-2-hydroxypropyl) isothiazolidine 1,1-dioxide (>99% ee) | (300 MHz, CDCl₃) δ 8.09 (d, 2H, J = 8.1 Hz), 7.47 (d, 4H, J = 3.3 Hz), 7.30-7.20 (m, 2H), 4.55-4.35 (m, 3H), 3.42-3.12 (m, 6H), 2.60 (d, 1H, J = 3.0 Hz), 2.35 (m, 2H). | 345.0 (M + H) |
| 40 | 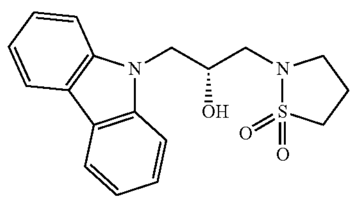 [SMILES: O=S1(=O)CCCN1C[C@H](O)Cn1c2ccccc2c2ccccc21] | (R)-N-(3-(9H-Carbazol-9-yl)-2-hydroxypropyl) isothiazolidine 1,1-dioxide (78.7% ee) | (300 MHz, CDCl₃) δ 8.09 (d, 2H, J = 7.5 Hz), 7.47 (d, 4H, J = 3.9 Hz), 7.30-7.20 (m, 2H), 4.55-4.35 (m, 3H), 3.40-3.10 (m, 6H), 2.60 (d, 1H, J = 3.0 Hz), 2.35 (m, 2H). | 345.0 (M + H) |
| 41 | 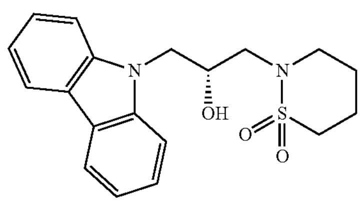 [SMILES: O=S1(=O)CCCCN1C[C@H](O)Cn1c2ccccc2c2ccccc21] | (R)-N-(3-(9H-Carbazol-9-yl)-2-hydroxypropyl)-1,2-thiazinane 1,1-dioxide (77.3% ee) | (300 MHz, CDCl₃) δ 8.09 (d, 2H, J = 7.8 Hz), 7.55-7.40 (m, 4H), 7.32-7.20 (m, 2H), 4.50-4.30 (m, 3H), 3.50-3.35 (m, 3H), 3.29 (dd, 1H, J = 14.4, 3.9 Hz), 3.16-2.98 (m, 2H), 2.45 (d, 1H, J = 3.0 Hz), 2.28-2.14 (m, 2H), 1.70-1.58 (m, 2H). | 359.1 (M + H) |
| 42 | 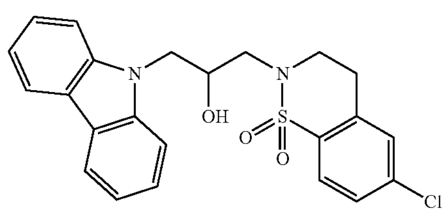 [SMILES: O=S1(=O)c2ccc(Cl)cc2CCN1CC(O)Cn1c2ccccc2c2ccccc21] | N-(3-(9H-Carbazol-9-yl)-2-hydroxypropyl)-6-chloro-3,4-dihydro-2H-benzo[e][1,2]thiazine 1,1-dioxide | (300 MHz, CDCl₃) δ 8.10 (d, 2H, J = 7.8 Hz), 7.80 (d, 1H, J = 8.4 Hz), 7.54-7.42 (m, 4H), 7.39 (dd, 1H, J = 8.1, 1.5 Hz), 7.32-7.20 (m, 3H), 4.60-4.35 (m, 3H), 3.98 (t, 2H, J = 6.3 Hz), 3.52-3.32 (m, 2H), 3.10-2.85 (m, 2H), 2.38 (d, 1H, J = 2.7 Hz). | 440.9 (M + H) |
| 43 | 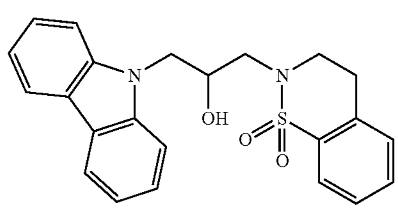 [SMILES: O=S1(=O)c2ccccc2CCN1CC(O)Cn1c2ccccc2c2ccccc21] | N-(3-(9H-Carbazol-9-yl)-2-hydroxypropyl)-3,4-dihydro-2H-benzo[e][1,2]thiazine 1,1-dioxide | (300 MHz, CDCl₃) δ 8.10 (d, 2H, J = 7.5 Hz), 7.87 (d, 1H, J = 7.2 Hz), 7.56-7.36 (m, 6H), 7.33-7.18 (m, 3H), 4.49 (m, 3H), 3.98 (t, 2H, J = 6.3 Hz), 3.44 (m, 2H), 3.01 (m, 2H), 2.43 (d, 1H, J = 2.4 Hz). | 407.0 (M + H) |
| 44 | 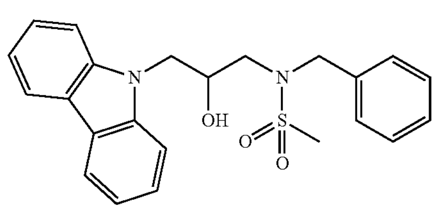 [SMILES: CS(=O)(=O)N(Cc1ccccc1)CC(O)Cn1c2ccccc2c2ccccc21] | N-(3-(9H-Carbazol-9-yl)-2-hydroxypropyl)-N-benzylmethane-sulfonamide | (CDCl₃, 300 MHz) δ 8.11-8.07 (d, 2H, J = 8.4 Hz), 7.45-7.41 (t, 2H, J = 7.7 Hz), 7.27-7.13 (m, 7H), 7.06-7.03 (m, 2H), 4.36-4.17 (m, 5H), 3.50-3.42 (dd, 1H, J = 8.3, 15.2 Hz), 3.22-3.16 (dd, 1H, J = 2.4, 15.0 Hz), 2.89 (s, 3H), 2.63-2.62 (d, 1H, J = 2.7 Hz). | 409.0 (M + H) |

-continued

| Cpd # | Structure | Name | $^1$H NMR | ESI (m/z) |
|---|---|---|---|---|
| 45 | 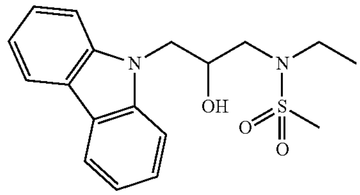 [SMILES: CCN(CC(O)Cn1c2ccccc2c2ccccc21)S(C)(=O)=O] | N-(3-(9H-Carbazol-9-yl)-2-hydroxypropyl)-N-ethylmethane-sulfonamide | (CDCl$_3$, 300 MHz) δ 8.14-8.08 (dt, 2H, J = 0.3, 7.8 Hz), 7.48-7.46 (m, 4H), 7.28-7.23 (m, 2H), 4.41-4.06 (d, 2H, J = 1.5 Hz), 4.41 (m, 1H), 3.47-3.38 (m, 1H), 3.30-3.23 (q, 2H, J = 7.2 Hz), 3.29 (m, 1H), 2.88 (s, 3H), 2.67 (br s, 1H), 1.12-1.07 (t, 3H, J = 7.2 Hz). | 346.8 (M + H) |
| 46 | 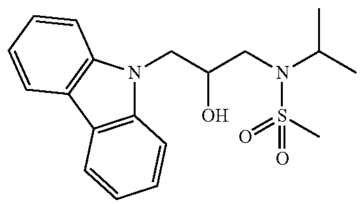 [SMILES: CC(C)N(CC(O)Cn1c2ccccc2c2ccccc21)S(C)(=O)=O] | N-(3-(9H-Carbazol-9-yl)-2-hydroxypropyl)-N-isopropylmethane-sulfonamide | (CDCl$_3$, 300 MHz) δ 8.11-8.08 (dd, 2H, J = 0.6, 7.5 Hz), 7.5-7.44 (m, 4H), 7.27-7.22 (m, 2H), 4.42-4.33 (m, 3H), 3.98-3.89 (septet, 1H, J = 6.8 Hz), 3.29 (br s, 1H), 3.29-3.22 (dd, 1H, J = 7.2, 15.6 Hz), 3.18-3.12 (dd, 1H, J = 2.4, 15.6 Hz), 2.86 (s, 3H), 0.91-0.89 (d, 3H, J = 6.6 Hz), 0.82-0.79 (d, 3H, J = 6.6 Hz). | 360.9 (M + H) |
| 47 | 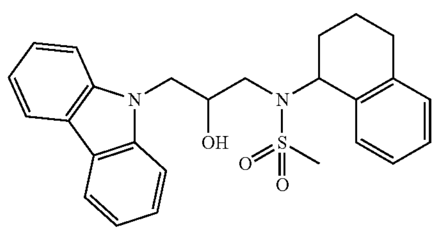 [SMILES: CS(=O)(=O)N(CC(O)Cn1c2ccccc2c2ccccc21)C1CCCc2ccccc21] | N-(3-(9H-Carbazol-9-yl)-2-hydroxypropyl)-N-(1,2,3,4-tetrahydro-naphthalen-1-yl)methanesulfon-amide | (CDCl$_3$, 300 MHz) (diastereomeric mixture) δ 8.04-8.01 (br d, 2H, J = 7.2 Hz), 7.41-7.14 (m, 2.5 H), 7.07-7.04 (m, 0.5H), 7.00-6.96 (m, 1H), 6.86-6.81 (br t, 0.5H, J = 7.5 Hz), 6.75-.6.71 (m, 1H), 6.75-6.55 (br d, 0.5H, J = 7.5 Hz), 5.04-4.99 (m, 0.5H), 4.92-4.87 (dd, 0.5H, J = 5.7, 10.2 Hz), 4.33-3.93 (m, 3H), 3.56-3.55 (d,.5H, J = 2.4 Hz), 3.36-3.09 (m, 2H), 3.08 (s, 1.5H), 3.03 (s, 1.5H), 2.97-2.92 (dd, 0.5H, J = 1.2 Hz, 15.9 Hz), 2.37-2.25 (m, 1H), 1.97-1.68 (m, 2H), 1.52-1.14 (m, 3H) | 449.0 (M + H) |
| 48 | 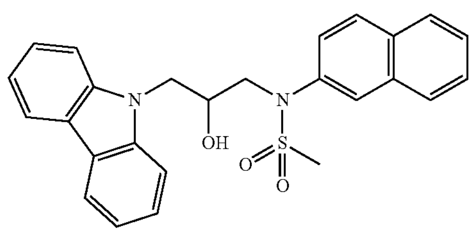 [SMILES: CS(=O)(=O)N(CC(O)Cn1c2ccccc2c2ccccc21)c1ccc2ccccc2c1] | N-(3-(9H-Carbazol-9-yl)-2-hydroxypropyl)-N-(naphthalen-2-yl)methanesulfon-amide | (CDCl$_3$, 300 MHz) δ 8.05-8.03 (dd, 2H, J = 0.9, 6.9 Hz), 7.85-7.77 (m, 4H), 7.54-7.44 (m, 3H), 7.39-7.32 (m, 3H), 7.27-7.17 (m, 3H), 4.51-4.34 (m, 3H), 4.10-4.34 (dd, 1H, J = 6.9, 14.4 Hz), 3.98-3.92 (dd, 1H, J = 5.1, 14.1 Hz), 2.97 (s, 3H), 2.38 (br s, 1H) | 444.9 (M + H) |
| 49 | 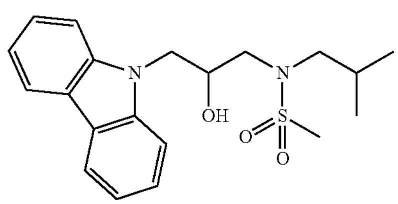 [SMILES: CC(C)CN(CC(O)Cn1c2ccccc2c2ccccc21)S(C)(=O)=O] | N-(3-(9H-Carbazol-9-yl)-2-hydroxypropyl)-N-isobutylmethane-sulfonamide | (CDCl$_3$, 300 MHz) δ 8.11-8.08 (br d, 2H, J = 7.8 Hz), 7.51-7.43 (m, 4H), 7.28-7.23 (m, 2H), 4.45-4.33 (m, 3H), 3.47-3.39 (dd, 1H, J = 7.8, 15 Hz), 3.18-3.12 (dd, 1H, J = 2.6, 15 Hz), 2.86-2.82 (m, 3H), 2.84 (s, 3H), 1.52-1.42 (nonet, 1H, J = 6.8 Hz), 0.79-0.77 (d, 3H, J = 6.6 Hz), 0.76-0.75 (d, 3H, J = 6.6 Hz) | 375.1 (M + H) |
| 50 | 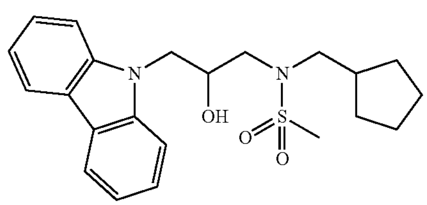 [SMILES: CS(=O)(=O)N(CC(O)Cn1c2ccccc2c2ccccc21)CC1CCCC1] | N-(3-(9H-Carbazol-9-yl)-2-hydroxypropyl)-N-(cyclopentylmeth-yl)methanesulfon-amide | (300 MHz, CDCl$_3$) δ 8.11-8.08 (d, 2H, J = 7.5 Hz), 7.51-7.44 (m, 4H), 7.28-7.23 (m, 2H), 4.45-4.34 (m, 3H), 3.45-3.38 (dd, 1H, J = 7.5, 15.0 Hz), 3.14-3.08 (dd, 1H, J = 2.1, 15.3 Hz), 3.03-3.02 (d, 1H, J = 2.4 Hz), 2.99-2.85 (m, 2H), 2.84 (s, 3H), 1.49-0.98 (m, 9H) | 401.1 (M + H) |

| Cpd # | Name | ¹H NMR | ESI (m/z) |
|---|---|---|---|
| 51 | N-(3-(9H-Carbazol-9-yl)-2-hydroxypropyl)-N-((tetrahydrofuran-2-yl)methyl)methanesulfonamide | (300 MHz, CDCl₃) (diastereomeric mixture) δ 8.10-8.07 (m, 2H), 7.51-7.43 (m, 4H), 7.26-7.21 (m, 2H), 4.55-4.47 (m, 1H), 4.39-4.32 (m, 2H), 4.30-4.22 (dd, 1H, J = 4.1, 20.1 Hz), 4.12-4.05 (m, 1H), 3.76-3.53 (m, 4H), 3.48-3.42 (dd, 1H, J = 2.0, 15.0 Hz), 3.24-3.10 (m, 1H), 2.96-2.86 (m, 1H), 2.91 (s, 1.5H), 2.87 (s, 1.5H), 1.98-1.75 (m, 3H), 1.43-1.30 (m, 1H) | 403.1 (M + H) |
| 52 | N-(3-(9H-Carbazol-9-yl)-2-hydroxypropyl)-N-(cyclohexylmethyl)methanesulfonamide | (300 MHz, CDCl₃) δ 8.11-8.08 (d, 2H, J = 7.8 Hz), 7.51-7.43 (m, 4H), 7.28-7.23 (m, 2H), 4.44-4.32 (m, 3H), 3.46-3.38 (m, 1H), 3.12-3.04 (dd, 1H, J = 1.8, 8.1 Hz), 3.09 (s, 1H), 2.88-2.68 (m, 2H), 2.84 (s, 3H), 1.56-0.63 (m, 11H) | 415.1 (M + H) |
| 53 | N-(3-(9H-Carbazol-9-yl)-2-hydroxypropyl)-N-((tetrahydro-2H-pyran-2-yl)methyl)methanesulfonamide | (300 MHz, CDCl₃) (diastereomeric mixture) δ 8.10-8.07 (m, 2H), 7.50-7.45 (m, 4H), 7.27-7.20 (m, 2H), 4.60-4.59 (d, 0.5H, J = 3.0 Hz), 4.52-4.32 (m, 3H), 4.14-4.13 (d, 0.5H, J = 4.2 Hz), 3.89-2.92 (m, 7H), 2.87 (s, 1.5H), 2.80 (s, 1.5H), 1.81-1.11 (m, 6H) | 417.1 (M + H) |
| 54 | N-(3-(9H-Carbazol-9-yl)-2-hydroxypropyl)-N-phenethylmethanesulfonamide | (300 MHz, CDCl₃) δ 8.12-8.10 (d, 2H, J = 7.8 Hz), 7.52-7.42 (m, 4H), 7.30-7.17 (m, 5H), 6.95-6.91 (m, 2H), 4.43-4.32 (m, 3H), 3.45-3.32 (m, 3H), 3.20-3.15 (m, 1H), 2.73-2.57 (m, 3H), 2.67 (s, 3H) | 423.0 (M + H) |
| 55 | N-(3-(9H-Carbazol-9-yl)-2-hydroxypropyl)-N-(2-(methylsulfonyl)ethyl)methanesulfonamide | (300 MHz, CDCl₃) δ 8.11-8.08 (d, 2H, J = 7.5 Hz), 7.51-7.43 (m, 4H), 7.29-7.23 (m, 2H), 4.48-4.35 (m, 3H), 3.70-3.63 (m, 2H), 3.50-3.31 (m, 4H), 2.94 (s, 3H), 2.91 (s, 3H), 2.74 (br s, 1H) | 425.1 (M + H) |
| 56 | N-(3-(9H-Carbazol-9-yl)-2-hydroxypropyl)-N-cyclopropylmethanesulfonamide | (300 MHz, CDCl₃) δ 8.10-8.08 (d, 2H, J = 7.8 Hz), 7.50-7.43 (m, 4H), 7.28-7.22 (m, 2H), 4.53-4.46 (m, 1H), 4.69-4.34 (d, 2H, J = 6.0 Hz), 3.54-3.46 (dd, 1H, J = 9.0, 15.0 Hz), 3.30-3.25 (dd, 1H, J = 3.2, 14.4 Hz), 2.93 (s, 3H), 2.60-2.59 (d, 1H, J = 2.7 Hz), 2.41-2.34 (m, 1H), 0.81-0.76 (m, 4H) | 359.1 (M + H) |
| 57 | N-(3-(9H-Carbazol-9-yl)-2-hydroxypropyl)-N-cyclobutylmethanesulfonamide | (300 MHz, CDCl₃) δ 8.11-8.07 (dt, 2H, J = 0.9, 7.5 Hz), 7.48-7.46 (m, 4H), 7.27-7.22 (m, 2H), 4.42-4.40 (d, 2H, J = 6.9 Hz), 4.35-4.28 (m, 1H), 4.15-4.09 (m, 1H), 3.29-3.26 (m, 2H), 3.02-3.01 (d, 1H, J = 3.0 Hz), 2.78 (s, 3H), 1.97-1.74 (m, 3H), 1.58-1.31 (m, 3H) | 373.0 (M + H) |

| Cpd # | Structure | Name | ¹H NMR | ESI (m/z) |
|---|---|---|---|---|
| 58 | 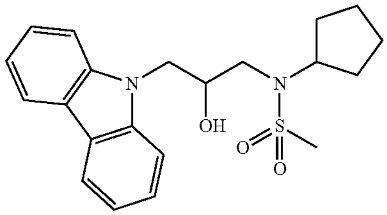 [SMILES: CS(=O)(=O)N(CC(O)Cn1c2ccccc2c2ccccc21)C1CCCC1] | N-(3-(9H-Carbazol-9-yl)-2-hydroxypropyl)-N-cyclopentylmethanesulfonamide | (300 MHz, CDCl₃) δ 8.10-8.07 (br d, 2H, J = 7.5 Hz), 7.51-7.44 (m, 4H), 7.27-7.22 (m, 2H), 4.45-4.32 (m, 3H), 4.05-3.93 (quint, 1H, J = 9.0 Hz), 3.49 (d, 1H, J = 1.8 Hz), 3.22-3.14 (dd, 1H, J = 6.9, 15.9 Hz), 3.05-2.99 (dd, 1H, J = 2.4, 15.6 Hz), 2.83 (s, 3H), 1.68-0.89 (m, 7H), 0.61-0.48 (m, 1H) | 387.0 (M + H) |
| 59 | 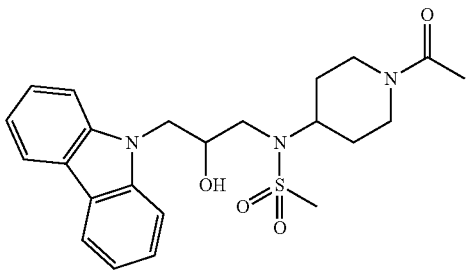 [SMILES: CC(=O)N1CCC(N(CC(O)Cn2c3ccccc3c3ccccc32)S(C)(=O)=O)CC1] | N-(3-(9H-Carbazol-9-yl)-2-hydroxypropyl)-N-(1-acetylpiperidin-4-yl)methanesulfonamide | (300 MHz, CDCl₃) δ 8.11-8.06 (m, 2H), 7.51-7.42 (m, 4H), 7.28-7.20 (m, 2H), 4.45-4.24 (m, 4H), 3.66-3.57 (m, 2H), 3.35-3.10 (m, 3H), 2.89 (s, 1.5H), 2.88 (s, 1.5H), 2.83-2.65 (m, 1H), 2.32-2.20 (m, 1H), 1.98 (s, 1.5H), 1.92 (s, 1.5H), 1.60-1.38 (m, 2H), 1.26-1.09 (m, 0.5H), 0.97-0.70 (m, 1H), 0.53-0.40 (qd, 0.5H, J = 4.5, 12.3 Hz) | 444.2 (M + H) |
| 60 | 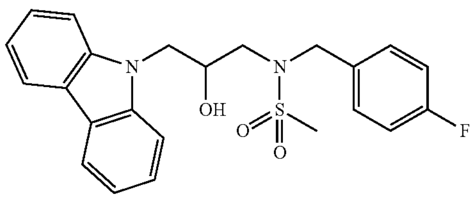 [SMILES: CS(=O)(=O)N(Cc1ccc(F)cc1)CC(O)Cn1c2ccccc2c2ccccc21] | N-(3-(9H-Carbazol-9-yl)-2-hydroxypropyl)-N-(4-fluorobenzyl)methanesulfonamide | (CDCl₃, 300 MHz) δ 8.11-8.08 (m, 2H), 7.46-7.38 (m, 2H), 7.29-7.23 (m, 4H), 6.94-6.90 (dd, 2H, J = 5.1, 8.7 Hz), 6.78-6.72 (t, 2H, J = 8.4 Hz), 4.30-4.10 (m, 5H), 3.49-3.42 (dd, 1H, J = 2.4, 15.3 Hz), 3.14-3.08 (dd, 1H, J = 2.7, 15.0 Hz), 2.90 (s, 3H), 2.78-2.77 (d, 1H, J = 2.4 Hz) | 427.3 (M + H) |
| 61 | 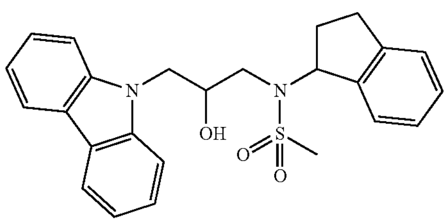 [SMILES: CS(=O)(=O)N(CC(O)Cn1c2ccccc2c2ccccc21)C1CCc2ccccc21] | N-(3-(9H-Carbazol-9-yl)-2-hydroxypropyl)-N-(2,3-dihydro-1H-inden-1-yl)methanesulfonamide | (300 MHz, CDCl₃) (diastereomer 1) δ 8.04-8.01 (m, 2H), 7.37-7.32 (m, 2H), 7.22-7.17 (m, 4H), 7.07-6.99 (m, 3H), 6.82-6.80 (m, 1H), 5.33-5.28 (m, 1H), 4.32-4.09 (m, 3H), 3.23-3.12 (dd, 1H, J = 7.8, 15.9 Hz), 3.09-3.08 (d, 1H, J = 3.0 Hz), 3.04 (s, 3H), 2.97-2.91 (dd, 1H, J = 2.4, 15.9 Hz), 2.53-2.42 (m, 1H), 2.30-2.13 (m, 2H), 1.55-1.48 (m, 1H) | 435.0 (M + H) |
| 62 | 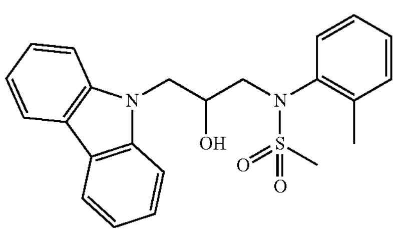 [SMILES: Cc1ccccc1N(CC(O)Cn1c2ccccc2c2ccccc21)S(C)(=O)=O] | N-(3-(9H-Carbazol-9-yl)-2-hydroxypropyl)-N-o-tolylmethanesulfonamide | (300 MHz, d6-DMSO) (rotameric mixture) δ 8.10-8.08 (d, 2H, J = 7.5 Hz), 7.49-7.44 (m, 2H), 7.39-7.34 (m, 2H), 7.31-7.20 (m, 3H), 7.17-7.12 (t, 2H, J = 7.2 Hz), 5.42 (d, 0.6H, J = 2.7 Hz), 5.15-5.13 (d, 0.4H, J = 3.0 Hz), 4.38-4.22 (m, 2H), 3.98-3.59 (m, 3H), 3.07 (s, 1.8H), 3.04 (s, 1.2H), 2.36 (s, 1.2H), 2.30 (s, 1.8H) | 409.1 (M + H) |
| 63 | 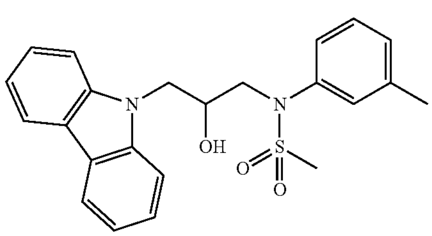 [SMILES: Cc1cccc(N(CC(O)Cn2c3ccccc3c3ccccc32)S(C)(=O)=O)c1] | N-(3-(9H-Carbazol-9-yl)-2-hydroxypropyl)-N-m-tolylmethanesulfonamide | (300 MHz, CDCl₃) δ 8.08-8.05 (d, 2H, J = 7.8 Hz), 7.45-7.14 (m, 10H), 4.49-4.43 (dd, 1H, J = 6.6, 14.4 Hz), 4.37-4.20 (m, 2H), 3.96-3.89 (dd, 1H, J = 7.1, 14.0 Hz), 3.85-3.79 (dd, 1H, J = 5.1, 13.8 Hz), 2.94 (s, 3H), 2.35 (s, 3H), 2.31-2.30 (d, 1H, J = 3.0 Hz) | 409.2 (M + H) |

| Cpd # | Structure | Name | ¹H NMR | ESI (m/z) |
|---|---|---|---|---|
| 64 | 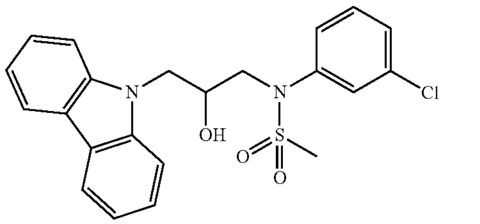 [SMILES: CS(=O)(=O)N(CC(O)Cn1c2ccccc2c2ccccc21)c1cccc(Cl)c1] | N-(3-(9H-Carbazol-9-yl)-2-hydroxypropyl)-N-(3-chlorophenyl)methanesulfonamide | (CDCl₃, 300 MHz) δ 8.08-8.05 (d, 2H, J = 8.4 Hz), 7.47-7.21 (m, 10H), 4.48-4.42 (dd, 1H, J = 3.8, 14.4 Hz), 4.39-4.27 (m, 2H), 3.97-3.95 (dd, 1H, J = 6.9, 14.1 Hz), 3.86-3.80 (dd, 1H, J = 4.8, 14.2 Hz), 2.95 (s, 3H), 2.23-2.22 (d, 1H, J = 3.6 Hz) | N/A |
| 65 | 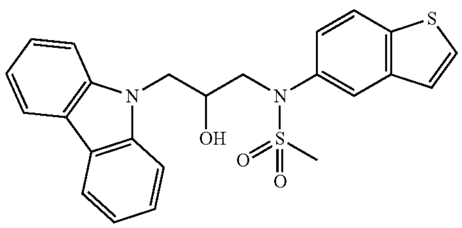 [SMILES: CS(=O)(=O)N(CC(O)Cn1c2ccccc2c2ccccc21)c1ccc2sccc2c1] | N-(3-(9H-Carbazol-9-yl)-2-hydroxypropyl)-N-(benzo[b]thiophen-5-yl)methanesulfonamide | (300 MHz, CDCl₃) δ 8.06-8.03 (d, 2H, J = 7.8 Hz), 7.89-7.86 (dd, 1H, J = 0.6, 8.4 Hz), 7.83-7.82 (d, 1H, J = 2.1 Hz), 7.54-7.52 (d, 1H, J = 5.4 Hz), 7.41-7.29 (m, 6H), 7.23-7.18 (m, 2H), 4.48-4.30 (m, 3H), 4.05-3.98 (dd, 1H, J = 7.2, 14.1 Hz), 3.91-3.84 (dd, 1H, J = 4.5, 14.1 Hz), 2.95 (s, 3H), 2.35-2.34 (d, 1H, J = 2.1 Hz) | 450.9 (M + H) |
| 66 | 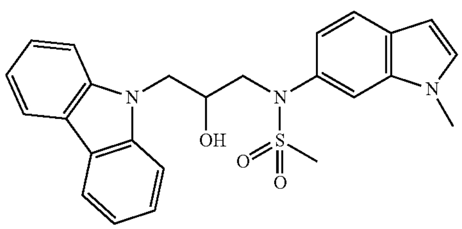 [SMILES: Cn1ccc2ccc(N(CC(O)Cn3c4ccccc4c4ccccc43)S(C)(=O)=O)cc21] | N-(3-(9H-Carbazol-9-yl)-2-hydroxypropyl)-N-(1-methyl-1H-indol-6-yl)methanesulfonamide | (300 MHz, CDCl₃) δ 8.06-8.04 (d, 2H, J = 7.5 Hz), 7.62-7.59 (d, 1H, J = 8.4 Hz), 7.40-7.34 (m, 5H), 7.23-7.18 (m, 4H), 7.13-7.12 (d, 1H, J = 3.0 Hz), 7.05-7.02 (dd, 1H, J = 2.0 Hz), 6.49-6.48 (dd, 1H, J = 0.6, 3.3 Hz), 4.54-4.48 (dd, 1H, J = 3.0, 14.1 Hz), 4.40-4.28 (m, 2H), 4.06-3.99 (dd, 1H, J = 7.1, 14.0 Hz), 3.78 (s, 3H), 2.96 (s, 3H), 2.35-2.34 (d, 1H, J = 3.6 Hz) | 447.9 (M + H) |
| 67 | 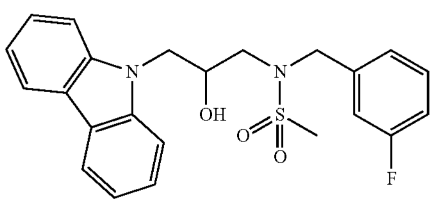 [SMILES: CS(=O)(=O)N(Cc1cccc(F)c1)CC(O)Cn1c2ccccc2c2ccccc21] | N-(3-(9H-Carbazol-9-yl)-2-hydroxypropyl)-N-(3-fluorobenzyl)methanesulfonamide | (300 MHz, CDCl₃) δ 8.10-8.07 (dt, 2H, J = 0.9, 7.5 Hz), 7.46-7.43 (m, 2H), 7.28-7.22 (m, 4H), 7.11-7.04 (m, 1H), 6.91-6.83 (m, 2H), 6.78-6.75 (br d, 1H, J = 7.5 Hz), 4.33-4.18 (m, 5H), 3.52-3.44 (dd, 1H, J = 7.7, 15.2 Hz), 3.21-3.15 (dd, 1H, J = 2.4, 15.0 Hz), 2.91 (s, 3H), 2.65 (br s, 1H) | 427.1 (M + H) |
| 68 | 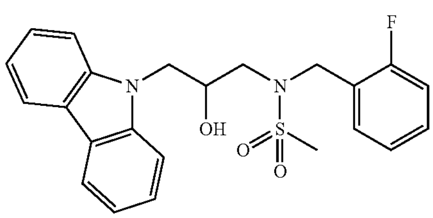 [SMILES: CS(=O)(=O)N(Cc1ccccc1F)CC(O)Cn1c2ccccc2c2ccccc21] | N-(3-(9H-Carbazol-9-yl)-2-hydroxypropyl)-N-(2-fluorobenzyl)methanesulfonamide | (300 MHz, CDCl₃) δ 8.10-8.08 (d, 2H, J = 7.5 Hz), 7.46-7.40 (m, 2H), 7.33-7.22 (m, 4H), 7.21-7.05 (m, 2H), 6.95-6.84 (m, 2H), 4.52-4.20 (m, 5H), 3.54-3.46 (m, 1H), 3.23-3.18 (m, 1H), 2.90 (s, 3H), 2.71-2.70 (d, 1H, J = 3.0 Hz) | 427.2 (M + H) |
| 69 | 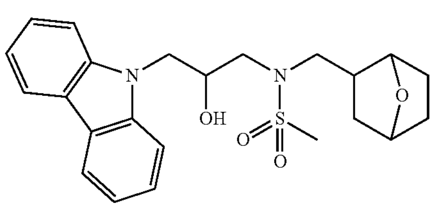 [SMILES: CS(=O)(=O)N(CC(O)Cn1c2ccccc2c2ccccc21)CC1CC2CCC1O2] | N-(7-Oxabicyclo[2.2.1]heptan-2-ylmethyl)-N-(3-(9H-carbazol-9-yl)-2-hydroxypropyl)methanesulfonamide | (CDCl₃, 300 MHz) (diastereomer 1) δ 8.10-8.08 (d, 2H, J = 7.52 Hz), 7.45-7.42 (m, 4H), 7.32-7.23 (m, 2H), 4.43-4.22 (m, 5H), 3.48 (s, 1H), 3.46-3.38 (dd, 1H, J = 8.1, 15.3 Hz), 3.26-3.03 (m, 3H), 2.86 (s, 3H), 2.11 (m, 1H), 1.77-1.22 (m, 5H), 0.86-0.74 (m, 1H) | 429.0 (M + H) |
| 70 | 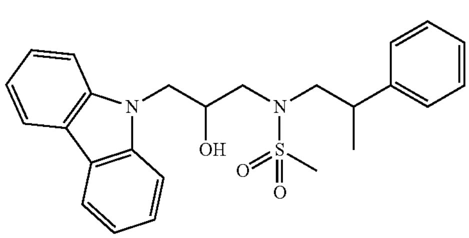 [SMILES: CC(CN(CC(O)Cn1c2ccccc2c2ccccc21)S(C)(=O)=O)c1ccccc1] | N-(3-(9H-Carbazol-9-yl)-2-hydroxypropyl)-N-(2-phenylpropyl)methanesulfonamide | (300 MHz, CDCl₃) δ 8.13-8.09 (m, 2H), 7.54-7.38 (m, 4H), 7.31-7.25 (m, 2H), 7.20-7.12 (m, 3H), 7.01-6.98 (m, 1H), 6.74-6.71 (m, 1H), 4.47-4.20 (m, 3H), 3.44-3.36 (m, 1H), 3.28-3.21 (m, 1H), 3.28-2.95 (m, 4H), 2.87-2.80 (m, 0.5H), 2.66 (s, 1.5H), 2.46-2.45 (d, 0.5H, J = 3.6 Hz), 2.38 (s, 1.5H), 2.18-2.10 (m, 0.5H), 1.17-1.15 (d, 1.5H, J = 6.9 Hz), 0.93-0.91 (d, 1.5H, J = 6.9 Hz) | 437.1 (M + H) |

-continued

| Cpd # | Structure | Name | ¹H NMR | ESI (m/z) |
|---|---|---|---|---|
| 71 | 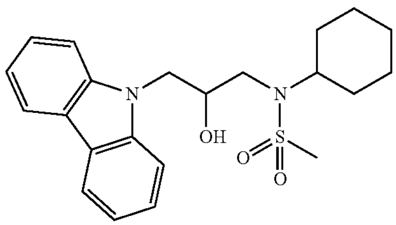 [SMILES: CS(=O)(=O)N(CC(O)Cn1c2ccccc2c2ccccc21)C1CCCCC1] | N-(3-(9H-Carbazol-9-yl)-2-hydroxypropyl)-N-cyclohexylmeth-anesulfonamide | (300 MHz, CDCl₃) δ 8.11-8.08 (dt, 2H, J = 0.9, 7.8 Hz), 7.49-7.46 (m, 4H), 7.27-7.22 (m, 2H), 4.47-4.27 (m, 3H), 3.48-3.47 (d, 1H, J = 6.9 Hz), 3.44-3.35 (tt, 1H, J = 3.8, 12.0 Hz), 3.26-3.19 (dd, 1H, J = 7.1, 15.9 Hz), 3.15-3.09 (dd, 1H, J = 2.6, 15.6 Hz), 2.84 (s, 3H), 1.55-1.28 (m, 5H), 1.16-0.94 (qd, 1H, J = 3.8, 12.0 Hz), 0.52-0.38 (qt, 1H, J = 3.6, 13.2 Hz), 0.34-0.21 (qd, 1H, J = 3.6, 12.5 Hz) | 401.1 (M + H) |
| 72 | 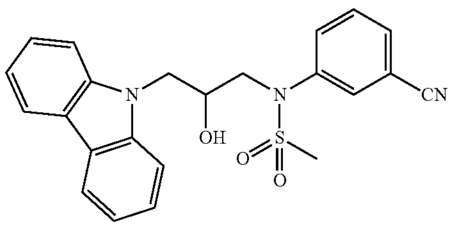 [SMILES: CS(=O)(=O)N(CC(O)Cn1c2ccccc2c2ccccc21)c1cccc(C#N)c1] | N-(3-(9H-Carbazol-9-yl)-2-hydroxypropyl)-N-(3-cyanophenyl)meth-anesulfonamide | (d6-DMSO, 300 MHz) δ 8.10-8.07 (d, 2H, J = 7.5 Hz), 8.00-7.98 (br t, 1H, J = 1.8 Hz), 7.81-7.76 (m, 2H), 7.62-7.57 (t, 1H, J = 7.8 Hz), 7.48-7.45 (d, 2H, J = 7.8 Hz), 7.4-7.34 (dt, 2H, J = 1.5, 7.2 Hz), 7.17-7.12 (br t, 2H, J = 6.9 Hz), 5.24-5.22 (d, 1H, J = 5.7 Hz), 4.42-4.25 (m, 2H), 3.93-3.83 (m, 3H), 3.08 (s, 3H) | N/A |
| 73 | 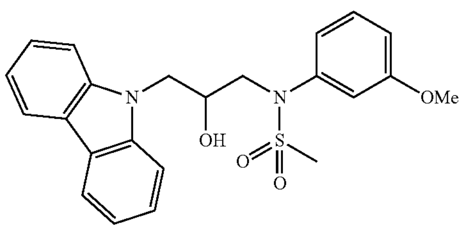 [SMILES: COc1cccc(N(CC(O)Cn2c3ccccc3c3ccccc32)S(C)(=O)=O)c1] | N-(3-(9H-Carbazol-9-yl)-2-hydroxypropyl)-N-(3-methoxyphenyl)methanesulfon-amide | (300 MHz, CDCl₃) δ 8.08-8.05 (dt, 2H, J = 0.9, 7.5 Hz), 7.45-7.20 (m, 7H), 6.96-6.86 (m, 3H), 4.50-4.44 (dd, 1H, J = 3.3, 14.4 Hz), 4.38-4.25 (m, 2H), 3.98-3.91 (dd, 1H, J = 6.9, 14.1 Hz), 3.87-3.82 (dd, 1H, J = 5.1, 14.1 Hz), 3.78 (s, 3H), 2.94 (s, 3H), 2.27-2.26 (d, 1H, J = 3.6 Hz) | 425.0 (M + H) |
| 74 | 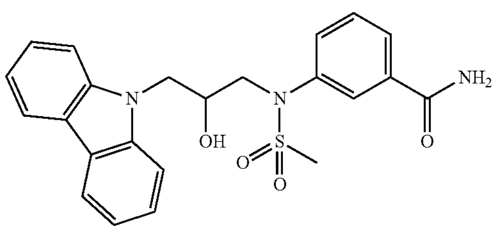 [SMILES: CS(=O)(=O)N(CC(O)Cn1c2ccccc2c2ccccc21)c1cccc(C(N)=O)c1] | 3-(N-(3-(9H-Carbazol-9-yl)-2-hydroxypropyl) methylsulfonamido) benzamide | (d6-DMSO, 300 MHz) δ 8.12 (br s, 1H), 8.09-8.06 (d, 2H, J = 7.8 Hz), 8.09 (s, 1H), 7.85-7.82 (d, 1H, J = 6.9 Hz), 7.65-7.63 (br d, 1H, J = 6.9 Hz), 7.53-7.47 (m, 3H), 7.43-7.41 (d, 2H, J = 7.8 Hz), 7.37-7.32 (t, 2H, J = 7.2 Hz), 7.15-7.11 (t, 2H, J = 7.2 Hz), 5.22-5.20 (d, 1H, J = 5.1 Hz), 4.45-4.40 (d, 1H, J = 14.7 Hz), 4.30-4.21 dd, 1H, J = 7.5, 15 Hz), 3.87 (br s, 3H), 3.06 (s, 3H) | 438.1 (M + H) |
| 75 | 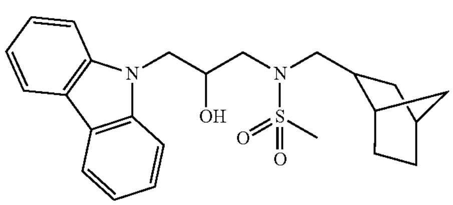 [SMILES: CS(=O)(=O)N(CC(O)Cn1c2ccccc2c2ccccc21)CC1CC2CCC1C2] | N-(3-(9H-Carbazol-9-yl)-2-hydroxypropyl)-N-(bicyclo[2.2.1]heptan-2-ylmethyl)methane-sulfonamide | (300 MHz, CDCl₃) (diastereomeric mixture) δ 8.11-8.08 (d, 2H, J = 7.8 Hz), 7.50-7.43 (m, 4H), 7.28-7.23 (m, 2H), 4.44-4.32 (m, 3H), 3.47-2.59 (m, 5H), 2.87 (s, 0.75H), 2.84 (s, 0.75H), 2.83 (s, 0.75H), 2.82 (s, 0.75H), 2.09-0.52 (m, 11H) | 427.4 (M + H) |
| 76 | 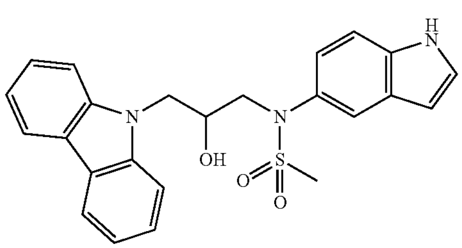 [SMILES: CS(=O)(=O)N(CC(O)Cn1c2ccccc2c2ccccc21)c1ccc2[nH]ccc2c1] | N-(3-(9H-Carbazol-9-yl)-2-hydroxypropyl)-N-(1H-indol-5-yl)methanesulfon-amide | (CDCl₃, 300 MHz) δ 8.28 (br s, 1H), 8.06-8.03 (dt, 2H, J = 0.9, 7.5 Hz), 7.67-7.66 (d, 1H, J = 1.8 Hz), 7.41-7.34 (m, 5H), 7.28-7.18 (m, 3H), 6.56-6.54 (m, 1H), 4.50-4.47 (dd, 1H, J = 3.0, 13.8 Hz), 4.39-4.32 (m, 2H), 4.05-3.98 (dd, 1H, J = 7.2, 13.8 Hz), 3.92-3.85 (dd, 1H, J = 5.1, 13.8 Hz), 2.97 (s, 3H), 2.34-2.33 (d, 1H, J = 3.6 Hz) | N/A |

-continued

| Cpd # | Structure | Name | ¹H NMR | ESI (m/z) |
|---|---|---|---|---|
| 77 | 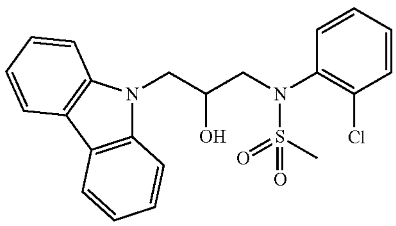 [SMILES: CS(=O)(=O)N(CC(O)Cn1c2ccccc2c2ccccc21)c1ccccc1Cl] | N-(3-(9H-Carbazol-9-yl)-2-hydroxypropyl)-N-(2-chlorophenyl)methanesulfonamide | (300 MHz, CDCl₃) (rotameric mixture) δ 8.08-8.05 (d, 2H, J = 7.5 Hz), 7.46-7.38 (m, 6H), 7.31-7.20 (m, 4H), 4.37-4.25 (m, 3H), 4.08-3.70 (m, 2H), 3.06 (s, 3H), 2.70 (br s, 0.6H). 2.32 (br s, 0.4H) | 429.0 (M + H) |
| 78 | 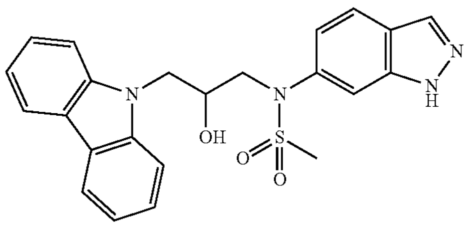 [SMILES: CS(=O)(=O)N(CC(O)Cn1c2ccccc2c2ccccc21)c1ccc2cn[nH]c2c1] | N-(3-(9H-Carbazol-9-yl)-2-hydroxypropyl)-N-(1H-indazol-6-yl)methanesulfonamide | (CDCl₃, 300 MHz) δ 10.02 (s, 1H), 8.06 (m, 3H), 7.75-7.72 (d, 1H, J = 8.7 Hz), 7.48 (br s, 1H), 7.46-7.32 (m, 4H), 7.26-7.19 (m, 2H), 7.12-7.09 (dd, 1H, J = 1.5, 8.4 Hz), 4.47-4.34 (m, 3H), 4.07-4.00 (dd, 1H, J = 6.9, 14.1 Hz), 3.90-3.84 (dd, 1H, J = 1.1, 14.7 Hz), 2.95 (s, 3H), 2.39-2.38 (d, 1H, J = 1.8 Hz) | 435.0 (M + H) |
| 79 | 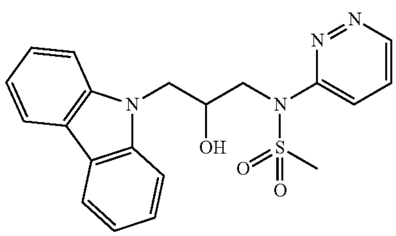 [SMILES: CS(=O)(=O)N(CC(O)Cn1c2ccccc2c2ccccc21)c1cccnn1] | N-(3-(9H-Carbazol-9-yl)-2-hydroxypropyl) N-(pyridazin-3-yl)methanesulfonamide | (300 MHz, CDCl₃) δ 8.10-8.08 (d, 2H, J = 7.8 Hz), 8.06-8.02 (dd, 1H, J = 1.5, 9.6 Hz), 7.95-7.93 (dd, 1H, J = 1.8, 4.2 Hz), 7.48-7.46 (m, 4H), 7.28-7.23 (m, 3H), 4.88-4.78 (br m, 1H), 4.54-4.44 (m, 3H), 4.32-4.25 (dd, 1H, J = 9.0, 13.5 Hz), 2.96-2.95 (d, 1H, J = 4.8 Hz), 2.58 (s, 3H) | 397.0 (M + H) |
| 80 | 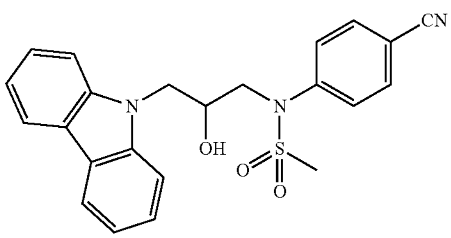 [SMILES: CS(=O)(=O)N(CC(O)Cn1c2ccccc2c2ccccc21)c1ccc(C#N)cc1] | N-(3-(9H-Carbazol-9-yl)-2-hydroxypropyl)-N-(4-cyanophenyl)methanesulfonamide | (CDCl₃, 300 MHz) δ 8.09-8.06 (ddd, 2H, J = 0.6, 1.3, 7.5 Hz), 7.60-7.57 (d, 2H, J = 6.6 Hz), 7.46-7.41 (ddd, 2H, J = 1.2, 6.9, 8.1 Hz), 7.39-7.36 (d, 2H, J = 6.0 Hz), 7.35-7.32 (dt, 2H, J = 3.0, 8.1 Hz), 7.27-7.22 (m, 2H), 4.46-4.31 (m, 3H), 4.01-3.93 (dd, 1H, J = 6.9, 14.7 Hz), 3.88-3.82 (dd, 1H, J = 3.6, 15 Hz), 2.94 (s, 3H), 2.28-2.27 (d, 1H, J = 3.6 Hz) | N/A |
| 81 | 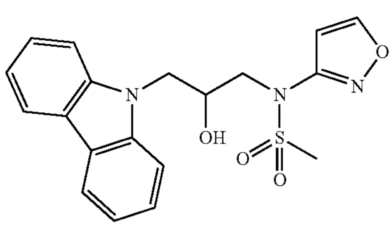 [SMILES: CS(=O)(=O)N(CC(O)Cn1c2ccccc2c2ccccc21)c1ccon1] | N-(3-(9H-Carbazol-9-yl)-2-hydroxypropyl) N-(isoxazol-3-yl)methanesulfonamide | (300 MHz, CDCl₃) δ 8.29 (d, 1H, J = 1.8 Hz), 8.10-8.07 (d, 2H, J = 7.8 Hz), 7.50-7.44 (m, 4H), 7.27-7.22 (m, 2H), 6.66-6.65 (d, 1H, J = 1.8 Hz), 4.69-4.63 (m, 1H), 4.51-4.45 (dd, 1H, J = 3.8, 15.0 Hz), 4.44-4.36 (dd, 1H, J = 8.1, 15.3 Hz), 4.18-4.15 (m, 2H), 3.09 (s, 3H), 2.50-2.48 (d, 1H, J = 4.8 Hz) | 386.1 (M + H) |
| 82 | 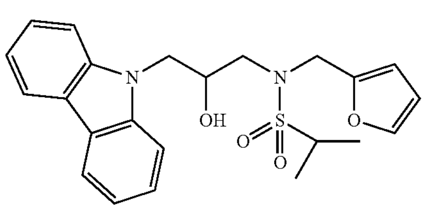 [SMILES: CC(C)S(=O)(=O)N(Cc1ccco1)CC(O)Cn1c2ccccc2c2ccccc21] | N-(3-(9H-Carbazol-9-yl)-2-hydroxypropyl)-N-(furan-2-ylmethyl)propane-2-sulfonamide | (300 MHz, CDCl₃) δ 8.11 (d, 2H, J = 7.5 Hz), 7.52-7.38 (m, 4H), 7.32-7.22 (m, 2H), 7.16 (d, 1H, J = 1.8 Hz), 6.09 (dd, 1H, J = 3.3, 1.8 Hz), 5.80 (d, 1H, J = 3.3 Hz), 4.51-4.25 (m, 5H), 3.49 (dd, 1H, J = 15.0, 7.2 Hz), 3.32 (m, 1H), 3.28 (dd, 1H, J = 15.0, 2.4 Hz), 2.87 (d, 1H, J = 2.4 Hz), 1.36 (d, 3H, J = 6.9 Hz), 1.30 (d, 3H, J = 6.9 Hz) | 427.1 (M + H) |

| Cpd # | Structure | Name | ¹H NMR | ESI (m/z) |
|---|---|---|---|---|
| 83 | 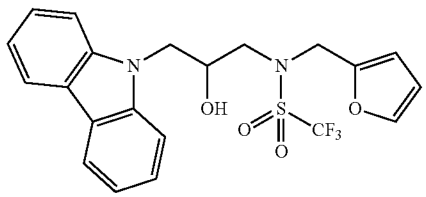 [SMILES: O=S(=O)(N(Cc1ccco1)CC(O)Cn1c2ccccc2c2ccccc21)C(F)(F)F] | N-(3-(9H-Carbazol-9-yl)-2-hydroxypropyl)-1,1,1-trifluoro-N-(furan-2-ylmethyl)methane-sulfonamide | (300 MHz, CDCl₃) δ 8.12 (d, 2H, J = 7.5 Hz), 7.49 (t, 2H, J = 7.5 Hz), 7.39 (d, 2H, J = 8.1 Hz), 7.28 (t, 2H, J = 7.5 Hz), 6.22 (br s, 2H), 4.62 (s, 2H), 4.33 (s, 3H), 3.56 (br s, 2H), 2.30 (br s, 1H). | N/A |
| 84 | 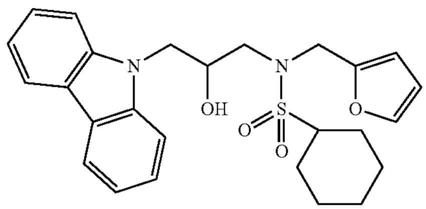 [SMILES: O=S(=O)(C1CCCCC1)N(Cc1ccco1)CC(O)Cn1c2ccccc2c2ccccc21] | N-(3-(9H-Carbazol-9-yl)-2-hydroxypropyl)-N-(furan-2-ylmethyl)cyclohex-anesulfonamide | (300 MHz, CDCl₃) δ 8.11 (d, 2H, J = 7.5 Hz), 7.52-7.40 (m, 4H), 7.31-7.23 (m, 2H), 7.17 (d, 1H, J = 1.8 Hz), 6.11 (dd, 1H, J = 3.0, 2.1 Hz), 5.82 (d, 1H, J = 3.0 Hz), 4.50-4.23 (m, 5H), 3.48 (dd, 1H, J = 15.0, 7.2 Hz), 3.29 (dd, 1H, J = 15.0, 2.4 Hz), 3.03 (tt, 1H, J = 12.0, 3.3 Hz), 2.87 (d, 1H, J = 1.8 Hz), 2.08 (m, 1H), 2.00-1.80 (m, 3H), 1.71 (m, 1H), 1.60-1.40 (m, 2H), 1.35-1.10 (m, 3H) | 467.2 (M + H) |
| 85 | 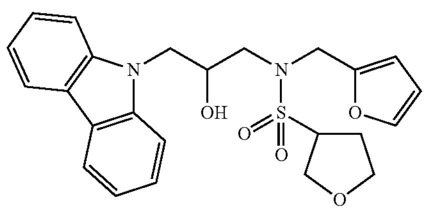 [SMILES: O=S(=O)(C1CCOC1)N(Cc1ccco1)CC(O)Cn1c2ccccc2c2ccccc21] | N-(3-(9H-Carbazol-9-yl)-2-hydroxypropyl)-N-(furan-2-ylmethyl)tetra-hydrofuran-3-sulfonamide | (300 MHz, CDCl₃) δ 8.11 (d, 2H, J = 7.8 Hz), 7.52-7.38 (m, 4H), 7.32-7.23 (m, 2H), 7.21 (m, 1H), 6.15 (m, 1H), 5.90 (m, 1H), 4.52 (dd, 1H, J = 15.9, 3.9 Hz), 4.46-4.22 (m, 4H), 4.15-3.75 (m, 5H), 3.51 (dd, 1H, J = 15.0, 7.5 Hz), 3.27 (ddd, 1H, J = 15.6, 7.5, 2.4 Hz), 2.71 (dd, 1H, J = 9.6, 3.0 Hz), 2.43-2.05 (m, 2H) | 455.2 (M + H) |
| 86 | 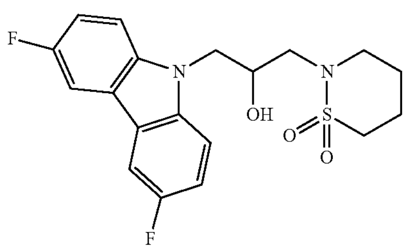 [SMILES: O=S1(=O)CCCCN1CC(O)Cn1c2ccc(F)cc2c2cc(F)ccc21] | N-(3-(3,6-Difluoro-9H-carbazol-9-yl)-2-hydroxypropyl)-1,2-thiazinane 1,1-dioxide | (300 MHz, CDCl₃) δ 7.69 (dd, 2H, J = 8.7, 2.4 Hz), 7.40 (dd, 2H, J = 8.7, 3.9 Hz), 7.23 (td, 2H, J = 9.0, 2.7 Hz), 4.44-4.28 (m, 3H), 3.46 (t, 2H, J = 5.7 Hz), 3.42-3.26 (m, 2H), 3.08 (td, 2H, J = 6.0, 2.1 Hz), 2.44 (d, 1H, J = 3.3 Hz), 2.30-2.18 (m, 2H), 1.73-1.62 (m, 2H) | N/A |
| 87 | 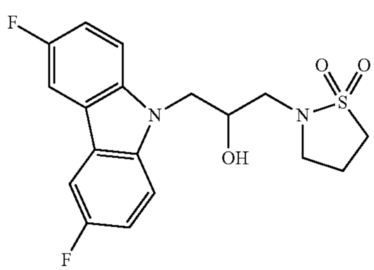 [SMILES: O=S1(=O)CCCN1CC(O)Cn1c2ccc(F)cc2c2cc(F)ccc21] | N-(3-(3,6-Difluoro-9H-carbazol-9-yl)-2-hydroxypropyl)-isothiazolidine-1,1-dioxide | (300 MHz, CDCl₃) δ 7.68 (dd, 2H, J = 8.7, 2.4 Hz), 7.41 (dd, 2H, J = 8.7, 3.9 Hz), 7.23 (td, 2H, J = 8.7, 2.4 Hz), 4.40 (s, 3H), 3.43-3.14 (m, 6H), 2.60 (d, 1H, J = 3.6 Hz), 2.45-2.33 (m, 2H) | N/A |
| 88 | 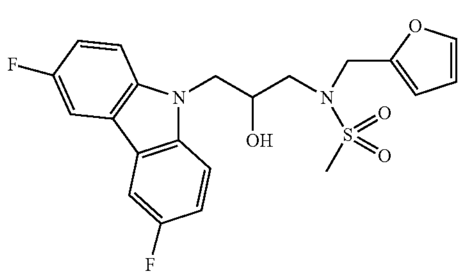 [SMILES: CS(=O)(=O)N(Cc1ccco1)CC(O)Cn1c2ccc(F)cc2c2cc(F)ccc21] | N-(3-(3,6-Difluoro-9H-carbazol-9-yl)-2-hydroxypropyl)-N-(furan-2-ylmethyl)methane-sulfonamide | (300 MHz, CDCl₃) δ 7.70 (dd, 2H, J = 8.7, 2.4 Hz), 7.35 (dd, 2H, J = 8.7, 4.2 Hz), 7.28 (m, 1H), 7.23 (td, 2H, J = 8.7, 2.4 Hz), 6.22 (dd, 1H, J = 3.3, 1.8 Hz), 6.03 (d, 1H, J = 3.3 Hz), 4.51 & 4.37 (AB, 2H, J = 15.9 Hz), 4.38-4.20 (m, 2H), 3.41 (dd, 1H, J = 14.7, 7.5 Hz), 3.25 (dd, 1H, J = 14.7, 3.3 Hz), 2.85 (s, 3H), 2.66 (d, 1H, J = 3.0 Hz) | N/A |

| Cpd # | Structure | Name | $^1$H NMR | ESI (m/z) |
|---|---|---|---|---|
| 89 | 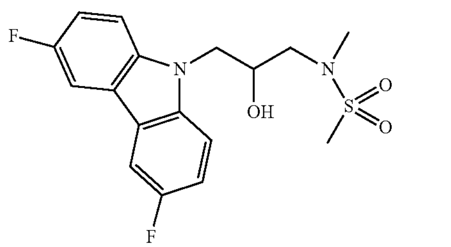 [SMILES: CN(CC(O)Cn1c2ccc(F)cc2c2cc(F)ccc21)S(C)(=O)=O] | N-(3-(3,6-Difluoro-9H-carbazol-9-yl)-2-hydroxypropyl)-N-methylmethane-sulfonamide | (300 MHz, CDCl$_3$) δ 7.69 (dd, 2H, J = 8.7, 2.4 Hz), 7.39 (dd, 2H, J = 9.0, 3.9 Hz), 7.24 (td, 2H, J = 9.0, 2.4 Hz), 4.50-4.32 (m, 3H), 3.41 (dd, 1H, J = 14.4, 6.9 Hz), 3.26 (dd, 1H, J = 14.4, 3.6 Hz), 2.97 (s, 3H), 2.88 (s, 3H), 2.38 (d, 1H, J = 3.3 Hz) | N/A |
| 90 | 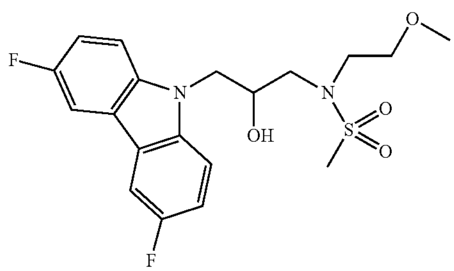 [SMILES: COCCN(CC(O)Cn1c2ccc(F)cc2c2cc(F)ccc21)S(C)(=O)=O] | N-(3-(3,6-Difluoro-9H-carbazol-9-yl)-2-hydroxypropyl)-N-(2-methoxyethyl)methanesulfonamide | (300 MHz, CDCl$_3$) δ 7.69 (dd, 2H, J = 8.7, 2.4 Hz), 7.41 (dd, 2H, J = 9.0, 3.9 Hz), 7.23 (td, 2H, J = 9.0, 2.7 Hz), 4.48-4.26 (m, 3H), 4.00 (d, 1H, J = 3.6 Hz), 3.62-3.18 (m, 9H), 2.88 (s, 3H) | 413.0 (M + H) |
| 91 | 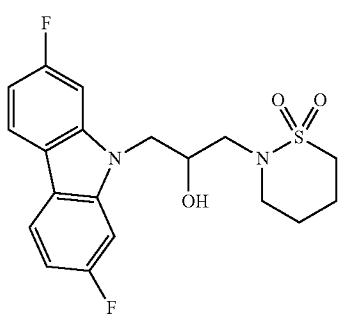 [SMILES: O=S1(=O)CCCCN1CC(O)Cn1c2cc(F)ccc2c2ccc(F)cc21] | N-(3-(2,7-Difluoro-9H-carbazol-9-yl)-2-hydroxypropyl)-1,2-thiazinane 1,1-dioxide | (300 MHz, CDCl$_3$) δ 7.93 (dd, 2H, J = 8.4, 5.4 Hz), 7.15 (dd, 2H, J = 9.9, 2.1 Hz), 6.99 (ddd, 2H, J = 9.6, 9.0, 2.4 Hz), 4.33 (s, 3H), 3.48 (t, 2H, J = 5.7 Hz), 3.45-3.25 (m, 2H), 3.10 (td, 2H, J = 6.0, 2.1 Hz), 2.47 (d, 1H, J = 2.1 Hz), 2.30-2.20 (m, 2H), 1.75-1.65 (m, 2H) | 394.8 (M + H) |
| 92 | 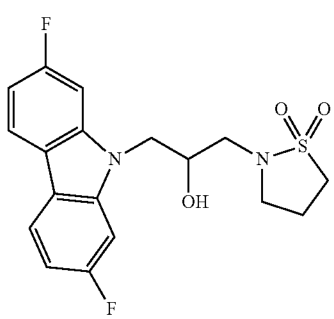 [SMILES: O=S1(=O)CCCN1CC(O)Cn1c2cc(F)ccc2c2ccc(F)cc21] | N-(3-(2,7-Difluoro-9H-carbazol-9-yl)-2-hydroxypropyl)-isothiazolidine-1,1-dioxide | (300 MHz, CDCl$_3$) δ 7.93 (dd, 2H, J = 8.7, 5.4 Hz), 7.17 (dd, 2H, J = 9.6, 2.4 Hz), 6.99 (td, 2H, J = 9.0, 2.4 Hz), 4.48-4.25 (m, 3H), 3.45-3.12 (m, 6H), 2.62 (d, 1H, J = 3.6 Hz), 2.42 (quin, 2H, J = 7.2 Hz) | 381.1 (M + H) |
| 93 | 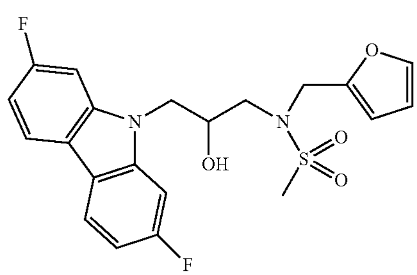 [SMILES: CS(=O)(=O)N(Cc1ccco1)CC(O)Cn1c2cc(F)ccc2c2ccc(F)cc21] | N-(3-(2,7-Difluoro-9H-carbazol-9-yl)-2-hydroxypropyl)-N-(furan-2-ylmethyl)methane-sulfonamide | (300 MHz, CDCl$_3$) δ 7.94 (dd, 2H, J = 8.7, 5.1 Hz), 7.30 (dd, 1H, J = 1.8, 0.9 Hz), 7.09 (dd, 2H, J = 9.6, 1.8 Hz), 7.00 (ddd, 2H, J = 9.6, 8.7, 2.1 Hz), 6.24 (dd, 1H, J = 3.3, 1.8 Hz), 6.07 (d, 1H, J = 3.3 Hz), 4.52 & 4.39 (AB, 2H, J = 15.6 Hz), 4.35-4.15 (m, 3H), 3.44 (dd, 1H, J = 14.7, 6.9 Hz), 3.27 (dd, 1H, J = 14.7, 2.7 Hz), 2.88 (s, 3H), 2.69 (d, 1H, J = 2.7 Hz) | N/A |

| Cpd # | Structure | Name | ¹H NMR | ESI (m/z) |
|---|---|---|---|---|
| 94 | 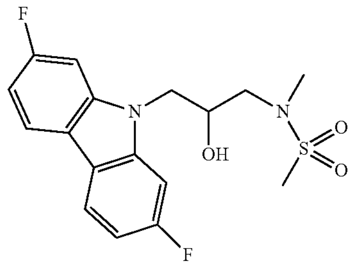 [SMILES: CN(CC(O)Cn1c2cc(F)ccc2c2ccc(F)cc21)S(C)(=O)=O] | N-(3-(2,7-Difluoro-9H-carbazol-9-yl)-2-hydroxypropyl)-N-methylmethane-sulfonamide | (300 MHz, CDCl₃) δ 7.94 (dd, 2H, J = 8.7, 5.4 Hz), 7.14 (dd, 2H, J = 9.9, 2.1 Hz), 7.00 (ddd, 2H, J = 9.6, 8.7, 2.1 Hz), 4.44-4.28 (m, 3H), 3.43 (dd, 1H, J = 14.4, 7.5 Hz), 3.27 (dd, 1H, J = 14.4, 3.9 Hz), 2.99 (s, 3H), 2.89 (s, 3H), 2.45 (d, 1H, J = 3.3 Hz) | 369.0 (M + H) |
| 95 | 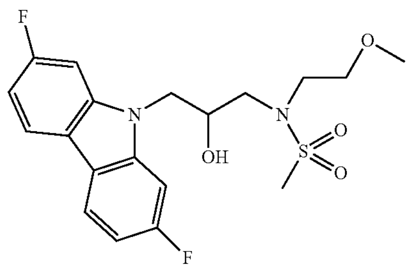 [SMILES: COCCN(CC(O)Cn1c2cc(F)ccc2c2ccc(F)cc21)S(C)(=O)=O] | N-(3-(2,7-Difluoro-9H-carbazol-9-yl)-2-hydroxypropyl)-N-(2-methoxyethyl)methanesulfonamide | (300 MHz, CDCl₃) δ 7.93 (dd, 2H, J = 8.4, 5.4 Hz), 7.16 (dd, 2H, J = 9.6, 2.4 Hz), 6.98 (td, 2H, J = 9.0, 2.4 Hz), 4.38 (m, 1H), 4.34-4.24 (m, 2H), 4.10 (d, 1H, J = 4.2 Hz), 3.65-3.22 (m, 9H), 2.90 (s, 3H) | 413.0 (M + H) |
| 96 | 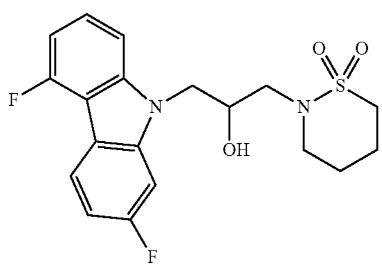 [SMILES: O=S1(=O)CCCCN1CC(O)Cn1c2cc(F)ccc2c2c(F)cccc21] | N-(3-(2,5-Difluoro-9H-carbazol-9-yl)-2-hydroxypropyl)-1,2-thiazinane 1,1-dioxide | (300 MHz, CDCl₃) δ 8.13 (dd, 1H, J = 8.4, 5.4 Hz), 7.37 (td, 1H, J = 8.4, 5.4 Hz), 7.23 (d, 1H, J = 8.1 Hz), 7.16 (dd, 1H, J = 9.6, 2.4 Hz), 7.02 (td, 1H, J = 9.0, 2.4 Hz), 6.94 (dd, 1H, J = 9.6, 8.1 Hz), 4.45-4.30 (m, 3H), 3.47 (t, 2H, J = 5.7 Hz), 3.45-3.25 (m, 2H), 3.09 (td, 2H, J = 6.0, 2.1 Hz), 2.45 (d, 1H, J = 3.3 Hz), 2.32-2.18 (m, 2H), 1.75-1.60 (m, 2H) | N/A |
| 97 | 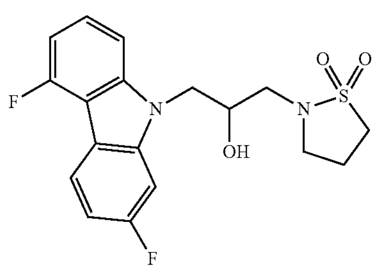 [SMILES: O=S1(=O)CCCN1CC(O)Cn1c2cc(F)ccc2c2c(F)cccc21] | N-(3-(2,5-Difluoro-9H-carbazol-9-yl)-2-hydroxypropyl)-isothiazolidine-1,1-dioxide | (300 MHz, CDCl₃) δ 8.13 (dd, 1H, J = 8.4, 5.4 Hz), 7.37 (td, 1H, J = 8.4, 5.1 Hz), 7.25 (d, 1H, J = 8.1 Hz), 7.18 (dd, 1H, J = 9.6, 2.1 Hz), 7.02 (td, 1H, J = 9.0, 2.4 Hz), 6.94 (dd, 1H, J = 9.9, 8.1 Hz), 4.50-4.35 (m, 3H), 3.45-3.15 (m, 6H), 2.59 (d, 1H, J = 3.6 Hz), 2.41 (quin, 2H, J = 7.2 Hz) | 380.9 (M + H) |
| 98 | 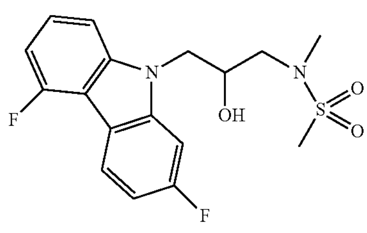 [SMILES: CN(CC(O)Cn1c2cc(F)ccc2c2c(F)cccc21)S(C)(=O)=O] | N-(3-(2,5-Difluoro-9H-carbazol-9-yl)-2-hydroxypropyl)-N-methylmethane-sulfonamide | (300 MHz, CDCl₃) δ 8.14 (dd, 1H, J = 8.4, 5.4 Hz), 7.38 (td, 1H, J = 8.1, 5.4 Hz), 7.22 (d, 1H, J = 8.4 Hz), 7.15 (dd, 1H, J = 9.6, 2.1 Hz), 7.03 (td, 1H, J = 9.0, 2.1 Hz), 6.95 (dd, 1H, J = 9.9, 8.1 Hz), 4.45-4.30 (m, 3H), 3.42 (dd, 1H, J = 14.4, 7.2 Hz), 3.27 (dd, 1H, J = 14.4, 3.3 Hz), 2.98 (s, 3H), 2.88 (s, 3H), 2.43 (d, 1H, J = 3.6 Hz) | N/A |
| 99 | 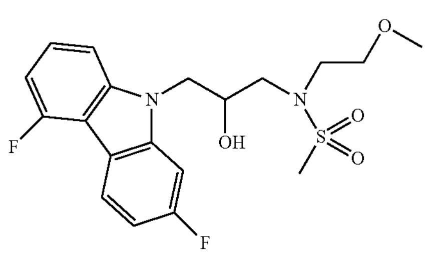 [SMILES: COCCN(CC(O)Cn1c2cc(F)ccc2c2c(F)cccc21)S(C)(=O)=O] | N-(3-(2,5-Difluoro-9H-carbazol-9-yl)-2-hydroxypropyl)-N-(2-methoxyethyl)methanesulfonamide | (300 MHz, CDCl₃) δ 8.13 (dd, 1H, J = 8.4, 5.4 Hz), 7.37 (td, 1H, J = 8.1, 5.1 Hz), 7.23 (d, 1H, J = 8.4 Hz), 7.18 (dd, 1H, J = 9.9, 2.4 Hz), 7.01 (td, 1H, J = 9.0, 2.4 Hz), 6.93 (dd, 1H, J = 9.9, 8.1 Hz), 4.48-4.25 (m, 3H), 4.04 (d, 1H, J = 3.9 Hz), 3.64-3.22 (m, 9H), 2.89 (s, 3H) | 413.0 (M + H) |

-continued

| Cpd # | Structure | Name | $^1$H NMR | ESI (m/z) |
|---|---|---|---|---|
| 100 | 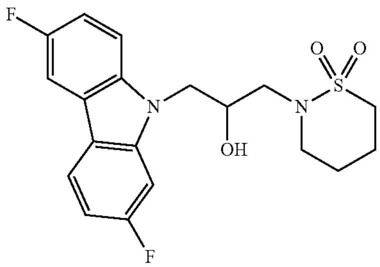 [SMILES: O=S1(=O)CCCCN1CC(O)Cn1c2ccc(F)cc2c2ccc(F)cc21] | N-(3-(2,6-Difluoro-9H-carbazol-9-yl)-2-hydroxypropyl)-1,2-thiazinane 1,1-dioxide | (300 MHz, CDCl$_3$) δ 7.94 (dd, 1H, J = 8.4, 5.4 Hz), 7.68 (dd, 1H, J = 8.7, 2.7 Hz), 7.38 (dd, 1H, J = 8.7, 4.2 Hz), 7.24-7.10 (m, 2H), 6.98 (td, 1H J = 9.0, 2.4 Hz), 4.45-4.25 (m, 3H), 3.47 (t, 2H, J = 5.7 Hz), 3.42-3.26 (m, 2H), 3.09 (td, 2H, J = 6.0, 2.1 Hz), 2.46 (d, 1H, J = 3.3 Hz), 2.30-2.18 (m, 2H), 1.74-1.62 (m, 2H) | N/A |
| 101 | 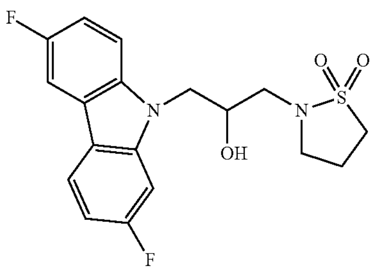 [SMILES: O=S1(=O)CCCN1CC(O)Cn1c2ccc(F)cc2c2ccc(F)cc21] | N-(3-(2,6-Difluoro-9H-carbazol-9-yl)-2-hydroxypropyl)-isothiazolidine-1,1-dioxide | (300 MHz, CDCl$_3$) δ 7.95 (dd, 1H, J = 8.4, 5.4 Hz), 7.68 (dd, 1H, J = 8.7, 2.7 Hz), 7.39 (dd, 1H, J = 8.7, 4.2 Hz), 7.23-7.12 (m, 2H), 6.98 (td, 1H, J = 9.0, 2.4 Hz), 4.48-4.32 (m, 3H), 3.45-3.15 (m, 6H), 2.58 (d, 1H, J = 3.6 Hz), 2.41 (quin, 2H, J = 7.2 Hz) | N/A |
| 102 | 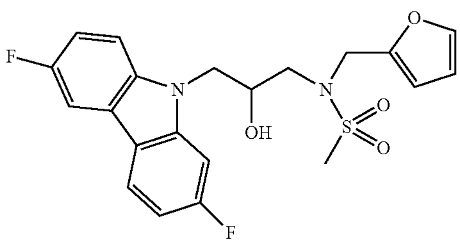 [SMILES: CS(=O)(=O)N(Cc1ccco1)CC(O)Cn1c2ccc(F)cc2c2ccc(F)cc21] | N-(3-(2,6-Difluoro-9H-carbazol-9-yl)-2-hydroxypropyl)-N-(furan-2-ylmethyl)methanesulfonamide | (300 MHz, CDCl$_3$) δ 7.96 (dd, 1H, J = 8.4, 5.4 Hz), 7.69 (dd, 1H, J = 8.7, 2.4 Hz), 7.34 (dd, 1H, J = 8.7, 4.2 Hz), 7.29 (m, 1H), 7.18 (td, 1H, J = 9.0, 2.4 Hz), 7.08 (dd, 1H, J = 9.6, 2.4 Hz), 6.99 (td, 1H, J = 9.0, 2.4 Hz), 6.23 (dd, 1H, J = 3.3, 2.1 Hz), 6.05 (d, 1H, J = 3.3 Hz), 4.52 & 4.39 (AB, 2H, J = 15.9 Hz), 4.35-4.20 (m, 3H), 3.43 (dd, 1H, J = 14.7, 6.9 Hz), 3.27 (dd, 1H, J = 14.7, 3.0 Hz), 2.86 (s, 3H), 2.66 (d, 1H, J = 3.3 Hz) | 435.0 (M + H) |
| 103 | 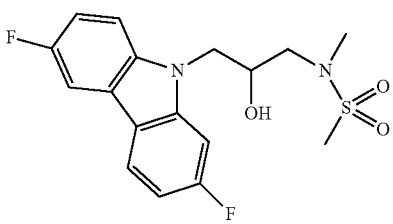 [SMILES: CN(CC(O)Cn1c2ccc(F)cc2c2ccc(F)cc21)S(C)(=O)=O] | N-(3-(2,6-Difluoro-9H-carbazol-9-yl)-2-hydroxypropyl)-N-methylmethanesulfonamide | (300 MHz, CDCl$_3$) δ 7.95 (dd, 1H, J = 8.4, 5.4 Hz), 7.69 (dd, 1H, J = 8.7, 2.7 Hz), 7.37 (dd, 1H, J = 8.7, 4.2 Hz), 7.19 (td, 1H, J = 9.0, 2.4 Hz), 7.13 (dd, 1H, J = 9.6, 2.4 Hz), 6.99 (td, 1H, J = 9.0, 2.4 Hz), 4.45-4.28 (m, 3H), 3.41 (dd, 1H, J = 14.4, 6.6 Hz), 3.26 (dd, 1H, J = 14.4, 3.6 Hz), 2.98 (s, 3H), 2.88 (s, 3H), 2.42 (d, 1H, J = 3.0 Hz) | 369.0 (M + H) |
| 104 | 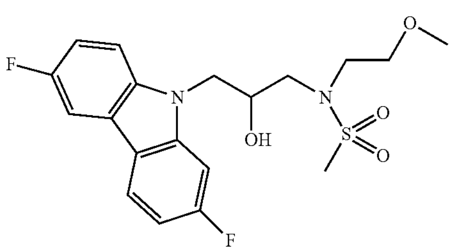 [SMILES: COCCN(CC(O)Cn1c2ccc(F)cc2c2ccc(F)cc21)S(C)(=O)=O] | N-(3-(2,6-Difluoro-9H-carbazol-9-yl)-2-hydroxypropyl)-N-(2-methoxyethyl)methanesulfonamide | (300 MHz, CDCl$_3$) δ 7.95 (dd, 1H, J = 8.4, 5.4 Hz), 7.68 (dd, 1H, J = 8.7, 2.7 Hz), 7.39 (dd, 1H, J = 8.7, 4.2 Hz), 7.23-7.12 (m, 2H), 6.97 (td, 1H, J = 9.0, 2.4 Hz), 4.45-4.25 (m, 3H), 4.02 (d, 1H, J = 3.9 Hz), 3.58 (t, 2H, J = 4.8 Hz), 3.58-3.20 (m, 7H), 2.89 (s, 3H) | 413.0 (M + H) |
| 105 | 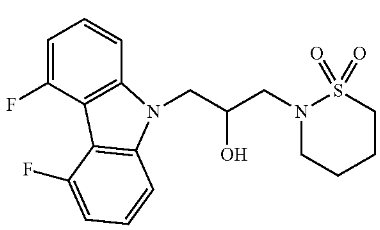 [SMILES: O=S1(=O)CCCCN1CC(O)Cn1c2cccc(F)c2c2c(F)cccc21] | N-(3-(4,5-Difluoro-9H-carbazol-9-yl)-2-hydroxypropyl)-1,2-thiazinane 1,1-dioxide | (300 MHz, CDCl$_3$) δ 7.44 (tt, 2H, J = 8.1, 2.4 Hz), 7.26 (d, 2H, J = 7.8 Hz), 6.98 (dt, 2H, J = 8.1, 5.1 Hz), 4.50-4.28 (m, 3H), 3.46 (t, 2H, J = 5.7 Hz), 3.39 (dd, 1H, J = 14.4, 6.9 Hz), 3.30 (dd, 1H, J = 14.4, 4.2 Hz), 3.08 (td, 2H, J = 6.0, 2.4 Hz), 2.46 (d, 1H, J = 3.3 Hz), 2.30-2.17 (m, 2H), 1.73-1.60 (m, 2H) | N/A |

-continued

| Cpd # | Structure | Name | ¹H NMR | ESI (m/z) |
|---|---|---|---|---|
| 106 | 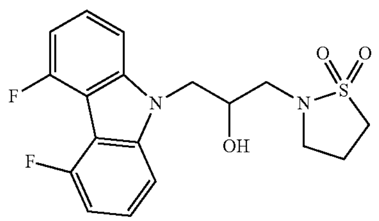 [SMILES: O=S1(=O)CCCN1CC(O)Cn1c2cccc(F)c2c2c(F)cccc21] | N-(3-(4,5-Difluoro-9H-carbazol-9-yl)-2-hydroxypropyl)-isothiazolidine-1,1-dioxide | (300 MHz, CDCl₃) δ 7.44 (tt, 2H, J = 8.1, 2.4 Hz), 7.27 (d, 2H, J = 8.1 Hz), 6.98 (dt, 2H, J = 8.1, 5.1 Hz), 4.52-4.35 (m, 3H), 3.44-3.14 (m, 6H), 2.60 (d, 1H, J = 3.6 Hz), 2.40 (quin, 2H, J = 7.2 Hz) | N/A |
| 107 | 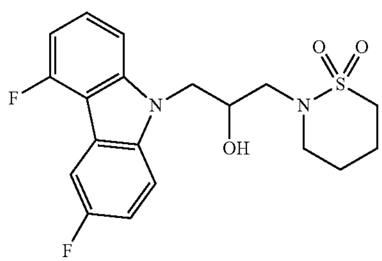 [SMILES: O=S1(=O)CCCCN1CC(O)Cn1c2ccc(F)cc2c2c(F)cccc21] | N-(3-(3,5-Difluoro-9H-carbazol-9-yl)-2-hydroxypropyl)-1,2-thiazinane 1,1-dioxide | (300 MHz, CDCl₃) δ 7.88 (dd, 1H, J = 8.7, 2.7 Hz), 7.46-7.35 (m, 2H), 7.27-7.18 (m, 2H), 6.92 (dd, 1H, J = 9.9, 7.8 Hz), 4.50-4.30 (m, 3H), 3.46 (t, 2H, J = 5.7 Hz), 3.38 (dd, 1H, J = 14.4, 6.9 Hz), 3.30 (dd, 1H, J = 14.4, 4.2 Hz), 3.08 (td, 2H, J = 6.0, 2.1 Hz), 2.45 (d, 1H, J = 3.3 Hz), 2.30-2.18 (m, 2H), 1.72-1.60 (m, 2H) | N/A |
| 108 | 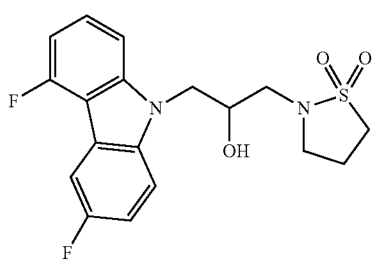 [SMILES: O=S1(=O)CCCN1CC(O)Cn1c2ccc(F)cc2c2c(F)cccc21] | N-(3-(3,5-Difluoro-9H-carbazol-9-yl)-2-hydroxypropyl)-isothiazolidine-1,1-dioxide | (300 MHz, CDCl₃) δ 7.88 (dd, 1H, J = 8.7, 2.7 Hz), 7.46-7.36 (m, 2H), 7.27-7.19 (m, 2H), 6.92 (dd, 1H, J = 9.3, 7.8 Hz), 4.50-4.30 (m, 3H), 3.44-3.12 (m, 6H), 2.58 (d, 1H, J = 3.6 Hz), 2.40 (quin, 2H, J = 7.2 Hz) | N/A |
| 109 | 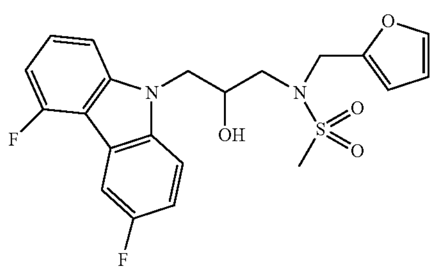 [SMILES: CS(=O)(=O)N(Cc1ccco1)CC(O)Cn1c2ccc(F)cc2c2c(F)cccc21] | N-(3-(3,5-Difluoro-9H-carbazol-9-yl)-2-hydroxypropyl)-N-(furan-2-ylmethyl)methane-sulfonamide | (300 MHz, CDCl₃) δ 7.89 (dd, 1H, J = 8.7, 2.7 Hz), 7.46-7.31 (m, 2H), 7.27-7.16 (m, 3H), 6.92 (dd, 1H, J = 9.9, 7.8 Hz), 6.21 (dd, 1H, J = 3.3, 1.8 Hz), 6.01 (d, 1H, J = 3.3 Hz), 4.50 (AB, 1H, J = 16.2 Hz), 4.44-4.20 (m, 4H), 3.42 (dd, 1H, J = 14.7, 7.5 Hz), 3.24 (dd, 1H, J = 14.7, 3.3 Hz), 2.86 (s, 3H), 2.67 (d, 1H, J = 3.6 Hz) | 434.9 (M + H) |
| 110 | 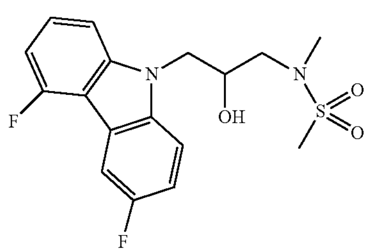 [SMILES: CN(CC(O)Cn1c2ccc(F)cc2c2c(F)cccc21)S(C)(=O)=O] | N-(3-(3,5-Difluoro-9H-carbazol-9-yl)-2-hdroxypropyl)-N-methylmethane-sulfonamide | (300 MHz, CDCl₃) δ 7.89 (dd, 1H, J = 8.7, 2.7 Hz), 7.47-7.36 (m, 2H), 7.28-7.20 (m, 2H), 6.93 (dd, 1H, J = 9.6, 8.1 Hz), 4.46-4.32 (m, 3H), 3.41 (dd, 1H, J = 14.1, 6.9 Hz), 3.26 (dd, 1H, J = 14.1, 3.6 Hz), 2.97 (s, 3H), 2.88 (s, 3H), 2.40 (d, 1H, J = 3.3 Hz) | N/A |
| 111 | 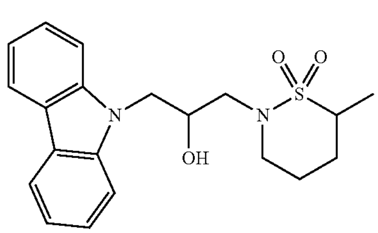 [SMILES: CC1CCCN(CC(O)Cn2c3ccccc3c3ccccc32)S1(=O)=O] | N-(3-(9H-Carbazol-9-yl)-2-hydroxypropyl)-6-methyl-1,2-thiazinane-1,1-dioxide | (300 MHz, CDCl₃) (diastereomers) δ 8.10 (d, 2H, J = 7.5 Hz), 7.52-7.44 (m, 4H), 7.32-7.22 (m, 2H)2H), 4.60-4.30 (m, 3H), 3.70-2.90 (m, 5H), 2.52 & 2.45 (d, 1H, J = 3.0 Hz), 2.15-1.85 (m, 2H), 1.80-1.60 (m, 2H), 1.42 (d, 3H, J = 6.6 Hz) | 373.1 (M + H) |

-continued

| Cpd # | Structure | Name | $^1$H NMR | ESI (m/z) |
|---|---|---|---|---|
| 112 | 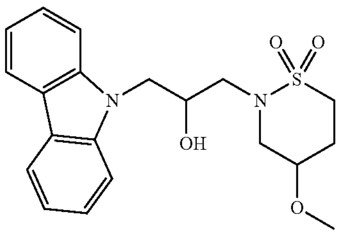 [SMILES: COC1CCS(=O)(=O)N(CC(O)Cn2c3ccccc3c3ccccc32)C1] | N-(3-(9H-Carbazol-9-yl)-2-hydroxypropyl)-4-methoxy-1,2-thiazinane-1,1-dioxide | (300 MHz, CDCl$_3$) (diastereomeric mixture) δ 8.10 (d, 2H, J = 7.5 Hz), 7.54-7.42 (m, 4H), 7.30-7.20 (m, 2H), 4.55-4.25 (m, 3H), 3.80-3.15 (m, 9H), 3.12-2.95 (m, 1.5 H), 2.79 (d, 0.5H, J = 3.6 HHz), 2.55-2.20 (m, 2H) | 389.1 (M + H) |
| 113 | 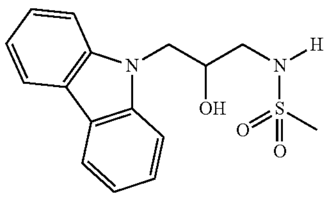 [SMILES: CS(=O)(=O)NCC(O)Cn1c2ccccc2c2ccccc21] | N-(3-(9H-Carbazol-9-yl)-2-hydroxypropyl)methanesulfonamide | (CDCl$_3$, 300 MHz) δ 8.10-8.07 (dt, 2H, J = 0.9, 7.5 Hz), 7.50-7.41 (m, 4H), 7.28-7.23 (m, 2H), 4.48-4.33 (m, 3H), 3.43-3.38 (dd, 1H, J = 3.0, 13.3 Hz), 3.24-3.18 (dd, 1H, J = 6.7, 13.5 Hz), 2.97 (s, 3H) | 319.0 (M + H) |
| 114 | 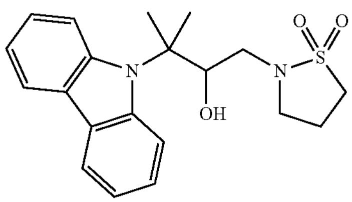 [SMILES: CC(C)(C(O)CN1CCCS1(=O)=O)n1c2ccccc2c2ccccc21] | 2-(3-(9H-Carbazol-9-yl)-2-hydroxy-3-methylbutyl)-isothiazolidine-1,1-dioxide | (300 MHz, CDCl$_3$) δ 8.09 (d, 2H, J = 7.2 Hz), 7.85 (d, 2H, J = 8.7 Hz), 7.37 (t, 2H, J = 7.8 Hz), 7.23 (t, 2H, J = 7.2 Hz), 4.98 (d, 1H, J = 9.3 Hz), 3.26 (dd, 1H, J = 14.7, 9.3 Hz), 3.20-3.00 (m, 3H), 2.92-2.70 (m, 3H), 2.20 (m, 2H), 2.14 (s, 3H), 2.10 (s, 3H) | N/A |
| 115 | 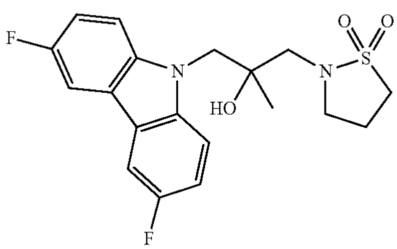 [SMILES: CC(O)(CN1CCCS1(=O)=O)Cn1c2ccc(F)cc2c2cc(F)ccc21] | 2-(3-(3,6-Difluoro-9H-carbazol-9-yl)-2-hydroxy-2-methylpropyl)-isothiazolidine-1,1-dioxide | (300 MHz, CDCl$_3$) δ 7.67 (dd, 2H, J = 8.7, 2.7 Hz), 7.44 (dd, 2H, J = 9.0, 4.2 Hz), 7.21 (td, 2H, J = 9.0, 2.7 Hz), 4.47 & 4.26 (AB, 2H, J = 15.3 Hz), 3.65-3.45 (m, 2H), 3.34 and 3.26 (AB, 2H, J = 15.0 Hz), 3.22 (t, 2H, J = 7.5 Hz), 2.54-2.38 (m, 2H), 2.02 (s, 1H), 1.32 (s, 3H) | N/A |
| 116 | 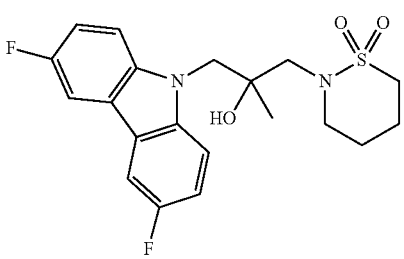 [SMILES: CC(O)(CN1CCCCS1(=O)=O)Cn1c2ccc(F)cc2c2cc(F)ccc21] | 2-(3-(3,6-Difluoro-9H-carbazol-9-yl)-2-hydroxy-2-methylpropyl)-1,2-thiazinane 1,1-dioxide | (300 MHz, CDCl$_3$) δ 7.68 (dd, 2H, J = 8.7, 2.7 Hz), 7.44 (dd, 2H, J = 9.0, 4.2 Hz), 7.21 (td, 2H, J = 9.0, 2.7 Hz), 4.48 & 4.26 (AB, 2H, J = 15.0 Hz), 3.70 (t, 2H, J = 5.7 Hz), 3.42 & 3.32(AB, 2H, J = 14.7 Hz), 3.08 (t, 2H, J = 6.0 Hz), 2.35-2.22 (m, 2H), 2.03 (s, 1H), 1.78-1.66 (m, 2H), 1.30 (s, 3H) | 409.0 (M + H) |
| 117 | 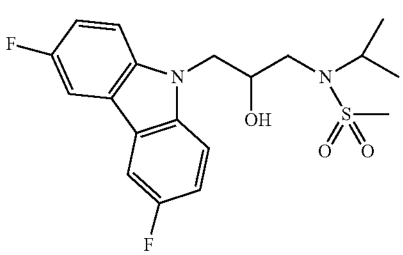 [SMILES: CC(C)N(CC(O)Cn1c2ccc(F)cc2c2cc(F)ccc21)S(C)(=O)=O] | N-(3-(3,6-Difluoro-9H-carbazol-9-yl)-2-hydroxypropyl)-N-isopropylmethane-sulfonamide | (300 MHz, CDCl$_3$) δ 7.69 (dd, 2H, J = 8.7, 2.4 Hz), 7.41 (dd, 2H, J = 8.7, 4.2 Hz), 7.24 (td, 2H, J = 9.0, 2.4 Hz), 4.44-4.26 (m, 3H), 4.00 (m, 1H), 3.30-3.10 (m, 3H), 2.89 (s, 3H), 0.98 (d, 3H, J = 6.6 Hz), 0.89 (d, 3H, J = 6.6 Hz) | 397.1 (M + H) |

-continued

| Cpd # | Structure | Name | ¹H NMR | ESI (m/z) |
|---|---|---|---|---|
| 118 | 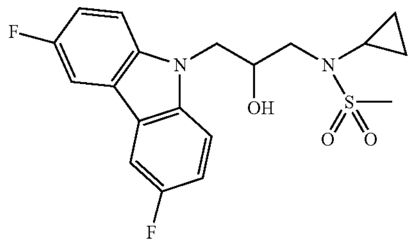 [SMILES: CS(=O)(=O)N(CC(O)Cn1c2ccc(F)cc2c2cc(F)ccc21)C1CC1] | N-Cyclopropyl-N-(3-(3,6-difluoro-9H-carbazol-9-yl)-2-hydroxypropyl)methanesulfonamide | (300 MHz, CDCl$_3$) δ 7.69 (dd, 2H, J = 9.0, 2.7 Hz), 7.39 (dd, 2H, J = 9.0, 4.2 Hz), 7.24 (td, 2H, J = 9.0, 2.7 Hz), 4.46 (m, 1H), 4.36 (s, 1H), 4.33 (d, 1H, J = 2.7 Hz), 3.47 (dd, 1H, J = 14.7, 8.4 Hz), 3.31 (dd, 1H, J = 14.7, 3.6 Hz), 2.97 (s, 3H), 2.58 (d, 1H, J = 3.9 Hz), 2.45 (m, 1H), 0.90-0.60 (m, 4H) | N/A |
| 119 | 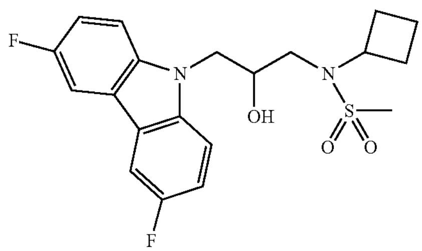 [SMILES: CS(=O)(=O)N(CC(O)Cn1c2ccc(F)cc2c2cc(F)ccc21)C1CCC1] | N-Cyclobutyl-N-(3-(3,6-difluoro-9H-carbazol-9-yl)-2-hydroxypropyl)methanesulfonamide | (300 MHz, CDCl$_3$) δ 7.69 (dd, 2H, J = 9.0, 2.4 Hz), 7.41 (dd, 2H, J = 9.0, 4.2 Hz), 7.24 (td, 2H, J = 9.0, 2.4 Hz), 4.50-4.10 (m, 4H), 3.40-3.20 (m, 2H), 2.92 (d, 1H, J = 2.7 Hz), 2.82 (s, 3H), 2.10-1.40 (m, 6H) | N/A |
| 120 | 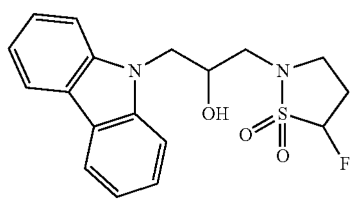 [SMILES: O=S1(=O)C(F)CCN1CC(O)Cn1c2ccccc2c2ccccc21] | 2-(3-(9H-Carbazol-9-yl)-2-hydroxypropyl)-5-fluoro-isothiazolidine-1,1-dioxide | (300 MHz, CDCl$_3$) δ 8.10-8.08 (dd, 2H, J = 0.9, 7.8 Hz), 7.47-7.44 (m, 4H), 7.28-7.23 (m, 2H), 5.54-5.36 (m, 1H), 4.50-4.39 (m, 3H), 3.53-3.28 (m, 2H), 2.78-2.38 (m, 2H), 2.34-2.31 (m, 1H) | 363.1 (M + H) |
| 121 | 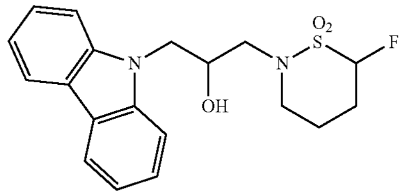 [SMILES: O=S1(=O)C(F)CCCN1CC(O)Cn1c2ccccc2c2ccccc21] | 2-(3-(9H-Carbazol-9-yl)-2-hydroxypropyl)-6-fluoro-1,2-thiazinane-1,1-dioxide | (300 MHz, CDCl$_3$) δ 8.10-8.07 (d, 2H, J = 7.5 Hz), 7.50-7.43 (m, 4H), 7.27-7.22 (m, 2H), 5.39-5.20 (m, 1H), 4.52-4.32 (m, 3H), 3.78-3.64 (m, 2H), 3.53-3.38 (m, 2H), 2.60-2.42 (m, 2H), 2.17-2.15 (t, 1H, J = 3.0 Hz), 2.04-1.96 (m, 1H), 1.50-1.42 (m, 1H) | 377.1 (M + H) |
| 122 | 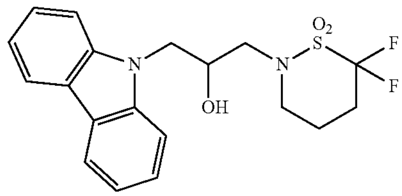 [SMILES: O=S1(=O)N(CC(O)Cn2c3ccccc3c3ccccc32)CCCC1(F)F] | 2-(3-(9H-Carbazol-9-yl)-2-hydroxypropyl)-6,6-difluoro-1,2-thiazinane-1,1-dioxide | (300 MHz, CDCl$_3$) δ 8.10-8.04 (dm, 2H, J = 7.5 Hz), 7.50-7.41 (m, 4H), 7.28-7.23 (m, 2H), 4.42-4.30 (m, 3H), 3.68-3.46 (m, 4H), 2.59-2.47 (m, 2H), 2.13 (br s, 1H), 1.99-1.91 (m, 2H) | 395.5 (M + H) |
| 123 | 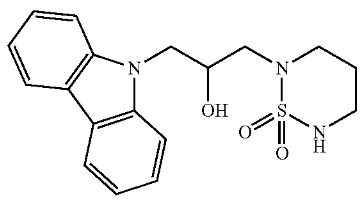 [SMILES: O=S1(=O)NCCCN1CC(O)Cn1c2ccccc2c2ccccc21] | 2-(3-(9H-Carbazol-9-yl)-2-hydroxypropyl)-1,2,6-thiadiazinane-1,1-dioxide | (300 MHz, CDCl$_3$) δ 8.08 (d, 2H, J = 8.1 Hz), 7.50-7.42 (m, 4H), 7.32-7.18 (m, 2H), 4.41 (s, 3H), 4.14 (t, 1H, J = 7.2 Hz), 3.49 (q, 2H, J = 6.0 Hz), 3.38 (t, 2H, J = 5.4 Hz), 3.35-3.15 (m, 2H), 2.54 (s, 1H), 1.75-1.64 (m, 2H) | 360.1 (M + H) |
| 124 | 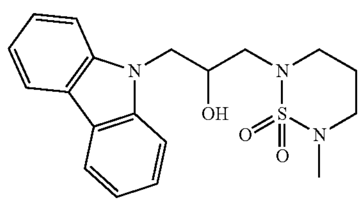 [SMILES: CN1CCCN(CC(O)Cn2c3ccccc3c3ccccc32)S1(=O)=O] | 2-(3-(9H-Carbazol-9-yl)-2-hydroxypropyl)-6-methyl-1,2,6-thiadiazinane-1,1-dioxide | (300 MHz, CDCl$_3$) δ 8.09 (d, 2H, J = 7.8 Hz), 7.47 (d, 4H, J = 3.9 Hz), 7.30-7.20 (m, 2H), 4.42 (s, 3H), 3.47 (t, 2H, J = 5.7 Hz), 3.36-3.25 (m, 4H), 2.81 (s, 3H), 2.48 (s, 1H), 1.85-1.70 (m, 2H) | 374.2 (M + H) |

| Cpd # | Structure | Name | ¹H NMR | ESI (m/z) |
|---|---|---|---|---|
| 125 | 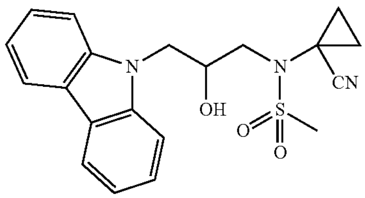 [SMILES: CS(=O)(=O)N(CC(O)Cn1c2ccccc2c2ccccc21)C1(C#N)CC1] | N-(3-(9H-Carbazol-9-yl)-2-hydroxypropyl)-N-(1-cyanocyclopropyl)methanesulfonamide | (300 MHz, CDCl₃) δ 8.11-8.09 (d, 2H, J = 7.8 Hz), 7.46-7.51-7.42 (m, 4H), 7.29-7.24 (ddd, 2H, J = 1.5, 6.6, 7.8 Hz), 4.59-4.52 (m, 1H), 4.36-4.33 (d, 2H, J = 6.6 Hz), 3.58-3.50 (dd, 1H, J = 8.3, 15.0 Hz), 3.49-3.43 (dd, 1H, J = 3.0, 15.0 Hz), 2.48-2.47 (d, 1H, J = 2.4 Hz), 1.64-1.38 (m, 4H) | 384.3 (M + H) |
| 126 | 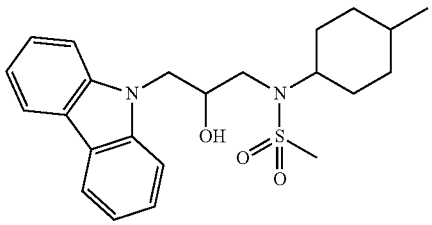 [SMILES: CC1CCC(N(CC(O)Cn2c3ccccc3c3ccccc32)S(C)(=O)=O)CC1] | N-(3-(9H-Carbazol-9-yl)-2-hydroxropyl)-N-(4-methylcyclohexyl)methanesulfonamide | (300 MHz, CDCl₃) (diastereomeric mixture) δ 8.10-8.08 (d, 0.33H, J = 7.8 Hz), 8.08-8.06 (d, 0.66H, J = 8.1 Hz), 7.51-7.44 (m, 4H), 7.27-7.20 (m, 2H), 4.49-4.26 (m, 3H), 3.64-3.63 (d, 0.6H, J = 1.8 Hz), 3.45-3.19 (m, 2.3H), 3.15-3.09 (m, 1H), 2.87 (s, 2H), 2.85 (s, 1H), 1.63-0.40 (m, 10H), 0.31-0.28 (d, 2H, J = 6.9 Hz) | 415.0 (M + H) |
| 127 | 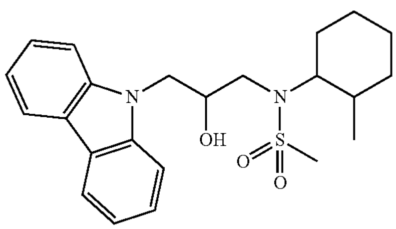 [SMILES: CC1CCCCC1N(CC(O)Cn1c2ccccc2c2ccccc21)S(C)(=O)=O] | N-(3-(9H-Carbazol-9-yl)-2-hydroxypropyl)-N-(2-methylcyclohexyl)methanesulfonamide | (300 MHz, CDCl₃) (diastereomeric mixture) δ 8.11-8.08 (br d, 2H, J = 7.2 Hz), 7.51-7.42 (m, 4H), 7.27-7.22 (m, 2H), 4.50-4.27 (m, 3H), 3.97 (br s, 0.3H), 3.66-3.52 (m, 0.7H), 3.33-2.93 (m, 2H), 2.88 (s), 2.86 (s), 2.85(s), 2.81(s) (3H total area for peaks 2.88-2.81), 1.45-0.21 (m, 12H) | 415.1 (M + H) |
| 128 | 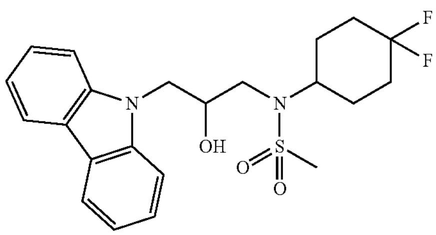 [SMILES: CS(=O)(=O)N(CC(O)Cn1c2ccccc2c2ccccc21)C1CCC(F)(F)CC1] | N-(3-(9H-Carbazol-9-yl)-2 hydroxypropyl)-N-(4,4-difluorocyclohexyl)methanesulfonamide | (300 MHz, CDCl₃) δ 8.21-8.09 (d, 2H, J = 7.8 Hz), 7.50-7.43 (m, 4H), 7.30-7.23 (m, 2H), 4.43-4.33 (m, 3H), 3.60 (m, 1H), 3.32-3.25 (dd, 1H, J = 7.2, 15.6 Hz), 3.19-3.14 (dd, 1H, J = 2.4, 15.6 Hz), 3.06-3.05 (d, 1H, J = 2.7 Hz), 2.85 (s, 3H), 2.01-1.05 (m, 8H) | 437.0 (M + H) |
| 129 | 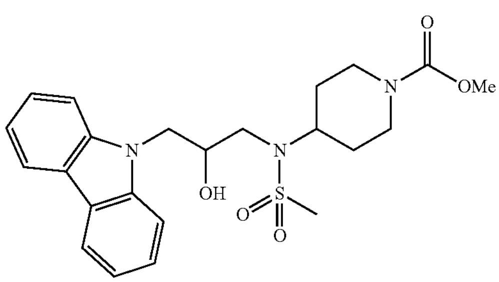 [SMILES: COC(=O)N1CCC(N(CC(O)Cn2c3ccccc3c3ccccc32)S(C)(=O)=O)CC1] | Methyl 4-(N-(3-(9H-carbazol-9-yl)-2-hydroxypropyl)methylsulfonamido)piperidine-1-carboxylate | (300 MHz, CDCl₃) δ 8.10-8.07 (d, 2H, J = 7.8 Hz), 7.51-7.43 (m, 4H), 7.28-7.22 (m, 2H), 4.39-4.36 (m, 2H), 4.34-4.27 (br m, 1H), 4.01 (br s, 2H), 3.72 (s, 3H), 3.67-3.50 (m, 1H), 3.31-3.23 (dd, 1H, J = 7.1, 15.6 Hz), 3.21-3.15 (dd, 1H, J = 2.4, 15.0 Hz), 2.89 (s, 3H), 2.57 (br m), 1.54-0.7 (m, 4H) | 460.0 (M + H) |
| 130 | 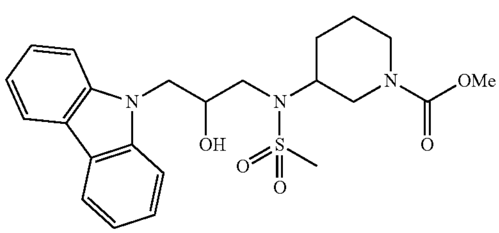 [SMILES: COC(=O)N1CCCC(N(CC(O)Cn2c3ccccc3c3ccccc32)S(C)(=O)=O)C1] | Methyl 3-(N-(3-(9H-carbazol-9-yl)-2-hydroxypropyl)methylsulfonamido)piperidine-1-carboxylate | (300 MHz, CDCl₃) δ 8.10-8.08 (d, 2H, J = 7.2 Hz), 7.52-7.45 (m, 4H), 7.28-7.23 (m, 2H), 4.46-4.31 (m, 3H), 3.93-3.83 (br m, 2H), 3.61 (s, 3H), 3.48-3.10 (br m, 4H), 2.91 (s, 3H), 2.30-1.12 (br m, 4H) | 460.1 (M + H) |

| Cpd # | Structure | Name | ¹H NMR | ESI (m/z) |
|---|---|---|---|---|
| 131 | 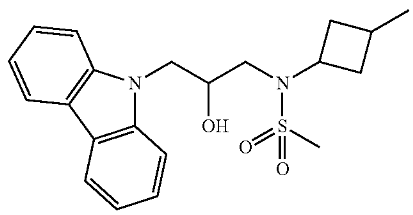 [SMILES: CC1CC(N(CC(O)Cn2c3ccccc3c3ccccc32)S(C)(=O)=O)C1] | N-(3-(9H-Carbazol-9-yl)-2-hydroxypropyl)-N-(3-methylcyclobutyl)methanesulfonamide | (300 MHz, CDCl₃) (diastereomeric mixture) δ 8.10-8.08 (d, 2H, J = 7.5 Hz), 7.48-7.47 (m, 4H), 7.28-7.22 (m, 2H), 4.44-4.27 (m, 3.4H), 3.99-3.87 (m, 0.6H), 3.28-3.14 (m, 3H), 3.06 (br s, 0.4H), 2.77 (s, 1H), 2.77 (s, 2H), 2.08-1.90 (m, 2H), 1.81-1.61 (m, 2H), 1.18-1.08 (q, .8H, J = 9.9 Hz), 1.02-1.00 (d, 1.2H, J = 6.6 Hz), 0.88-0.78 (q, 0.6H, J = 6.6 Hz), 0.56-0.53 (d, 1.8H, J = 6.6 Hz) | 387.1 (M + H) |
| 132 | 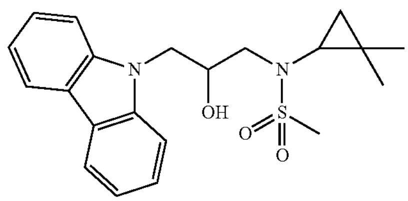 [SMILES: CC1(C)CC1N(CC(O)Cn1c2ccccc2c2ccccc21)S(C)(=O)=O] | N-(3-(9H-Carbazol-9-yl)-2-hydroxypropyl)-N-(2,2-dimethylcyclopropyl)methanesulfonamide | (300 MHz, CDCl₃) (diastereomeric mixture) δ 8.11-8.08 (d, 2H, J = 7.5 Hz), 7.50-7.42 (m, 4H), 7.28-7.23 (m, 2H), 4.58-4.28 (m, 3H), 3.69-3.61 (dd, 0.4H, J = 9.0, 15.3 Hz), 3.52-3.44 (dd, 0.6H, J = 8.6, 15.0 Hz), 3.20-3.14 (dd, 0.6H, J = 2.4, 15.0 Hz), 3.11-3.05 (dd, 0.4H, J = 2.4, 15.0 Hz), 2.95 (s, 1.3H), 2.93 (s, 1.7H), 2.89-2.88 (d, 0.4H, J = 6.6 Hz), 2.13-2.09 (dd, 0.6H, J = 4.2, 7.5 Hz), 2.09-2.05 (dd, 0.4H, J = 4.4, 7.5 Hz), 0.93 (s, 1.7H), 0.86 (s, 1.3H), 0.84 (s, 1.7H), 0.70 (s, 1.3H), 0.62-0.50 (m, 2H) | 386.7 (M + H) |
| 133 | 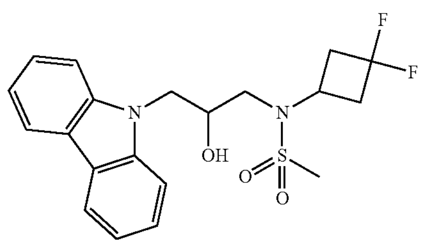 [SMILES: CS(=O)(=O)N(CC(O)Cn1c2ccccc2c2ccccc21)C1CC(F)(F)C1] | N-(3-(9H-Carbazol-9-yl)-2-hydroxypropyl)-N-(3,3-difluorocyclobutyl)methanesulfonamide | (CDCl₃, 300 MHz) δ 8.11-8.08 (d, 2H, J = 7.8 Hz), 7.51-7.43 (m, 4H), 7.29-7.23 (m, 2H), 4.44-4.36 (m, 3H), 4.05-3.98 (quin d, 1H, J = 1.3, 3.9 Hz), 3.27-3.25 (d, 2H, J = 5.1 Hz), 2.85 (s, 3H), 2.74-2.42 (m, 5H) | N/A |
| 134 | 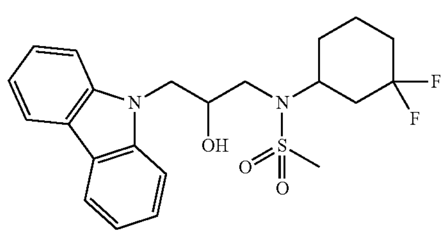 | N-(3-(9H-Carbazol-9-yl)-2-hydroxypropyl)-N-(3,3-difluorocyclohexyl)methanesulfonamide | (300 MHz, CDCl₃) (diastereomeric mixture) δ 8.11-8.08 (dt, 2H, J = 0.9, 7.5 Hz), 7.53-7.44 (m, 4H), 7.29-7.24 (m, 2H), 4.47-4.25 (m, 3H), 3.64-3.57 (br m, 1H), 3.36-3.07 (m, 3H), 2.88 (s, 1.7H), 2.86 (s, 1.3H), 1.86-0.20 (m, 8H) | 454.9 (M + H₂O) |
| 135 | 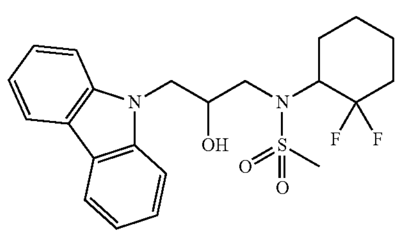 [SMILES: CS(=O)(=O)N(CC(O)Cn1c2ccccc2c2ccccc21)C1CCCCC1(F)F] | N-(3-(9H-Carbazol-9-yl)-2-hydroxypropyl)-N-(2,2-difluorocyclohexyl)methanesulfonamide | (300 MHz, CDCl₃) (diastereomeric mixture) δ 8.10-8.07 (d, 2H, J = 7.5 Hz), 7.51-7.43 (m, 4H), 7.27-7.21 (m, 2H), 4.58-4.50 (br m, 0.4H), 4.46-4.27 (m, 2.6H), 4.10-3.83 (m, 1.4H), 3.81-3.73 (dd, 0.6H, J = 7.8, 15.8 Hz), 3.66-3.60 (br d, 0.4H, J = 16.5 Hz), 3.46-3.41 (br d, 0.6H, J = 15.6 Hz), 3.35-3.28 (dd, 0.4H, J = 6.8, 16.4 Hz), 3.06 (s, 1.7H), 2.99 (s, 1.3H), 2.41-2.39 (d, 0.6H, J = 4.5 Hz), 2.25-2.15 (m, 0.6H), 1.85-0.72 (m, 7H), 0.37-0.25 (qd, 0.4H, J = 3.6, 12.8 Hz) | 436.8 (M + H) |

-continued

| Cpd # | Structure | Name | ¹H NMR | ESI (m/z) |
|---|---|---|---|---|
| 136 | 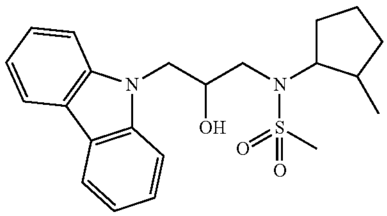 [SMILES: CC1CCCC1N(CC(O)Cn1c2ccccc2c2ccccc21)S(C)(=O)=O] | N-(3-(9H-Carbazol-9-yl)-2-hydroxypropyl)-N-(2-methylcyclopent-yl)methanesulfon-amide | (CDCl$_3$, 300 MHz) (diastereomeric mixture) δ 8.10-8.07 (m, 2H), 7.48-7.43 (m, 4H), 7.27-7.22 (m, 4H), 4.46-4.29 (m, 3H), 4.00 (br s, 0.25H), 3.88-3.80 (m, 0.5H), 3.65 (br s, 0.25H), 3.50-3.08 (m, 3H), 2.91 (s, 0.75H), 2.90 (s, 0.75H), 2.86 (s, 0.75H), 2.85 (s, 0.75H), 2.05-0.60 (m, 7H), 0.90-0.88 (d, 0.75H, J = 6.0 Hz), 0.76-0.73 (d, 0.75H, J = 7.2 Hz), 0.48-0.46 (d, 0.75H, J = 7.5 Hz), 0.47-0.45 (d, 0.75H, J = 6.3 Hz) | 401.0 (M + H) |
| 137 | 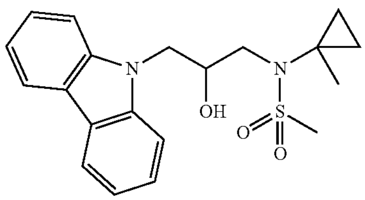 [SMILES: CC1(N(CC(O)Cn2c3ccccc3c3ccccc32)S(C)(=O)=O)CC1] | N-(3-(9H-Carbazol-9-yl)-2-hydroxypropyl)-N-(1-methylcycloprop-yl)methanesulfon-amide | (300 MHz, CDCl$_3$) δ 8.11-8.08 (d, 2H, J = 7.8 Hz), 7.51-7.43 (m, 4H), 7.28-7.23 (m, 2H), 4.49-4.42 (m, 3H), 3.46-3.39 (dd, 1H, J = 7.8, 15.0 Hz), 3.37-3.31 (dd, 1H, J = 3.0, 15.0 Hz), 2.90 (s, 3H), 1.24 (s, 3H), 0.98-0.91 (m, 1H), 0.82-0.75 (m, 1H), 0.56-0.40 (m, 2H) | 373.0 (M + H) |
| 138 | 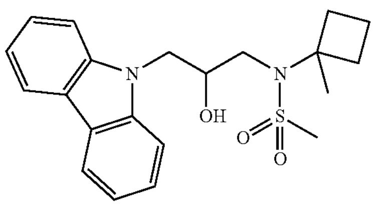 [SMILES: CC1(N(CC(O)Cn2c3ccccc3c3ccccc32)S(C)(=O)=O)CCC1] | N-(3-(9H-Carbazol-9-yl)-2-hydroxypropyl)-N-(1-methylcyclobutyl)methanesulfon-amide | (300 MHz, CDCl$_3$) δ 8.10-8.07 (d, 2H, J = 7.5 Hz), 7.51-7.44 (m, 4H), 7.28-7.22 (m, 2H), 4.43-4.30 (m, 3H), 3.35-3.34 (d, 1H, J = 2.7 Hz), 3.21-3.14 (dd, 1H, J = 4.4, 15.5 Hz), 3.09-3.04 (dd, 1H, J = 2.3, 15.5 Hz), 2.94 (s, 3H), 2.21-2.12 (q, 1H, J = 9.6 Hz), 1.95-1.86 (q, 1H, J = 9.6 Hz), 1.66-1.40 (m, 4H), 1.30 (s, 3H) | 387.0 (M + H) |
| 139 | 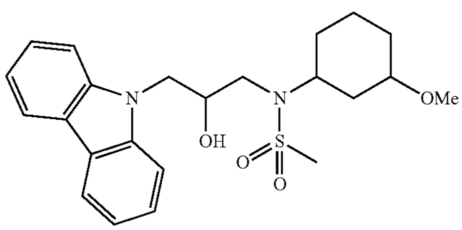 [SMILES: COC1CCCC(N(CC(O)Cn2c3ccccc3c3ccccc32)S(C)(=O)=O)C1] | N-(3-(9H-Carbazol-9-yl)-2-hydroxypropyl)-N-(3-methoxycyclohex-yl)methanesulfon-amide | (300 MHz, CDCl$_3$) (diastereomeric mixture) δ 8.10-8.08 (d, 2H, J = 7.5 Hz), 7.49-7.45 (m, 4H), 7.28-7.22 (m, 2H), 4.48-4.24 (m, 3H), 3.76-3.66 (m, 1H), 3.51 (br s, 0.5H), 3.37-3.20 (m, 2H), 3.16 (s, 1.5H), 3.12-3.09 (m, 0.5H), 3.11 (s, 1.5H), 3.09-3.03 (m, 1H), 2.85 (s, 1.5H), 2.84 (s, 1.5H), 1.70-1.04 (m, 5H), 0.85-0.76 (td, 0.5H, J = 2.1, 12.6 Hz), 0.68-0.63 (m, 0.5H), 0.59-0.46 (m, 1H), 0.37-0.32 (dd, 0.5H, J = 4.1, 12.6 Hz), 0.27-0.18 (td, 0.5H, J = 2.4, 12.6 Hz) | 431.0 (M + H) |
| 140 A | 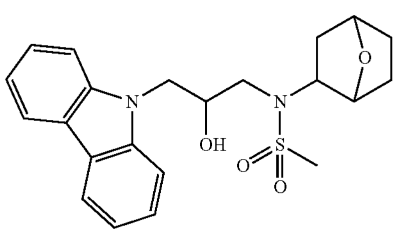 [SMILES: CS(=O)(=O)N(CC(O)Cn1c2ccccc2c2ccccc21)C1CC2CCC1O2] | N-(3-(9H-Carbazol-9-yl)-2-hydroxypropyl)-N-(7-oxabicyclo[2.2.1]heptan-2-yl)methanesulfon-amide | (300 MHz, CDCl$_3$) (diastereomer 1) δ 8.10-8.07 (m, 2H), 7.55-7.43 (m, 4H), 7.27-7.21 (m, 2H), 4.58-4.25 (m, 5H), 4.11-4.07 (dd, 0.7H, J = 4.1, 8.3 Hz), 4.03-3.98 (dd, 0.3H, J = 4.1, 8.6 Hz), 3.61-3.55, (dd, 0.7H, J = 2.7, 15.3 Hz), 3.58-3.52 (dd, 0.3H, J = 2.7, 15.3 Hz), 3.48-3.41 (dd, 0.3H, J = 7.4, 15.6 Hz), 3.39-3.31 (dd, 0.7H, J = 8.3, 15.6 Hz), 2.84 (s, 1H), 2.81 (s, 2H), 1.95-1.92 (d, 0.2H, J = 8.4 Hz), 1.91-1.88 (d, 0.7H, J = 8.7 Hz), 1.83-1.26 (m, 6H) | 414.7 (M + H) |
| 140 B | 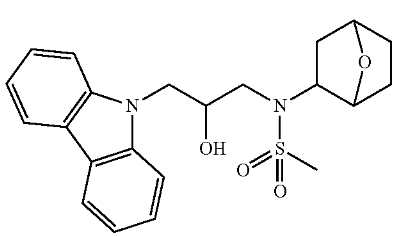 [SMILES: CS(=O)(=O)N(CC(O)Cn1c2ccccc2c2ccccc21)C1CC2CCC1O2] | N-(3-(9H-Carbazol-9-yl)-2-hydroxypropyl)-N-(7-oxabicyclo[2.2.1]heptan-2-yl)methanesulfon-amide | (300 MHz, CDCl$_3$) (diastereomer 2) δ 8.10-8.08 (d, 2H, J = 7.2 Hz), 7.51-7.42 (m, 4H), 7.28-7.23 (m, 2H), 4.49-4.31 (m, 4H), 4.22-4.13 (m, 1H), 3.67-3.02 (m, 4H), 2.92 (s, 1.5H), 2.85 (s, 1.5H), 1.87-1.32 (m, 4H), 0.98-0.92 (m, 0.5H), 0.86-0.80 (dd, 0.5H, J = 5.6, 12.6 Hz), 0.67-0.58 (m, 1H) | 414.7 (M + H) |

| Cpd # | Structure | Name | $^1$H NMR | ESI (m/z) |
|---|---|---|---|---|
| 141 | 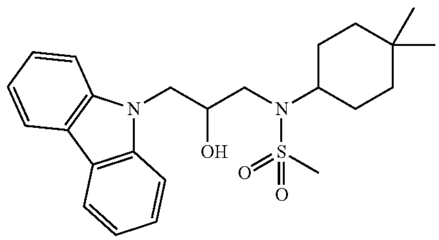 [SMILES: CC1(C)CCC(N(CC(O)Cn2c3ccccc3c3ccccc32)S(C)(=O)=O)CC1] | N-(3-(9H-Carbazol-9-yl)-2-hydroxypropyl)-N-(4,4-dimethylcyclohexyl)methanesulfonamide | (CDCl$_3$, 300 MHz) δ 8.08-8.05 (d t, 2H, J = 0.9, 7.5 Hz), 7.47-7.43 (m, 4H), 7.26-7.21 (m, 2H), 4.46-4.28 (m, 3H), 3.61-3.60 (d, 1H, J = 2.1 Hz), 3.42-3.34 (m, 1H), 3.31-3.24 (dd, 1H, J = 7.5, 15.9 Hz), 3.15-3.09 (dd, 1H, J = 0.6, 15.6 Hz), 2.86 (s, 3H), 1.20-0.92 (m, 7H), 0.71 (s, 3H), 0.23 (s, 3H) | N/A |
| 142 | 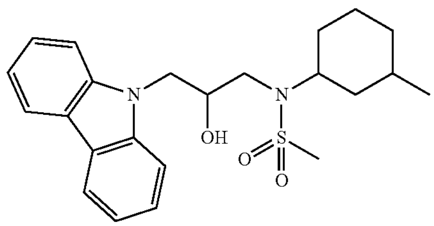 [SMILES: CC1CCCC(N(CC(O)Cn2c3ccccc3c3ccccc32)S(C)(=O)=O)C1] | N-(3-(9H-Carbazol-9-yl)-2-hydroxypropyl)-N-(3-methylcyclohexyl)methanesulfonamide | (300 MHz, CDCl$_3$) (diastereomeric mixture) δ 8.10-8.08 (d, 2H, J = 7.5 Hz), 7.51-7.45 (m, 4H), 7.28-7.22 (m, 2H), 4.48-4.24 (m, 3H), 3.69-3.08 (m, 4H), 2.85 (s, 1.4H), 2.83 (s, 1.3H), 2.83 (s, 0.3H), 1.50-0.03 (m, 8H), 0.67-0.64 (d, 1.8H, J = 6.6 Hz), 0.41-0.38 (d, 1.2H, J = 6.6 Hz) | 415.5 (M + H) |
| 143 | 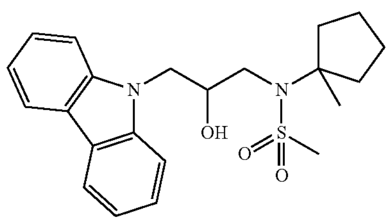 [SMILES: CC1(N(CC(O)Cn2c3ccccc3c3ccccc32)S(C)(=O)=O)CCCC1] | N-(3-(9H-Carbazol-9-yl)-2-hydroxypropyl)-N-(1-methylcyclopentyl)methanesulfonamide | (CDCl$_3$, 300 MHz) δ 8.10-8.07 (dt, 2H, J = 0.9, 7.8 Hz), 7.48-7.44 (m, 4H), 7.27-7.22 (m, 2H), 4.41-4.29 (m, 3H), 3.47-3.38 (m, 2H), 3.30-3.24 (dd, 1H, J = 2.0, 15.3 Hz), 2.95 (s, 3H), 1.69-1.28 (m, 8H), 1.15 (s, 3H) | N/A |
| 144 | 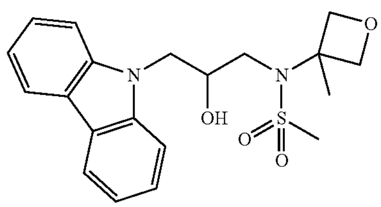 [SMILES: CC1(N(CC(O)Cn2c3ccccc3c3ccccc32)S(C)(=O)=O)COC1] | N-(3-(9H-Carbazol-9-yl)-2-hydroxypropyl)-N-(3-methyloxetan-3-yl)methanesulfonamide | (d4-MeOH, 300 MHz) δ 8.09-8.06 (m, 2H), 7.57-7.54 (br d, 2H, J = 7.5 Hz), 7.47-7.41 (m, 4H), 7.22-7.17 (m, 2H), 4.83-4.80 (br d, 1H, J = 6.6 Hz), 4.62-4.59 (br d, 1H), 4.37-4.30 (m, 3H), 4.01-3.83 (dd, 1H, J = 1.2, 6.0 Hz), 3.86-3.83 (dd, 1H, J = 1.2, 5.7 Hz), 3.18-3.15 (m, 2H), 3.37 (s, 3H), 1.63 (s, 3H) | 389.0 (M + H) |
| 145 | 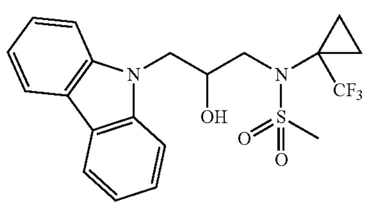 | N-(3-(9H-Carbazol-9-yl)-2-hydroxypropyl)-N-(1-(trifluoromethyl)cyclopropyl)methanesulfonamide | (300 MHz, d6-DMSO) δ 8.13-8.11 (d, 2H, J = 7.8 Hz), 7.61-7.58 (d, 2H, J = 8.1 Hz), 7.45-7.40 (td, 2H, J = 0.6, 7.8 Hz), 7.20-7.15 (t, 2H, J = 7.2 Hz), 5.41-5.32 (m, 1H), 4.39-4.26 (m, 3H), 3.80-3.60 (m, 1H), 3.03 (s, 3H), 1.58-0.95 (m, 4H) | 427.0 (M + H) |
| 146 | 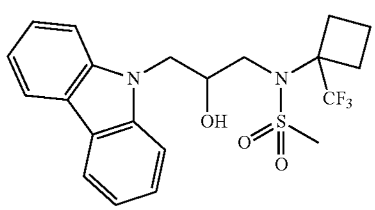 [SMILES: CS(=O)(=O)N(CC(O)Cn1c2ccccc2c2ccccc21)C1(C(F)(F)F)CCC1] | N-(3-(9H-Carbazol-9-yl)-2-hydroxypropyl)-N-(1-(trifluoromethyl)cyclobutyl)methanesulfonamide | (CDCl$_3$, 300 MHz) δ 8.10-8.07 (dt, 2H, J = 0.9, 7.2 Hz), 7.51-7.44 (m, 4H), 7.28-7.23 (m, 2H), 4.57-4.54 (m, 1H), 4.35-4.32 (dd, 2H, J = 2.2, 6.6 Hz), 3.38 (br s, 1H), 3.27-3.18 (m, 2H), 2.97 (s, 3H), 2.76-2.65 (m, 1H), 2.33-2.23 (m, 1H), 2.13-1.61 (m, 4H) | N/A |
| 147 | 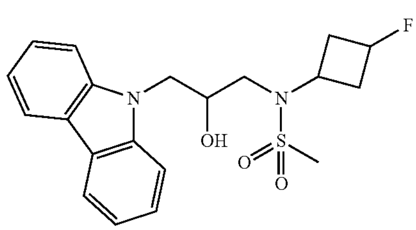 [SMILES: CS(=O)(=O)N(CC(O)Cn1c2ccccc2c2ccccc21)C1CC(F)C1] | N-(3-(9H-Carbazol-9-yl)-2-yl)hydroxypropyl)-N-(3-fluorocyclobutyl)methanesulfonamide | (300 MHz, CDCl$_3$) (diastereomeric mixture) δ 8.11-8.08 (d, 2H, J = 7.5 Hz), 7.51-7.44 (m, 4H), 7.29-7.23 (m, 2H), 4.72-4.63 (m, 0.5H), 4.54-4.30 (m, 4H), 3.75-3.68 (m, 0.5H), 3.34-3.05 (m, 2H), 3.05-3.04 (d, 0.5H, J = 2.4 Hz), 2.82 (s, 1.5H), 2.81 (s, 1.5H), 2.77-2.76 (d, 0.5H, J = 3.0 Hz), 2.58-2.50 (m, 1H), 2.26-1.74 (m, 3H) | 391.0 (M + H) |

-continued

| Cpd # | Structure | Name | ¹H NMR | ESI (m/z) |
|---|---|---|---|---|
| 148 | 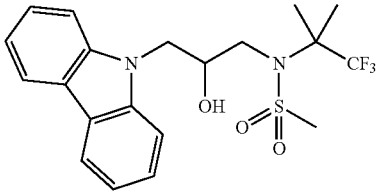 [SMILES: CC(C)(N(CC(O)Cn1c2ccccc2c2ccccc21)S(C)(=O)=O)C(F)(F)F] | N-(3-(9H-Carbazol-9-yl)-2-hydroxypropyl)-N-(1,1,1-trifluoro-2-methylpropan-2-yl)methanesulfonamide | (d4-MeOH, 300 MHz) δ 8.07-8.04 (m, 2H), 7.57-7.54 (br d, 2H, J = 6.1 Hz), 7.45-7.40 (m, 2H), 7.21-7.16 (m, 2H), 4.42-4.27 (m, 3H), 3.75-3.67 (dd, 1H, J = 7.8, 16.2 Hz), 3.61-3.55 (dd, 1H, J = 2.6, 16.2 Hz), 3.10 (s, 3H), 1.62 (s, 3H), 1.47 (s, 3H) | 428.9 (M + H) |
| 149 | 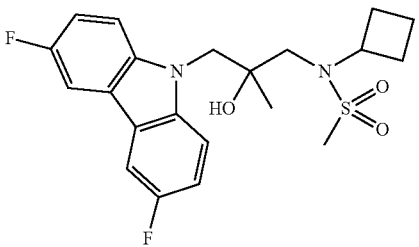 [SMILES: CC(O)(CN(C1CCC1)S(C)(=O)=O)Cn1c2ccc(F)cc2c2cc(F)ccc21] | N-Cyclobutyl-N-(3-(3,6-difluoro-9H-carbazol-9-yl)-2-hydroxy-2-methylpropyl)methanesulfonamide | (300 MHz, CDCl₃) δ 7.68 (dd, 2H, J = 8.4, 2.7 Hz), 7.45 (dd, 2H, J = 9.0, 4.2 Hz), 7.22 (td, 2H, J = 9.0, 2.7 Hz), 4.40 & 4.28 (AB, 2H, J = 15.3 Hz), 4.23 (m, 1H), 3.43 (s, 3H), 3.16 (s, 1H), 2.88 (s, 3H), 2.30-2.10 (m, 4H), 1.75-1.55 (m, 2H), 1.30 (s, 3H) | 405.0 (M + H − H₂O) |
| 150 | 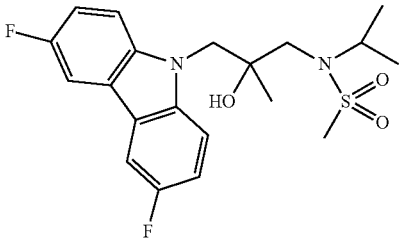 [SMILES: CC(C)N(CC(C)(O)Cn1c2ccc(F)cc2c2cc(F)ccc21)S(C)(=O)=O] | N-(3-(3,6-Difluoro-9H-carbazol-9-yl)-2-hydroxy-2-methylpropyl)-N-isopropylmethanesulfonamide | (300 MHz, CDCl₃) δ 7.68 (dd, 2H, J = 8.7, 2.7 Hz), 7.44 (dd, 2H, J = 9.0, 4.2 Hz), 7.21 (td, 2H, J = 9.0, 2.7 Hz), 4.44 & 4.29 (AB, 2H, J = 15.3 Hz), 4.02 (m, 1H), 3.45 & 3.33 (AB, 2H, J = 15.3 Hz), 3.00 (s, 1H), 2.95 (s, 3H), 1.36-1.26 (m, 9H) | 392.9 (M + H − H₂O) |
| 151 | 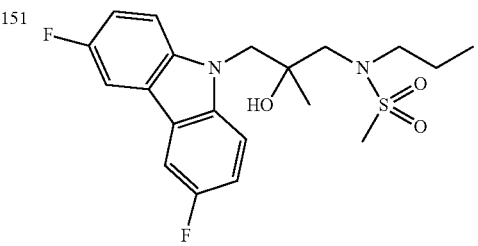 | N-(3-(3,6-Difluoro-9H-carbazol-9-yl)-2-hydroxy-2-methylpropyl)-N-propylmethanesulfonamide | (300 MHz, CDCl₃) δ 7.68 (dd, 2H, J = 8.7, 2.7 Hz), 7.43 (dd, 2H, J = 9.0, 4.2 Hz), 7.21 (td, 2H, J = 9.0, 2.7 Hz), 4.46 & 4.27 (AB, 2H, J = 15.3 Hz), 3.52 (AB, 1H, J = 15.0 Hz), 3.45-3.35 (m, 3H), 2.95 (s, 3H), 2.42 (s, 1H), 1.88-1.72 (m, 2H), 1.32 (s, 3H), 0.97 (t, 3H, J = 7.5 Hz) | 392.8 (M + H − H₂O) |
| 152 | 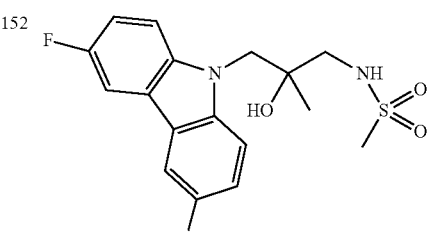 | N-(3-(3,6-Difluoro-9H-carbazol-9-yl)-2-hydroxy-2-methylpropyl)methanesulfonamide | (300 MHz, d6 DMSO) δ 7.98 (dd, 2H, J = 9.3, 2.7 Hz), 7.69 (dd, 2H, J = 9.3, 4.5 Hz), 7.29 (td, 2H, J = 9.3, 2.7 Hz), 7.09 (t, 1H, J = 6.3 Hz), 4.91 (s, 1H), 3.35 & 3.29 (AB, 2H, J = 15.3 Hz), 3.22-3.04 (m, 2H), 2.95 (s, 3H), 1.06 (s, 3H) | 366.8 (M − H) |
| 153 | 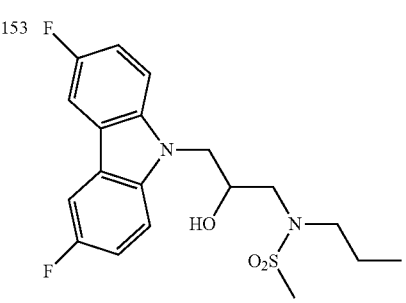 | N-(3-(3,6-Difluoro-9H-carbazol-9-yl)-2-hydroxypropyl)-N-propylmethanesulfonamide | (CDCl₃, 300 MHz) δ 7.69-7.66 (dd, 2H, J = 2.6, 8.7 Hz), 7.40-7.35 (dd, 2H, J = 4.2, 8.7 Hz), 7.25-7.19 (td, 2H, J = 2.6, 9.0 Hz), 4.38-4.35 (m, 3H), 3.41-3.33 (m, 1H), 3.24-3.20 (m, 1H), 3.15-3.10 (t, 2H, J = 7.7 Hz), 2.88 (s, 3H), 2.69-2.68 (d, 1H, J = 2.7 Hz), 1.52-1.45 (sext, 2H, J = 7.8 Hz), 0.87-0.82 (t, 3H, J = 7.4 Hz) | 396.9 (M + H) |

-continued

| Cpd # | Structure | Name | $^1$H NMR | ESI (m/z) |
|---|---|---|---|---|
| 154 | 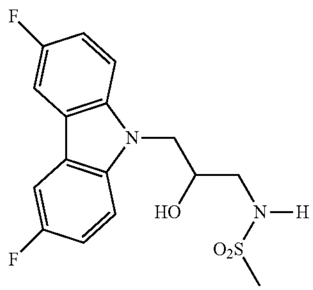 [SMILES: CS(=O)(=O)NCC(O)Cn1c2ccc(F)cc2c2cc(F)ccc21] | N-(3-(3,6-Difluoro-9H-carbazol-9-yl)-2-hydroxypropyl) methanesulfonamide | (d4-MeOH, 300 MHz) δ 7.77-7.74 (dd, 2H, J = 2.4, 8.7 Hz), 7.56-7.52 (dd, 2H, J = 4.2, 9.0 Hz), 7.25-7.18 (td, 2H, J = 2.7, 9.0 Hz), 4.50-4.48 (dd, 1H, J = 3.8, 14.9 Hz), 4.35-4.43 (dd, 1H, J = 8.0, 15.0 Hz), 4.19-4.12 (m, 1H), 3.25-3.21 (dd, 2H, J = 4.5, 6.0 Hz), 2.98 (s, 3H) | N/A |
| 155 | 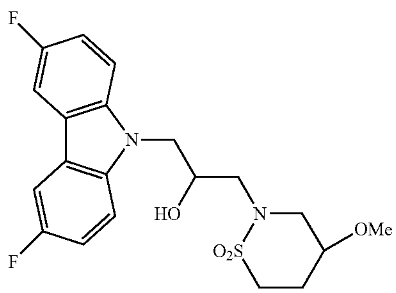 [SMILES: COC1CCS(=O)(=O)N(CC(O)Cn2c3ccc(F)cc3c3cc(F)ccc32)C1] | N-(3-(3,6-Difluoro-9H-carbazol-9-yl)-2-hydroxypropyl)-4-methoxy-1,2-thiazinane-1,1-dioxide | (CDCl$_3$, 300 MHz) (diastereomeric mixture) δ 7.68-7.64 (ddd, 2H, J = 0.9, 2.4, 8.4 Hz), 7.42-7.36 (dt, 2H, J = 3.6, 8.7 Hz), 7.25-7.17 (td, 2H, J = 2.4, 9.0 Hz), 4.37-4.32 (m, 3H), 3.75-2.99 (m, 10H), 3.34 (s, 1.5H), 3.28 (s, 1.5H), 2.82-2.81 (d, 0.5H, J = 3.9 Hz), 2.44-2.30 (m, 2H) | 425.0 (M + H) |
| 156 | 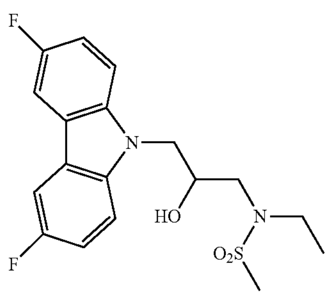 [SMILES: CCN(CC(O)Cn1c2ccc(F)cc2c2cc(F)ccc21)S(C)(=O)=O] | N-(3-(3,6-ifluoro-9H-carbazol-9-yl)-2-hydroxypropyl)-N-ethylmethane-sulfonamide | (300 MHz, CDCl$_3$) δ 7.69-7.65 (dd, 2H, J = 2.4, 8.4 Hz), 7.40-7.35 (dd, 2H, J = 4.2, 9.0 Hz), 7.25-7.19 (td, 2H, J = 2.7, 9.0 Hz), 4.41-4.36 (m, 3H), 3.41-3.21 (m, 4H), 2.88 (s, 3H), 2.64-2.63 (d, 1H, J = 3.3 Hz), 1.16-1.11 (t, 3H, J = 7.0 Hz) | N/A |
| 157 | 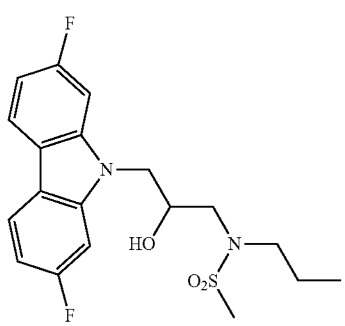 [SMILES: CCCN(CC(O)Cn1c2cc(F)ccc2c2ccc(F)cc21)S(C)(=O)=O] | N-(3-(2,7-Difluoro-9H-carbazol-9-yl)-2-hydroxypropyl)-N-propylmethane-sulfonamide | (CDCl$_3$, 300 MHz) δ 7.95-7.90 (dd, 2H, J = 5.2, 8.7 Hz), 7.14-7.10 (dd, 2H, J = 2.3, 9.9 Hz), 7.02-6.95 (ddd, 2H, J = 2.1, 8.7, 9.3 Hz), 4.38-4.34 (m, 1H), 4.28-4.26 (m, 2H), 3.42-3.35 (dd, 1H, J = 7.5, 14.7 Hz), 3.27-3.21 (dd, 1H, J = 3.3, 14.7 Hz), 3.17-3.12 (m, 2H), 2.89 (s, 3H), 2.76-2.75 (d, 1H, J = 3.3 Hz), 1.52-1.45 (sext, 2H, J = 7.7 Hz), 0.88-0.83 (t, 3H, J = 7.2 Hz) | 397.0 (M + H) |
| 158 | 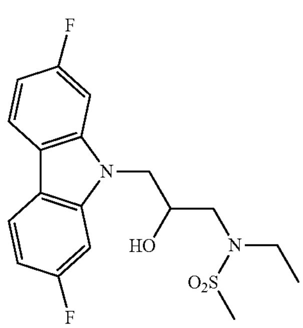 [SMILES: CCN(CC(O)Cn1c2cc(F)ccc2c2ccc(F)cc21)S(C)(=O)=O] | N-(3-(2,7-Difluoro-9H-carbazol-9-yl)-2-hydroxypropyl)-N-ethylmethane-sulfonamide | (CDCl$_3$, 300 MHz) δ 7.94-7.89 (dd, 2H, J = 4.8, 8.4 Hz), 7.14-7.10 (dd, 2H, J = 2.3, 9.9 Hz), 7.01-6.95 (ddd, 2H, J = 2.4, 8.4, 10.8 Hz), 4.36-4.34 (m, 1H), 4.29-4.26 (m, 2H), 3.42-3.23 (m, 4H), 2.89 (s, 3H), 2.73 (br s, 1H), 1.18-1.3 (t, 3H, J = 7.2 Hz) | 382.9 (M + H) |

-continued

| Cpd # | Structure | Name | ¹H NMR | ESI (m/z) |
|---|---|---|---|---|
| 159 | 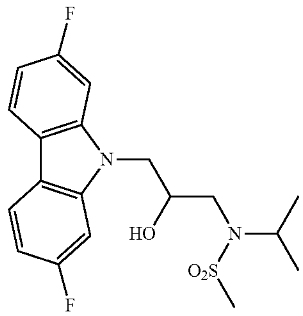 [SMILES: CC(C)N(CC(O)Cn1c2cc(F)ccc2c2ccc(F)cc21)S(C)(=O)=O] | N-(3-(2,7-Difluoro-9H-carbazol-9-yl)-2-hydroxypropyl)-N-isopropylmethane-sulfonamide | (CDCl₃, 300 MHz) δ 7.93-7.88 (dd, 2H, J = 5.1, 8.7 Hz), 7.14-7.10 (dd, 2H, J = 2.1, 9.9 Hz), 7.00-6.93 (ddd, 2H, J = 2.4, 8.7, 9.9 Hz), 4.31-4.22 (m, 3H), 4.04-3.95 (sept, 1H, J = 6.9 Hz), 3.28 (br s, 1H), 3.25-3.12 (m, 2H), 2.88 (s, 3H), 1.02-0.98 (d, 3H, J = 6.5 Hz) 0.95-0.92 (d, 3H, J = 6.5 Hz) | 396.8 (M + H) |
| 160 | 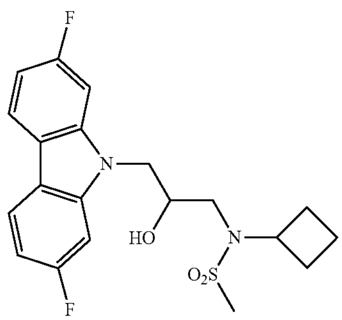 [SMILES: CS(=O)(=O)N(CC(O)Cn1c2cc(F)ccc2c2ccc(F)cc21)C1CCC1] | N-Cyclobutyl-N-(3-(2,7-difluoro-9H-carbazol-9-yl)-2-hydroxypropyl)methanesulfonamide | (CDCl₃, 300 MHz) δ 7.94-7.90 (dd, 2H, J = 5.4, 8.4 Hz), 7.16-7.12 (dd, 2H, J = 2.1, 9.9 Hz), 7.01-6.94 (ddd, 2H, J = 2.4, 8.7, 9.3 Hz), 4.34-4.15 (m, 4H), 3.29-3.27 (d, 2H, J = 4.5 Hz), 2.82 (s, 3H), 2.05-1.98 (m, 2H), 1.92-1.86 (m, 1H), 1.75-1.67 (m, 1H), 1.54-1.44 (m, 2H) | 408.9 (M + H) |
| 161 | 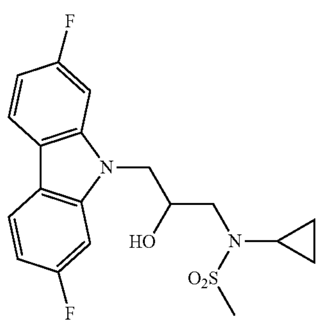 [SMILES: CS(=O)(=O)N(CC(O)Cn1c2cc(F)ccc2c2ccc(F)cc21)C1CC1] | N-Cyclopropyl-N-(3-(2,7-difluoro-9H-carbazol-9-yl)-2-hydroxypropyl)methanesulfonamide | (CDCl₃, 300 MHz) δ 7.94-7.90 (dd, 2H, J = 5.1, 8.7 Hz), 7.14-7.10 (dd, 2H, J = 2.3, 9.9 Hz), 7.01-6.94 (td, 2H, J = 2.1, 9.0 Hz), 4.47-4.41 (m, 1H), 4.26-4.24 (m, 2H), 3.15-3.43 (dd, 1H, J = 8.4, 14.4 Hz), 3.34-3.28 (dd, 2H, J = 3.3, 14.7 Hz), 2.97 (s, 3H), 2.62-2.61 (d, 1H, J = 3.9 Hz), 2.48-2.42 (m, 1H), 0.84-0.73 (m, 4H) | 394.9 (M + H) |
| 162 | 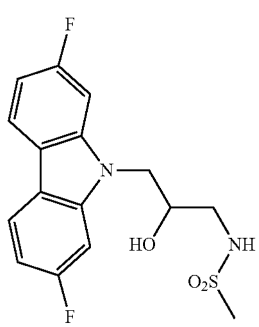 [SMILES: CS(=O)(=O)NCC(O)Cn1c2cc(F)ccc2c2ccc(F)cc21] | N-(3-(2,7-Difluoro-9H-carbazol-9-yl)-2-hydroxypropyl)methanesulfonamide | (d4-MeOH, 300 MHz) δ 8.00-7.95 (dd, 2H, J = 2.4, 8.7 Hz), 7.32-7.28 (dd, 2H, J = 2.1, 10.5 Hz), 7.25-7.18 (ddd, 2H, J = 2.4, 8.7, 9.9 Hz), 4.43-4.37 (dd, 1H, J = 3.6, 15.0 Hz), 4.29-4.21 (dd, 1H, J = 8.1, 14.7 Hz), 4.19-4.12 (m, 1H), 3.25-3.21 (dd, 2H, J = 5.7, 6.9 Hz), 2.99 (s, 3H) | N/A |

| Cpd # | Structure | Name | ¹H NMR | ESI (m/z) |
|---|---|---|---|---|
| 163 | 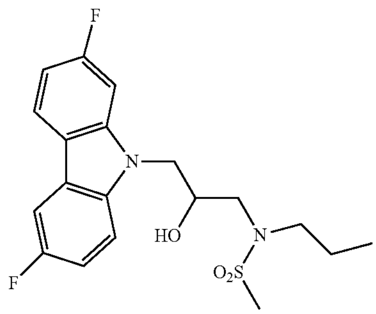 [SMILES: CCCN(CC(O)Cn1c2ccc(F)cc2c2ccc(F)cc21)S(C)(=O)=O] | N-(3-(2,6-Difluoro-9H-carbazol-9-yl)-2-hydroxypropyl)-N-propylmethane-sulfonamide | (CDCl₃, 300 MHz) δ 7.95-7.90 (dd, 1H, J = 5.6, 8.7 Hz), 7.68-7.64 (dd, 1H, J = 2.4, 8.7 Hz), 7.37-7.33 (dd, 1H, J = 10.0, 8.7 Hz), 7.20-7.16 (dd, 1H, J = 2.6, 9.0 Hz), 7.13-7.09 (dd, 1H, J = 2.3, 32.0 Hz), 6.99-6.93 (ddd, 1H, J = 2.1, 8.4, 9.3 Hz), 4.38-4.25 (m, 3H), 3.41-3.33 (dd, 1H, J = 7.6, 15.0 Hz), 3.25-3.19 (dd, 1H, J = 3.3, 14.7 Hz), 3.15-3.10 (m, 2H), 2.88 (s, 3H), 2.75-2.73 (d, 1H, J = 3.3 Hz), 1.52-1.45 (sext, 2H, J = 7.5 Hz), 0.87-0.82 (t, 3H, J = 7.5 Hz) | N/A |
| 164 | 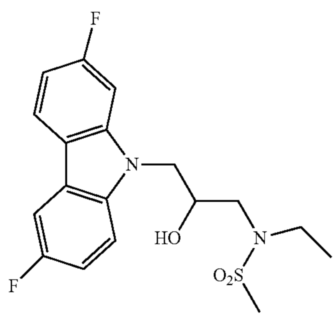 [SMILES: CCN(CC(O)Cn1c2ccc(F)cc2c2ccc(F)cc21)S(C)(=O)=O] | N-(3-(2,6-Difluoro-9H-carbazol-9-yl)-2-hydroxypropyl)-N-ethylmethane-sulfonamide | (CDCl₃, 300 MHz) δ 7.96-7.91 (dd, 1H, J = 5.4, 9.0 Hz), 7.69-7.65 (dd, 1H, J = 2.4, 8.7 Hz), 7.38-7.34 (dd, 1H, J = 3.9, 9.0 Hz), 7.20-7.16 (dd, 1H, J = 2.4, 8.7 Hz), 7.14-7.10 (dd, 1H, J = 2.4, 4.0 Hz), 7.00-6.93 (ddd, 1H, J = 2.1, 8.4, 9.0 Hz), 4.38-4.25 (m, 3H), 3.41-3.22 (m, 4H), 2.89 (s, 3H), 2.66-2.65 (d, 1H, J = 3.3 Hz), 1.17-1.12 (t, 3H, J = 7.1 Hz) | N/A |
| 165 | 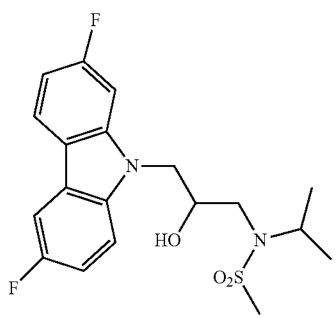 [SMILES: CC(C)N(CC(O)Cn1c2ccc(F)cc2c2ccc(F)cc21)S(C)(=O)=O] | N-(3-(2,6-Difluoro-9H-carbazol-9-yl)-2-hydroxypropyl)-N-isopropylmethane-sulfonamide | (CDCl₃, 300 MHz) δ 7.96-7.91 (dd, 1H, J = 5.4, 9.0 Hz), 7.69-7.65 (dd, 1H, J = 2.6, 8.7 Hz), 7.38-7.34 (dd, 1H, J = 4.2, 8.7 Hz), 7.20-7.16 (dd, 1H, J = 2.4, 9.0 Hz), 7.14-7.10 (dd, 1H, J = 2.1, 9.9 Hz), 7.00-6.93 (ddd, 1H, J = 2.4, 8.4, 9.0 Hz), 4.30 (br m, 3H), 4.04-3.95 (sept, 1H, J = 6.9 Hz), 3.28-3.11 (m, 3H), 2.88 (s, 3H), 0.99-0.97 (d, 3H, J = 6.6 Hz), 0.91-0.89 (d, 3H, J = 6.9 Hz) | 396.8 (M + H) |
| 166 | 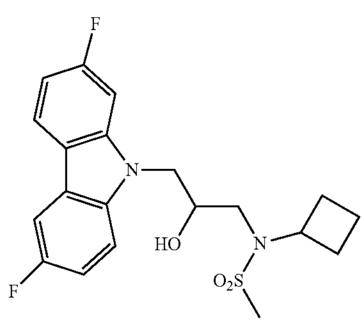 [SMILES: CS(=O)(=O)N(CC(O)Cn1c2ccc(F)cc2c2ccc(F)cc21)C1CCC1] | N-Cyclobutyl-N-(3-(2,6-difluoro-9H-carbazol-9-yl)-2-hydroxypropyl)methanesulfonamide | (CDCl₃, 300 MHz) δ 7.94-7.90 (dd, 1H, J = 5.3, 8.7 Hz), 7.67-7.63 (dd, 1H, J = 2.3, 8.7 Hz), 7.38-7.34 (dd, 1H, J = 4.0, 8.7 Hz), 7.20-7.16 (dd, 1H, J = 2.6, 9.0 Hz), 7.14-7.10 (m, 1H), 7.00-6.93 (ddd, 1H, J = 2.3, 8.4, 9.0 Hz), 4.35-4.13 (m, 4H), 3.27-3.25 (m, 2H), 2.97-2.97 (d, 1H, J = 1.8 Hz), 2.78 (s, 3H), 2.04-1.94 (m, 2H), 1.91-1.84 (t, 1H, J = 10.6 Hz), 1.75-1.65 (t, 1H, J = 10.4 Hz), 1.58-1.42 (m, 2H) | 409.0 (M + H) |
| 167 | 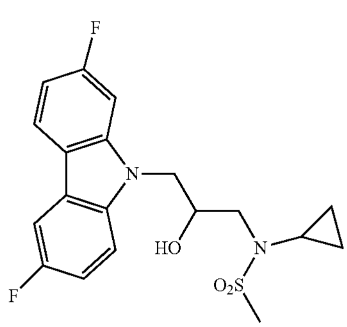 [SMILES: CS(=O)(=O)N(CC(O)Cn1c2ccc(F)cc2c2ccc(F)cc21)C1CC1] | N-Cyclopropyl-N-(3-(2,6-difluoro-9H-carbazol-9-yl)-2-hydroxypropyl)methanesulfonamide | (CDCl₃, 300 MHz) δ 7.95-7.90 (dd, 1H, J = 5.4, 8.4 Hz), 7.68-7.64 (dd, 1H, J = 2.4, 8.7 Hz), 7.37-7.33 (dd, 1H, J = 1.9, 8.7 Hz), 7.20-7.16 (dd, 1H, J = 2.6, 9.0 Hz), 7.14-7.10 (m, 1H), 7.00-6.93 (m, 1H), 4.45-4.48 (m, 1H), 4.28-4.26 (m, 2H), 3.49-3.42 (dd, 1H, J = 8.7, 14.7 Hz), 3.32-3.26 (dd, 1H, J = 3.6, 14.7 Hz), 2.95 (s, 3H), 2.63-2.62 (d, 1H, J = 3.6 Hz), 2.47-2.40 (m, 1H), 0.83-0.67 (m, 4H) | 394.9 (M + H) |

| Cpd # | Structure | Name | ¹H NMR | ESI (m/z) |
|---|---|---|---|---|
| 168 | 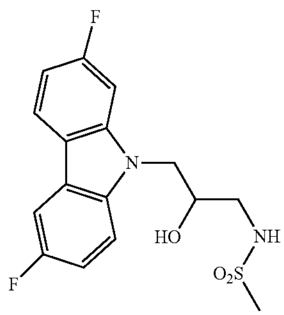 [SMILES: CS(=O)(=O)NCC(O)Cn1c2ccc(F)cc2c2ccc(F)cc21] | N-(3-(2,6-Difluoro-9H-carbazol-9-yl)-2-hydroxypropyl)methanesulfonamide | (d4-MeOH, 300 MHz) δ 8.03-7.99 (dd, 1H, J = 5.7, 8.4 Hz), 7.75-7.71 (dd, 1H, J = 2.4, 9.3 Hz), 7.54-7.50 (dd, 1H, J = 2.3, 10.5 Hz), 7.20-7.13 (td, 1H, J = 2.4, 9.0 Hz), 6.96-6.89 (ddd, 1H, J = 2.2, 8.4, 9.6 Hz), 4.47-4.41 (dd, 1H, J = 8.1, 15.0 Hz), 4.19-4.13 (m, 1H), 3.29-3.18 (m, 2H), 2.98 (s, 3H) | N/A |
| 169 | 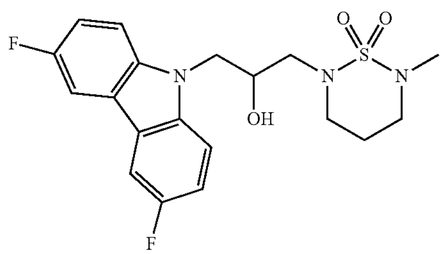 [SMILES: CN1CCCN(CC(O)Cn2c3ccc(F)cc3c3cc(F)ccc32)S1(=O)=O] | 2-(3-(3,6-Difluoro-9H-carbazol-9-yl)-2-hydroxypropyl)-6-methyl-1,2,6-thiadiazinane-1,1-dioxide | (300 MHz, CDCl₃) δ 7.68 (dd, 2H, J = 8.7, 2.7 Hz), 7.40 (dd, 2H, J = 9.0, 4.2 Hz), 7.23 (td, 2H, J = 9.0, 2.7 Hz), 4.45-4.30 (m, 3H), 3.51 (t, 2H, J = 5.7 Hz), 3.40-3.25 (m, 4H), 2.82 (s, 3H), 2.47 (s, 1H), 1.90-1.70 (m, 2H) | 410.0 (M + H) |
| 170 | 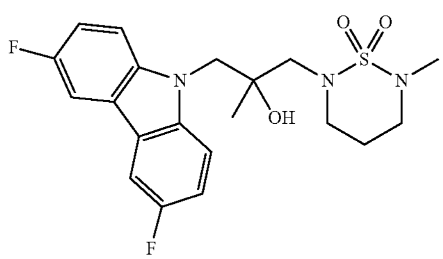 [SMILES: CN1CCCN(CC(C)(O)Cn2c3ccc(F)cc3c3cc(F)ccc32)S1(=O)=O] | 2-(3-(3,6-Difluoro-9H-carbazol-9-yl)-2-hydroxy-2-methylpropyl)-6-methyl-1,2,6-thiadiazinane-1,1-dioxide | (300 MHz, CDCl₃) δ 7.68 (dd, 2H, J = 8.7, 2.7 Hz), 7.44 (dd, 2H, J = 9.0, 4.2 Hz), 7.22 (td, 2H, J = 9.0, 2.7 Hz), 4.50 & 4.25 (AB, 2H, J = 15.3 Hz), 3.75 (t, 2H, J = 5.7 Hz), 3.45-3.30 (m, 4H), 2.84 (s, 3H), 2.01 (s, 1H), 1.98-1.80 (m, 2H), 1.30 (s, 3H) | 423.9 (M + H) |
| 171 | 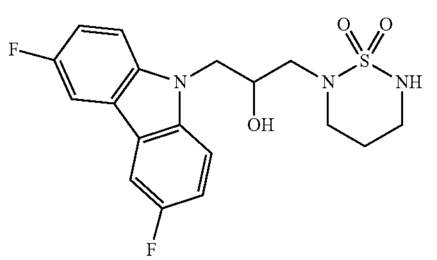 [SMILES: O=S1(=O)NCCCN1CC(O)Cn1c2ccc(F)cc2c2cc(F)ccc21] | 2-(3-(3,6-Difluoro-9H-carbazol-9-yl)-2-hydroxypropyl)-1,2,6-thiadiazinane-1,1-dioxide | (300 MHz, d6-DMSO) δ 8.00 (dd, 2H, J = 9.3, 2.7 Hz), 7.59 (dd, 2H, J = 9.0, 4.2 Hz), 7.32 (td, 2H, J = 9.3, 2.7 Hz), 6.94 (t, 1H, J = 6.6 Hz), 5.15 (d, 1H, J = 5.7 Hz), 4.44 (dd, 1H, J = 14.7, 3.0 Hz), 4.29 (dd, 1H, J = 14.7, 8.7 Hz), 4.05 (m, 1H), 3.50-3.20 (m, 4H), 3.15-3.00 (m, 2H), 1.70-1.55 (m, 2H) | 393.9 (M + H) |
| 172 | 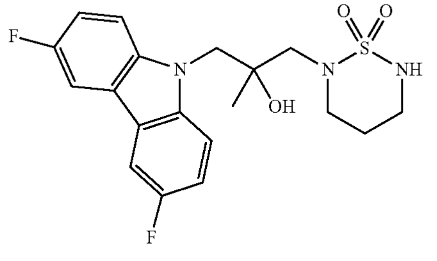 [SMILES: CC(O)(CN1CCCNS1(=O)=O)Cn1c2ccc(F)cc2c2cc(F)ccc21] | 2-(3-(3,6-Difluoro-9H-carbazol-9-yl)-2-hydroxy-2-methylpropyl)-1,2,6-thiadiazinane-1,1-dioxide | (300 MHz, CDCl₃) δ 7.68 (dd, 2H, J = 8.7, 2.7 Hz), 7.43 (dd, 2H, J = 9.0, 4.2 Hz), 7.22 (td, 2H, J = 9.0, 2.4,Hz.), 4.49 & 4.25 (AB, 2H, J = 15.3 Hz), 4.12 (t, 1H, J = 6.6 Hz), 3.80-3.65 (m, 2H), 3.59 (q, 2H, J = 6.0 Hz), 3.36 & 3.24 (AB, 2H, J = 14.4 Hz), 2.02 (s, 1H), 1.90-1.70 (m, 2H), 1.31 (s, 3H) | 409.9 (M + H) |

-continued

| Cpd # | Structure | Name | ¹H NMR | ESI (m/z) |
|---|---|---|---|---|
| 173 | 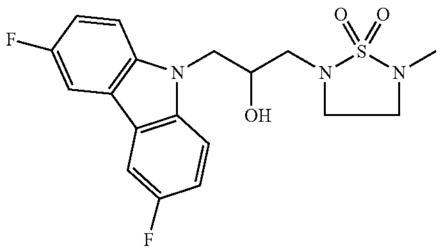 [SMILES: CN1CCN(CC(O)Cn2c3ccc(F)cc3c3cc(F)ccc32)S1(=O)=O] | 2-(3-(3,6-Difluoro-9H-carbazol-9-yl)-2-hydroxypropyl)-5-methyl-1,2,5-thiadiazinane-1,1-dioxide | (300 MHz, CDCl₃) δ 7.68 (dd, 2H, J = 8.7, 2.7 Hz), 7.43 (dd, 2H, J = 9.0, 4.2 Hz), 7.23 (td, 2H, J = 9.0, 2.4 Hz), 4.53-4.35 (m, 3H), 3.48-3.28 (m, 4H), 3.26 (d, 2H, J = 5.4 Hz), 2.81 (s, 3H), 2.42 (d, 1H, J = 3.6 Hz) | 396.0 (M + H) |
| 174 | 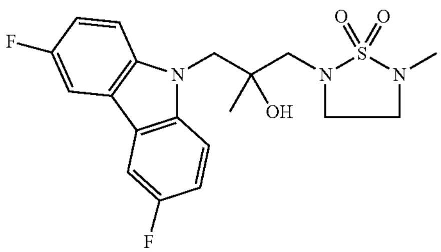 [SMILES: CN1CCN(CC(C)(O)Cn2c3ccc(F)cc3c3cc(F)ccc32)S1(=O)=O] | 2-(3-(3,6-Difluoro-9H-carbazol-9-yl)-2-hydroxy-2-methylpropyl)-5-methyl-1,2,5-thiadiazinane-1,1-dioxide | (300 MHz, d6-DMSO) δ 7.97 (dd, 2H, J = 9.0, 2.7 Hz), 7.70 (dd, 2H, J = 9.0, 4.2 Hz), 7.29 (td, 2H, J = 9.0, 2.7 Hz), 4.91 (s, 1H), 4.35 (s, 2H), 3.60-3.40 (m, 2H), 3.40-3.20 (m, 3H), 3.11 (AB, 1H, J = 14.1 Hz), 2.63 (s, 3H), 1.11 (s, 3H) | 410.0 (M + H) |
| 175 | 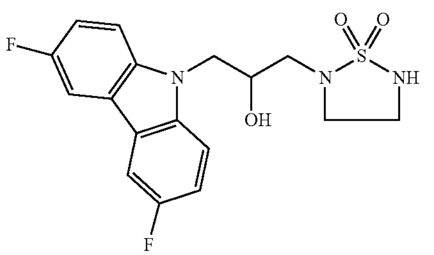 [SMILES: O=S1(=O)NCCN1CC(O)Cn1c2ccc(F)cc2c2cc(F)ccc21] | 2-(3-(3,6-Difluoro-9H-carbazol-9-yl)-2-hydroxypropyl)-1,2,5-thiadiazinane-1,1-dioxide | (300 MHz, CDCl₃) δ 7.67 (dd, 2H, J = 8.7, 2.7 Hz), 7.40 (dd, 2H, J = 9.0, 4.2 Hz), 7.22 (td, 2H, J = 9.0, 2.7 Hz), 4.54-4.35 (m, 3H), 4.26 (br s, 1H), 3.60-3.40 (m, 4H), 3.24 (d, 2H, J = 5.4 Hz), 2.40 (d, 1H, J = 3.6 Hz) | 382.0 (M + H) |
| 176 | 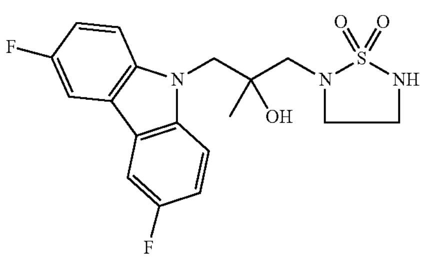 [SMILES: CC(O)(CN1CCNS1(=O)=O)Cn1c2ccc(F)cc2c2cc(F)ccc21] | 2-(3-(3,6-Difluoro-9H-carbazol-9-yl)-2-hydroxy-2-methylpropyl)-1,2,5-thiadiazinane-1,1-dioxide | (300 MHz, CDCl₃) δ 7.68 (dd, 2H, J = 8.4, 2.4 Hz), 7.43 (dd, 2H, J = 9.0, 4.2 Hz), 7.22 (td, 2H, J = 9.0, 2.4 Hz), 4.51 & 4.27 (AB, 2H, J = 15.6 Hz), 4.25 (br s, 1H), 3.82-3.45 (m, 4H), 3.37 & 3.29 (AB, 2H, J = 14.7 Hz), 1.91 (s, 1H), 1.35 (s, 3H) | 396.0 (M + H) |
| 177 | 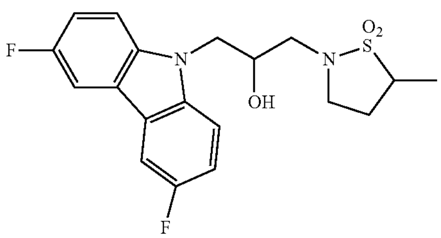 [SMILES: CC1CCN(CC(O)Cn2c3ccc(F)cc3c3cc(F)ccc32)S1(=O)=O] | 2-(3-(3,6-Difluoro-9H-carbazol-9-yl)-2-hydroxy-2-methylpropyl)-5-methylisothiazolidine-1,1-dioxide | (CDCl₃, 300 MHz) (diastereomeric mixture) δ 7.68-7.64 (dd, 2H, J = 2.4, 9.0 Hz), 7.41-7.36 (ddd, 2H, J = 1.8, 3.9, 8.7 Hz), 7.25-7.17 (td, 2H, J = 2.4, 8.7 Hz), 4.37 (m, 3H), 3.4-3.09 (m, 5H), 2.65-2.57 (dd, 1H, J = 3.3, 19.2 Hz), 2.48-2.42 (m, 1H), 2.03-1.95 (m, 1H), 1.46-1.42 (t, 3H, J = 6.9 Hz) | 395.0 (M + H) |
| 178 | 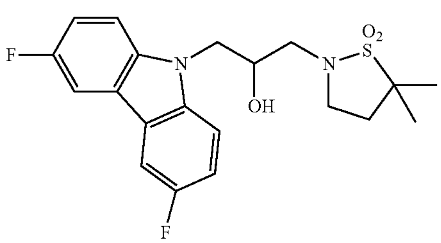 [SMILES: CC1(C)CCN(CC(O)Cn2c3ccc(F)cc3c3cc(F)ccc32)S1(=O)=O] | 2-(3-(3,6-Difluoro-9H-carbazol-9-yl)-2-hydroxypropyl)-5,5-dimethylisothiazolidine-1,1-dioxide | (CDCl₃, 300 MHz) δ 7.68-7.64 (dd, 2H, J = 2.7, 8.7 Hz), 7.41-7.36 (dd, 2H, J = 4.2, 9.0 Hz), 7.24-7.17 (td, 2H, J = 2.4, 9.0 Hz), 4.37-4.35 (m, 3H), 3.39-3.14 (m, 4H), 2.65-2.64 (d, 1H, J = 3.3 Hz), 2.19-2.14 (t, 2H, J = 7.1 Hz), 1.47-1.44 (d, 3H, J = 3.3 Hz) | 409.0 (M + H) |

| Cpd # | Structure | Name | $^1$H NMR | ESI (m/z) |
|---|---|---|---|---|
| 179 | 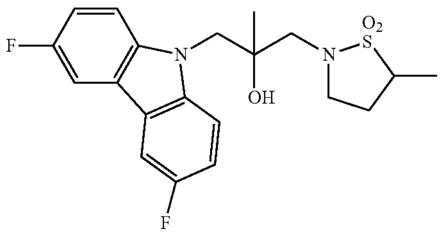 [SMILES: CC1CCN(CC(C)(O)Cn2c3ccc(F)cc3c3cc(F)ccc32)S1(=O)=O] | 2-(3-(3,6-Difluoro-9H-carbazol-9-yl)-2-hydroxy-2-methylpropyl)-5-methylisothiazolidine-1,1-dioxide | (CDCl$_3$, 300 MHz) (diastereomeric mixture) δ 7.67-7.63 (dd, 2H, J = 2.4, 8.7 Hz), 7.44-7.39 (ddd, 2H, J = 1.8, 4.2, 9.3 Hz), 7.23-7.16 (td, 2H, J = 2.4, 8.7 Hz), 4.50-4.39 (dd, 1H, J = 15.0, 17.1 Hz), 4.28-4.20 (dd, 1H, J = 7.5, 15.0 Hz), 3.62-3.15 (m, 5H), 2.56-2.44 (m, 1H), 2.14-1.98 (m, 2H), 1.48-1.47 (d, 1.5H, J = 3.3 Hz), 1.46-1.45 (d, 1.5H, J = 3.3 Hz), 1.30-1,28 (d, 3H, J = 6.6 Hz) | 409.0 (M + H) |
| 180 | 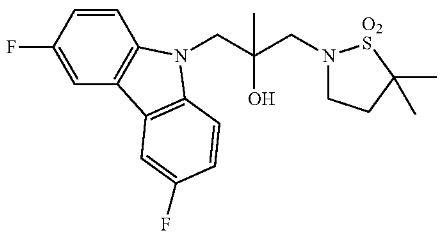 [SMILES: CC(O)(CN1CCC(C)(C)S1(=O)=O)Cn1c2ccc(F)cc2c2cc(F)ccc21] | 2-(3-(3,6-Difluoro-9H-carbazol-9-yl)-2-hydroxy-2-methylpropyl)-5,5-dimethylisothiazolidine-1,1-dioxide | (CDCl$_3$, 300 MHz) δ 7.67-7.63 (dd, 2H, J = 2.4, 8.7 Hz), 7.44-7.40 (dd, 2H, J = 4.2, 9.3 Hz), 7.22-7.16 (td, 2H, J = 2.7, 9.0 Hz), 4.46-4.41 (d, 1H, J = 15.3 Hz), 4.27-4.22 (d, 1H, J = 15.3 Hz), 3.52-3.26 (m, 4H), 2.24-2.20 (t, 2H, J = 7.2 Hz), 1.47-1.46 (d, 6H, J = 2.7 Hz), 1.28 (s, 3H) | 423.0 (M + H) |
| 181 | 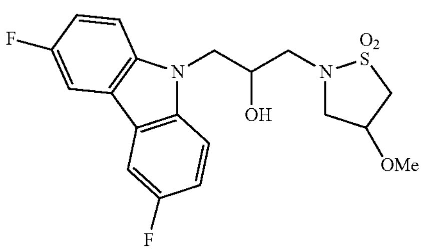 [SMILES: COC1CN(CC(O)Cn2c3ccc(F)cc3c3cc(F)ccc32)S(=O)(=O)C1] | 2-(3-(3,6-Difluoro-9H-carbazol-9-yl)-2-hydroxypropyl)-4-methoxyisothiazolidine-1,1-dioxide | (300 MHz, CDCl$_3$) δ 7.67-7.63 (dd, 2H, J = 2.4, 8.7 Hz), 7.40-7.36 (dd, 2H, J = 4.1, 9.0 Hz), 7.23-7.16 (tdd, 2H, J = 0.9, 2.7, 8.7 Hz), 4.43-4.30 (m, 3H), 4.23-4.19 (m, 1H), 3.56-3.16 (m, 6H), 3.36 (s, 1.5H), 3.34 (s, 1.5H), 2.68 (br s, 0.5H), 2.60 (br s, 0.5H) | 411.0 (M + H) |
| 182 | 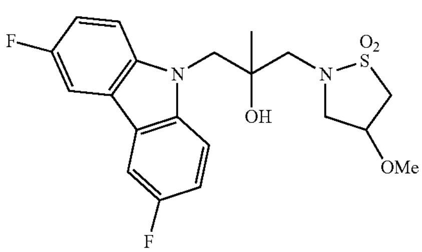 [SMILES: COC1CN(CC(C)(O)Cn2c3ccc(F)cc3c3cc(F)ccc32)S(=O)(=O)C1] | 2-(3-(3,6-Difluoro-9H-carbazol-9-yl)-2-hydroxy-2-methylpropyl)-4-methoxyisothiazolidine-1,1-dioxide | (300 MHz, CDCl$_3$) (diastereomeric mixture) δ 7.62-7.58 (dd, 2H, J = 2.3, 9.0 Hz), 7.43-7.37 (m, 2H), 7.17-7.10 (tdd, 2H, J = 1.2, 2.4, 9.0 Hz), 4.49-4.13 (m, 3H), 3.76-3.53 (m, 2H), 3.49-3.40 (m, 1H), 3.37 (s, 1.5 H), 3.34 (s, 1.5H), 3.32-3.12 (m, 3H), 1.23 (s, 1.5H), 1.22 (s, 1.5H) | 424.9 (M + H) |
| 183 | 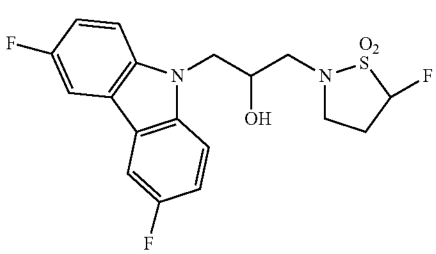 [SMILES: O=S1(=O)C(F)CCN1CC(O)Cn1c2ccc(F)cc2c2cc(F)ccc21] | 2-(3-(3,6-Difluoro-9H-carbazol-9-yl)-2-hydroxypropyl)-5-fluoroisothiazolidine-1,1-dioxide | (CDCl$_3$, 300 MHz) δ 7.68-7.65 (dd, 2H, J = 2.4, 8.7 Hz), 7.39-7.35 (dd, 2H, J = 4.2, 8.7 Hz), 7.25-7.18 (td, 2H, J = 2.4, 9.0 Hz), 5.56-5.35 (m, 1H), 4.43-4.34 (m, 3H), 3.51-3.23 (m, 4H), 2.76-2.33 (m, 3H) | N/A |
| 184 | 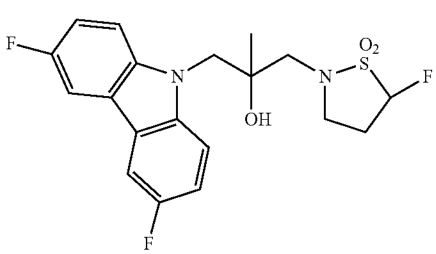 [SMILES: CC(O)(CN1CCC(F)S1(=O)=O)Cn1c2ccc(F)cc2c2cc(F)ccc21] | 2-(3-(3,6-Difluoro-9H-carbazol-9-yl)-2-hydroxy-2-methylpropyl)-5-fluoroisothiazolidine-1,1-dioxide | (CDCl$_3$, 300 MHz) (diastereomeric mixture) δ 7.67-7.63 (dd, 2H, J = 2.4, 8.4 Hz), 7.43-7.38 (ddd, 2H, J = 1.5, 4.2, 9.0 Hz), 7.23-7.16 (tdd, 2H, J = 0.9, 2.7, 9.3 Hz), 5.59-5.38 (dtd, 1H, J = 1.5, 4.2, 53.1 Hz), 4.53-4.40 (dd, 1H, J = 15.3, 24.9 Hz), 4.27-4.19 (dd, 1H, J = 9.9, 15.3 Hz), 3.76-3.52 (m, 3H), 3.25-3.16 (dd, 1H, J = 9.3, 14.7 Hz), 1.84-1.83 (d, 1H, J = 2.7 Hz), 1.33 (s, 1.5H), 1.29 (s, 1.5H) | 413.1 (M + H) |

-continued

| Cpd # | Structure | Name | ¹H NMR | ESI (m/z) |
|---|---|---|---|---|
| 185 | 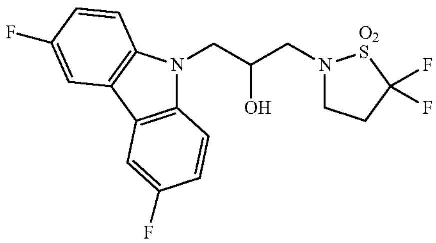 [SMILES: O=S1(=O)N(CC(O)Cn2c3ccc(F)cc3c3cc(F)ccc32)CCC1(F)F] | 2-(3-(3,6-Difluoro-9H-carbazol-9-yl)-2-hydroxypropyl)-5,5-difluoroisothiazol-idine-1,1-dioxide | (CDCl₃, 300 MHz) δ 7.68-7.64 (dd, 2H, J = 2.6, 8.7 Hz), 7.38-7.33 (dd, 2H, J = 4.2, 9.0 Hz), 7.24-7.18 (td, 2H, J = 2.7, 8.7 Hz), 4.42-4.35 (m, 3H), 3.45-3.35 (m, 4H), 2.76-2.67 (m, 2H), 2.33-2.32 (d, 1H, J = 3.3 Hz) | N/A |
| 186 | 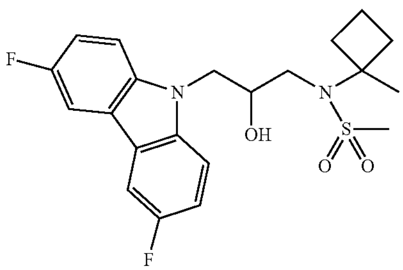 [SMILES: CC1(N(CC(O)Cn2c3ccc(F)cc3c3cc(F)ccc32)S(C)(=O)=O)CCC1] | N-(3-(3,6-Difluoro-9H-carbazol-9-yl)-2-hydroxypropyl)-N-(1-methylcyclobutyl)methanesulfon-amide | (300 MHz, CDCl₃) δ 7.69 (dd, 2H, J = 9.0, 2.4 Hz), 7.40 (dd, 2H, J = 9.0, 4.2 Hz), 7.25 (td, 2H, J = 9.0, 2.4 Hz), 4.45-4.25 (m, 3H), 3.33 (d, 1H, J = 3.0 Hz), 3.15 (dd, 1H, J = 15.3, 7.5 Hz), 3.05 (dd, 1H, J = 15.3, 2.4 Hz), 2.96 (s, 3H), 2.21 (m, 1H), 1.97 (m, 1H), 1.73-1.50 (m, 4H), 1.35 (s, 3H) | 423.0 (M + H) |
| 187 | 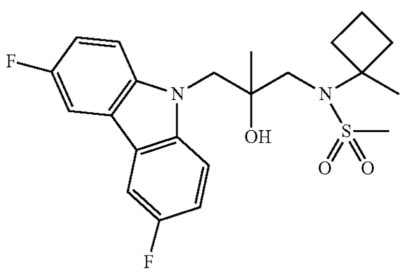 [SMILES: CC(O)(CN(C1(C)CCC1)S(C)(=O)=O)Cn1c2ccc(F)cc2c2cc(F)ccc21] | N-(3-(3,6-Difluoro-9H-carbazol-9-yl)-2-hydroxy-2-methylpropyl)-N-(1-methylcyclobutyl)methanesulfon-amide | (300 MHz, CDCl₃) δ 7.68 (dd, 2H, J = 8.7, 2.4 Hz), 7.41 (dd, 2H, J = 9.0, 4.2 Hz), 7.22 (td, 2H, J = 9.0, 2.4 Hz), 4.38 & 4.26 (AB, 2H, J = 15.3 Hz), 3.55 (s, 1H), 3.45 (d, 1H, J = 15.0 Hz), 3.12 (d, 1H, J = 15.3 Hz), 3.11 (s, 3H), 2.50-2.00 (m, 3H), 1.85-1.70 (m, 3H), 1.51 (s, 3H), 1.38 (s, 3H) | 437.1 (M + H) |
| 188 | 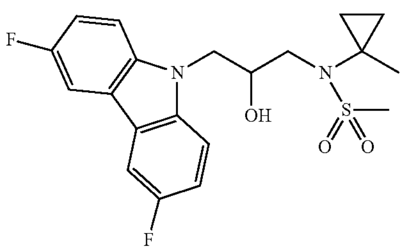 [SMILES: CC1(N(CC(O)Cn2c3ccc(F)cc3c3cc(F)ccc32)S(C)(=O)=O)CC1] | N-(3-(3,6-Difluoro-9H-carbazol-9-yl)-2-hydroxypropyl)-N-(1-methylcycloprop-yl)methanesulfon-amide | (300 MHz, CDCl₃) δ 7.69 (dd, 2H, J = 9.0, 2.4 Hz), 7.40 (dd, 2H, J = 9.0, 4.2 Hz), 7.24 (td, 2H, J = 9.0, 2.4 Hz), 4.42 (m, 1H), 4.33 (d, 2H, J = 6.0 Hz), 3.41 (dd, 1H, J = 15.0, 7.5 Hz), 3.34 (dd, 1H, J = 15.0, 3.6 Hz), 3.00-2.85 (m, 4H), 1.29 (s, 3H), 1.00 (m, 1H), 0.85 (m, 1H), 0.63-0.45 (m, 2H) | 409.1 (M + H) |
| 189 | 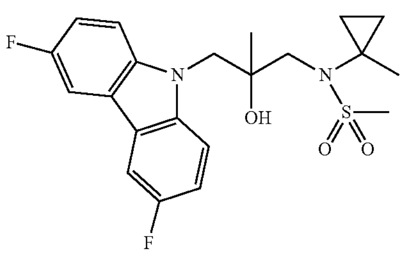 [SMILES: CC(O)(CN(C1(C)CC1)S(C)(=O)=O)Cn1c2ccc(F)cc2c2cc(F)ccc21] | N-(3-(3,6-Difluoro-9H-carbazol-9-yl)-2-hydroxy-2-methylpropyl)-N-(1-methylcycloprop-yl)methanesulfon-amide | (300 MHz, CDCl₃) δ 7.68 (dd, 2H, J = 8.7, 2.4 Hz), 7.43 (dd, 2H, J = 9.0, 4.2 Hz), 7.22 (td, 2H, J = 9.0, 2.4 Hz), 4.35 & 4.26 (AB, 2H, J = 15.0 Hz), 3.70 & 3.46 (AB, 2H, J = 15.0 Hz), 3.18 (s, 1H), 3.03 (s, 3H), 1.45 (s, 3H), 1.30 (s, 3H), 1.20 (m, 1H), 1.07 (m, 1H), 0.85 (m, 1H), 0.68 (m, 1H) | 405.0 (M + H − H₂O) |
| 190 | 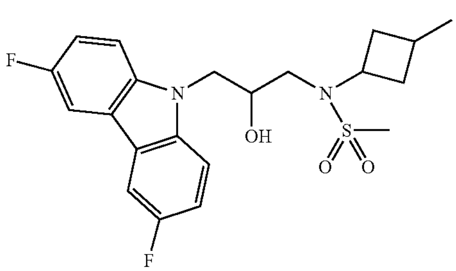 [SMILES: CC1CC(N(CC(O)Cn2c3ccc(F)cc3c3cc(F)ccc32)S(C)(=O)=O)C1] | N-(3-(3,6-Difluoro-9H-carbazol-9-yl)-2-hydroxypropyl)-N-(3-methylcyclobutyl)methanesulfon-amide | (300 MHz, CDCl₃) (diastereomeric mixture) δ 7.69 (dd, 2H, J = 9.0, 2.4 Hz), 7.41 (dd, 2H, J = 9.0, 4.2 Hz), 7.31-7.20 (m, 2H), 4.50-4.20 (m, 3.4H), 3.98 (m, 0.6H), 3.34-3.10 (m, 2.6H), 2.99 (d, 0.4H, J = 3.0 Hz), 2.80 (s, 3H), 2.20-1.60 (m, 4H), 1.24 & 0.94 (m, 1H), 1.08 & 0.67 (d, 3H, J = 6.6 Hz) | 422.9 (M + H) |

-continued

| Cpd # | Structure | Name | ¹H NMR | ESI (m/z) |
|---|---|---|---|---|
| 191 | 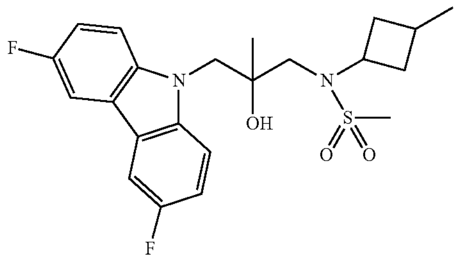 [SMILES: CC1CC(N(CC(C)(O)Cn2c3ccc(F)cc3c3cc(F)ccc32)S(C)(=O)=O)C1] | N-(3-(3,6-Difluoro-9H-carbazol-9-yl)-2-hydroxy-2-methylpropyl)-N-(3-methylcyclobutyl)methanesulfonamide | (300 MHz, CDCl₃) (diastereomeric mixture) δ 7.72-7.65 (m, 2H), 7.50-7.40 (m, 2H), 7.28-7.18 (m, 2H), 4.55-4.25 (m, 2.4H), 4.04 (m, 0.6H), 3.46-3.28 (m, 3H), 2.86 (s, 3H), 2.40-1.50 (m, 5H), 1.30 (m, 3H), 1.18 & 0.95 (d, 3H, J = 6.9 Hz) | 437.0 (M + H) |
| 192 | 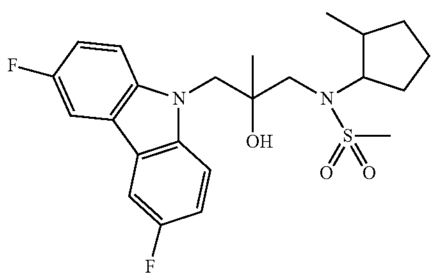 [SMILES: CC1CCCC1N(CC(C)(O)Cn1c2ccc(F)cc2c2cc(F)ccc21)S(C)(=O)=O] | N-(3-(3,6-Difluoro-9H-carbazol-9-yl)-2-hydroxy-2-methylpropyl)-N-(2-methylcyclopentyl)methanesulfonamide | (300 MHz, CDCl₃) (diastereomeric mixture) δ 7.72-7.64 (m, 2H), 7.49-7.38 (m, 2H), 7.28-7.16 (m, 2H), 4.52-4.20 (m, 1.8H), 4.00 (m, 0.2H), 3.70-2.85 (m, 6H), 2.50-0.80 (m, 14H) | 432.9 (M + H − H₂O) |
| 193 A | 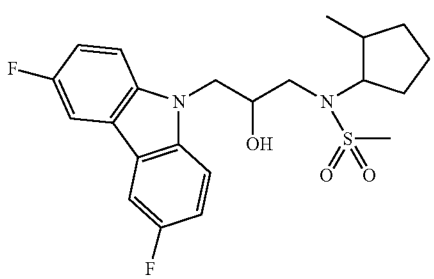 [SMILES: CC1CCCC1N(CC(O)Cn1c2ccc(F)cc2c2cc(F)ccc21)S(C)(=O)=O] | N-(3-(3,6-Difluoro-9H-carbazol-9-yl)-2-hydroxypropyl)-N-(2-methylcyclopentyl)methanesulfonamide | (300 MHz, CDCl₃) (1:1 mixture of two diastereomers) δ 7.69 (dd, 2H, J = 8.7, 2.4 Hz), 7.45-7.35 (m, 2H), 7.28-7.20 (m, 2H), 4.50-4.20 (m, 3H), 3.93 & 3.53 (m, 1H), 3.40 & 2.78 (d, 1H, J = 2.7 Hz), 3.35-3.10 (m, 2H), 2.89 & 2.88 (s, 3H), 2.10-1.00 & 0.70 (m, 7H), 0.95 (d, 1.5H, J = 6.3 Hz), 0.79 (d, 1.5H, J = 7.2 Hz) | 418.9 (M + H) |
| 193 B | 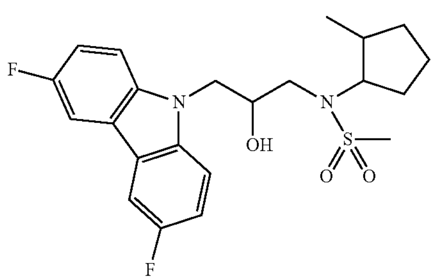 [SMILES: CC1CCCC1N(CC(O)Cn1c2ccc(F)cc2c2cc(F)ccc21)S(C)(=O)=O] | N-(3-(3,6-Difluoro-9H-carbazol-9-yl)-2-hydroxypropyl)-N-(2-methylcyclopentyl)methanesulfonamide | (300 MHz, CDCl₃) (single diastereomer) δ 7.70 (dd, 2H, J = 8.7, 2.4 Hz), 7.40 (dd, 2H, J = 8.7, 4.2 Hz), 7.26 (dt, 2H, J = 9.0, 2.4 Hz), 4.44 (dd, 1H, J = 14.7, 4.8 Hz), 4.35-4.15 (m, 2H), 3.97 (d, 1H, J = 1.5 Hz), 3.41 & 3.35 (AB, 1H, J = 9.0 Hz), 3.17 (dd, 1H, J = 15.6, 7.5 Hz), 2.85 (d, 1H, J = 15.6 Hz), 2.81 (s, 3H), 1.60 (m, 1H), 1.30 (m, 1H), 1.12 (m, 1H), 0.92 (m, 1H), 0.85-0.50 (m, 5H), 0.23 (m, 1H) | 418.9 (M + H) |
| 193 C | 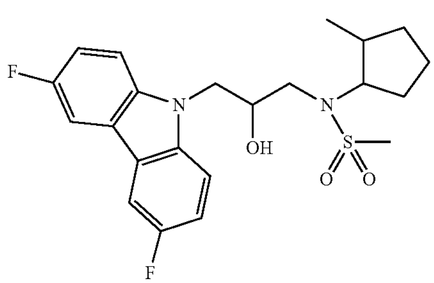 [SMILES: CC1CCCC1N(CC(O)Cn1c2ccc(F)cc2c2cc(F)ccc21)S(C)(=O)=O] | N-(3-(3,6-Difluoro-9H-carbazol-9-yl)-2-hydroxypropyl)-N-(2-methylcyclopentyl)methanesulfonamide | (300 MHz, CDCl₃) (single diastereomer) δ 7.70 (dd, 2H, J = 8.7, 2.4 Hz), 7.38 (dd, 2H, J = 9.0, 4.2 Hz), 7.25 (dt, 2H, J = 9.0, 2.4 Hz), 4.50-4.10 (m, 3H), 3.88 (dt, 1H, J = 10.5, 7.8 Hz), 3.67 (d, 1H, J = 3.0 Hz), 3.45 (dd, 1H, J = 15.6, 7.8 Hz), 3.10 (dd, 1H, J = 15.6, 1.5 Hz), 2.94 (s, 3H), 2.03 (m, 1H), 1.70-1.00 (m, 4H), 0.78 (m, 1H), 0.56 (m, 1H), 0.55 (d, 3H, J = 7.2 Hz) | 436.9 (M + H + H₂O) |

| Cpd # | Structure | Name | ¹H NMR | ESI (m/z) |
|---|---|---|---|---|
| 194 | 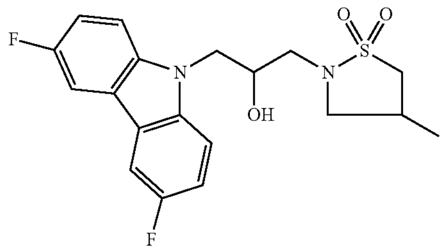 [SMILES: CC1CN(CC(O)Cn2c3ccc(F)cc3c3cc(F)ccc32)S(=O)(=O)C1] | 2-(3-(3,6-Difluoro-9H-carbazol-9-yl)-2-hydroxypropyl)-4-methylisothiazolidine-1,1-dioxide | (300 MHz, CDCl₃) (1:1 mixture of two diastereomers) δ 7.68 (dd, 2H, J = 8.7, 2.7 Hz), 7.44-7.37 (m, 2H), 7.23 (td, 2H, J = 9.0, 2.7 Hz), 4.50-4.30 (m, 3H), 3.55-2.70 (m, 7H), 2.66 (d, 0.5H, J = 3.6 Hz), 2.55 (d, 0.5H, J = 3.0 Hz), 1.30-1.20 (m, 3H) | 395.0 (M + H) |
| 195 | 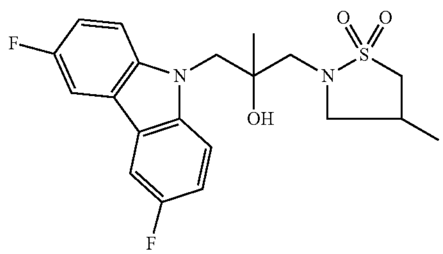 [SMILES: CC1CN(CC(C)(O)Cn2c3ccc(F)cc3c3cc(F)ccc32)S(=O)(=O)C1] | 2-(3-(3,6-Difluoro-9H-carbazol-9-yl)-2-hydroxy-2-methylpropyl)-4-methylisothiazolidine-1,1-dioxide | (300 MHz, CDCl₃) (1:1 mixture of two diastereomers) δ 7.68 (dd, 2H, J = 8.7, 2.7 Hz), 7.48-7.40 (m, 2H), 7.22 (td, 2H, J = 9.0, 2.7 Hz), 4.52 & 4.42 (d, 1H, J = 15.3 Hz), 4.28 & 4.23 (d, 1H, J = 13.2 Hz), 3.79 (dd, 0.5H, J = 9.3, 6.3 Hz), 3.65 (dd, 0.5H, J = 9.3, 6.3 Hz), 3.52-3.35 (m, 2H), 3.20-3.00 (m, 2H), 2.95-2.75 (m, 2H), 2.02 (d, 1H, J = 4.2 Hz), 1.35-1.25 (m, 6H) | 408.9 (M + H) |
| 196 | 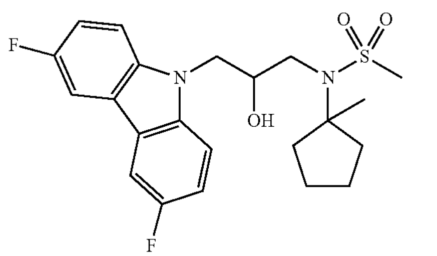 [SMILES: CC1(N(CC(O)Cn2c3ccc(F)cc3c3cc(F)ccc32)S(C)(=O)=O)CCCC1] | N-(3-(3,6-Difluoro-9H-carbazol-9-yl)-2-hydroxypropyl)-N-(1-methylcyclopentyl)methanesulfonamide | (300 MHz, CDCl₃) δ 7.69 (dd, 2H, J = 8.7, 2.4 Hz), 7.40 (dd, 2H, J = 9.0, 4.2 Hz), 7.25 (td, 2H, J = 9.0, 2.4 Hz), 4.42-4.25 (m, 3H), 3.50-3.20 (m, 3H), 2.98 (s, 3H), 1.85-1.30 (m, 8H), 1.20 (s, 3H) | N/A |
| 197 | 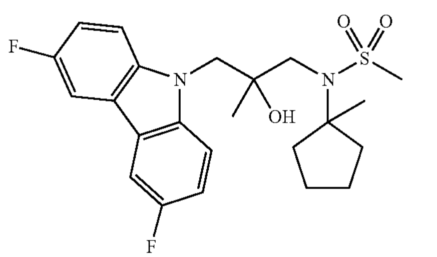 [SMILES: CC(O)(CN(C1(C)CCCC1)S(C)(=O)=O)Cn1c2ccc(F)cc2c2cc(F)ccc21] | N-(3-(3,6-Difluoro-9H-carbazol-9-yl)-2-hydroxy-2-methylpropyl)-N-(1-methylcyclopentyl)methanesulfonamide | (300 MHz, CDCl₃) δ 7.68 (dd, 2H, J = 8.7, 2.4 Hz), 7.42 (dd, 2H, J = 8.7, 4.2 Hz), 7.22 (td, 2H, J = 9.0, 2.4 Hz), 4.35 & 4.25 (AB, 2H, J = 15.3 Hz), 3.77 (d, 1H, J = 15.6 Hz), 3.67 (s, 1H), 3.44 (d, 1H, J = 15.9 Hz), 3.13 (s, 3H), 2.20-1.50 (m, 8H), 1.35 (s, 3H), 1.33 (s, 3H) | N/A |
| 198 | 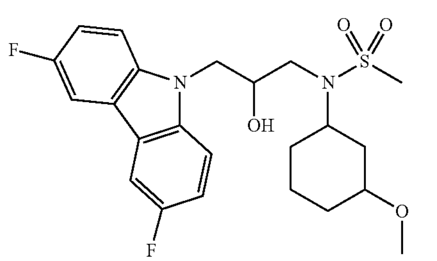 [SMILES: COC1CCCC(N(CC(O)Cn2c3ccc(F)cc3c3cc(F)ccc32)S(C)(=O)=O)C1] | N-(3-(3,6-Difluoro-9H-carbazol-9-yl)-2-hydroxypropyl)-N-(3-methoxycyclohexyl)methanesulfonamide | (300 MHz, CDCl₃) (diastereomeric mixture) δ 7.70 (dd, 2H, J = 8.7, 2.4 Hz), 7.41 (dd, 2H, J = 9.0, 4.2 Hz), 7.30-7.21 (m, 2H), 4.50-4.20 (m, 3H), 3.80 (tt, 1H, J = 12.3, 3.6 Hz), 3.50-3.00 (m, 7H), 2.88 (s, 3H), 1.90-0.40 (m, 8H) | N/A |
| 199 | 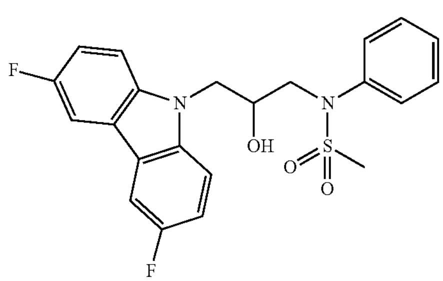 [SMILES: CS(=O)(=O)N(CC(O)Cn1c2ccc(F)cc2c2cc(F)ccc21)c1ccccc1] | N-(3-(3,6-Difluoro-9H-carbazol-9-yl)-2-hydroxypropyl)-N-phenylmethanesulfonamide | (300 MHz, CDCl₃) δ 7.66-7.62 (dd, 2H, J = 2.1, 8.7 Hz), 7.47-7.36 (m, 7H), 7.21-7.14 (td, 2H, J = 2.4, 9.0 Hz), 4.36,4.4.21 (ABq, 2H, J_{AB} = 15.3 Hz), 4.03,3.96 (ABq, 2H, J_{AB} = 14.7 Hz), 2.90 (s, 3H), 2.34 (s, 1H), 1.22 (s, 3H) | N/A |

| Cpd # | Structure | Name | ¹H NMR | ESI (m/z) |
|---|---|---|---|---|
| 200 | 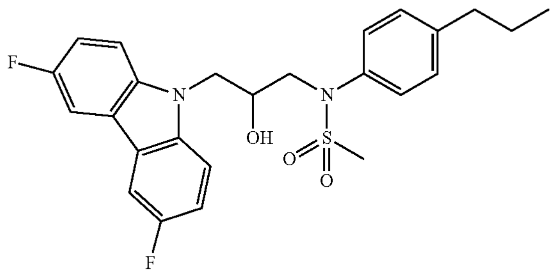 [SMILES: CCCc1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-propylphenyl)methanesulfonamide | (300 MHz, CDCl₃) δ 7.66-7.62 (dd, 2H, J = 2.4, 9.0 Hz), 7.29-7.13 (m, 8H), 4.45-4.25 (m, 3H), 3.93-3.86 (dd, 1H, J = 6.6, 14.1 Hz), 3.83-3.77 (dd, 1H, J = 5.3, 14.0 Hz), 2.92 (s, 3H), 2.62-2.57 (t, 2H, J = 7.7 Hz), 2.32-2.31 (d, 1H, J = 3.3 Hz), 1.71-1.61 (m, 2H), 0.98-0.93 (t, 3H, J = 7.4 Hz) | 473.1 (M + H) |
| 201 | 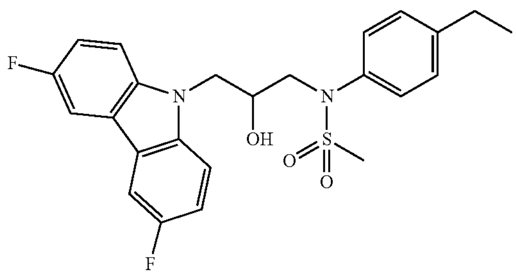 [SMILES: CCc1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-ethylphenyl)methanesulfonamide | (300 MHz, CDCl₃) δ 7.66-7.62 (dd, 2H, J = 2.4, 9.0 Hz), 7.29-7.21 (m, 8H), 7.20-7.13 (td, 2H, J = 2.7, 6.0 Hz), 4.45-4.41 (m, 1H), 4.32-4.25 (m, 2H), 3.93-3.86 (dd, 1H, J = 6.6, 14.1 Hz), 3.83-3.77 (dd, 1H, J = 5.3, 14.1 Hz), 2.92 (s, 3H), 2.71-2.63 (q, 2H, J = 7.5 Hz), 2.32-2.31 (d, 1H, J = 3.0 Hz), 1.28-1.23 (t, 3H, J = 7.5 Hz) | 459.1 (M + H) |
| 202 | 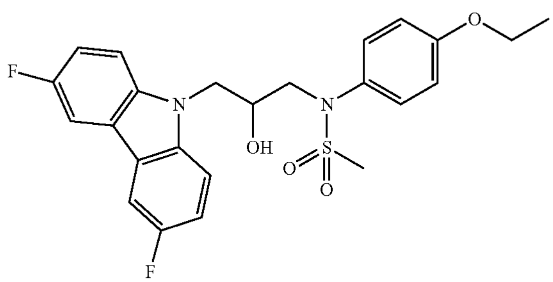 [SMILES: CCOc1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-ethoxyphenyl)methanesulfonamide | (300 MHz, CDCl₃) δ 7.66-7.62 (dd, 2H, J = 2.4, 8.7 Hz), 7.30-7.25 (m, 4H), 7.20-7.14 (td, 2H, J = 2.4, 8.9 Hz), 6.90-6.87 (d, 2H, J = 8.7 Hz), 4.45-4.39 (dd, 1H, J = 3.0, 14.1 Hz), 4.32-4.30 (d, 1H, J = 7.8 Hz), 4.26-4.22 (m, 1H), 4.06-3.99 (q, 2H, J = 7.0 Hz), 3.92-3.85 (dd, 1H, J = 7.1, 14.0 Hz), 3.78-3.72 (dd, 1H, J = 5.0, 14.0 Hz), 2.91 (s, 3H), 2.34-2.33 (d, 1H, J = 3.9 Hz), 1.45-1.41 (t, 3H, J = 6.9 Hz) | 475.0 (M + H) |
| 203 | 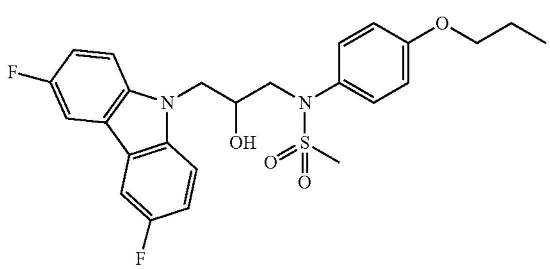 [SMILES: CCCOc1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-propoxyphenyl)methanesulfonamide | (300 MHz, CDCl₃) δ 7.66-7.62 (dd, 2H, J = 2.4, 8.7 Hz), 7.30-7.24 (m, 4H), 7.20-7.13 (td, 2H, J = 2.4, 9.0 Hz), 6.90-6.87 (m, 2H), 4.43-4.25 (m, 3H), 3.93-3.89 (t, 2H, J = 6.6 Hz), 3.90-3.71 (m, 2H), 2.91 (s, 3H), 2.36 (br s, 1H), 1.85-1.78 (m, 2H), 1.07-1.02 (t, 2H, J = 7.5 Hz) | 489.1 (M + H) |
| 204 | 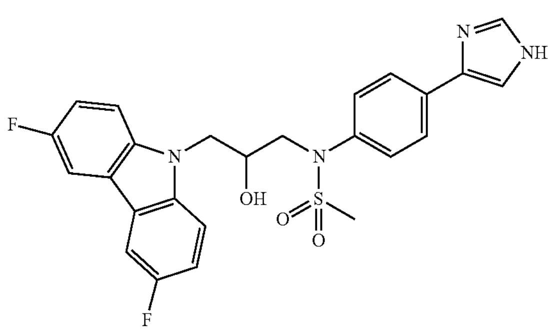 [SMILES: CS(=O)(=O)N(CC(O)Cn1c2ccc(F)cc2c2cc(F)ccc21)c1ccc(-c2c[nH]cn2)cc1] | N-(4-(1H-Imidazol-4-yl)phenyl)-N-(3-(3,6-difluoro-9H-carbazol-9-yl)-2-hydroxypropyl)methanesulfonamide | (300 MHz, CDCl₃) δ 12.20 (s, 1H), 7.97-7.94 (dd, 2H, J = 2.5, 9.0 Hz), 7.82-7.79 (d, 2H, J = 8.4 Hz), 7.70-7.65 (m, 2H), 7.46-7.41 (m, 4H), 7.27-7.20 (td, 2H, J = 2.7, 9.3 Hz), 5.28-5.26 (d, 1H, J = 5.4 Hz), 4.40-4.20 (m, 2H), 3.82-3.81 (m, 2H), 3.02 (s, 3H) | 497.0 (M + H) |

| Cpd # | Structure | Name | ¹H NMR | ESI (m/z) |
|---|---|---|---|---|
| 205 | 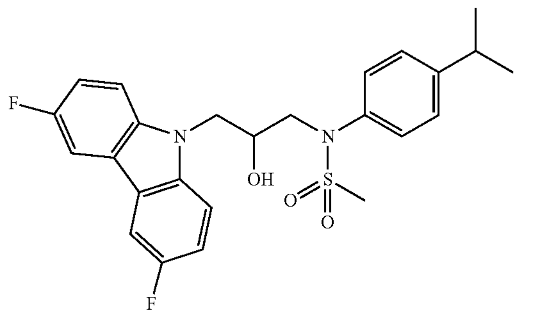 [SMILES: CC(C)c1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-isopropylphenyl)methanesulfonamide | (300 MHz, CDCl₃) δ 7.66-7.62 (dd, 2H, J = 2.4, 8.7 Hz), 7.29-7.23 (m, 4H), 7.19-7.13 (td, 2H, J = 2.4, 9.0 Hz), 4.45-4.41 (m, 1H), 4.32-4.29 (d, 1H, J = 8.1 Hz), 4.25-4.24 (m, 1H), 3.93-3.86 (dd, 1H, J = 6.6, 14.1 Hz), 3.84-3.77 (dd, 1H, J = 5.4, 14.1 Hz), 2.97-2.86 (sept, 1H, J = 6.9 Hz), 2.92 (s, 3H), 2.33 (br s, 1H), 1.27-1.25 (d, 6H, J = 7.2 Hz) | 473.1 (M + H) |
| 206 | 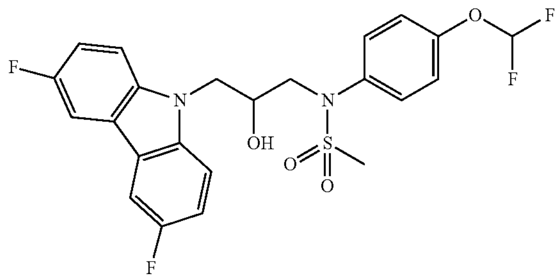 [SMILES: CS(=O)(=O)N(CC(O)Cn1c2ccc(F)cc2c2cc(F)ccc21)c1ccc(OC(F)F)cc1] | N-(3-(3,6-Difluoro-9H-carbazol-9-yl)-2-hydroxypropyl)-N-(4-(difluoromethoxy)phenyl)methanesulfonamide | (300 MHz, CDCl₃) δ 7.66-7.62 (dd, 2H, J = 2.4, 8.7 Hz), 7.36-7.25 (m, 3H), 7.21-7.13 (m, 3H), 6.76-6.28 (t, 1H, J = 72.9 Hz), 4.42-4.26 (m, 3H), 3.93-3.86 (dd, 1H, J = 7.0, 14.3 Hz), 3.84-3.77 (dd, 1H, J = 4.5, 14.0 Hz), 2.92 (s, 3H), 2.33-2.32 (d, 1H, J = 3.6 Hz) | 497.1 (M + H) |
| 207 | 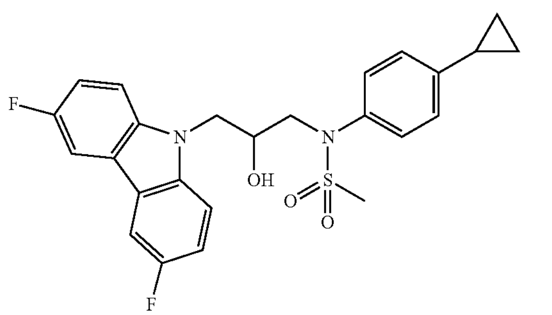 [SMILES: CS(=O)(=O)N(CC(O)Cn1c2ccc(F)cc2c2cc(F)ccc21)c1ccc(C2CC2)cc1] | N-(4-Cyclopropylphenyl)-N-(3-(3,6-difluoro-9H-carbazol-9-yl)-2-hydroxypropyl)methanesulfonamide | (300 MHz, CDCl₃) δ 7.66-7.62 (dd, 2H, J = 2.4, 8.7 Hz), 7.28-7.22 (m, 4H), 7.20-7.13 (td, 2H, J = 3.5, 8.9 Hz), 7.09-7.06 (d, 2H, J = 8.4 Hz), 4.44-4.40 (m, 1H), 4.31-4.29 (d, 1H, J = 8.1 Hz), 4.24 (br m, 1H), 3.92-3.85 (dd, 1H, J = 6.8, 14.0 Hz), 3.82-3.76 (dd, 1H, J = 4.8, 14.1 Hz), 2.91 (s, 3H), 2.31-2.30 (d, 1H, J = 3.0 Hz), 1.95-1.86 (m, 1H), 1.06-1.00 (m, 2H), 0.73-0.68 (m, 2H) | 471.1 (M + H) |
| 208 | 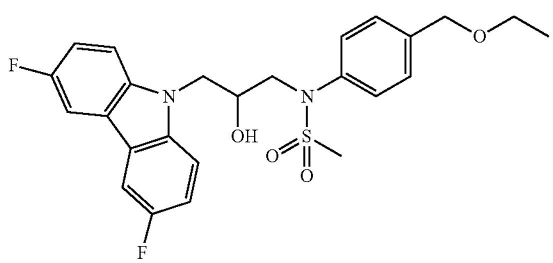 [SMILES: CCOCc1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-(ethoxymethyl)phenyl)methanesulfonamide | (300 MHz, CDCl₃) δ 7.64-7.60 (dd, 2H, J = 2.7, 8.7 Hz), 7.39-7.31 (m, 4H), 7.23-7.23 (m, 2H), 7.19-7.12 (td, 2H, J = 2.7, 9.3 Hz), 4.48 (s, 2H), 4.41-4.26 (m, 2H), 4.21 (br s, 1H), 3.93 (dd, 1H, J = 6.9, 14.1 Hz), 3.81-3.75 (dd, 1H, J = 4.8, 14.1 Hz), 3.60-3.53 (q, 2H, J = 6.9 Hz), 2.90 (s, 3H), 2.44-2.43 (d, 1H, J = 2.7 Hz), 1.29-1.24 (t, 3H, J = 6.7 Hz) | 489.3 (M + H) |
| 209 | 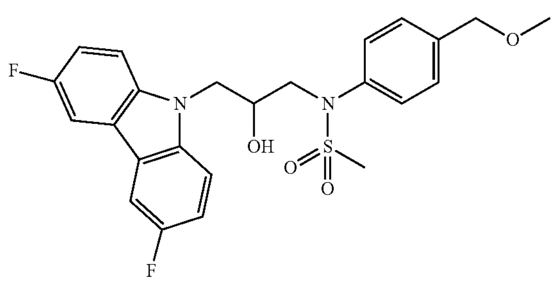 [SMILES: COCc1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-(methoxymethyl)phenyl)methanesulfonamide | (300 MHz, CDCl₃) δ 7.66-7.62 (dd, 2H, J = 2.4, 8.7 Hz), 7.39-7.33 (m, 4H), 7.29-7.24 (m, 2H), 7.20-7.13 (td, 2H, J = 2.4, 9.0 Hz), 4.45 (s, 2H), 4.44-4.29 (m, 2H), 4.25-4.23 (m, 1H), 3.95-3.88 (dd, 1H, J = 6.6, 14.4 Hz), 3.84-3.77 (dd, 1H, J = 5.1, 14.4 Hz), 3.42 (s, 3H), 2.92 (s, 3H), 2.33-2.32 (d, 1H, J = 3.9 Hz) | N/A |

-continued

| Cpd # | Structure | Name | ¹H NMR | ESI (m/z) |
|---|---|---|---|---|
| 210 | 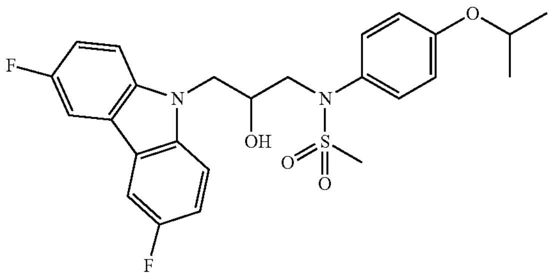 [SMILES: CC(C)Oc1ccc(N(CC(O)Cn2c3ccc(F)cc3c3cc(F)ccc32)S(C)(=O)=O)cc1] | N-(3-(3,6-Difluoro-9H-carbazol-9-yl)-2-hydroxypropyl)-N-(4-isopropoxyphenyl)methanesulfonamide | (300 MHz, CDCl₃) δ 7.65-7.61 (dd, 2H, J = 2.6, 8.6 Hz), 7.29-7.22 (m, 4H), 7.20-7.14 (td, 2H, J = 2.5, 9.0 Hz), 6.88-6.85 (d, 2H, J = 8.7 Hz), 4.59-4.47 (sept, 1H, J = 6.0 Hz), 4.43-4.36 (dd, 1H, J = 3.0, 13.8 Hz), 4.31-4.28 (d, 1H, J = 8.1 Hz), 4.24-4.20 (m, 1H), 3.90-3.83 (dd, 1H, J = 6.6, 14.1 Hz), 3.77-3.71 (dd, 1H, J = 4.8, 14.1 Hz), 2.91 (s, 3H), 2.39(br s, 1H). 1.36-1.32 (d, 6H, J = 6.3 Hz) | 489.0 (M + H) |
| 211 | 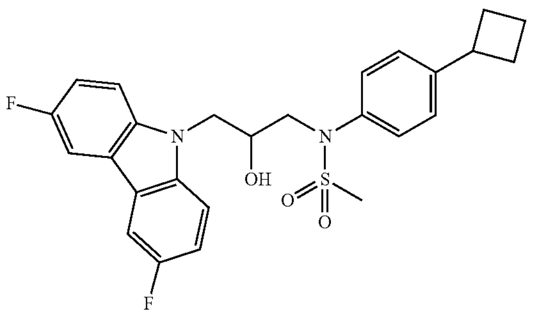 [SMILES: CS(=O)(=O)N(CC(O)Cn1c2ccc(F)cc2c2cc(F)ccc21)c1ccc(C2CCC2)cc1] | N-(4-Cyclobutylphenyl)-N-(3-(3,6-difluoro-9H-carbazol-9-yl)-2-hydroxypropyl)methanesulfonamide | (300 MHz, CDCl₃) δ 7.66-7.62 (dd, 2H, J = 2.4, 8.7 Hz), 7.29-7.22 (m, 6H), 7.19-7.13 (td, 2H, J = 2.7, 8.7 Hz), 4.45-4.38 (m, 2H), 4.24 (br s, 1H), 3.93-3.86 (dd, 1H, J = 6.6, 14.1 Hz), 3.83-3.77 (dd, 1H, J = 5.4, 14.1 Hz), 3.58-3.49 (q, 1H, J = 8.6 Hz), 2.92 (s, 3H), 2.41-2.34 (m, 2H), 2.20-1.82 (m, 4H) | 485.1 (M + H) |
| 212 | 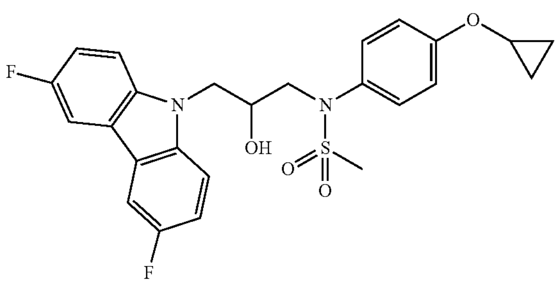 [SMILES: CS(=O)(=O)N(CC(O)Cn1c2ccc(F)cc2c2cc(F)ccc21)c1ccc(OC2CC2)cc1] | N-(4-Cyclopropoxyphenyl)-N-(3-(3,6-difluoro-9H-carbazol-9-yl)-2-hydroxypropyl)methanesulfonamide | (300 MHz, CDCl₃) δ 7.67-7.63 (dd, 2H, J = 2.6, 8.6 Hz), 7.31-7.26 (m, 4H), 7.20-7.14 (td, 2H, J = 2.7, 8.9 Hz), 7.06-7.03 (d, 2H, J = 9.0 Hz), 4.46-4.40 (dd, 1H, J = 2.7, 14.1 Hz), 4.33-4.30 (d, 1H, J = 7.8 Hz), 4.26-4.22 (br m, 1H), 3.92-3.85 (dd, 1H, J = 6.8, 14.1 Hz), 3.79-3.70 (m, 2H), 2.92 (s, 3H), 2.33-2.32 (d, 1H, J = 3.6 Hz), 0.83-0.77 (m, 4H) | 487.0 (M + H) |
| 213 | 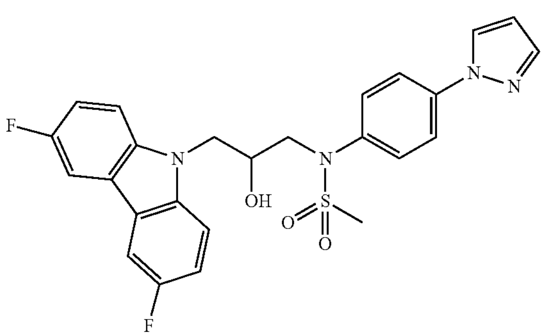 [SMILES: CS(=O)(=O)N(CC(O)Cn1c2ccc(F)cc2c2cc(F)ccc21)c1ccc(-n2cccn2)cc1] | N-(4-(1H-Pyrazol-1-yl)phenyl)-N-(3-(3,6-difluoro-9H-carbazol-9-yl)-2-hydroxypropyl)methanesulfonamide | (300 MHz, CDCl₃) δ 7.91-7.90 (d, 1H, J = 2.4 Hz), 7.74-7.71 (m, 3H), 7.66-7.62 (dd, 2H, J = 2.4, 8.7 Hz), 7.46-7.43 (d, 2H, J = 8.7 Hz), 7.31-7.27 (dd, 2H, J = 4.2, 9.0 Hz), 7.21-7.14 (td, 2H, J = 2.6, 9.0 Hz), 6.50-6.48 (m, 1H), 4.44-4.28 (m, 3H), 3.99-3.92 (dd, 1H, J = 6.8, 14.4 Hz), 3.86-3.79 (dd, 1H, J = 4.4, 14.4 Hz), 2.96 (s, 3H), 2.37-2.36 (d, 1H, J = 3.6 Hz) | 497.0 (M + H) |
| 214 | 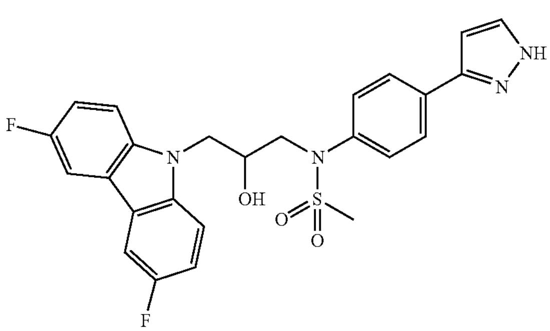 [SMILES: CS(=O)(=O)N(CC(O)Cn1c2ccc(F)cc2c2cc(F)ccc21)c1ccc(-c2cc[nH]n2)cc1] | N-(4-(1H-Pyrazol-3-yl)phenyl)-N-(3-(3,6-difluoro-9H-carbazol-9-yl)-2-hydroxypropyl)methanesulfonamide | (300 MHz, CDCl₃) δ 7.78-7.75 (d, 1H, J = 8.1 Hz), 7.63-7.59 (dd, 2H, J = 2.4, 8.7 Hz), 7.58 (d, 1H, J = 2.1 Hz), 7.40-7.37 (d, 2H, J = 8.7 Hz), 7.28-7.25 (m, 3H), 7.17-7.10 (td, 2H, J = 2.4, 9.0 Hz), 6.60-6.59 (d, 1H, J = 2.1 Hz), 4.46-4.26 (m, 3H), 3.99-3.81 (dd, 1H, J = 6.3, 14.1 Hz), 3.88-3.81 (dd, 1H, J = 5.1, 14.4 Hz), 2.94 (s, 3H) | N/A |

-continued

| Cpd # | Structure | Name | ¹H NMR | ESI (m/z) |
|---|---|---|---|---|
| 215 | 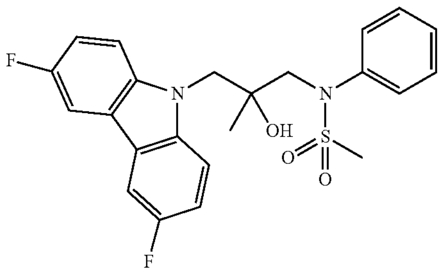 [SMILES: CC(O)(CN(c1ccccc1)S(C)(=O)=O)Cn1c2ccc(F)cc2c2cc(F)ccc21] | N-(3-(3,6-Difluoro-9H-carbazol-9-yl)-2-hydroxy-2-methylpropyl)-N-phenylmethane-sulfonamide | (300 MHz, CDCl₃) δ 7.66-7.62 (dd, 2H, J = 2.1, 8.7 Hz), 7.47-7.36 (m, 7H), 7.21-7.14 (td, 2H, J = 2.4, 9.0 Hz), 4.36,4.4.21 (ABq, 2H, $J_{AB}$ = 15.3 Hz), 4.03,3.96 (ABq, 2H, $J_{AB}$ = 14.7 Hz), 2.90 (s, 3H), 2.34 (s, 1H), 1.22 (s, 3H) | N/A |
| 216 | 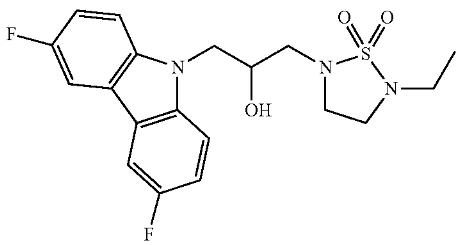 [SMILES: CCN1CCN(CC(O)Cn2c3ccc(F)cc3c3cc(F)ccc32)S1(=O)=O] | 2-(3-(3,6-Difluoro-9H-carbazol-9-yl)-2-hydroxypropyl)-5-ethyl-1,2,5-thiadiazinane-1,1-dioxide | (300 MHz, CDCl₃) δ 7.67-7.63 (dd, 2H, J = 9.0, 2.7 Hz), 7.41-7.37 (dd, 2H, J = 9.0, 3.9 Hz), 7.25-7.16 (td, 2H, J = 9.0, 2.7 Hz), 4.43-4.36 (m, 3H), 3.38-3.27 (m, 4H), 3.22-3.20 (d, 2H, J = 5.4 Hz), 3.15-3.07 (q, 2H, J = 7.4 Hz), 2.60 (br s, 1H), 1.30-1.25 (t, 3H, J = 7.4 Hz) | 410.0 (M + H) |
| 217 | 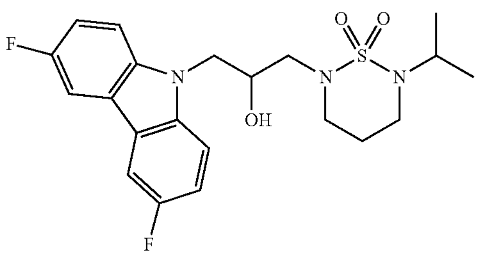 [SMILES: CC(C)N1CCCN(CC(O)Cn2c3ccc(F)cc3c3cc(F)ccc32)S1(=O)=O] | 2-(3-(3,6-Difluoro-9H-carbazol-9-yl)-2-hydroxypropyl)-6-isopropyl-1,2,6-thiadiazinane-1,1-dioxide | (300 MHz, CDCl₃) δ 7.65-7.61 (dd, 2H, J = 8.7, 2.7 Hz), 7.38-7.34 (dd, 2H, J = 8.7, 4.2 Hz), 7.22-7.15 (td, 2H, J = 8.7, 2.7 Hz), 4.39-4.24 (m, 3H), 4.13-4.04 (sept, 1H, J = 6.9 Hz), 3.59-3.45 (m, 2H), 3.27-3.12 (m, 4H), 2.59-2.58 (d, 1H, J = 2.7 Hz), 1.73-1.67 (m, 2H), 1.18-1.15 (dd, 6H, J = 1.2, 6.9 Hz) | 438.0 (M + H) |
| 218 | 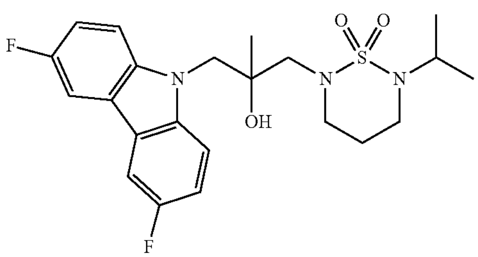 [SMILES: CC(C)N1CCCN(CC(C)(O)Cn2c3ccc(F)cc3c3cc(F)ccc32)S1(=O)=O] | 2-(3-(3,6-Difluoro-9H-carbazol-9-yl)-2-hydroxy-2-methylpropyl)-6-isopropyl-1,2,6-thiadiazinane-1,1-dioxide | (300 MHz, CDCl₃) δ 7.67-7.63 (dd, 2H, J = 8.9, 2.8 Hz), 7.45-7.40 (dd, 2H, J = 8.9, 4.0 Hz), 7.22-7.15 (td, 2H, J = 9.0, 2.8 Hz), 4.49-4.44 & 4.26-4.21 (ABq, 2H, J = 15.0 Hz), 4.18-4.05 (sept, 1H, J = 6.8 Hz), 3.79-3.74 (m, 2H), 3.28-3.14 (m, 4H), 2.06 (s, 1H), 1.26 (s, 3H), 1.21-1.18 (dd, 6H, J = 2.4, 6.6 Hz) | 452.0 (M + H) |
| 219 | 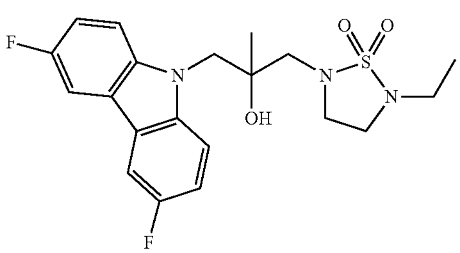 [SMILES: CCN1CCN(CC(C)(O)Cn2c3ccc(F)cc3c3cc(F)ccc32)S1(=O)=O] | 2-(3-(3,6-Difluoro-9H-carbazol-9-yl)-2-hydroxy-2-methylpropyl)-5-ethyl-1,2,5-thiadiazinane-1,1-dioxide | (300 MHz, CDCl₃) δ 7.67-7.63 (dd, 2H, J = 2.4, 8.4 Hz), 7.44-7.39 (dd, 2H, J = 4.2, 9.0 Hz), 7.23-7.16 (td, 2H, J = 2.7, 9.0 Hz), 4.50-4.45 & 4.27-4.22 (ABq, 2H, J = 15.6 Hz), 3.63-3.49 (m, 2H), 3.38-3.31 (m, 4H), 3.18-3.11 (q, 2H, J = 7.2 Hz), 1.33-1.28 (t, 3H, J = 7.4 Hz), 1.31 (s, 3H) | 424.0 (M + H) |
| 220 | 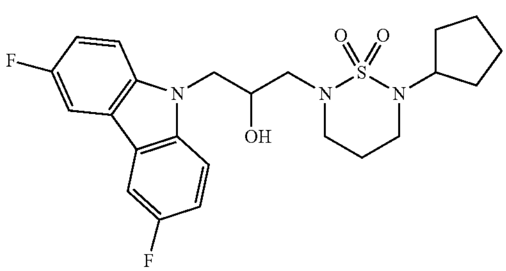 [SMILES: O=S1(=O)N(CC(O)Cn2c3ccc(F)cc3c3cc(F)ccc32)CCCN1C1CCCC1] | 2-(3-(3,6-Difluoro-9H-carbazol-9-yl)-2-hydroxypropyl)-6-cyclopentyl-1,2,6-thiadiazinane-1,1-dioxide | (300 MHz, CDCl₃) δ 7.66-7.62 (dd, 2H, J = 2.4, 9.0 Hz), 7.39-7.35 (dd, 2H, J = 4.2, 8.7 Hz), 7.25-7.16 (td, 2H, J = 2.7, 9.0 Hz), 4.40-4.26 (m, 3H), 4.12-4.07 (m, 1H), 3.58-3.46 (m, 2H), 3.29-3.15 (m, 4H), 2.56-2.55 (d, 1H, J = 3.3 Hz), 1.87-1.82 (m, 2H), 1.75-1.53 (m, 8H) | 464.0 (M + H) |

-continued

| Cpd # | Structure | Name | ¹H NMR | ESI (m/z) |
|---|---|---|---|---|
| 221 | 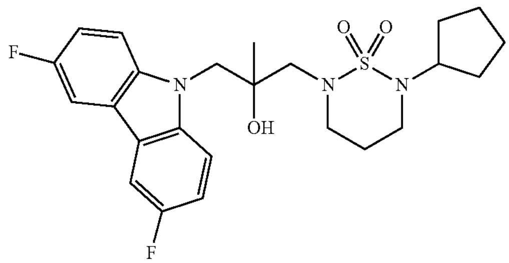 [SMILES: CC(O)(CN1CCCN(C2CCCC2)S1(=O)=O)Cn1c2ccc(F)cc2c2cc(F)ccc21] | 2-(3-(3,6-Difluoro-9H-carbazol-9-yl)-2-hydroxy-2-methylpropyl)-6-cyclopentyl-1,2,6-thiadiazinane-1,1-dioxide | (300 MHz, CDCl₃) δ 7.66-7.62 (dd, 2H, J = 9.0, 2.3 Hz), 7.44-7.40 (dd, 2H, J = 9.0, 4.2 Hz), 7.22-7.15 (td, 2H, J = 9.0, 2.7 Hz), 4.49-4.44 & 4.25-4.20 (ABq, 2H, J = 15.3 Hz), 4.17-4.05 (quint, 1H, J = 8.1 Hz), 3.77-3.73 (m, 2H), 3.31-3.27 (m, 4H), 2.08 (s, 1H), 1.89-1.54 (m, 10H), 1.25 (s, 3H) | 478.0 (M + H) |
| 222 | 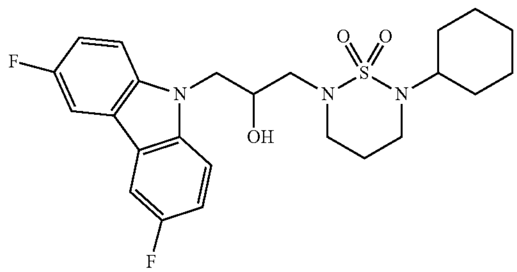 [SMILES: O=S1(=O)N(CC(O)Cn2c3ccc(F)cc3c3cc(F)ccc32)CCCN1C1CCCCC1] | 2-(3-(3,6-Difluoro-9H-carbazol-9-yl)-2-hydroxypropyl)-6-cyclohexyl-1,2,6-thiadiazinane-1,1-dioxide | (300 MHz, CDCl₃) δ 7.65-7.61 (dd, 2H, J = 2.6, 8.6 Hz), 7.39-7.34 (dd, 2H, J = 4.2, 8.7 Hz), 7.22-7.15 (td, 2H, J = 9.0, 2.7 Hz), 4.42-4.26 (m, 3H), 3.66-3.44 (m, 3H), 3.28-3.24 (m, 2H), 3.21-3.12 (m, 2H), 2.59-2.58 (d, 1H, J = 3.0 Hz), 1.87-1.62 (m, 7H), 1.42-1.03 (m, 5H) | 478.0 (M + H) |
| 223 | 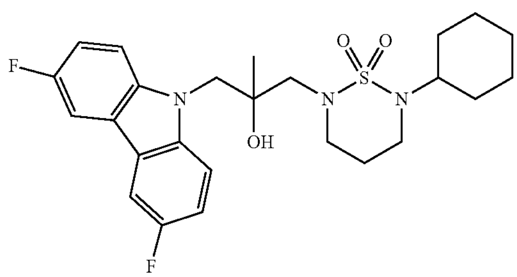 | 2-(3-(3,6-Difluoro-9H-carbazol-9-yl)-2-hydroxy-2-methylpropyl)-6-cyclohexyl-1,2,6-thiadiazinane-1,1-dioxide | (300 MHz, CDCl₃) δ 7.65-7.62 (dd, 2H, J = 2.6, 8.6 Hz), 7.43-7.39 (dd, 2H, J = 4.2, 9.0 Hz), 7.21-7.14 (td, 2H, J = 2.7, 9.0 Hz), 4.47-4.42 & 4.25-4.20 (ABq, 2H, J = 15.3 Hz), 3.76-3.61 (m, 3H), 3.32-3.61 (m, 2H), 3.25 (s, 2H), 2.13 (s, 1H), 1.84-1.67 (m, 7H), 1.45-1.03 (m, 5H), 1.24 (s, 3H) | 492.0 (M + H) |
| 224 | 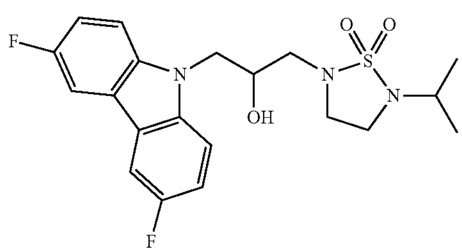 [SMILES: CC(C)N1CCN(CC(O)Cn2c3ccc(F)cc3c3cc(F)ccc32)S1(=O)=O] | 2-(3-(3,6-Difluoro-9H-carbazol-9-yl)-2-hydroxypropyl)-5-isopropyl-1,2,5-thiadiazinane 1,1-dioxide | (300 MHz, CDCl₃) δ 7.68-7.64 (dd, 2H, J = 2.6, 8.6 Hz), 7.43-7.39 (dd, 2H, J = 4.2, 8.7 Hz), 7.25-7.18 (td, 2H, J = 2.4, 9.0 Hz), 4.47-4.36 (m, 3H), 3.77-3.68 (sept, 1H, J = 6.6 Hz), 3.38-3.27 (m, 4H), 3.20-3.19 (d, 2H, J = 5.4 Hz), 2.53-2.52 (d, 1H, J = 2.4 Hz), 1.31-1.29 (dd, 6H, J = 0.9, 6.8 Hz) | 424.1 (M + H) |
| 225 | 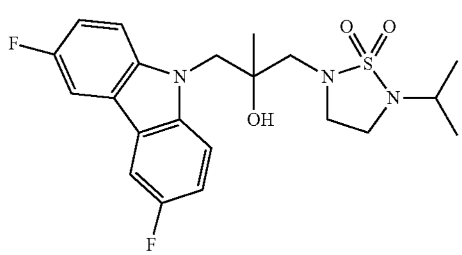 [SMILES: CC(C)N1CCN(CC(C)(O)Cn2c3ccc(F)cc3c3cc(F)ccc32)S1(=O)=O] | 2-(3-(3,6-Difluoro-9H-carbazol-9-yl)-2-hydroxy-2-methylpropyl)-5-isopropyl-1,2,5-thiadiazinane 1,1-dioxide | (300 MHz, CDCl₃) δ 7.65-7.62 (dd, 2H, J = 2.6, 8.4 Hz), 7.42-7.38 (dd, 2H, J = 4.1, 9.0 Hz), 7.21-7.14 (td, 2H, J = 2.7, 9.0 Hz), 4.48-4.43 & 4.25-4.20 (ABq, 2H, J = 15.3 Hz), 3.75-3.65 (sept, 1H, J = 6.6 Hz), 3.61-3.21 (m, 6H), 2.06 (s, 1H), 1.32-1.29 (d, 6H, J = 8.4 Hz), 1.30 (s, 3H) | 438.0 (M + H) |
| 226 | 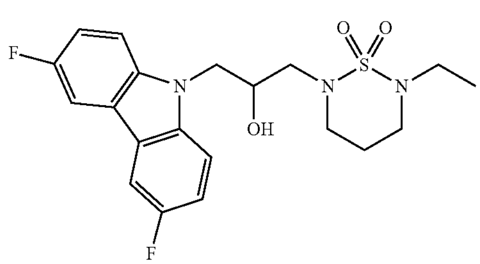 [SMILES: CCN1CCCN(CC(O)Cn2c3ccc(F)cc3c3cc(F)ccc32)S1(=O)=O] | 2-(3-(3,6-Difluoro-9H-carbazol-9-yl)-2-hydroxypropyl)-6-ethyl-1,2,6-thiadiazinane-1,1-dioxide | (300 MHz, CDCl₃) δ 7.66-7.62 (dd, 2H, J = 2.4, 9.0 Hz), 7.39-7.34 (dd, 2H, J = 4.2, 8.7 Hz), 7.25-7.16 (td, 2H, J = 2.4, 9.0 Hz), 4.39-4.24 (m, 3H), 3.48-3.44 (m, 2H), 3.38-3.34 (t, 2H, J = 5.7 Hz), 3.24-3.14 (m, 4H), 2.55 (s, 1H), 1.79-1.70 (m, 2H), 1.22-1.17 (t, 3H, J = 7.2 Hz) | 424.0 (M + H) |

| Cpd # | Structure | Name | ¹H NMR | ESI (m/z) |
|---|---|---|---|---|
| 227 | 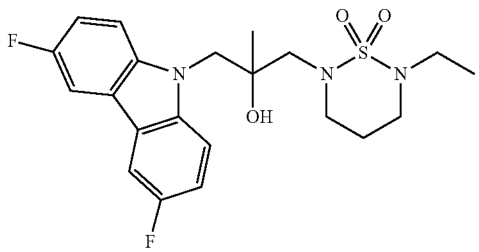 [SMILES: CCN1CCCN(CC(C)(O)Cn2c3ccc(F)cc3c3cc(F)ccc32)S1(=O)=O] | 2-(3-(3,6-Difluoro-9H-carbazol-9-yl)-2-hydroxy-2-methylpropyl)-6-ethyl-1,2,6-thiadiazinane-1,1-dioxide | (300 MHz, CDCl₃) δ 7.66-7.62 (dd, 2H, J = 2.7, 9.0 Hz), 7.43-7.39 (dd, 2H, J = 4.2, 8.7 Hz), 7.25-7.15 (td, 2H, J = 2.7, 9.0 Hz), 4.49-4.44 & 4.24-4.19 (ABq, 2H, J = 15.3 Hz), 3.72-3.68 (t, 2H, J = 5.7 Hz), 3.41-3.15 (m, 6H), 2.06 (s, 1H), 1.84-1.80 (m, 2H), 1.26 (s, 3H), 1.23-1.18 (t, 3H, J = 7.2 Hz) | 437.9 (M + H) |
| 228 | 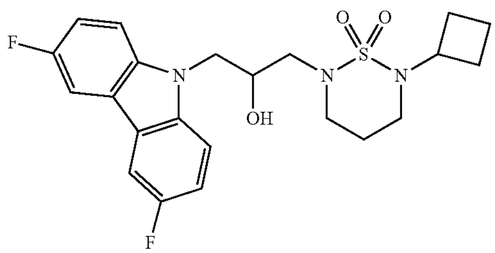 [SMILES: O=S1(=O)N(CC(O)Cn2c3ccc(F)cc3c3cc(F)ccc32)CCCN1C1CCC1] | 2-(3-(3,6-Difluoro-9H-carbazol-9-yl)-2-hydroxypropyl)-6-cyclobutyl-1,2,6-thiadiazinane-1,1-dioxide | (300 MHz, CDCl₃) δ 7.67-7.63 (dd, 2H, J = 2.3, 8.7 Hz), 7.40-7.36 (dd, 2H, J = 4.2, 9.3 Hz), 7.24-7.17 (td, 2H, J = 2.4, 9.0 Hz), 4.41-4.31 (m, 3H), 3.96-3.84 (m, 1H), 3.48-3.43 (m, 2H), 3.29-3.24 (m, 4H), 2.53-2.52 (d, 1H, J = 3.3 Hz), 2.20-2.08 (m, 4H), 1.78-1.60 (m, 4H) | 450.1 (M + H) |
| 229 | 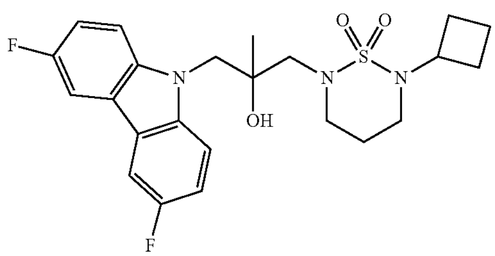 [SMILES: CC(O)(CN1CCCN(C2CCC2)S1(=O)=O)Cn1c2ccc(F)cc2c2cc(F)ccc21] | 2-(3-(3,6-Difluoro-9H-carbazol-9-yl)-2-hydroxy-2-methylpropyl)-6-cyclobutyl-1,2,6-thiadiazinane-1,1-dioxide | (300 MHz, CDCl₃) δ 7.65-7.62 (dd, 2H, J = 2.4, 8.6 Hz), 7.43-7.39 (dd, 2H, J = 4.2, 9.0 Hz), 7.21-7.15 (td, 2H, J = 2.7, 9.0 Hz), 4.48-4.42 & 4.23-4.18 (ABq, 2H, J = 15.3 Hz), 3.97-3.85 (m, 1H), 3.70-3.67 (t, 2H, J = 5.7 Hz), 3.36-3.24 (m, 4H), 2.10 (s, 1H), 2.21-2.05 (m, 4H), 1.80-1.61 (m, 4H), 1.26 (s, 3H) | 464.0 (M + H) |
| 230 | 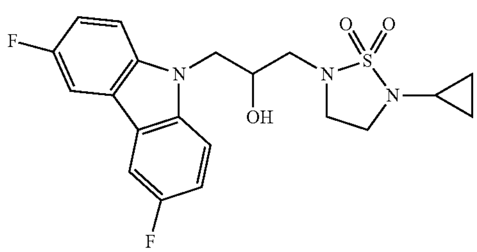 [SMILES: O=S1(=O)N(CC(O)Cn2c3ccc(F)cc3c3cc(F)ccc32)CCN1C1CC1] | 2-(3-(3,6-Difluoro-9H-carbazol-9-yl)-2-hydroxypropyl)-5-cyclopropyl-1,2,5-thiadiazinane-1,1-dioxide | (300 MHz, CDCl₃) δ 7.67-7.63 (dd, 2H, J = 2.4, 9.0 Hz), 7.42-7.38 (dd, 2H, J = 4.0, 9.0 Hz), 7.24-7.17 (td, 2H, J = 2.4, 9.0 Hz), 4.45-4.35 (m, 3H), 3.41-3.19 (m, 6H), 2.54-2.53 (d, 1H, J = 3.3 Hz), 2.37-2.30 (m, 1H), 0.86-0.72 (m, 4H) | N/A |
| 231 | 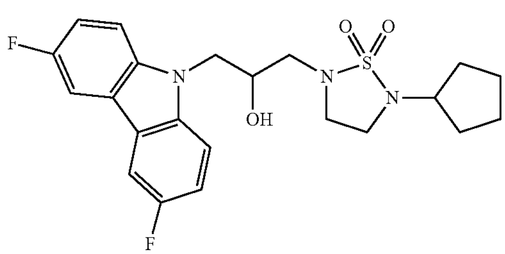 [SMILES: O=S1(=O)N(CC(O)Cn2c3ccc(F)cc3c3cc(F)ccc32)CCN1C1CCCC1] | 2-(3-(3,6-Difluoro-9H-carbazol-9-yl)-2-hydroxypropyl)-5-cyclopentyl-1,2,5-thiadiazinane-1,1-dioxide | (300 MHz, CDCl₃) δ 7.67-7.63 (dd, 2H, J = 2.4, 8.7 Hz), 7.43-7.39 (dd, 2H, J = 4.1, 8.9 Hz), 7.23-7.17 (td, 2H, J = 2.5, 9.0 Hz), 4.44-4.34 (m, 3H), 3.52-3.20 (m, 7H), 2.63-2.62 (m, 1H, J = 3.0 Hz), 2.03-1.96 (m, 2H), 1.77-1.61 (m, 6H) | 450.1 (M + H) |

-continued

| Cpd # | Structure | Name | ¹H NMR | ESI (m/z) |
|---|---|---|---|---|
| 232 | 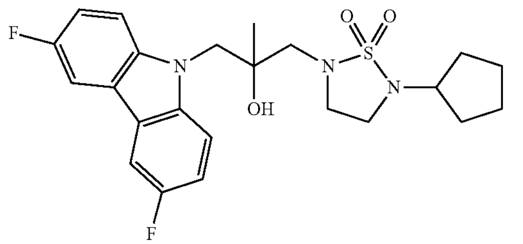 [SMILES: CC(O)(CN1CCN(C2CCCC2)S1(=O)=O)Cn1c2ccc(F)cc2c2cc(F)ccc21] | 2-(3-(3,6-Difluoro-9H-carbazol-9-yl)-2-hydroxy-2-methylpropyl)-5-cyclopentyl-1,2,5-thiadiazinane-1,1-dioxide | (300 MHz, CDCl₃) δ 7.68-7.64 (dd, 2H, J = 2.4, 8.7 Hz), 7.45-7.40 (dd, 2H, J = 4.1, 9.0 Hz), 7.23-7.16 (td, 2H, J = 2.5, 9.0 Hz), 4.51-4.46 & 4.28-4.23 (ABq, 2H, J = 15.0 Hz), 3.63-3.31 (m, 7H), 2.05-2.00 (m, 2H), 1.94 (s, 1H), 1.80-1.62 (m, 6H), 1.32 (s, 3H) | 464.0 (M + H) |
| 233 | 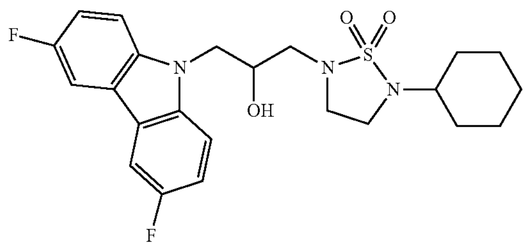 [SMILES: O=S1(=O)N(CC(O)Cn2c3ccc(F)cc3c3cc(F)ccc32)CCN1C1CCCCC1] | 2-(3-(3,6-Difluoro-9H-carbazol-9-yl)-2-hydroxypropyl)-5-cyclohexyl-1,2,5-thiadiazinane-1,1-dioxide | (300 MHz, CDCl₃) δ 7.68-7.64 (dd, 2H, J = 2.6, 8.7 Hz), 7.43-7.39 (dd, 2H, J = 4.2, 8.7 Hz), 7.24-7.18 (td, 2H, J = 2.5, 9.0 Hz), 4.46-4.37 (m, 3H), 3.37-3.36 (m, 5H), 3.20-3.19 (d, 2H, J = 5.4 Hz), 2.55-2.53 (br m, 1H), 2.05-2.01 (m, 2H), 1.84-1.80 (m, 2H), 1.62-1.13 (m, 6H) | 464.0 (M + H) |
| 234 | 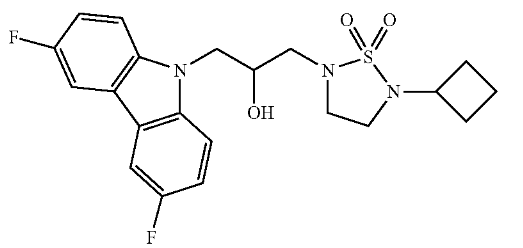 [SMILES: O=S1(=O)N(CC(O)Cn2c3ccc(F)cc3c3cc(F)ccc32)CCN1C1CCC1] | 2-(3-(3,6-Difluoro-9H-carbazol-9-yl)-2-hydroxypropyl)-5-cyclobutyl-1,2,5-thiadiazinane-1,1-dioxide | (300 MHz, CDCl₃) δ 7.67-7.63 (dd, 2H, J = 2.4, 9.0 Hz), 7.42-7.37 (dd, 2H, J = 4.1, 9.0 Hz), 7.24-7.17 (td, 2H, J = 2.5, 9.0 Hz), 4.43-4.34 (m, 3H), 3.83-3.72 (quint, 1H, J = 7.8 Hz), 3.40-3.18 (m, 6H), 2.64(br s, 1H), 2.26-2.17 (m, 4H), 1.88-1.79 (m, 2H) | 436.1 (M + H) |
| 235 | 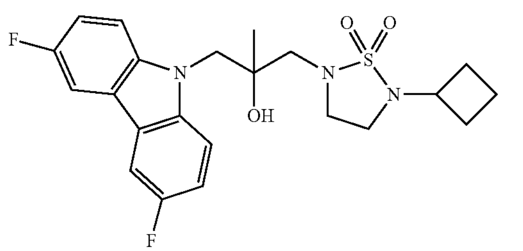 [SMILES: CC(O)(CN1CCN(C2CCC2)S1(=O)=O)Cn1c2ccc(F)cc2c2cc(F)ccc21] | 2-(3-(3,6-Difluoro-9H-carbazol-9-yl)-2-hydroxy-2-methylpropyl)-5-cyclobutyl-1,2,5-thiadiazinane-1,1-dioxide | (300 MHz, CDCl₃) δ 7.67-7.63 (dd, 2H, J = 2.6, 8.9 Hz), 7.45-7.40 (dd, 2H, J = 4.4, 8.7 Hz), 7.22-7.15 (td, 2H, J = 2.6, 9.0 Hz), 4.49-4.44 & 4.26-4.21 (ABq, 2H, J = 15.3 Hz), 3.86-3.74 (quint, 1H, J = 7.8 Hz), 3.63-3.46 (m, 2H), 3.35-3.29 (m, 4H), 2.29-2.21 (m, 4H), 1.95 (s, 1H), 1.89-1.81 (m, 2H), 1.30 (s, 3H) | 450.0 (M + H) |

Compound 236: N-(3-(1-Fluoro-9H-carbazol-9-yl)-2-hydroxypropyl)-N-(furan-2-ylmethyl)methanesulfonamide

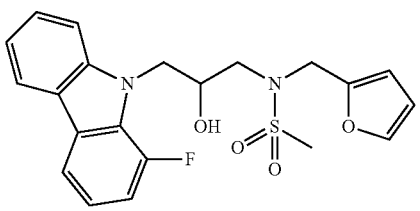 [SMILES: CS(=O)(=O)N(Cc1ccco1)CC(O)Cn1c2ccccc2c2cccc(F)c21]

A suspension of 1-fluoro-9H-carbazole (0.099 g, 0.54 mmol) and N-(furan-2-ylmethyl)-N-(oxiran-2-ylmethyl)methanesulfonamide (0.142 g, 0.62 mmol), and cesium carbonate (0.174 g, 0.54 mmol) in anhydrous N,N-dimethylformamide (1 mL) was heated at 110° C. for 30 mins in a microwave reactor. The reaction mixture was cooled and poured into water and ethyl acetate. The organic layer was isolated, washed with water and saturated aqueous sodium chloride, dried (anhydrous sodium sulfate), filtered, and concentrated in vacuo. The crude residue was purified by silica gel column chromatography (10-80% ethyl acetate in hexanes) to give a white solid (0.103 g, 46%). ¹H NMR (CDCl₃, 300 MHz) δ 8.08-8.06 (dt, 1H, J=0.9 Hz, 7.5 Hz), 7.88-7.85 (m, 1H), 7.50-7.48 (m, 2H), 7.29-7.27 (m 1H), 2.24-2.12 (m, 3H), 6.16-6.14 (dd, 1H, J=2.1, 3.3 Hz), 5.97-5.96 (d, 1H, J=3.3 Hz), 4.54-4.31 (m, 5H), 3.51-3.43 (dd, 1H, J=8.3, 14.8 Hz), 3.27-3.22 (dd, 1H, J=3.0, 15 Hz), 2.85 (s, 3H), 2.65-2.64 (d, 1H, J=3.3 Hz). ESI (m/z): 417.1 (M+H), 349.3 (M-Furan). HPLC analysis: (C18, 10-90% acetonitrile in water+0.1% trifluoroacetic acid over 10 min: retention time, % area at 254 nm): 9.73 min, 100%.

Compounds 237 to 245

Compounds 237 to 245 were prepared by procedures analogous to those used for Compound 236.

| Cpd # | Structure | Name | ¹H NMR | ESI (m/z) |
|---|---|---|---|---|
| 237 | 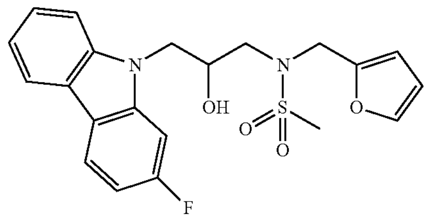 [SMILES: CS(=O)(=O)N(Cc1ccco1)CC(O)Cn1c2ccccc2c2ccc(F)cc21] | N-(3-(2-Fluoro-9H-carbazol-9-yl)-2-hydroxypropyl)-N-(furan-2-ylmethyl)methane-sulfonamide | (CDCl₃, 300 MHz) δ 8.04-7.97 (m, 2H), 7.40-7.38 (m, 2H), 7.28-7.23 (m, 3H), 7.11-7.07 (dd, 1H, J = 2.1, 9.9 Hz), 7.01-6.95 (td, 1H, J = 2.4, 9 Hz), 6.19-6.17 (dd, 1H, J = 3.3, 1.8 Hz), 5.98-5.97 (d, 1H, J = 3.3 Hz), 4.51-4.24 (m, 5H), 3.46-3.39 (dd, 1H, J = 7.1, 14.9 Hz), 3.27-3.21 (dd, 1H, J = 2.9, 14.9 Hz), 2.85 (s, 3H), 2.67-2.66 (d, 1H, J = 3 Hz) | 416.8 (M + H), 349.1 (M-furan) |
| 238 | 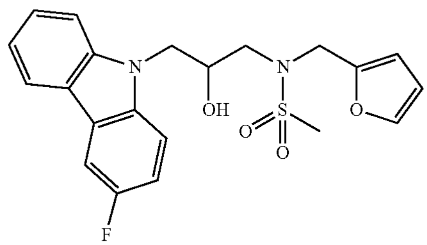 [SMILES: CS(=O)(=O)N(Cc1ccco1)CC(O)Cn1c2ccccc2c2cc(F)ccc21] | N-(3-(3-Fluoro-9H-carbazol-9-yl)-2-hydroxypropyl)-N-(furan-2-ylmethyl)methane-sulfonamide | (CDCl₃, 300 MHz) δ 8.05-8.02 (d, 1H, J = 7.8 Hz), 7.76-7.72 (dd, 1H, J = 2.4, 8.7 Hz), 7.51-7.45 (m, 1H), 7.41-7.38 (d, 1H, J = 8.4 Hz), 7.36-7.32 (dd, 1H, J = 4.0, 9.0 Hz), 7.27-7.16 (m, 3H) 6.18-6.17 (dd, 1H, J = 1.7, 3.3 Hz), 5.95-5.94 (m, 1H), 4.51-4.26 (m, 5H), 3.45-3.38 (dd, 1H, J = 7.8, 15 Hz), 3.26-3.20 (dd, 1H, J = 2.7, 15 Hz), 2.84 (s, 3H), 2.65-2.64 (d, 1H, J = 2.7 Hz) | 416.8 (M + H), 349.1 (M-furan) |
| 239 | 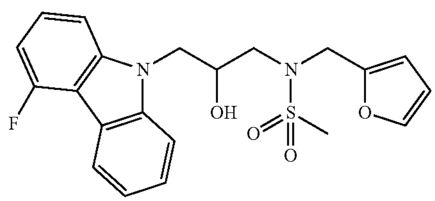 [SMILES: CS(=O)(=O)N(Cc1ccco1)CC(O)Cn1c2ccccc2c2c(F)cccc21] | N-(3-(4-Fluoro-9H-carbazol-9-yl)-2-hydroxypropyl)-N-(furan-2-ylmethyl)methane-sulfonamide | (CDCl₃, 300 MHz) δ 8.23-8.21 (d, 1H, J = 7.5 Hz), 7.51-7.46 (m, 1H), 7.42-7.26 (m, 3H), 7.22-7.17 (m, 2H), 6.95-6.89 (dd, 1H, J = 8.0, 10.2 Hz), 6.17-6.16 (dd, 1H, J = 1.7, 3 Hz), 5.94-5.93 (d, 1H, J = 3.3 Hz), 4.50-4.29 (m, 5H), 3.45-3.81 (dd, 1H, J = 7.8, 14.7 Hz), 3.24-3.18 (dd, 1H, J = 3.0, 14.7 Hz), 2.83 (s, 3H), 2.68-2.67 (d, 1H, J = 3.0 Hz) | 417.1 (M + H), 349.2 (M-furan) |
| 240 | 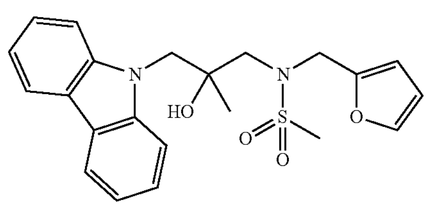 [SMILES: CC(O)(CN(Cc1ccco1)S(C)(=O)=O)Cn1c2ccccc2c2ccccc21] | N-(3-(9H-Carbazol-9-yl)-2-hydroxy-2-methylpropyl)-N-(furan-2-ylmethyl)methane-sulfonamide | (CDCl₃, 300 MHz) δ 8.11-8.08 (m, 2H), 7.52-7.38 (m, 5H), 7.27-7.22 (m, 2H), 6.36-6.33 (m, 2H), 4.86-4.74 (dd, 2H, J = 16.4, 22 Hz), 4.59-4.54 (d, 1H, J = 15.3 Hz), 4.33-4.28 (d, 1H, J = 14.7 Hz), 3.47 (s, 2H), 2.78 (s, 3H), 2.32 (s, 1H), 1.33 (s, 3H) | 413.0 (M + H) |
| 241 | 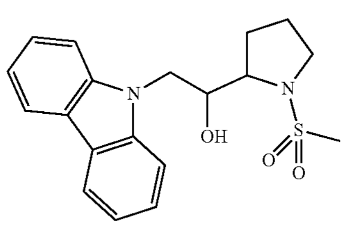 [SMILES: CS(=O)(=O)N1CCCC1C(O)Cn1c2ccccc2c2ccccc21] | 2-(9H-Carbazol-9-yl)-1-(1-(methylsulfonyl)pyrrolidin-2-yl)ethanol | (CDCl₃, 300 MHz) (diastereomeric mixture) δ 8.09-8.07 (d, 2H, J = 8.1 Hz), 7.52-7.43 (m, 4H), 7.26-7.21 (m, 2H), 4.51-4.33 (m, 2H), 4.26-4.22 (m, 1H), 3.96-3.92 (m, 0.5H), 3.84-3.79 (m, 0.5H), 3.49-3.45 (t, 1H, J = 6.6 Hz), 3.44-3.39 (t, 1H, J = 6.6 Hz), 2.86 (s, 1.5H), 2.81 (s, 1.5H), 2.22-1.85 (m, 4H) | 359.1 (M + H) |
| 242 | 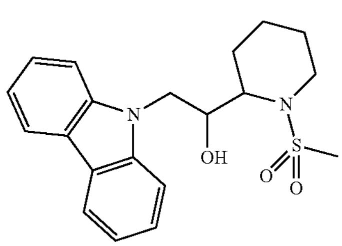 [SMILES: CS(=O)(=O)N1CCCCC1C(O)Cn1c2ccccc2c2ccccc21] | 2-(9H-Carbazol-9-yl)-1-(1-(methylsulfonyl)piperidin-2-yl)ethanol | (CDCl₃, 300 MHz) (diastereomeric mixture) δ 8.11-8.09 (d, 2H, J = 7.5 Hz), 7.50-7.42 (m, 4H), 7.29-7.23 (m, 2H), 4.51-4.35 (m, 3H), 4.17-4.15 (m, 1H), 3.82-3.78 (m, 1H), 3.12-3.04 (td, 1H, J = 11.1, 3.0 Hz), 2.95 (s, 3H), 2.09-2.08 (d, 1H, J = 3.9 Hz), 1.95-1.58 (m, 6H) | 373.1 (M + H) |
| 243 | 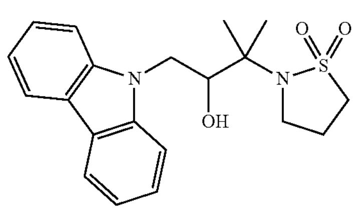 [SMILES: CC(C)(C(O)Cn1c2ccccc2c2ccccc21)N1CCCS1(=O)=O] | 2-(4-(9H-Carbazol-9-yl)-3-hydroxy-2-methylbutan-2-yl)-isothiazolidine-1,1-dioxide | (300 MHz, CDCl₃) δ 8.10 (d, 2H, J = 7.5 Hz), 7.55-7.42 (m, 4H), 7.30-7.20 (m, 2H), 4.60-4.28 (m, 3H), 3.65-3.48 (m, 2H), 3.26 (t, 2H, J = 7.5 Hz), 2.60 (d, 1H, J = 3.6 Hz), 2.34 (quin, 2H, J = 7.2 Hz) | 372.9 (M + H) |

-continued

| Cpd # | Structure | Name | ¹H NMR | ESI (m/z) |
|---|---|---|---|---|
| 244 | 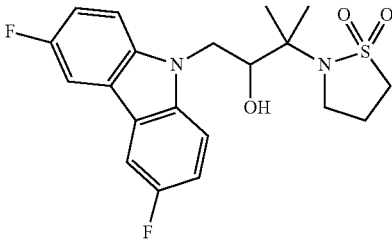 [SMILES: CC(C)(C(O)Cn1c2ccc(F)cc2c2cc(F)ccc21)N1CCCS1(=O)=O] | 2-(4-(3,6-Difluoro-9H-carbazol-9-yl)-3-hydroxy-2-methylbutan-2-yl)isothiazolidine-1,1-dioxide | (300 MHz, d6-DMSO) δ 7.99 (dd, 2H, J = 9.6, 2.7 Hz), 7.58 (dd, 2H, J = 9.0, 4.2 Hz), 7.31 (td, 2H, J = 9.3, 2.7 Hz), 5.24 (d, 1H, J = 6.0 Hz), 4.54 (d, 1H, J = 13.8 Hz), 4.29 (dd, 1H, J = 15.0, 9.9 Hz), 4.00 (m, 1H), 3.60-3.20 (m, 4H), 2.32-2.10 (m, 2H), 1.50 (s, 3H), 1.46 (s, 3H) | 409.1 (M + H) |
| 245 | 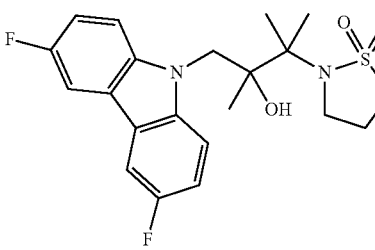 | 2-(4-(3,6-Difluoro-9H-carbazol-9-yl)-3-hydroxy-2,3-dimethylbutan-2-yl)isothiazolidine-1,1-dioxide | (300 MHz, d6-DMSO) δ 7.99 (dd, 2H, J = 9.6, 2.7 Hz), 7.61 (dd, 2H, J = 9.0, 4.2 Hz), 7.30 (td, 2H, J = 9.3, 2.7 Hz), 4.91 (s, 1H), 4.48 & 4.42 (AB, 2H, J = 15.3 Hz), 3.92 (dt, 1H, J = 9.9, 6.3 Hz), 3.54 (dt, 1H, J = 9.9, 6.6 Hz), 3.40-3.20 (m, 2H), 2.35-2.10 (m, 2H), 1.71 (s, 3H), 1.51 (s, 3H), 0.97 (s, 3H) | 422.7 (M + H) |

Specific assays useful for evaluating the compounds of formula I include the Per2 Assay for Evaluating the Potency of Test Compounds and the Cry1 Assay for Evaluating the Target of Test Compounds, as described below.

Example 3

Per2 Assay for Evaluating the Potency of Test Compounds

Compounds were screened by using a high-throughput circadian assay system as previously described in Zhang, E. E. et al. *Cell*, 2009, 139, 199-210. In brief, stable U2OS reporter cells harboring Per2-dLuc were plated at a density of 8,000 cells/well in Corning 96-well, solid white, flat bottom, TC-treated microplates (Corning®), and incubated for 24 hours at 37° C. in the presence of 5% $CO_2$. The cells were then synchronized by serum shock by media exchange to a minimal explant media (10 mM HEPES (pH 7.0), 2% B27, 1×PSG (Invitrogen®), and 1.0 mM beetle luciferin (Promega®)) followed by the addition of the compounds of formula I dissolved in dimethylsulfoxide (0.5% final dimethylsulfoxide concentration). Gene expression was monitored by measuring luminescence (Tecan® M200) over 4-5 days at 35° C. The period, amplitude, and phase of the associated circadian rhythms were determined using Multicycle™ software (Actimetrics, Inc). $EC_{50}$ values of the compounds of formula I were calculated using Graphpad™ (Prism®).

The following table provides Per2 $EC_{50}$ data for the specified Examples. The $EC_{50}$, are reported as micromolar concentration.

Table of Per2 Assay Data

| Example | Per2 $EC_{50}$ (μM) |
|---|---|
| 1 | 0.340 |
| 2 | 0.742 |
| 3 | 0.650 |
| 4 | 2.498 |
| 5 | 8.185 |
| 6 | 0.964 |
| 7 | 2.105 |
| 8 | 6.956 |
| 9 | 2.861 |
| 10 | 1.133 |
| 11 | 1.791 |
| 12 | 1.013 |
| 13 | 0.454 |
| 14 | 0.652 |
| 15 | 0.592 |
| 16 | 1.669 |
| 17 | 2.486 |
| 18 | 3.765 |
| 19 | 2.098 |
| 20 | 0.029 |
| 21 | 0.440 |
| 22 | 0.510 |
| 23 | 0.09 |
| 24 | 0.210 |
| 25 | 0.170 |
| 26 | 1.300 |
| 27 | 0.250 |
| 28 | 2.090 |
| 29 | 0.710 |
| 30 | 0.390 |
| 31 | 1.400 |
| 32 | 0.100 |
| 33 | 0.035 |
| 34 | 0.031 |
| 35 | 1.500 |
| 36 | 0.539 |
| 37 | 0.034 |
| 38 | 0.011 |
| 39 | 0.021 |
| 40 | 0.179 |
| 41 | 0.343 |
| 42 | N/A |
| 43 | 2.999 |
| 44 | 8.273 |
| 45 | 0.398 |
| 46 | 0.100 |
| 47 | 3.355 |
| 48 | 1.500 |

| Example | Per2 EC$_{50}$ (μM) |
|---|---|
| 49 | 0.100 |
| 50 | 0.148 |
| 51 | 0.371 |
| 52 | 0.306 |
| 53 | 0.578 |
| 54 | 0.824 |
| 55 | 2.308 |
| 56 | 0.128 |
| 57 | 0.035 |
| 58 | 0.150 |
| 59 | 9.582 |
| 60 | 1.222 |
| 61 | 4.474 |
| 62 | 1.329 |
| 63 | 0.199 |
| 64 | 1.003 |
| 65 | 9.500 |
| 66 | 9.900 |
| 67 | 3.143 |
| 68 | 1.986 |
| 69 | 0.759 |
| 70 | 8.966 |
| 71 | 3.300 |
| 72 | 2.580 |
| 73 | 2.986 |
| 74 | 7.623 |
| 75 | 0.842 |
| 76 | 2.178 |
| 77 | 0.750 |
| 78 | 6.348 |
| 79 | 2.799 |
| 80 | 4.225 |
| 81 | 0.964 |
| 82 | 0.158 |
| 83 | 0.413 |
| 84 | 0.892 |
| 85 | 0.510 |
| 86 | 0.046 |
| 87 | 0.020 |
| 88 | 0.940 |
| 89 | 0.360 |
| 90 | 0.406 |
| 91 | 0.150 |
| 92 | 0.040 |
| 93 | 2.886 |
| 94 | 3.448 |
| 95 | 2.743 |
| 96 | 0.456 |
| 97 | 0.319 |
| 98 | 8.104 |
| 99 | 3.554 |
| 100 | 0.032 |
| 101 | 0.050 |
| 102 | 3.247 |
| 103 | 2.213 |
| 104 | 3.499 |
| 105 | 5.198 |
| 106 | 8.600 |
| 107 | 0.240 |
| 108 | 0.388 |
| 109 | 7.421 |
| 110 | 3.634 |
| 111 | 0.084 |
| 112 | 0.044 |
| 113 | 0.123 |
| 114 | 0.521 |
| 115 | 0.232 |
| 116 | 0.540 |
| 117 | 0.127 |
| 118 | 0.081 |
| 119 | 0.037 |
| 120 | 0.023 |
| 121 | 0.051 |
| 122 | 0.329 |
| 123 | 0.033 |
| 124 | 0.154 |
| 125 | 2.612 |
| 126 | 0.425 |
| 127 | 4.006 |
| 128 | 0.372 |
| 129 | 0.386 |
| 130 | 0.636 |
| 131 | 0.079 |
| 132 | 0.348 |
| 133 | 1.527 |
| 134 | 1.078 |
| 135 | 0.609 |
| 136 | 0.113 |
| 137 | 0.076 |
| 138 | 0.041 |
| 139 | 0.263 |
| 140A | 0.503 |
| 140B | 0.823 |
| 141 | 0.846 |
| 142 | 0.813 |
| 143 | 0.028 |
| 144 | 2.155 |
| 145 | 1.347 |
| 146 | 1.161 |
| 147 | 0.980 |
| 148 | 0.489 |
| 149 | 7.619 |
| 150 | 5.047 |
| 151 | 2.258 |
| 152 | 1.912 |
| 153 | 0.396 |
| 154 | 0.680 |
| 155 | 0.324 |
| 156 | 0.471 |
| 157 | 0.895 |
| 158 | 0.811 |
| 159 | 0.505 |
| 160 | 0.605 |
| 161 | 1.136 |
| 162 | 1.992 |
| 163 | 0.206 |
| 164 | 0.200 |
| 165 | 0.095 |
| 166 | 0.147 |
| 167 | 0.267 |
| 168 | 0.391 |
| 169 | 0.504 |
| 170 | 1.256 |
| 171 | 0.025 |
| 172 | 0.375 |
| 173 | 0.086 |
| 174 | 0.080 |
| 175 | 0.035 |
| 176 | 0.125 |
| 177 | 0.202 |
| 178 | 0.073 |
| 179 | 1.199 |
| 180 | 1.651 |
| 181 | 0.174 |
| 182 | 0.241 |
| 183 | 0.053 |
| 184 | 0.155 |
| 185 | 0.045 |
| 186 | 0.083 |
| 187 | 2.750 |
| 188 | 0.147 |
| 189 | 1.293 |
| 190 | 0.211 |
| 191 | 1.189 |
| 192 | 0.686 |
| 193A | 0.427 |
| 193B | 0.654 |
| 193C | 4.469 |
| 194 | 0.078 |
| 195 | 0.254 |
| 196 | 0.149 |
| 197 | 0.873 |
| 198 | 1.227 |
| 199 | 0.544 |

203
-continued

| Example | Per2 EC$_{50}$ (µM) |
|---|---|
| 200 | 1.889 |
| 201 | 1.574 |
| 202 | 2.100 |
| 203 | 1.767 |
| 204 | 2.553 |
| 205 | 1.210 |
| 206 | 2.847 |
| 207 | 2.949 |
| 208 | 4.714 |
| 209 | 4.808 |
| 210 | 7.212 |
| 211 | 9.239 |
| 212 | 1.796 |
| 213 | 2.954 |
| 214 | 6.560 |
| 215 | 7.876 |
| 216 | 0.150 |
| 217 | 1.667 |
| 218 | 9.778 |
| 219 | 1.575 |
| 220 | 1.663 |
| 221 | 5.516 |
| 222 | 7.115 |
| 223 | 6.786 |
| 224 | 0.059 |
| 225 | 3.092 |
| 226 | 0.314 |
| 227 | 5.286 |
| 228 | 3.425 |
| 229 | 4.985 |
| 230 | 0.643 |
| 231 | 1.498 |
| 232 | 2.582 |
| 233 | 0.418 |
| 234 | 0.289 |
| 235 | 6.457 |
| 236 | 0.620 |
| 237 | 0.594 |
| 238 | 0.535 |
| 239 | 1.577 |
| 240 | 1.060 |
| 241 | 0.488 |
| 242 | 0.494 |
| 243 | 0.042 |
| 244 | 0.057 |
| 245 | 1.154 |

One of ordinary skill in the art could readily optimize this assay to determine Per2 EC$_{50}$ data for any of the compounds described herein.

Example 4

Cry1 Assay for Evaluating the Target of Test Compounds

HEK293 cells (2.5×10$^6$ cells) were reverse transfected on 6-well plates with 2 µg expression vector by Lipofectamine 2000. After 28 hours, the cells were collected in ice-cold PBS and re-suspended in 100 µL of incubation buffer (50 mM Tris, 50 mM NaCl, 2 mM EDTA, 10% glycerol, 1 mM DTT, Complete Protease Inhibitor Cocktail, Phosphatase Inhibitor Cocktail 1 and 3; pH 8.0). The mixture was supplemented with NP-40 (final 1%) and incubated on ice for 15 mins, followed by centrifugation (16,000×g) at 4° C. for 10 mins. The supernatant was used for assays. Expression vectors for C-terminally 3×Flag-tagged mCRY1 were based on p3×FLAG-CMV-14 (Sigma).

Cry1::Luc or Luc reporter HEK293 cells (1.0×10$^4$ cells) were plated onto 384-well white solid-bottom plates at 50 µL per well. After 24 hours, 500 nl of the compound (final 1% dimethylsulfoxide) was applied to the medium. After 24 hours, the medium was supplemented with luciferin (final 1 mM) and HEPES-NaOH (pH7.2; final 10 mM), and the luminescence was recorded every 7.5 min for 1 hour with a microplate reader. The luminescence intensity parameter was calculated by averaging the intensity during the experiment. The first data point was excluded from the analysis because of transient luminescence changes. Cry::Luc intensity is normalized to Luc intensity to provide final EC$_{50}$ values. EC$_{50}$ values of the compounds of formula I were calculated using Graphpad™ (Prism®).

The following table provides Cry1 EC$_{50}$ data for the specified Examples. The EC$_{50}$, are reported as micromolar concentration.

Table of Cry1 Assay Data

| Example | Cry1 EC$_{50}$ (µM) |
|---|---|
| 1 | 9.41 |
| 20 | 50.86 |
| 23 | 23.84 |
| 28 | 7.06 |
| 32 | 43.47 |
| 33 | 4.46 |
| 237 | 12.00 |
| 238 | 7.35 |
| 239 | 8.53 |

Example 5

Transient Assay for Steady-State CRY1 Protein Stabilization

HEK293 cells are transfected in 24 well plates with a mammalian expression vector (0.5 µg/well) containing a cDNA encoding full-length CRY1 with a C-terminally-encoded MycDDK tag (Origene) or FLAG-tag (Sigma) using Lipofectamine 2000 or an equivalent reagent. After 24 hours the cells are treated with test compounds with up to a final concentration of 1% DMSO. After a further 24 hours, the cells are lysed in RIPA buffer (150 mM NaCl, 1.0% IGEPAL® CA-630 (or NP-40), 0.5% sodium deoxycholate, 0.1% SDS, and 50 mM Tris, pH 8.0) containing protease inhibitor cocktail. Protein gel sample buffer is added to equivalent amounts of each sample and they are separated on a SDS-polyacrylamide gel and electrophoretically transferred to a PVDF membrane. Tagged proteins are detected with a tag-directed primary antibody and a secondary antibody conjugated to HRP. Tagged CRY1 protein is revealed by chemi-luminescence with ECL+ or other similar reagent and recorded with a digital camera as a RAW file. Photoshop and ImageJ software are employed to quantitate individual bands. The amount of tagged CRY1 protein can be compared to total protein in the loaded sample or to a subsequently detected internal control protein such as GAPDH. The relative amount of tagged CRY1 protein can be determined by comparing compound-treated cell samples to DMSO-treated cell samples. Increases in tagged CRY1 protein compared to control samples indicate that the compound increases CRY1 stability. Decreases in tagged CRY1 protein compared to control samples indicate that the compound decreases CRY1 stability. The assay described supra can be readily modified and optimized by those skilled in the art to measure or determine endogenous protein levels of any of the proteins involved in circadian rhythm and/or CRY-regulated pathways, for example, Cry2, Per1, Per2, CLOCK, BMAL1, TIM protein, or VEGF.

Example 6

Stable Cell Line Assay for Steady-State CRY1 Protein Stabilization

A stable cell line expressing a tagged CRY1 protein is treated with test compounds for 24 hours in up to 1% DMSO. After a further 24 hours, the cells are lysed in RIPA buffer (150 mM NaCl, 1.0% IGEPAL® CA-630 (or NP-40), 0.5% sodium deoxycholate, 0.1% SDS, and 50 mM Tris, pH 8.0) containing protease inhibitor cocktail. SDS-containing protein gel sample buffer is added to equivalent amounts of each sample and they are separated on a SDS-polyacrylamide gel and electrophoretically transferred to a PVDF membrane. Tagged proteins are detected with a tag-directed primary antibody and a secondary antibody conjugated to HRP. Tagged CRY1 protein is detected by chemi-luminescence with ECL+ or other similar reagent and recorded with a digital camera as a RAW file. Photoshop and ImageJ software are employed to quantitate individual bands. The amount of tagged CRY1 protein can be compared to total protein in the loaded sample or to a subsequently detected internal control protein such as GAPDH. The relative amount of tagged CRY1 protein can be determined by comparing compound-treated cell samples to control or DMSO-treated cell samples. Increases in tagged CRY1 protein compared to control samples indicate that the compound increases CRY1 stability. Decreases in tagged CRY1 protein compared to control samples indicate that the compound decreases CRY1 stability. The assay described supra can be readily modified and optimized by those skilled in the art to measure or determine endogenous protein levels of any of the proteins involved in circadian rhythm and/or CRY-regulated pathways, for example, Cry2, Per1, Per2, CLOCK, BMAL1, TIM protein, or VEGF.

Example 7

Determination of Half-Life of CRY1-Tagged Protein

Transiently transfected HEK293 cells or stable cell lines expressing a tagged-CRY1 protein are exposed to test compounds for 24 hours and then exposed to cycloheximide (1 µg/ml). The cells are lysed in RIPA buffer after incubating from 15 min to 6 hours. SDS-containing protein gel sample buffer is added to equivalent amounts of each sample and they are separated on a SDS-polyacrylamide gel and electrophoretically transferred to a PVDF membrane. Tagged proteins are detected with a tag-directed primary antibody and a secondary antibody conjugated to HRP. Tagged CRY1 protein is detected by chemi-luminescence with ECL+ OR OTHER SIMILAR REAGENT and recorded with a digital camera as a RAW file. Photoshop and ImageJ software are employed to quantitate individual bands. The amount of tagged CRY1 protein can be compared to total protein in the loaded sample or to a subsequently detected internal control protein such as GAPDH. The rate of the decline in tagged CRY1 protein abundance can be compared between test compound-treated samples and control or DMSO-treated samples. A faster rate of decline of tagged CRY1 protein in compound-treated samples compared to control samples indicates that the compound decreases CRY1 stability. A slower rate of decline of tagged CRY1 protein in compound-treated samples compared to control samples indicates that the compound increases CRY1 stability. The assay described supra can be readily modified and optimized by those skilled in the art to measure or determine the half-life of any of the proteins involved in circadian rhythm and/or CRY-regulated pathways, for example, Cry2, Per2, Per2, CLOCK, BMAL1, TIM protein, or VEGF.

Example 8

Endogenous CRY Protein Assay

Cells or tissues are exposed to test compounds or vehicle for 2 hours to 4 days prior to harvest and homogenization in RIPA buffer containing protease inhibitor cocktail. SDS-containing protein gel sample buffer is added to equivalent amounts of each sample and they are separated on a SDS-polyacrylamide gel and electrophoretically transferred to a PVDF membrane. The amounts of endogenous proteins are detected with specific antibodies directed to CRY proteins and a secondary antibody conjugated to HRP. CRY protein is revealed by chemi-luminescence with ECL+ or other similar reagent and recorded with a digital camera as a RAW file. Photoshop and ImageJ software are employed to quantitate individual bands. The amount of tagged CRY1 protein can be compared to total protein in the loaded sample or to a subsequently detected internal control protein such as GAPDH. The relative amount of CRY protein can be determined by comparing compound-treated cell or tissue samples to control, or DMSO-treated, cell or tissue samples. Increases in CRY protein compared to control samples indicate that the compound increases CRY stability. Decreases in CRY protein compared to control samples indicate that the compound decreases CRY stability. The assay described supra can be readily modified and optimized by those skilled in the art to measure or determine endogenous protein levels of any of the proteins involved in circadian rhythm and/or CRY-regulated pathways, for example, Cry2, Per1, Per2, CLOCK, BMAL1, TIM protein, or VEGF.

All documents cited in this application, including scientific publications, patents, and patent applications, are hereby incorporated by reference in their entirety.

What is claimed is:
1. A compound of formula I

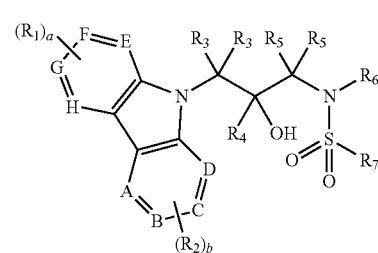

or a pharmaceutically acceptable salt or hydrate thereof, wherein each of A, B, C', D, E, F, G, and H' is independently C;

each of $R_1$ and $R_2$, is independently selected from the group consisting of H, halo, cyano, nitro, —$CF_3$, —$CHF_2$, —$CH_2F$, trifluoromethoxy, azido, hydroxyl, ($C_1$-$C_6$) alkoxy, ($C_1$-$C_6$)alkyl, ($C_2$-$C_6$)alkenyl, ($C_2$-$C_6$)alkynyl, —(C=O)—$R_8$, —(C=O)—O—$R_8$, —O—(C=O)—$R_8$, —$NR_8$(C=O)—$R_{10}$, —(C=O)—$NR_8R_9$, —$NR_8R_9$, —$NR_8OR_9$, —S(O)$_c$$NR_8R_9$, —S(O)$_d$($C_1$-$C_8$)alkyl, —O—$SO_2$—$R_8$, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_f$(C=O)

$(CR_8R_9)_e(C_6\text{-}C_{10})$aryl, $-(CR_8R_9)_f(C=O)(CR_8R_9)_e$(4-10)-membered heterocyclyl, $-(CR_8R_9)_eO(CR_8R_9)_f$ $(C_6\text{-}C_{10})$aryl, $-(CR_8R_9)_eO(CR_8R_9)_f$(4-10)-membered heterocyclyl, $-(CR_8R_9)_fS(O)_d(CR_8R_9)_e(C_6\text{-}C_{10})$aryl, and $-(CR_8R_9)_fS(O)_d(CR_8R_9)_e$(4-10)-membered heterocyclyl;

each of $R_3$ and each of $R_5$ is independently selected from the group consisting of H, cyano, $-CF_3$, $-CHF_2$, $-CH_2F$, $(C_1\text{-}C_6)$alkyl, $(C_2\text{-}C_6)$alkenyl, $(C_2\text{-}C_6)$alkynyl, $-(C=O)-R_8$, $-(C=O)-O-R_8$, $-(C=O)-NR_8R_9$, $-S(O)_cNR_8R_9$, $-S(O)_d(C_1\text{-}C_8)$alkyl, $-(CR_8R_9)_d$(3-10)-membered cycloalkyl, $-(CR_8R_9)_e$ $(C_6\text{-}C_{10})$aryl, $-(CR_8R_9)_e$(4-10)-membered heterocyclyl, $-(CR_8R_9)_f(C=O)(CR_8R_9)_e(C_6\text{-}C_{10})$aryl, $-(CR_8R_9)_f(C=O)(CR_8R_9)_e$(4-10)-membered heterocyclyl, $-(CR_8R_9)_eO(CR_8R_9)_f(C_6\text{-}C_{10})$aryl, $-(CR_8R_9)_eO(CR_8R_9)_f$(4-10)-membered heterocyclyl, $-(CR_8R_9)_fS(O)_d(CR_8R_9)_e(C_6\text{-}C_{10})$aryl, and $-(CR_8R_9)_fS(O)_d(CR_8R_9)_e$(4-10)-membered heterocyclyl;

wherein each of the $R_3$ groups are optionally linked to each other as a 4-12 membered mono- or bicyclic ring;

wherein each of the $R_5$ groups are optionally linked to each other as a 4-12 membered mono- or bicyclic ring;

$R_4$ is selected from the group consisting of H, $-CF_3$, $-CHF_2$, $-CH_2F$, $(C_1\text{-}C_6)$alkyl, $(C_2\text{-}C_6)$alkenyl, $(C_2\text{-}C_6)$alkynyl, $-(C=O)-R_8$, $-(C=O)-O-R_8$, $-(C=O)-NR_8R_9$, $-(CR_8R_9)_d$(3-10)-membered cycloalkyl, $-(CR_8R_9)_e(C_6\text{-}C_{10})$aryl, $-(CR_8R_9)_e$(4-10)-membered heterocyclyl, $-(CR_8R_9)_f(C=O)$ $(CR_8R_9)_e(C_6\text{-}C_{10})$aryl, $-(CR_8R_9)_f(C=O)(CR_8R_9)_e$(4-10)-membered heterocyclyl, $-(CR_8R_9)_eO(CR_8R_9)_f$ $(C_6\text{-}C_{10})$aryl, $-(CR_8R_9)_eO(CR_8R_9)_f$(4-10)-membered heterocyclyl, $-(CR_8R_9)_fS(O)_d(CR_8R_9)_e(C_6\text{-}C_{10})$aryl, and $-(CR_8R_9)_fS(O)_d(CR_8R_9)_e$(4-10)-membered heterocyclyl;

$R_6$ is selected from the group consisting of H, $-CF_3$, $-CHF_2$, $-CH_2F$, $(C_1\text{-}C_6)$alkyl, $(C_2\text{-}C_6)$alkenyl, $(C_2\text{-}C_6)$alkynyl, $-(C=O)-R_8$, $-(C=O)-O-R_8$, $-(C=O)-NR_8R_9$, $-(CR_8R_9)_d$(3-10)-membered cycloalkyl, $-(CR_8R_9)_e(C_6\text{-}C_{10})$aryl, $-(CR_8R_9)_e$(4-10)-membered heterocyclyl, $-(CR_8R_9)_f(C=O)$ $(CR_8R_9)_e(C_6\text{-}C_{10})$aryl, $-(CR_8R_9)_f(C=O)(CR_8R_9)_e$(4-10)-membered heterocyclyl, $-(CR_8R_9)_eO(CR_8R_9)_f$ $(C_6\text{-}C_{10})$aryl, $-(CR_8R_9)_eO(CR_8R_9)_f$(4-10)-membered heterocyclyl, $-(CR_8R_9)_fS(O)_d(CR_8R_9)_e(C_6\text{-}C_{10})$aryl, and $-(CR_8R_9)_fS(O)_d(CR_8R_9)_e$(4-10)-membered heterocyclyl;

wherein one $R_5$ group and $R_6$ are optionally linked to each other as a 4-12 membered mono- or bicyclic ring;

$R_7$ is selected from the group consisting of $-CF_3$, $-CHF_2$, $-CH_2F$, $(C_1\text{-}C_6)$alkyl, $(C_2\text{-}C_6)$alkenyl, $(C_2\text{-}C_6)$alkynyl, $-(C=O)-R_8$, $-(C=O)-O-R_8$, $-NR_8(C=O)-R_{10}$, $-(C=O)-NR_8R_9$, $-NR_8R_9$, $-NR_8OR_9$, $-(CR_8R_9)_d$(3-10)-membered cycloalkyl, $-(CR_8R_9)_e$(4-10)-membered heterocyclyl, $-(CR_8R_9)_f(C=O)(CR_8R_9)_e(C_6\text{-}C_{10})$aryl, $-(CR_8R_9)_f(C=O)$ $(CR_8R_9)_e$(4-10)-membered heterocyclyl, $-(CR_8R_9)_eO$ $(CR_8R_9)_f(C_6\text{-}C_{10})$aryl, $-(CR_8R_9)_eO(CR_8R_9)_f$(4-10)-membered heterocyclyl, $-(CR_8R_9)_fS(O)_d(CR_8R_9)_e$ $(C_6\text{-}C_{10})$aryl, and $-(CR_8R_9)_fS(O)_d(CR_8R_9)_e$(4-10)-membered heterocyclyl;

$R_6$ and $R_7$ can be linked to each other as a 4-12 membered mono- or bicyclic ring;

each of $R_8$, $R_9$ and $R_{10}$ are independently selected from the group consisting of H, $(C_1\text{-}C_6)$alkyl, $-(CR_{11}R_{12})_e$(3-10)-membered cycloalkyl, $-(CR_{11}R_{12})_g(C_6\text{-}C_{10})$aryl, and $-(CR_{11}R_{12})_g$(4-10)-membered heterocyclyl;

any carbon atoms of the $(C_1\text{-}C_6)$alkyl, the (3-10)-membered cycloalkyl, the $(C_6\text{-}C_{10})$aryl and the (4-10)-membered heterocyclyl of the foregoing $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{15}$, and $R_{16}$ are independently optionally substituted with 1 to 3 $R_{14}$ substituents each independently selected from the group consisting of halo, cyano, nitro, $-CF_3$, $-CHF_2$, $-CH_2F$, trifluoromethoxy, azido, hydroxyl, $-O-R_{15}$, $(C_1\text{-}C_6)$alkoxy, $-(CR_8R_9)_e(C_1\text{-}C_6)$alkoxy, $(C_1\text{-}C_6)$alkyl, $(C_2\text{-}C_6)$alkenyl, $(C_2\text{-}C_6)$alkynyl, $-(C=O)-R_{11}$, $-(C=O)-R_{15}$, $-(C=O)-O-R_{11}$, $-(C=O)-O-R_{15}$, $-O-(C=O)-R_{11}$, $-O-(C=O)-R_{15}$, $-NR11(C=O)-R_{13}$, $-(C=O)-NR_{11}R_{12}$, $-(C=O)-NR_{11}R_{15}$, $-NR_{11}R_{12}$, $-NR_{11}R_{15}$, $-NR_{11}OR_{12}$, $-NR_{11}OR_{15}$, $-S(O)_cNR_{11}R_{12}$, $-S(O)_cNR_{11}R_{15}$, $-S(O)_d(C_1\text{-}C_6)$alkyl, $-S(O)_dR_{15}$, $-O-SO_2-R_{11}$, $-O-SO_2-R_{15}$, $-(CR_{11}R_{12})_e$(3-10)-membered cycloalkyl, $-(CR_{11}R_{12})_e(C_6\text{-}C_{10})$aryl, $-(CR_{11}R_{12})_e$(4-10)-membered heterocyclyl, $-(CR_{11}R_{12})_f(C=O)(CR_{11}R_{12})_e$ $(C_6\text{-}C_{10})$aryl, $-(CR_{11}R_{12})_f(C=O)(CR_{11}R_{12})_e$(4-10)-membered heterocyclyl, $-(CR_{11}R_{12})_eO(CR_{11}R_{12})_f$ $(C_6\text{-}C_{10})$aryl, $-(CR_{11}R_{12})_eO(CR_{11}R_{12})_e$(4-10)-membered heterocyclyl, $-(CR_{11}R_{12})_fS(O)_d(CR_{11}R_{12})_e(C_6\text{-}C_{10})$aryl, and $-(CR_{11}R_{12})_fS(O)_d(CR_{11}R_{12})_e$(4-10)-membered heterocyclyl;

any carbon atoms of the $(C_1\text{-}C_6)$alkyl, the (3-10)-membered cycloalkyl, the $(C_6\text{-}C_{10})$aryl and the (4-10)-membered heterocyclyl of the foregoing $R_{14}$ are independently optionally substituted with 1 to 3 $R_{16}$ substituents each independently selected from the group consisting of halo, cyano, nitro, $-CF_3$, $-CHF_2$, $-CH_2F$, trifluoromethoxy, azido, $(CH_2)_eOH$, $(C_1\text{-}C_6)$alkoxy, $(C_1\text{-}C_6)$alkyl, $(C_2\text{-}C_6)$alkenyl, $(C_2\text{-}C_6)$alkynyl, $-(C=O)-R_{11}$, $-(C=O)-R_{15}$, $-(C=O)-O-R_{11}$, $-(C=O)-O-R_{15}$, $-O-(C=O)-R_{11}$, $-O-(C=O)-R_{15}$, $-NR_{11}(C=O)-R_{13}$, $-(C=O)-NR_{11}R_{12}$, $-NR_{11}R_{12}$, and $-NR_{11}R_{15}$;

any nitrogen atoms of the (4-10)-membered heterocyclyl of the foregoing $R_1$, $R_2$, $R_3$, $R_4$, $R_5$, $R_6$, $R_7$, $R_8$, $R_9$, $R_{10}$, $R_{14}$, and $R_{15}$ are independently optionally substituted with $(C_1\text{-}C_6)$alkyl, $(C_2\text{-}C_6)$alkenyl, $(C_2\text{-}C_6)$alkynyl, $-(C=O)-R_{11}$, $-(C=O)-O-R_{11}$, $-(C=O)-NR_{11}R_{12}$, $-(CR_{11}R_{12})_e$(3-10)- membered cycloalkyl, $-(CR_{11}R_{12})_e(C_6\text{-}C_{10})$aryl, $-(CR_{11}R_{12})_e$(4-10)-membered heterocyclyl, $-(CR_{11}R_{12})_f(C=O)(CR_{11}R_{12})_e$ $(C_6\text{-}C_{10})$aryl, or $-(CR_{11}R_{12})_f(C=O)(CR_{11}R_{12})_e$(4-10)-membered heterocyclyl;

each $R_{11}$, $R_{12}$, and $R_{13}$ are independently H or $(C_1\text{-}C_6)$alkyl;

$R_{15}$ is $-(CR_{11}R_{12})_e$(3-10)-membered cycloalkyl, $-(CR_{11}R_{12})_e(C_6\text{-}C_{10})$aryl, or $-(CR_{11}R_{12})_e$(4-10)-membered heterocyclyl;

a and b are each independently 1, 2, 3, or 4;

c is 1 or 2;

d is 0, 1, or 2; and e, f, and g are each independently 0, 1, 2, 3, 4, or 5, and wherein when $R_7$ is $(C_1\text{-}C_6)$alkyl, $R_6$ is selected from the group consisting of $-CF_3$, $-CHF_2$, $-CH_2F$, $(C_2\text{-}C_6)$alkenyl, $(C_2\text{-}C_6)$alkynyl, $-(C=O)-R_8$, $-(C=O)-O-R_8$, $-(C=O)-NR_8R_9$, $-(CR_8R_9)_d$(3-10)-membered cycloalkyl, $-(CR_8R_9)_e$(4-10)-membered non-aromatic heterocyclyl, $-(CR_8R_9)_f(C=O)$ $(CR_8R_9)_e(C_6\text{-}C_{10})$aryl, $-(CR_8R_9)_f(C=O)(CR_8R_9)_e$(4-10)-membered heterocyclyl, $-(CR_8R_9)_eO(CR_8R_9)_f$ ($C_6$-$C_{10}$)aryl, —($CR_8R_9$)$_e$O($CR_8R_9$)$_f$(4-10)-membered heterocyclyl, —($CR_8R_9$)$_e$S(O)$_d$($CR_8R_9$)$_e$($C_6$-$C_{10}$)aryl, and —($CR_8R_9$)$_f$S(O)$_d$($CR_8R_9$)$_e$(4-10)-membered heterocyclyl.

2. The compound according to claim 1, wherein each of $R_1$ and $R_2$ is independently selected from H or halo; $R_4$ is H or ($C_1$-$C_6$)alkyl; $R_3$ and $R_5$ are H; $R_6$ is —$CF_3$, —$CHF_2$, —$CH_2F$, ($C_1$-$C_6$)alkyl, ($C_2$-$C_6$)alkenyl, ($C_2$-$C_6$)alkynyl, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_e$S(O)$_d$($CR_8R_9$)$_e$($C_6$-$C_{10}$)aryl, or —($CR_8R_9$)$_f$S(O)$_d$($CR_8R_9$)$_e$(4-10)-membered heterocyclyl; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —($CR_8R_9$)$_d$(3-10)-membered cycloalkyl, —($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_e$S(O)$_d$($CR_8R_9$)$_e$($C_6$-$C_{10}$)aryl, or —($CR_8R_9$)$_f$S(O)$_d$($CR_8R_9$)$_e$(4-10)-membered heterocyclyl.

3. The compound according to claim 1, wherein each of $R_1$ and $R_2$ is independently selected from H or halo; $R_4$ is H or ($C_1$-$C_6$)alkyl; $R_3$ and $R_5$ are H; $R_6$ and $R_7$ are linked to each other as a 4-12 membered mono- or bicyclic ring.

4. The compound according to claim 1, wherein each of $R_1$ and $R_2$ is independently selected from H or halo; $R_4$ is H or ($C_1$-$C_6$)alkyl; $R_3$ and one $R_5$ are H; one $R_5$ and $R_6$ are linked to each other as a 4-12 membered mono- or bicyclic ring; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —($CR_8R_9$)$_d$(3-10)-membered cycloalkyl, —($CR_8R_9$)$_e$(4-10)-membered heterocyclyl, —($CR_8R_9$)$_e$O ($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_e$S(O)$_d$($CR_8R_9$)$_e$($C_6$-$C_{10}$)aryl, or —($CR_8R_9$)$_f$S(O)$_d$($CR_8R_9$)$_e$(4-10)-membered heterocyclyl.

5. The compound according to claim 1, wherein the compound is the single enantiomer bearing an (S)-configuration at C-3; each of $R_1$ and $R_2$ is independently selected from H or halo; $R_4$ is H or ($C_1$-$C_6$)alkyl, $R_3$ and $R_5$ are H; $R_6$ is —$CF_3$, —$CHF_2$, —$CH_2F$, ($C_1$-$C_6$)alkyl, ($C_2$-$C_6$)alkenyl, ($C_2$-$C_6$)alkynyl, —($CR_8R_9$)$_d$(3-10)-membered cycloalkyl, —($CR_8R_9$)$_e$($C_6$-$C_{10}$)aryl, —($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_e$S(O)$_d$($CR_8R_9$)$_e$($C_6$-$C_{10}$)aryl, or —($CR_8R_9$)$_f$S(O)$_d$($CR_8R_9$)$_e$(4-10)-membered heterocyclyl; $R_7$ is —$CF_3$, —$CHF_2$, —$CH_2F$, ($C_1$-$C_6$)alkyl, ($C_2$-$C_6$)alkenyl, ($C_2$-$C_6$)alkynyl, —($CR_8R_9$)$_d$(3-10)-membered cycloalkyl, —($CR_8R_9$)$_e$(4-10)-membered heterocyclyl, —($CR_8R_9$)$_e$O($CR_8R_9$)$_f$($C_6$-$C_{10}$)aryl, —($CR_8R_9$)$_e$O($CR_8R_9$)$_f$(4-10)-membered heterocyclyl, —($CR_8R_9$)$_e$S(O)$_d$($CR_8R_9$)$_e$($C_6$-$C_{10}$)aryl, or —($CR_8R_9$)$_f$S(O)$_d$($CR_8R_9$)$_e$(4-10)-membered heterocyclyl.

6. The compound according to claim 1, wherein the compound is the single enantiomer bearing an (S)-configuration at C-3; each of $R_1$ and $R_2$ is independently selected from H or halo; $R_4$ is H or ($C_1$-$C_6$)alkyl; $R_3$ and $R_5$ are H; $R_6$ and $R_7$ are linked to each other as a 4-12 membered mono- or bicyclic ring.

7. A compound selected from the group consisting of:
(S)—N-(3-(9H-Carbazol-9-yl)-2-hydroxypropyl)-1,2-thiazinane-1,1-dioxide;
N-(3-(3,6-Difluoro-9H-carbazol-9-yl)-2-hydroxypropyl)-isothiazolidine-1,1-dioxide;
(S)—N-(3-(9H-Carbazol-9-yl)-2-hydroxypropyl)isothiazolidine-1,1-dioxide;
2-(3-(9H-Carbazol-9-yl)-2-hydroxypropyl)-5-fluoro-isothiazolidine-1,1-dioxide;
2-(3-(3,6-Difluoro-9H-carbazol-9-yl)-2-hydroxypropyl)-1,2,6-thiadiazinane-1,1-dioxide;
N-(3-(9H-Carbazol-9-yl)-2-hydroxypropyl)-N-(1-methylcyclopentyl)methanesulfonamide;
N-(3-(9H-Carbazol-9-yl)-2-hydroxypropyl)isothiazolidine-1,1-dioxide;
N-(3-(9H-Carbazol-9-yl)-2-hydroxypropyl)-2,3-dihydrobenzo[d]isothiazole-1,1-dioxide;
N-(3-(2,6-Difluoro-9H-carbazol-9-yl)-2-hydroxypropyl)-1,2-thiazinane-1,1-dioxide; and
2-(3-(9H-Carbazol-9-yl)-2-hydroxypropyl)-1,2,6-thiadiazinane-1,1-dioxide;
or a pharmaceutically acceptable salt or hydrate thereof.

8. The compound according to claim 7 which is (S)—N-(3-(9H-Carbazol-9-yl)-2-hydroxypropyl)-1,2-thiazinane-1,1-dioxide; or a pharmaceutically acceptable salt thereof.

9. The compound according to claim 7 which is N-(3-(3,6-Difluoro-9H-carbazol-9-yl)-2-hydroxypropyl)-isothiazolidine-1,1-dioxide; or a pharmaceutically acceptable salt or hydrate thereof.

10. The compound according to claim 7 which is (S)—N-(3-(9H-Carbazol-9-yl)-2-hydroxypropyl)isothiazolidine-1,1-dioxide; or a pharmaceutically acceptable salt or hydrate thereof.

11. The compound according to claim 7 which is 2-(3-(9H-Carbazol-9-yl)-2-hydroxypropyl)-5-fluoro-isothiazolidine-1,1-dioxide; or a pharmaceutically acceptable salt or hydrate thereof.

12. The compound according to claim 7 which is 2-(3-(3,6-Difluoro-9H-carbazol-9-yl)-2-hydroxypropyl)-1,2,6-thiadiazinane-1,1-dioxide; or a pharmaceutically acceptable salt or hydrate thereof.

13. The compound according to claim 7 which is N-(3-(9H-Carbazol-9-yl)-2-hydroxypropyl)-N-(1-methylcyclopentyl)methanesulfonamide; or a pharmaceutically acceptable salt or hydrate thereof.

14. The compound according to claim 7 which is N-(3-(9H-Carbazol-9-yl)-2-hydroxypropyl)isothiazolidine-1,1-dioxide; or a pharmaceutically acceptable salt or hydrate thereof.

15. The compound according to claim 7 which is N-(3-(9H-Carbazol-9-yl)-2-hydroxypropyl)-2,3-dihydrobenzo[d]isothiazole-1,1-dioxide; or a pharmaceutically acceptable salt or hydrate thereof.

16. The compound according to claim 7 which is N-(3-(2,6-Difluoro-9H-carbazol-9-yl)-2-hydroxypropyl)-1,2-thiazinane-1,1-dioxide; or a pharmaceutically acceptable salt or hydrate thereof.

17. The compound according to claim 7 which is 2-(3-(9H-Carbazol-9-yl)-2-hydroxypropyl)-1,2,6-thiadiazinane-1,1-dioxide; or a pharmaceutically acceptable salt or hydrate thereof.

18. The compound according to claim 1, wherein said compound modulates Cry1 or Cry2.

19. The compound according to claim 18, wherein said modulation comprises any one of the following:
(i) binding to Cry1 or Cry2;
(ii) inhibiting modification of Cry1 or Cry2;
(iii) altering Cry1 or Cry2 localization;
(iv) increasing or decreasing Cry1 or Cry2 stabilization;
(v) increasing or decreasing the binding between Cry1 or Cry2 to a target;
(vi) increasing or decreasing Cry1 or Cry2 activity; and
(vii) increasing or decreasing activity of a Cry1 or Cry2 target.

20. The compound according to claim 19, wherein said target is Per1, Per2, glucocorticoid receptor (GR), CLOCK, BMAL1, or a CLOCK-BMAL1 promoter sequence.

21. A pharmaceutical composition comprising a compound according to claim 1, or a pharmaceutically acceptable salt or hydrate thereof, and a pharmaceutically acceptable carrier, adjuvant, or diluent.

22. The pharmaceutical composition according to claim 21, further comprising one or more additional therapeutic agents.

* * * * *

UNITED STATES PATENT AND TRADEMARK OFFICE
CERTIFICATE OF CORRECTION

PATENT NO. : 9,265,772 B2
APPLICATION NO. : 13/891407
DATED : February 23, 2016
INVENTOR(S) : Bersot et al.

It is certified that error appears in the above-identified patent and that said Letters Patent is hereby corrected as shown below:

Title page, item (57), Abstract,

"The subject matter herein is directed to carbazole-containing sulfonamide derivatives and pharmaceutically acceptable salts or hydrates thereof of structural formula I wherein the variable $R_1$, $R_2$, $R_3$, $R_4$, $R_5$, $R_6$, $R_7$, A, B, C, D, E, F, G, H, a, and b are accordingly described. Also provided are pharmaceutical compositions comprising the compounds of formula I to treat a Cry-mediated disease or disorder, such as diabetes, obesity, metabolic syndrome, Cushing's syndrome, and glaucoma.

I

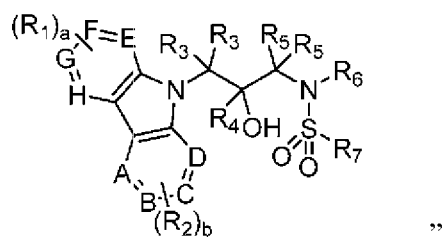

"

should read

--The subject matter herein is directed to carbazole-containing sulfonamide derivatives and pharmaceutically acceptable salts or hydrates thereof of structural formula I wherein the variable $R_1$, $R_2$, $R_3$, $R_4$, $R_5$, $R_6$, $R_7$, A, B, C', D, E, F, G, H', a, and b are accordingly described. Also provided are pharmaceutical compositions comprising the compounds of formula I to treat a Cry-mediated disease or disorder, such as diabetes, obesity, metabolic syndrome, Cushing's syndrome, and glaucoma.

Signed and Sealed this
Ninth Day of August, 2016

Michelle K. Lee
*Director of the United States Patent and Trademark Office*

CERTIFICATE OF CORRECTION (continued)

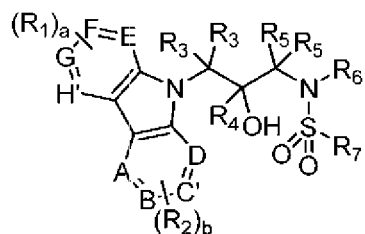

In the Specification

Column 3, Lines 12-31:

"In one aspect, the subject matter disclosed herein is directed to a compound of formula I:

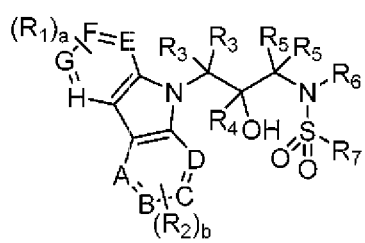

or a pharmaceutically acceptable salt or hydrate thereof, wherein:

each of A, B, C, D, E, F, G, and H is independently N or C;

each of $R_1$ and $R_2$, when A, B, C, D, E, F, G, or H is C, is"

should read

--In one aspect, the subject matter disclosed herein is directed to a compound of formula I:

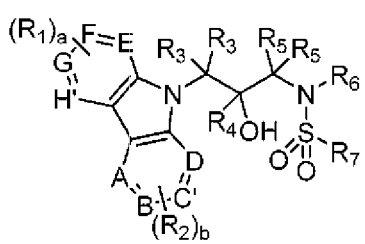

or a pharmaceutically acceptable salt or hydrate thereof, wherein:

each of A, B, C', D, E, F, G, and H' is independently N or C;

each of $R_1$ and $R_2$, when A, B, C', D, E, F, G, or H' is C, is--

Column 11, Lines 16-36:

"The subject matter disclosed herein provides carbazole-containing sulfonamide compounds that modulate one or more cryptochrome molecules. These compounds have the general structure set forth in formula I:

I

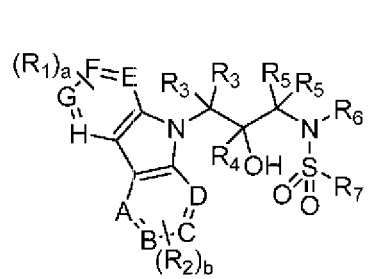

or a pharmaceutically acceptable salt or hydrate thereof, wherein:

each of A, B, C, D, E, F, G, and H is independently N or C;

each of $R_1$ and $R_2$, when A, B, C, D, E, F, G, or H is C, is"

should read

--The subject matter disclosed herein provides carbazole-containing sulfonamide compounds that modulate one or more cryptochrome molecules. These compounds have the general structure set forth in formula I:

I

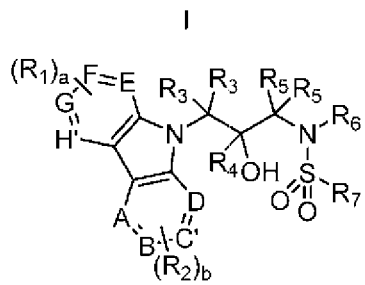

or a pharmaceutically acceptable salt or hydrate thereof, wherein:

each of A, B, C', D, E, F, G, and H' is independently N or C;

each of $R_1$ and $R_2$, when A, B, C', D, E, F, G, or H' is C, is--

CERTIFICATE OF CORRECTION (continued)
U.S. Pat. No. 9,265,772 B2

In the Claims

Claim 1, Column 206, Lines 42-54:

"
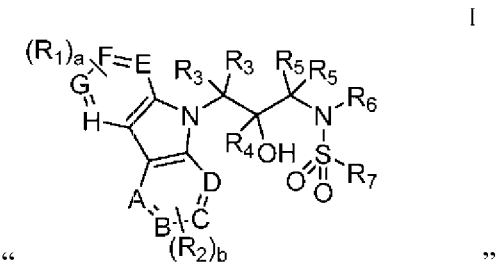
"

should read

--
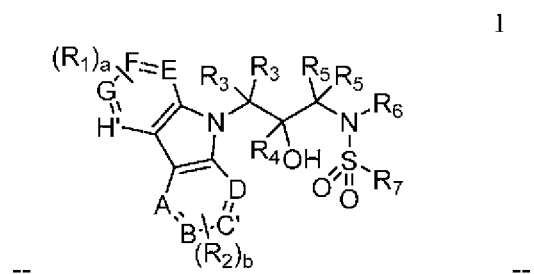
--